US012036243B2

(12) United States Patent
Lin et al.

(10) Patent No.: US 12,036,243 B2
(45) Date of Patent: Jul. 16, 2024

(54) BCMA CAR-T CELLS WITH ENHANCED ACTIVITIES

(71) Applicant: Allogene Therapeutics, Inc., South San Francisco, CA (US)

(72) Inventors: Regina Junhui Lin, San Mateo, CA (US); Siler Panowski, Berkeley, CA (US); Cesar Adolfo Sommer, San Mateo, CA (US); Thomas John Van Blarcom, Oakland, CA (US); Barbra Johnson Sasu, San Francisco, CA (US); Arun Balakumaran, Westfield, NJ (US)

(73) Assignee: Allogene Therapeutics, Inc., South San Francisco, CA (US)

( * ) Notice: Subject to any disclaimer, the term of this patent is extended or adjusted under 35 U.S.C. 154(b) by 278 days.

(21) Appl. No.: 17/183,689

(22) Filed: Feb. 24, 2021

(65) Prior Publication Data

US 2021/0260118 A1 Aug. 26, 2021

Related U.S. Application Data

(60) Provisional application No. 63/092,681, filed on Oct. 16, 2020, provisional application No. 63/053,409, filed on Jul. 17, 2020, provisional application No. 63/020,713, filed on May 6, 2020, provisional application No. 62/980,914, filed on Feb. 24, 2020.

(51) Int. Cl.

| | |
|---|---|
| ***A61K 35/17*** | (2015.01) |
| ***A61P 35/00*** | (2006.01) |
| ***C07K 14/715*** | (2006.01) |
| ***C07K 16/28*** | (2006.01) |
| ***C12N 15/86*** | (2006.01) |

(52) U.S. Cl.

CPC .............. *A61K 35/17* (2013.01); *A61P 35/00* (2018.01); *C07K 14/7151* (2013.01); *C07K 16/2878* (2013.01); *C12N 15/86* (2013.01)

(58) Field of Classification Search

CPC ..... A61K 35/17; A61P 35/00; C07K 14/7151; C07K 16/2878; C12N 15/86

See application file for complete search history.

(56) References Cited

U.S. PATENT DOCUMENTS

| | | | | |
|---|---|---|---|---|
| 8,389,282 | B2 | 3/2013 | Sadelain et al. | |
| 9,434,935 | B2 | 9/2016 | Spencer et al. | |
| 9,913,882 | B2 | 3/2018 | Slawin et al. | |
| 9,944,690 | B2 | 4/2018 | Spencer et al. | |
| 10,287,354 | B2 | 3/2019 | Brogdon et al. | |
| 10,294,304 | B2 * | 5/2019 | Pfizer | C07K 14/7051 |
| 10,336,810 | B2 | 7/2019 | Tanaka | |
| 10,548,921 | B2 | 2/2020 | Leen et al. | |
| 2014/0050709 | A1 | 2/2014 | Leen et al. | |
| 2014/0087468 | A1 | 3/2014 | Spencer et al. | |
| 2015/0111294 | A1 | 4/2015 | Spencer et al. | |
| 2016/0175359 | A1 | 6/2016 | Spencer et al. | |
| 2016/0297884 | A1 | 10/2016 | Kuo et al. | |
| 2016/0297885 | A1 * | 10/2016 | Kuo | A61K 39/39558 |
| 2018/0037630 | A1 | 2/2018 | Tanaka et al. | |
| 2019/0000881 | A1 | 1/2019 | Sadelain et al. | |
| 2019/0292533 | A1 * | 9/2019 | Nager | C07K 14/72 |

FOREIGN PATENT DOCUMENTS

| | | | |
|---|---|---|---|
| CA | 2842368 | A1 | 2/2013 |
| WO | 199802558 | A1 | 1/1998 |
| WO | WO9802558 | A2 | 1/1998 |
| WO | WO2007075899 | A2 | 7/2007 |
| WO | WO2011069004 | A1 | 6/2011 |
| WO | WO2012138858 | A1 | 10/2012 |
| WO | WO2014151960 | A2 | 9/2014 |
| WO | WO2016055551 | A1 | 4/2016 |
| WO | 2016127257 | A1 | 8/2016 |
| WO | WO2017029512 | A1 | 2/2017 |
| WO | 2017068360 | A1 | 4/2017 |
| WO | WO2017103596 | A1 | 6/2017 |

(Continued)

OTHER PUBLICATIONS

Wilms, S., et al., "Mechanism of homodimeric cytokine receptor activation and dysregulation by oncogenic mutations," Science 367(6478): 643-652. doi: 10.1126/science.aaw3242. Feb. 7, 2020. (Year: 2020).*
GenBank AAB08425.1; submitted Aug. 27, 1996. (Year: 1996).*
Floss, D. M., and Scheller, J., "Naturally occurring and synthetic constitutive-active cytokine receptors in disease and therapy," Cytokine & Growth Factor Reviews 47:1-20. doi: 10.1016/j.cytogfr.2019.05.007. Epub May 21, 2019. (Year: 2019).*
GenBank MN366105.1; submitted Aug. 22, 2019. (Year: 2019).*
Bajgain, Pradip , "CAR T Cell Therapy for Breast Cancer: Harnessing the Tumor Milieu to Drive T Cell Activation", Research Article, J Immunother Cancer. May 10, 2018;6(1):34. doi: 10.1186/s40425-018-0347-5.
Behrmann, Iris , et al., "A single STAT recruitment module in a chimeric cytokine receptor complex is sufficient for STAT activation.", J Biol Chem.;272(8):5269-74., 1997.

(Continued)

*Primary Examiner* — Tracy Vivlemore
*Assistant Examiner* — Eric J Rogers

(57) ABSTRACT

Provided here are engineered immune cells that comprise a constitutively active chimeric cytokine receptor (CACCR) and a B-cell maturation antigen (BCMA) specific chimeric antigen receptor (CAR). Also provided herein are engineered immune cells that comprise one or more nucleic acids e.g. a bicistronic vector such as a viral vector that encode the CACCRs and BCMA CARs and engineered immune cells e.g. engineered autologous or allogeneic T cells that express both CACCRs and BCMA CARs from the nucleic acids. When present on chimeric antigen receptor (CAR)-bearing engineered immune cells, the CACCRs allow for increased immune cell activation, proliferation, persistence, and/or potency. Further provided herein are methods of making and using the engineered immune cells described herein, such as methods of treating a disease or condition by administering at least one appropriate dose of the cells to a patient suffering from the condition.

32 Claims, 51 Drawing Sheets

Specification includes a Sequence Listing.

(56) References Cited

FOREIGN PATENT DOCUMENTS

| | | | |
|---|---|---|---|
| WO | WO2018038945 A1 | 3/2018 | |
| WO | WO2018094244 A1 | 5/2018 | |
| WO | WO2018104473 A1 | 6/2018 | |
| WO | 2018150187 A1 | 8/2018 | |
| WO | 2018161064 A1 | 9/2018 | |
| WO | 2019055946 A1 | 3/2019 | |
| WO | 2019102207 A1 | 5/2019 | |
| WO | WO2019118508 A1 | 6/2019 | |
| WO | 2019169290 A1 | 9/2019 | |
| WO | 2019246563 A1 | 12/2019 | |
| WO | WO-2019232425 A1 * | 12/2019 | ............ A61K 35/17 |
| WO | 2020044055 A1 | 3/2020 | |
| WO | WO2020180664 | 9/2020 | |
| WO | WO2020180694 A1 | 9/2020 | |
| WO | WO2016168612 A1 | 10/2020 | |

OTHER PUBLICATIONS

Boger, Dale L., et al., "Cytokine receptor dimerization and activation: prospects for small molecule agonists.", Bioorg Med Chem. ;9(3):557-62., 2001.

Boyerinas, B. , et al., "Abstract 602: A novel TGF-B/IL-12R signal conversion platform that protects CAR T cells from TGF-B-mediated immune suppression and concurrently amplifies effector function", Proceedings of the American Association for Cancer Research Annual Meeting 2017; Apr. 1-5, 2017; Washington, DC. Philadelphia (PA): AACR; Cancer Res 2017;77(13 Suppl):Abstract 602, 4 total pages.

Cherkassky, L., et al., "Human CAR T cells with cell-intrinsic PD-1 checkpoint blockade resist tumor-mediated inhibition", J. Clin. Invest. 126:3130-3144, 2016.

Defour, J P, et al., "Oncogenic activation of MPL/thrombopoietin receptor by 17 mutations at W515: implications for myeloproliferative neoplasms", Leukemia 30, 1214-1216; doi:10.1038/leu.2015.271, 2016.

Defour, J P, et al., "Tryptophan at the transmembrane-cytosolic junction modulates thrombopoietin receptor dimerization and activation", PNAS 110:2540-2545, 2013.

EPO , "International Search Report & Written Opinion", mailed on Nov. 17, 2020 for PCT/US2020/048402.

EPO , "International Search Report & Written Opinion", Mailed on Jun. 21, 2021 for International Application No. PCT/US2021/019362.

EPO , "International Search Report & Written Opinion", mailed on May 29, 2020 for PCT Application No. PCT/US2020/020415; 17 pages.

EPO , "International Search Report and Written Opinion", mailed on Jun. 4, 2020 for PCT Application No. PCT/US2020/020340; 15 pages.

EPO , "International Search Report and Written Opinion", mailed on May 31, 2019 for PCT Application No. PCT/US2019/020340; 18 pages.

Friedmann, Michael C., et al., "Different interleukin 2 receptor beta-chain tyrosines couple to at least two signaling pathways and synergistically mediate interleukin 2-induced proliferation", Immunology; Proc. Natl. Acad. Sci. USA, vol. 93, pp. 2077-2082, Mar. 1996.

Hoyos, V. , et al., "Engineering CD19-specific T lymphocytes with interleukin-15 and a suicide gene to enhance their anti-lymphoma/leukemia effects and safety", Leukemia 24:1160-1170, 2010.

Hurton, L. V., et al., "Tethered IL-15 augments antitumor activity and promotes a stem-cell memory subset in tumor-specific T cells", PNAS E7788-E7797, 2016.

Johnson, L.A. , et al., "Rational development and characterization of humanized anti-EGFR variant III chimeric antigen receptor T cells for glioblastoma", Science Translational Medicine, vol. 7, No. 275, Feb. 18, 2015, pp. 1-16, XP055362795, US ISSN: 1946-6234, DOI: 10.1126/scitranslmed.aaa4963.

Kagoya, Yuki , et al., "A Novel Chimeric Antigen Receptor Containing a JAK-STAT Signaling Domain Mediates Superior Antitumor Effects", Nat Med. Feb. 2018; 24(3): 352-359; doi: 10.1038/nm.4478, Feb. 5, 2018.

Kloss, C. , "TGFBeta signaling blockade within PSMA targeted CAR human T cells for the eradication of metastatic prostate cancer", Abstract 638, Molucular Therapy vol. 24, Supplement 1, 2 total pages, 2016.

Leen, Ann M, et al., "Reversal of Tumor Immune Inhibition Using a Chimeric Cytokine Receptor", Molecular Therapy vol. 22 No. 6, 1211-1220 Jun. 2014, Mar. 2014.

Leroy, Emilie , et al., "His 499 Regulates Dimerization and Prevents Oncogenic Activation by Asparagine Mutations of the Human Thrombopoietin Receptor", Journal of Biological Chemistry, vol. 291, No. 6, pp. 2974-2987, XP055696813, US ISSN: 0021-9258, DOI: 10.1074/jbc.M115.696534, 2015.

Liu, X. , et al., "A chimeric switch-receptor targeting PD1 augments the efficacy of second-generation CAR T cells in advanced solid tumors", Cancer Res. 76:1578-1590, 2016.

Lu, Xiaohui , et al., "Dimerization by a Cytokine Receptor Is Necessary for Constitutive Activation of JAK2V617F", J Biol Chem; Feb. 29, 2008;283(9):5258-66. doi: 10.1074/jbc.M707125200; Epub Dec. 23, 2007.

Malek, Thomas R., et al., "Interleukin-2 Receptor Signaling: At the Interface between Tolerance and Immunity", Immunity. Aug. 27, 2010; 33(2): 153-165. doi:10.1016/j.immuni.2010.08.004, 2010.

Matthews, E E, et al., "Thrombopoietin receptor activation: Transmembrane helix dimerization, rotation, and allosteric modulation", FASEB J. 25:2234-2244, 2011.

Maute, R L, "Engineering high-affinity PD-1 variants for optimized immunotherapy and immuno-PET imaging", PNAS 112:E6506-E6514, 2015.

Morris, Rhiannon , et al., "The molecular details of cytokine signaling via the JAK/STAT pathway", Protein Science 2018 ; vol. 27; pp. 1984-2009;, Dec. 1, 2018.

Murray, P J, "The JAK-STAT signaling pathway: input and output integration.", J Immunol. Mar. 1, 2007;178(5):2623-9., Feb. 2007.

Nakamura, T , et al., "A selective switch-on system for self-renewal of embryonic stem cells using chimeric cytokine receptors.", Biochem Biophys Res Commun. Jul. 9, 1998;248(1):22-7., Jul. 1998.

Saur, Sebastian J., et al., "Ubiquitination and degradation of the thrombopoietin receptor c-Mpl", Blood, Feb. 11, 2010 vol. 115, No. 6, pp. 1254-1263.

Shum, T , et al., "Constitutive signaling from an engineered IL7 receptor promotes durable tumor elimination by tumor-redirected T cells", Cancer Discovery 7:1-10, 2017.

Sukumaran, S. , "Enhancing the potency and specificity of engineered T cells for cancer treatment", Cancer Discovery 8:972-987, 2018.

Tokarew, Nicholas , et al., "Teaching an old dog new tricks: next-generation CAR T cells", British Journal Cancer, Nature Publishing Group; 120, 26-37. https://doi.org/10.1038/s41416-018-0325-1, Nov. 6, 2018.

Varghese, Lelia N., et al., "The Thrombopoietin Receptor: Structural Basis of Traffic and Activation by Ligand, Mutations, Agonists, and Mutated Calreticulin", Frontiers in Endocrinology, Mar. 2017, vol. 8, Article 59; doi: 10.3389/fendo.2017.00059.

Vong, Q , et al., "Inhibiting TGFbeta signaling in CAR T-cells may significantly enhance efficacy of tumor immunotherapy", Blood 130:1791, 5 total pages, 2017.

Wu, C-Y , et al., "Remote control of therapeutic T cells through a small molecule-gated chimeric receptor", Science 350:aab4077, 21 total pages, 2015.

Ajina, Adam , et al., "Strategies to Address Chimeric Antigen Receptor Tonic Signaling", Mol Cancer Ther, Sep. 2018;17(9):1795-1815. doi: 10.1158/1535-7163.MCT-17-1097.

Behncken, Stuart N., et al., "Growth Hormone (GH)-independent Dimerization of GH Receptor by a Leucine Zipper Results in Constitutive Activation", Journal of Biological Chemistry; vol. 275 Issue 22 pp. 17000-17007 (Jun. 2000) DOI: 10.1074/jbc.275.22.17000.

Ding, Jiamin , et al., "Asn 505 Mutation of the C-MPL Gene, A Cause of Familial Essential Thrombocythemia, Induces the Autono-

(56) References Cited

OTHER PUBLICATIONS mous Homodimerizaton of the C-Mpl Independent of Ligand Stimulation.", Blood; vol. 104, Issue 11, Nov. 16, 2004, p. 738.
Gacerez, Albert T., et al., "How Chimeric Antigen Receptor Design Affects Adoptive T Cell Therapy", J Cell Physiol; Dec. 2016;231(12):2590-8. doi: 10.1002/jcp.25419.
Grotzinger, Joachim , "Molecular mechanisms of cytokine receptor activation", Biochim Biophys Acta; Nov. 11, 2002;1592(3):215-23.
Hu, Yuan , et al., "Chimeric antigen receptor (CAR)-transduced natural killer cells in tumor immunotherapy", Acta Pharmacol Sin; Feb. 2018;39(2):167-176. doi: 10.1038/aps.2017.125.
Kim, Jin Hee, et al., "High cleavage efficiency of a 2A peptide derived from porcine teschovirus-1 in human cell lines, zebrafish and mice", PLoS One; 2011;6(4):e18556. doi: 10.1371/journal.pone.0018556.
Metcalfe, Riley D., et al., "Structural Understanding of Interleukin 6 Family Cytokine Signaling and Targeted Therapies: Focus on Interleukin 11", Front. Immunol., Jul. 16, 2020; Sec. Cytokines and Soluble Mediators in Immunity https://doi.org/10.3389/fimmu.2020.01424.
Shao, Huang , "Structural requirements for signal transducer and activator of transcription 3 binding to phosphotyrosine ligands containing the YXXQ motif", J Biol Chem; Apr. 30, 2004;279(18):18967-73. doi: 10.1074/jbc.M314037200. Epub Feb. 13, 2004.
Shochat, Chen , et al., "Gain-of-function mutations in interleukin-7 receptor-α (IL7R) in childhood acute lymphoblastic leukemias", Journal of Experimental Medicine; 2(2011) 208 (5): 901-908; https://doi.org/10.1084/jem.20110580.
Suthaus, Jan , et al., "Forced Homo- and Heterodimerization of All gp130-Type Receptor Complexes Leads to Constitutive Ligand-independent Signaling and Cytokine-independent Growth", Molecular Biology of the Cell vol. 21, No. 15; 2797-2807; Aug. 1, 2010; https://doi.org/10.1091/mbc.e10-03-0240.
Xie, Jiasen , et al., "Construction of an anti-programmed death-ligand 1 chimeric antigen receptor and determination of its antitumor function with transduced cells", Oncology Letters; Jul. 2018; vol. 16 Issue 1; DOI: https://doi.org/10.3892/ol.2018.8617.
Zenatti, Priscila P., et al., "Oncogenic IL7R gain-of-function mutations in childhood T-cell acute lymphoblastic leukemia", Nature Genetics; Sep. 4, 2011;43(10):932-9. doi: 10.1038/ng.924.
Zhang, Cheng , et al., "Engineering CAR-T cells", Biomarker Research vol. 5, Article No. 22 (2017).
Itaya, Miki, "Regulation of Dimerization and Activation of the Thrombopoietin Receptor", Stony Brook University . Dec. 2012.
Plo, Isabelle et al., Genetic Alterations of the Thrombopoietin/MPL/JAK2 Axis Impacting Megakaryopoiesis Front. Endocrinol. 2017, 8:234. doi: 10.3389/fendo.2017.00234.

* cited by examiner

FIG. 22C
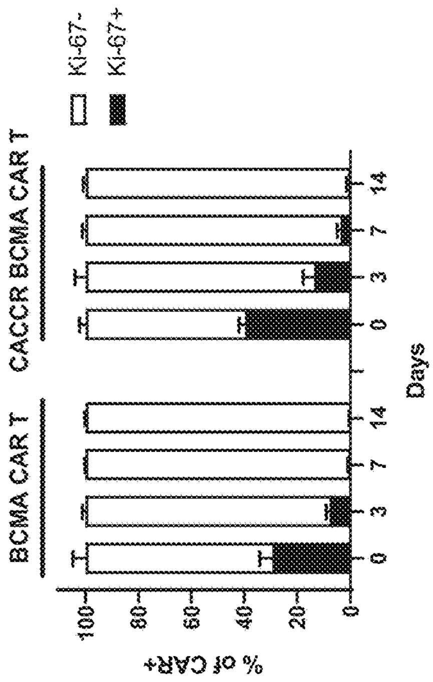
FIG. 22B
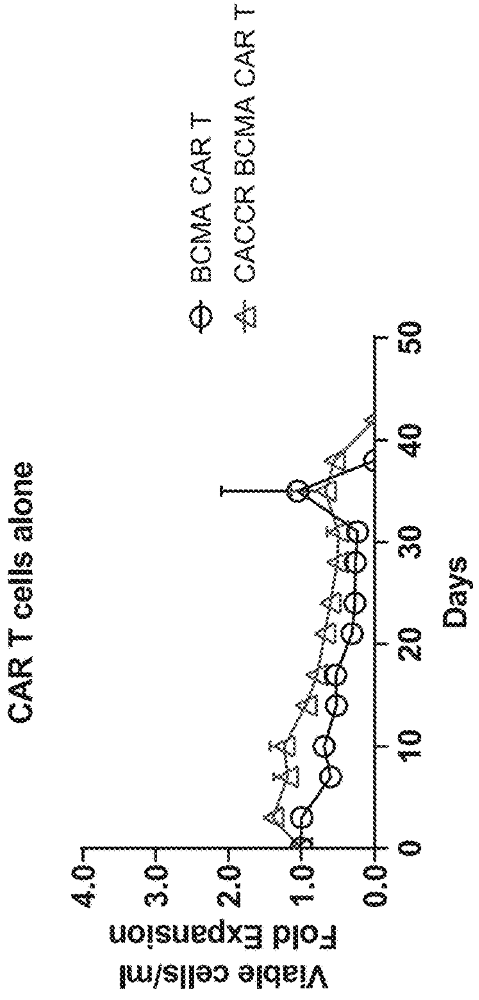
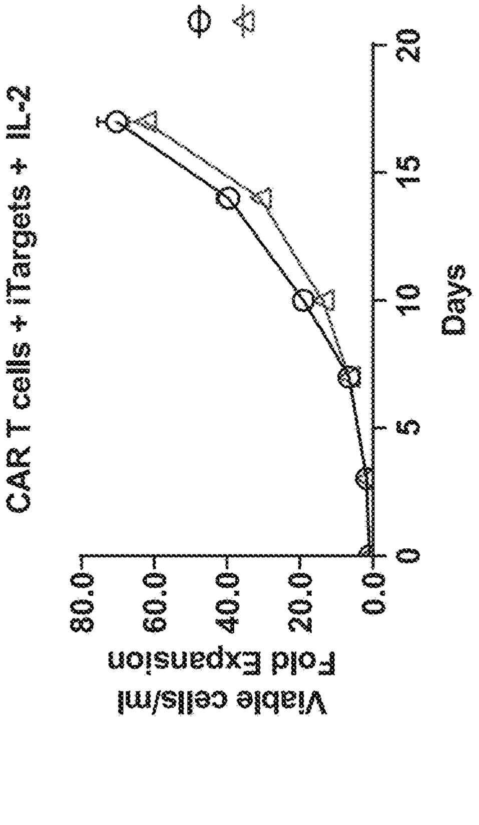
FIG. 22D

SEQUENCE LISTING

<160> NUMBER OF SEQ ID NOS: 188

<210> SEQ ID NO 1
<211> LENGTH: 508
<212> TYPE: PRT
<213> ORGANISM: Homo sapiens

<400> SEQUENCE: 1

Met Asp His Leu Gly Ala Ser Leu Trp Pro Gln Val Gly Ser Leu Cys
1               5                   10                  15

Leu Leu Leu Ala Gly Ala Ala Trp Ala Pro Pro Pro Asn Leu Pro Asp

-continued

```
            20                  25                  30

Pro Lys Phe Glu Ser Lys Ala Ala Leu Leu Ala Ala Arg Gly Pro Glu
        35                  40                  45

Glu Leu Leu Cys Phe Thr Glu Arg Leu Glu Asp Leu Val Cys Phe Trp
    50                  55                  60

Glu Glu Ala Ala Ser Ala Gly Val Gly Pro Gly Asn Tyr Ser Phe Ser
65                  70                  75                  80

Tyr Gln Leu Glu Asp Glu Pro Trp Lys Leu Cys Arg Leu His Gln Ala
                85                  90                  95

Pro Thr Ala Arg Gly Ala Val Arg Phe Trp Cys Ser Leu Pro Thr Ala
            100                 105                 110

Asp Thr Ser Ser Phe Val Pro Leu Glu Leu Arg Val Thr Ala Ala Ser
        115                 120                 125

Gly Ala Pro Arg Tyr His Arg Val Ile His Ile Asn Glu Val Val Leu
    130                 135                 140

Leu Asp Ala Pro Val Gly Leu Val Ala Arg Leu Ala Asp Glu Ser Gly
145                 150                 155                 160

His Val Val Leu Arg Trp Leu Pro Pro Pro Glu Thr Pro Met Thr Ser
                165                 170                 175

His Ile Arg Tyr Glu Val Asp Val Ser Ala Gly Asn Gly Ala Gly Ser
            180                 185                 190

Val Gln Arg Val Glu Ile Leu Glu Gly Arg Thr Glu Cys Val Leu Ser
        195                 200                 205

Asn Leu Arg Gly Arg Thr Arg Tyr Thr Phe Ala Val Arg Ala Arg Met
    210                 215                 220

Ala Glu Pro Ser Phe Gly Gly Phe Trp Ser Ala Trp Ser Glu Pro Val
225                 230                 235                 240

Ser Leu Leu Thr Pro Ser Asp Leu Asp Pro Leu Ile Leu Thr Leu Ser
                245                 250                 255

Leu Ile Leu Val Val Ile Leu Val Leu Leu Thr Val Leu Ala Leu Leu
            260                 265                 270

Ser His Arg Arg Ala Leu Lys Gln Lys Ile Trp Pro Gly Ile Pro Ser
        275                 280                 285

Pro Glu Ser Glu Phe Glu Gly Leu Phe Thr Thr His Lys Gly Asn Phe
    290                 295                 300

Gln Leu Trp Leu Tyr Gln Asn Asp Gly Cys Leu Trp Trp Ser Pro Cys
305                 310                 315                 320

Thr Pro Phe Thr Glu Asp Pro Pro Ala Ser Leu Glu Val Leu Ser Glu
                325                 330                 335

Arg Cys Trp Gly Thr Met Gln Ala Val Glu Pro Gly Thr Asp Asp Glu
            340                 345                 350

Gly Pro Leu Leu Glu Pro Val Gly Ser Glu His Ala Gln Asp Thr Tyr
        355                 360                 365

Leu Val Leu Asp Lys Trp Leu Leu Pro Arg Asn Pro Pro Ser Glu Asp
    370                 375                 380

Leu Pro Gly Pro Gly Gly Ser Val Asp Ile Val Ala Met Asp Glu Gly
385                 390                 395                 400

Ser Glu Ala Ser Ser Cys Ser Ser Ala Leu Ala Ser Lys Pro Ser Pro
                405                 410                 415

Glu Gly Ala Ser Ala Ala Ser Phe Glu Tyr Thr Ile Leu Asp Pro Ser
            420                 425                 430

Ser Gln Leu Leu Arg Pro Trp Thr Leu Cys Pro Glu Leu Pro Pro Thr
        435                 440                 445
```

```
Pro Pro His Leu Lys Tyr Leu Tyr Leu Val Val Ser Asp Ser Gly Ile
    450                 455                 460

Ser Thr Asp Tyr Ser Ser Gly Asp Ser Gln Gly Ala Gln Gly Gly Leu
465                 470                 475                 480

Ser Asp Gly Pro Tyr Ser Asn Pro Tyr Glu Asn Ser Leu Ile Pro Ala
                485                 490                 495

Ala Glu Pro Leu Pro Pro Ser Tyr Val Ala Cys Ser
            500                 505


<210> SEQ ID NO 2
<211> LENGTH: 918
<212> TYPE: PRT
<213> ORGANISM: Homo sapiens

<400> SEQUENCE: 2

Met Leu Thr Leu Gln Thr Trp Leu Val Gln Ala Leu Phe Ile Phe Leu
1               5                   10                  15

Thr Thr Glu Ser Thr Gly Glu Leu Leu Asp Pro Cys Gly Tyr Ile Ser
            20                  25                  30

Pro Glu Ser Pro Val Val Gln Leu His Ser Asn Phe Thr Ala Val Cys
        35                  40                  45

Val Leu Lys Glu Lys Cys Met Asp Tyr Phe His Val Asn Ala Asn Tyr
    50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
    130                 135                 140

Glu Trp Asp Arg Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205

Ser Asp His Ile Asn Phe Asp Pro Val Tyr Lys Val Lys Pro Asn Pro
    210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255

Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
        275                 280                 285

Leu Lys Pro Phe Thr Glu Tyr Val Phe Arg Ile Arg Cys Met Lys Glu
    290                 295                 300

Asp Gly Lys Gly Tyr Trp Ser Asp Trp Ser Glu Glu Ala Ser Gly Ile
```

-continued

```
305                 310                 315                 320

Thr Tyr Glu Asp Arg Pro Ser Lys Ala Pro Ser Phe Trp Tyr Lys Ile
                325                 330                 335

Asp Pro Ser His Thr Gln Gly Tyr Arg Thr Val Gln Leu Val Trp Lys
            340                 345                 350

Thr Leu Pro Pro Phe Glu Ala Asn Gly Lys Ile Leu Asp Tyr Glu Val
        355                 360                 365

Thr Leu Thr Arg Trp Lys Ser His Leu Gln Asn Tyr Thr Val Asn Ala
    370                 375                 380

Thr Lys Leu Thr Val Asn Leu Thr Asn Asp Arg Tyr Val Ala Thr Leu
385                 390                 395                 400

Thr Val Arg Asn Leu Val Gly Lys Ser Asp Ala Ala Val Leu Thr Ile
                405                 410                 415

Pro Ala Cys Asp Phe Gln Ala Thr His Pro Val Met Asp Leu Lys Ala
            420                 425                 430

Phe Pro Lys Asp Asn Met Leu Trp Val Glu Trp Thr Thr Pro Arg Glu
        435                 440                 445

Ser Val Lys Lys Tyr Ile Leu Glu Trp Cys Val Leu Ser Asp Lys Ala
    450                 455                 460

Pro Cys Ile Thr Asp Trp Gln Gln Glu Asp Gly Thr Val His Arg Thr
465                 470                 475                 480

Tyr Leu Arg Gly Asn Leu Ala Glu Ser Lys Cys Tyr Leu Ile Thr Val
                485                 490                 495

Thr Pro Val Tyr Ala Asp Gly Pro Gly Ser Pro Glu Ser Ile Lys Ala
            500                 505                 510

Tyr Leu Lys Gln Ala Pro Pro Ser Lys Gly Pro Thr Val Arg Thr Lys
        515                 520                 525

Lys Val Gly Lys Asn Glu Ala Val Leu Glu Trp Asp Gln Leu Pro Val
    530                 535                 540

Asp Val Gln Asn Gly Phe Ile Arg Asn Tyr Thr Ile Phe Tyr Arg Thr
545                 550                 555                 560

Ile Ile Gly Asn Glu Thr Ala Val Asn Val Asp Ser Ser His Thr Glu
                565                 570                 575

Tyr Thr Leu Ser Ser Leu Thr Ser Asp Thr Leu Tyr Met Val Arg Met
            580                 585                 590

Ala Ala Tyr Thr Asp Glu Gly Gly Lys Asp Gly Pro Glu Phe Thr Phe
        595                 600                 605

Thr Thr Pro Lys Phe Ala Gln Gly Glu Ile Glu Ala Ile Val Val Pro
    610                 615                 620

Val Cys Leu Ala Phe Leu Leu Thr Thr Leu Leu Gly Val Leu Phe Cys
625                 630                 635                 640

Phe Asn Lys Arg Asp Leu Ile Lys Lys His Ile Trp Pro Asn Val Pro
                645                 650                 655

Asp Pro Ser Lys Ser His Ile Ala Gln Trp Ser Pro His Thr Pro Pro
            660                 665                 670

Arg His Asn Phe Asn Ser Lys Asp Gln Met Tyr Ser Asp Gly Asn Phe
        675                 680                 685

Thr Asp Val Ser Val Val Glu Ile Glu Ala Asn Asp Lys Lys Pro Phe
    690                 695                 700

Pro Glu Asp Leu Lys Ser Leu Asp Leu Phe Lys Lys Glu Lys Ile Asn
705                 710                 715                 720

Thr Glu Gly His Ser Ser Gly Ile Gly Gly Ser Ser Cys Met Ser Ser
                725                 730                 735
```

Ser Arg Pro Ser Ile Ser Ser Ser Asp Glu Asn Glu Ser Ser Gln Asn
740 745 750

Thr Ser Ser Thr Val Gln Tyr Ser Thr Val Val His Ser Gly Tyr Arg
755 760 765

His Gln Val Pro Ser Val Gln Val Phe Ser Arg Ser Glu Ser Thr Gln
770 775 780

Pro Leu Leu Asp Ser Glu Glu Arg Pro Glu Asp Leu Gln Leu Val Asp
785 790 795 800

His Val Asp Gly Gly Asp Gly Ile Leu Pro Arg Gln Gln Tyr Phe Lys
805 810 815

Gln Asn Cys Ser Gln His Glu Ser Ser Pro Asp Ile Ser His Phe Glu
820 825 830

Arg Ser Lys Gln Val Ser Ser Val Asn Glu Glu Asp Phe Val Arg Leu
835 840 845

Lys Gln Gln Ile Ser Asp His Ile Ser Gln Ser Cys Gly Ser Gly Gln
850 855 860

Met Lys Met Phe Gln Glu Val Ser Ala Ala Asp Ala Phe Gly Pro Gly
865 870 875 880

Thr Glu Gly Gln Val Glu Arg Phe Glu Thr Val Gly Met Glu Ala Ala
885 890 895

Thr Asp Glu Gly Met Pro Lys Ser Tyr Leu Pro Gln Thr Val Arg Gln
900 905 910

Gly Gly Tyr Met Pro Gln
915

<210> SEQ ID NO 3
<211> LENGTH: 622
<212> TYPE: PRT
<213> ORGANISM: Homo sapiens

<400> SEQUENCE: 3

Met Lys Glu Asn Val Ala Ser Ala Thr Val Phe Thr Leu Leu Leu Phe
1 5 10 15

Leu Asn Thr Cys Leu Leu Asn Gly Gln Leu Pro Pro Gly Lys Pro Glu
20 25 30

Ile Phe Lys Cys Arg Ser Pro Asn Lys Glu Thr Phe Thr Cys Trp Trp
35 40 45

Arg Pro Gly Thr Asp Gly Gly Leu Pro Thr Asn Tyr Ser Leu Thr Tyr
50 55 60

His Arg Glu Gly Glu Thr Leu Met His Glu Cys Pro Asp Tyr Ile Thr
65 70 75 80

Gly Gly Pro Asn Ser Cys His Phe Gly Lys Gln Tyr Thr Ser Met Trp
85 90 95

Arg Thr Tyr Ile Met Met Val Asn Ala Thr Asn Gln Met Gly Ser Ser
100 105 110

Phe Ser Asp Glu Leu Tyr Val Asp Val Thr Tyr Ile Val Gln Pro Asp
115 120 125

Pro Pro Leu Glu Leu Ala Val Glu Val Lys Gln Pro Glu Asp Arg Lys
130 135 140

Pro Tyr Leu Trp Ile Lys Trp Ser Pro Pro Thr Leu Ile Asp Leu Lys
145 150 155 160

Thr Gly Trp Phe Thr Leu Leu Tyr Glu Ile Arg Leu Lys Pro Glu Lys
165 170 175

Ala Ala Glu Trp Glu Ile His Phe Ala Gly Gln Gln Thr Glu Phe Lys

```
            180                 185                 190

Ile Leu Ser Leu His Pro Gly Gln Lys Tyr Leu Val Gln Val Arg Cys
        195                 200                 205

Lys Pro Asp His Gly Tyr Trp Ser Ala Trp Ser Pro Ala Thr Phe Ile
    210                 215                 220

Gln Ile Pro Ser Asp Phe Thr Met Asn Asp Thr Thr Val Trp Ile Ser
225                 230                 235                 240

Val Ala Val Leu Ser Ala Val Ile Cys Leu Ile Ile Val Trp Ala Val
                245                 250                 255

Ala Leu Lys Gly Tyr Ser Met Val Thr Cys Ile Phe Pro Pro Val Pro
            260                 265                 270

Gly Pro Lys Ile Lys Gly Phe Asp Ala His Leu Leu Glu Lys Gly Lys
        275                 280                 285

Ser Glu Glu Leu Leu Ser Ala Leu Gly Cys Gln Asp Phe Pro Pro Thr
    290                 295                 300

Ser Asp Tyr Glu Asp Leu Leu Val Glu Tyr Leu Glu Val Asp Asp Ser
305                 310                 315                 320

Glu Asp Gln His Leu Met Ser Val His Ser Lys Glu His Pro Ser Gln
                325                 330                 335

Gly Met Lys Pro Thr Tyr Leu Asp Pro Asp Thr Asp Ser Gly Arg Gly
            340                 345                 350

Ser Cys Asp Ser Pro Ser Leu Leu Ser Glu Lys Cys Glu Glu Pro Gln
        355                 360                 365

Ala Asn Pro Ser Thr Phe Tyr Asp Pro Glu Val Ile Glu Lys Pro Glu
    370                 375                 380

Asn Pro Glu Thr Thr His Thr Trp Asp Pro Gln Cys Ile Ser Met Glu
385                 390                 395                 400

Gly Lys Ile Pro Tyr Phe His Ala Gly Gly Ser Lys Cys Ser Thr Trp
                405                 410                 415

Pro Leu Pro Gln Pro Ser Gln His Asn Pro Arg Ser Ser Tyr His Asn
            420                 425                 430

Ile Thr Asp Val Cys Glu Leu Ala Val Gly Pro Ala Gly Ala Pro Ala
        435                 440                 445

Thr Leu Leu Asn Glu Ala Gly Lys Asp Ala Leu Lys Ser Ser Gln Thr
    450                 455                 460

Ile Lys Ser Arg Glu Glu Gly Lys Ala Thr Gln Gln Arg Glu Val Glu
465                 470                 475                 480

Ser Phe His Ser Glu Thr Asp Gln Asp Thr Pro Trp Leu Leu Pro Gln
                485                 490                 495

Glu Lys Thr Pro Phe Gly Ser Ala Lys Pro Leu Asp Tyr Val Glu Ile
            500                 505                 510

His Lys Val Asn Lys Asp Gly Ala Leu Ser Leu Leu Pro Lys Gln Arg
        515                 520                 525

Glu Asn Ser Gly Lys Pro Lys Lys Pro Gly Thr Pro Glu Asn Asn Lys
    530                 535                 540

Glu Tyr Ala Lys Val Ser Gly Val Met Asp Asn Asn Ile Leu Val Leu
545                 550                 555                 560

Val Pro Asp Pro His Ala Lys Asn Val Ala Cys Phe Glu Glu Ser Ala
                565                 570                 575

Lys Glu Ala Pro Pro Ser Leu Glu Gln Asn Gln Ala Glu Lys Ala Leu
            580                 585                 590

Ala Asn Phe Thr Ala Thr Ser Ser Lys Cys Arg Leu Gln Leu Gly Gly
        595                 600                 605
```

```
Leu Asp Tyr Leu Asp Pro Ala Cys Phe Thr His Ser Phe His
    610                 615                 620


<210> SEQ ID NO 4
<211> LENGTH: 638
<212> TYPE: PRT
<213> ORGANISM: Homo sapiens

<400> SEQUENCE: 4

Met Asp Leu Trp Gln Leu Leu Leu Thr Leu Ala Leu Ala Gly Ser Ser
1               5                   10                  15

Asp Ala Phe Ser Gly Ser Glu Ala Thr Ala Ala Ile Leu Ser Arg Ala
            20                  25                  30

Pro Trp Ser Leu Gln Ser Val Asn Pro Gly Leu Lys Thr Asn Ser Ser
        35                  40                  45

Lys Glu Pro Lys Phe Thr Lys Cys Arg Ser Pro Glu Arg Glu Thr Phe
    50                  55                  60

Ser Cys His Trp Thr Asp Glu Val His His Gly Thr Lys Asn Leu Gly
65                  70                  75                  80

Pro Ile Gln Leu Phe Tyr Thr Arg Arg Asn Thr Gln Glu Trp Thr Gln
                85                  90                  95

Glu Trp Lys Glu Cys Pro Asp Tyr Val Ser Ala Gly Glu Asn Ser Cys
            100                 105                 110

Tyr Phe Asn Ser Ser Phe Thr Ser Ile Trp Ile Pro Tyr Cys Ile Lys
        115                 120                 125

Leu Thr Ser Asn Gly Gly Thr Val Asp Glu Lys Cys Phe Ser Val Asp
    130                 135                 140

Glu Ile Val Gln Pro Asp Pro Pro Ile Ala Leu Asn Trp Thr Leu Leu
145                 150                 155                 160

Asn Val Ser Leu Thr Gly Ile His Ala Asp Ile Gln Val Arg Trp Glu
                165                 170                 175

Ala Pro Arg Asn Ala Asp Ile Gln Lys Gly Trp Met Val Leu Glu Tyr
            180                 185                 190

Glu Leu Gln Tyr Lys Glu Val Asn Glu Thr Lys Trp Lys Met Met Asp
        195                 200                 205

Pro Ile Leu Thr Thr Ser Val Pro Val Tyr Ser Leu Lys Val Asp Lys
    210                 215                 220

Glu Tyr Glu Val Arg Val Arg Ser Lys Gln Arg Asn Ser Gly Asn Tyr
225                 230                 235                 240

Gly Glu Phe Ser Glu Val Leu Tyr Val Thr Leu Pro Gln Met Ser Gln
                245                 250                 255

Phe Thr Cys Glu Glu Asp Phe Tyr Phe Pro Trp Leu Leu Ile Ile Ile
            260                 265                 270

Phe Gly Ile Phe Gly Leu Thr Val Met Leu Phe Val Phe Leu Phe Ser
        275                 280                 285

Lys Gln Gln Arg Ile Lys Met Leu Ile Leu Pro Pro Val Pro Val Pro
    290                 295                 300

Lys Ile Lys Gly Ile Asp Pro Asp Leu Leu Lys Glu Gly Lys Leu Glu
305                 310                 315                 320

Glu Val Asn Thr Ile Leu Ala Ile His Asp Ser Tyr Lys Pro Glu Phe
                325                 330                 335

His Ser Asp Asp Ser Trp Val Glu Phe Ile Glu Leu Asp Ile Asp Glu
            340                 345                 350

Pro Asp Glu Lys Thr Glu Glu Ser Asp Thr Asp Arg Leu Leu Ser Ser
```

```
        355                 360                 365

Asp His Glu Lys Ser His Ser Asn Leu Gly Val Lys Asp Gly Asp Ser
    370                 375                 380

Gly Arg Thr Ser Cys Cys Glu Pro Asp Ile Leu Glu Thr Asp Phe Asn
385                 390                 395                 400

Ala Asn Asp Ile His Glu Gly Thr Ser Glu Val Ala Gln Pro Gln Arg
                405                 410                 415

Leu Lys Gly Glu Ala Asp Leu Leu Cys Leu Asp Gln Lys Asn Gln Asn
            420                 425                 430

Asn Ser Pro Tyr His Asp Ala Cys Pro Ala Thr Gln Gln Pro Ser Val
        435                 440                 445

Ile Gln Ala Glu Lys Asn Lys Pro Gln Pro Leu Pro Thr Glu Gly Ala
    450                 455                 460

Glu Ser Thr His Gln Ala Ala His Ile Gln Leu Ser Asn Pro Ser Ser
465                 470                 475                 480

Leu Ser Asn Ile Asp Phe Tyr Ala Gln Val Ser Asp Ile Thr Pro Ala
                485                 490                 495

Gly Ser Val Val Leu Ser Pro Gly Gln Lys Asn Lys Ala Gly Met Ser
            500                 505                 510

Gln Cys Asp Met His Pro Glu Met Val Ser Leu Cys Gln Glu Asn Phe
        515                 520                 525

Leu Met Asp Asn Ala Tyr Phe Cys Glu Ala Asp Ala Lys Lys Cys Ile
    530                 535                 540

Pro Val Ala Pro His Ile Lys Val Glu Ser His Ile Gln Pro Ser Leu
545                 550                 555                 560

Asn Gln Glu Asp Ile Tyr Ile Thr Thr Glu Ser Leu Thr Thr Ala Ala
                565                 570                 575

Gly Arg Pro Gly Thr Gly Glu His Val Pro Gly Ser Glu Met Pro Val
            580                 585                 590

Pro Asp Tyr Thr Ser Ile His Ile Val Gln Ser Pro Gln Gly Leu Ile
        595                 600                 605

Leu Asn Ala Thr Ala Leu Pro Leu Pro Asp Lys Glu Phe Leu Ser Ser
    610                 615                 620

Cys Gly Tyr Val Ser Thr Asp Gln Leu Asn Lys Ile Met Pro
625                 630                 635


<210> SEQ ID NO 5
<211> LENGTH: 863
<212> TYPE: PRT
<213> ORGANISM: Homo sapiens

<400> SEQUENCE: 5

Met Ala Arg Leu Gly Asn Cys Ser Leu Thr Trp Ala Ala Leu Ile Ile
1               5                   10                  15

Leu Leu Leu Pro Gly Ser Leu Glu Glu Cys Gly His Ile Ser Val Ser
            20                  25                  30

Ala Pro Ile Val His Leu Gly Asp Pro Ile Thr Ala Ser Cys Ile Ile
        35                  40                  45

Lys Gln Asn Cys Ser His Leu Asp Pro Glu Pro Gln Ile Leu Trp Arg
    50                  55                  60

Leu Gly Ala Glu Leu Gln Pro Gly Gly Arg Gln Gln Arg Leu Ser Asp
65                  70                  75                  80

Gly Thr Gln Glu Ser Ile Ile Thr Leu Pro His Leu Asn His Thr Gln
                85                  90                  95
```

```
Ala Phe Leu Ser Cys Cys Leu Asn Trp Gly Asn Ser Leu Gln Ile Leu
            100                 105                 110

Asp Gln Val Glu Leu Arg Ala Gly Tyr Pro Pro Ala Ile Pro His Asn
        115                 120                 125

Leu Ser Cys Leu Met Asn Leu Thr Thr Ser Ser Leu Ile Cys Gln Trp
    130                 135                 140

Glu Pro Gly Pro Glu Thr His Leu Pro Thr Ser Phe Thr Leu Lys Ser
145                 150                 155                 160

Phe Lys Ser Arg Gly Asn Cys Gln Thr Gln Gly Asp Ser Ile Leu Asp
                165                 170                 175

Cys Val Pro Lys Asp Gly Gln Ser His Cys Cys Ile Pro Arg Lys His
            180                 185                 190

Leu Leu Leu Tyr Gln Asn Met Gly Ile Trp Val Gln Ala Glu Asn Ala
        195                 200                 205

Leu Gly Thr Ser Met Ser Pro Gln Leu Cys Leu Asp Pro Met Asp Val
    210                 215                 220

Val Lys Leu Glu Pro Pro Met Leu Arg Thr Met Asp Pro Ser Pro Glu
225                 230                 235                 240

Ala Ala Pro Pro Gln Ala Gly Cys Leu Gln Leu Cys Trp Glu Pro Trp
                245                 250                 255

Gln Pro Gly Leu His Ile Asn Gln Lys Cys Glu Leu Arg His Lys Pro
            260                 265                 270

Gln Arg Gly Glu Ala Ser Trp Ala Leu Val Gly Pro Leu Pro Leu Glu
        275                 280                 285

Ala Leu Gln Tyr Glu Leu Cys Gly Leu Leu Pro Ala Thr Ala Tyr Thr
    290                 295                 300

Leu Gln Ile Arg Cys Ile Arg Trp Pro Leu Pro Gly His Trp Ser Asp
305                 310                 315                 320

Trp Ser Pro Ser Leu Glu Leu Arg Thr Thr Glu Arg Ala Pro Thr Val
                325                 330                 335

Arg Leu Asp Thr Trp Trp Arg Gln Arg Gln Leu Asp Pro Arg Thr Val
            340                 345                 350

Gln Leu Phe Trp Lys Pro Val Pro Leu Glu Glu Asp Ser Gly Arg Ile
        355                 360                 365

Gln Gly Tyr Val Val Ser Trp Arg Pro Ser Gly Gln Ala Gly Ala Ile
    370                 375                 380

Leu Pro Leu Cys Asn Thr Thr Glu Leu Ser Cys Thr Phe His Leu Pro
385                 390                 395                 400

Ser Glu Ala Gln Glu Val Ala Leu Val Ala Tyr Asn Ser Ala Gly Thr
                405                 410                 415

Ser Arg Pro Thr Pro Val Val Phe Ser Glu Ser Arg Gly Pro Ala Leu
            420                 425                 430

Thr Arg Leu His Ala Met Ala Arg Asp Pro His Ser Leu Trp Val Gly
        435                 440                 445

Trp Glu Pro Pro Asn Pro Trp Pro Gln Gly Tyr Val Ile Glu Trp Gly
    450                 455                 460

Leu Gly Pro Pro Ser Ala Ser Asn Ser Asn Lys Thr Trp Arg Met Glu
465                 470                 475                 480

Gln Asn Gly Arg Ala Thr Gly Phe Leu Leu Lys Glu Asn Ile Arg Pro
                485                 490                 495

Phe Gln Leu Tyr Glu Ile Ile Val Thr Pro Leu Tyr Gln Asp Thr Met
            500                 505                 510

Gly Pro Ser Gln His Val Tyr Ala Tyr Ser Gln Glu Met Ala Pro Ser
```

```
        515                 520                 525

His Ala Pro Glu Leu His Leu Lys His Ile Gly Lys Thr Trp Ala Gln
    530                 535                 540

Leu Glu Trp Val Pro Glu Pro Pro Glu Leu Gly Lys Ser Pro Leu Thr
545                 550                 555                 560

His Tyr Thr Ile Phe Trp Thr Asn Ala Gln Asn Gln Ser Phe Ser Ala
                565                 570                 575

Ile Leu Asn Ala Ser Ser Arg Gly Phe Val Leu His Gly Leu Glu Pro
            580                 585                 590

Ala Ser Leu Tyr His Ile His Leu Met Ala Ala Ser Gln Ala Gly Ala
        595                 600                 605

Thr Asn Ser Thr Val Leu Thr Leu Met Thr Leu Thr Pro Glu Gly Ser
    610                 615                 620

Glu Leu His Ile Ile Leu Gly Leu Phe Gly Leu Leu Leu Leu Leu Thr
625                 630                 635                 640

Cys Leu Cys Gly Thr Ala Trp Leu Cys Cys Ser Pro Asn Arg Lys Asn
                645                 650                 655

Pro Leu Trp Pro Ser Val Pro Asp Pro Ala His Ser Ser Leu Gly Ser
            660                 665                 670

Trp Val Pro Thr Ile Met Glu Glu Leu Pro Gly Pro Arg Gln Gly Gln
        675                 680                 685

Trp Leu Gly Gln Thr Ser Glu Met Ser Arg Ala Leu Thr Pro His Pro
    690                 695                 700

Cys Val Gln Asp Ala Phe Gln Leu Pro Gly Leu Gly Thr Pro Pro Ile
705                 710                 715                 720

Thr Lys Leu Thr Val Leu Glu Glu Asp Glu Lys Lys Pro Val Pro Trp
                725                 730                 735

Glu Ser His Asn Ser Ser Glu Thr Cys Gly Leu Pro Thr Leu Val Gln
            740                 745                 750

Thr Tyr Val Leu Gln Gly Asp Pro Arg Ala Val Ser Thr Gln Pro Gln
        755                 760                 765

Ser Gln Ser Gly Thr Ser Asp Gln Val Leu Tyr Gly Gln Leu Leu Gly
    770                 775                 780

Ser Pro Thr Ser Pro Gly Pro Gly His Tyr Leu Arg Cys Asp Ser Thr
785                 790                 795                 800

Gln Pro Leu Leu Ala Gly Leu Thr Pro Ser Pro Lys Ser Tyr Glu Asn
                805                 810                 815

Leu Trp Phe Gln Ala Ser Pro Leu Gly Thr Leu Val Thr Pro Ala Pro
            820                 825                 830

Ser Gln Glu Asp Asp Cys Val Phe Gly Pro Leu Leu Asn Phe Pro Leu
        835                 840                 845

Leu Gln Gly Ile Arg Val His Gly Met Glu Ala Leu Gly Ser Phe
    850                 855                 860


<210> SEQ ID NO 6
<211> LENGTH: 635
<212> TYPE: PRT
<213> ORGANISM: Homo sapiens

<400> SEQUENCE: 6

Met Pro Ser Trp Ala Leu Phe Met Val Thr Ser Cys Leu Leu Leu Ala
1               5                   10                  15

Pro Gln Asn Leu Ala Gln Val Ser Ser Gln Asp Val Ser Leu Leu Ala
            20                  25                  30
```

```
Ser Asp Ser Glu Pro Leu Lys Cys Phe Ser Arg Thr Phe Glu Asp Leu
        35                  40                  45

Thr Cys Phe Trp Asp Glu Glu Glu Ala Ala Pro Ser Gly Thr Tyr Gln
    50                  55                  60

Leu Leu Tyr Ala Tyr Pro Arg Glu Lys Pro Arg Ala Cys Pro Leu Ser
65                  70                  75                  80

Ser Gln Ser Met Pro His Phe Gly Thr Arg Tyr Val Cys Gln Phe Pro
                85                  90                  95

Asp Gln Glu Glu Val Arg Leu Phe Phe Pro Leu His Leu Trp Val Lys
            100                 105                 110

Asn Val Phe Leu Asn Gln Thr Arg Thr Gln Arg Val Leu Phe Val Asp
        115                 120                 125

Ser Val Gly Leu Pro Ala Pro Pro Ser Ile Ile Lys Ala Met Gly Gly
    130                 135                 140

Ser Gln Pro Gly Glu Leu Gln Ile Ser Trp Glu Glu Pro Ala Pro Glu
145                 150                 155                 160

Ile Ser Asp Phe Leu Arg Tyr Glu Leu Arg Tyr Gly Pro Arg Asp Pro
                165                 170                 175

Lys Asn Ser Thr Gly Pro Thr Val Ile Gln Leu Ile Ala Thr Glu Thr
            180                 185                 190

Cys Cys Pro Ala Leu Gln Arg Pro His Ser Ala Ser Ala Leu Asp Gln
        195                 200                 205

Ser Pro Cys Ala Gln Pro Thr Met Pro Trp Gln Asp Gly Pro Lys Gln
    210                 215                 220

Thr Ser Pro Ser Arg Glu Ala Ser Ala Leu Thr Ala Glu Gly Gly Ser
225                 230                 235                 240

Cys Leu Ile Ser Gly Leu Gln Pro Gly Asn Ser Tyr Trp Leu Gln Leu
                245                 250                 255

Arg Ser Glu Pro Asp Gly Ile Ser Leu Gly Gly Ser Trp Gly Ser Trp
            260                 265                 270

Ser Leu Pro Val Thr Val Asp Leu Pro Gly Asp Ala Val Ala Leu Gly
        275                 280                 285

Leu Gln Cys Phe Thr Leu Asp Leu Lys Asn Val Thr Cys Gln Trp Gln
    290                 295                 300

Gln Gln Asp His Ala Ser Ser Gln Gly Phe Phe Tyr His Ser Arg Ala
305                 310                 315                 320

Arg Cys Cys Pro Arg Asp Arg Tyr Pro Ile Trp Glu Asn Cys Glu Glu
                325                 330                 335

Glu Glu Lys Thr Asn Pro Gly Leu Gln Thr Pro Gln Phe Ser Arg Cys
            340                 345                 350

His Phe Lys Ser Arg Asn Asp Ser Ile Ile His Ile Leu Val Glu Val
        355                 360                 365

Thr Thr Ala Pro Gly Thr Val His Ser Tyr Leu Gly Ser Pro Phe Trp
    370                 375                 380

Ile His Gln Ala Val Arg Leu Pro Thr Pro Asn Leu His Trp Arg Glu
385                 390                 395                 400

Ile Ser Ser Gly His Leu Glu Leu Glu Trp Gln His Pro Ser Ser Trp
                405                 410                 415

Ala Ala Gln Glu Thr Cys Tyr Gln Leu Arg Tyr Thr Gly Glu Gly His
            420                 425                 430

Gln Asp Trp Lys Val Leu Glu Pro Pro Leu Gly Ala Arg Gly Gly Thr
        435                 440                 445

Leu Glu Leu Arg Pro Arg Ser Arg Tyr Arg Leu Gln Leu Arg Ala Arg
```

```
    450                 455                 460

Leu Asn Gly Pro Thr Tyr Gln Gly Pro Trp Ser Ser Trp Ser Asp Pro
465                 470                 475                 480

Thr Arg Val Glu Thr Ala Thr Glu Thr Ala Trp Ile Ser Leu Val Thr
                485                 490                 495

Ala Leu His Leu Val Leu Gly Leu Ser Ala Val Leu Gly Leu Leu Leu
            500                 505                 510

Leu Arg Trp Gln Phe Pro Ala His Tyr Arg Arg Leu Arg His Ala Leu
        515                 520                 525

Trp Pro Ser Leu Pro Asp Leu His Arg Val Leu Gly Gln Tyr Leu Arg
    530                 535                 540

Asp Thr Ala Ala Leu Ser Pro Pro Lys Ala Thr Val Ser Asp Thr Cys
545                 550                 555                 560

Glu Glu Val Glu Pro Ser Leu Leu Glu Ile Leu Pro Lys Ser Ser Glu
                565                 570                 575

Arg Thr Pro Leu Pro Leu Cys Ser Ser Gln Ala Gln Met Asp Tyr Arg
            580                 585                 590

Arg Leu Gln Pro Ser Cys Leu Gly Thr Met Pro Leu Ser Val Cys Pro
        595                 600                 605

Pro Met Ala Glu Ser Gly Ser Cys Cys Thr Thr His Ile Ala Asn His
    610                 615                 620

Ser Tyr Leu Pro Leu Ser Tyr Trp Gln Gln Pro
625                 630                 635


<210> SEQ ID NO 7
<211> LENGTH: 105
<212> TYPE: PRT
<213> ORGANISM: Homo sapiens

<400> SEQUENCE: 7

Ser Asp Pro Thr Arg Val Glu Thr Ala Thr Glu Thr Ala Trp Ile Ser
1               5                   10                  15

Leu Val Thr Ala Leu His Leu Val Leu Gly Leu Ser Ala Val Leu Gly
            20                  25                  30

Leu Leu Leu Leu Arg Trp Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu
            100                 105


<210> SEQ ID NO 8
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Ser Asp Pro Thr Arg Val Glu Thr Ala Thr Glu Thr Ala Trp Ile Ser
1               5                   10                  15

Leu Val Thr Ala Leu Leu Leu Val Leu Gly Leu Asn Ala Val Leu Gly
```

-continued

```
            20                  25                  30

Leu Leu Leu Leu Arg Trp Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu
            100                 105


<210> SEQ ID NO 9
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Ser Asp Pro Thr Arg Val Glu Thr Ala Thr Glu Thr Ala Trp Ile Ser
1               5                   10                  15

Leu Val Thr Ala Leu His Leu Val Leu Gly Leu Asn Ala Val Leu Gly
            20                  25                  30

Leu Leu Leu Leu Arg Trp Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu
            100                 105


<210> SEQ ID NO 10
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Ser Asp Pro Thr Arg Val Glu Thr Ala Thr Glu Thr Ala Trp Ile Ser
1               5                   10                  15

Leu Val Thr Ala Leu Leu Leu Val Leu Gly Leu Ser Ala Val Leu Gly
            20                  25                  30

Leu Leu Leu Leu Arg Lys Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu
```

```
            100                 105


<210> SEQ ID NO 11
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Ser Asp Pro Thr Arg Val Glu Thr Ala Thr Glu Thr Ala Trp Ile Ser
1               5                   10                  15

Leu Val Thr Ala Leu His Leu Val Leu Gly Leu Ser Ala Val Leu Gly
            20                  25                  30

Leu Leu Leu Leu Arg Lys Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu
            100                 105


<210> SEQ ID NO 12
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Ser Asp Pro Thr Arg Val Glu Thr Ala Thr Glu Thr Ala Trp Ile Ser
1               5                   10                  15

Leu Val Thr Ala Leu Leu Leu Val Leu Gly Leu Asn Ala Val Leu Gly
            20                  25                  30

Leu Leu Leu Leu Arg Lys Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu
            100                 105


<210> SEQ ID NO 13
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ser Asp Pro Thr Arg Val Glu Thr Ala Thr Glu Thr Ala Trp Ile Ser
1               5                   10                  15
```

```
Leu Val Thr Ala Leu His Leu Val Leu Gly Leu Asn Ala Val Leu Gly
            20                  25                  30

Leu Leu Leu Leu Arg Lys Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu
            100                 105


<210> SEQ ID NO 14
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Ser Asp Pro Thr Arg Val Glu Thr Ala Thr Glu Thr Ala Trp Ile Ser
1               5                   10                  15

Leu Val Thr Ala Leu Leu Leu Val Leu Gly Leu Ser Ala Val Leu Asn
            20                  25                  30

Leu Leu Leu Leu Arg Trp Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu
            100                 105


<210> SEQ ID NO 15
<211> LENGTH: 97
<212> TYPE: PRT
<213> ORGANISM: Unknown
<220> FEATURE:
<223> OTHER INFORMATION: Description of Unknown:
      GCSFR(614-710) sequence

<400> SEQUENCE: 15

Leu Thr Leu Met Thr Leu Thr Pro Glu Gly Ser Glu Leu His Ile Ile
1               5                   10                  15

Leu Gly Leu Phe Gly Leu Leu Leu Leu Leu Thr Cys Leu Cys Gly Thr
            20                  25                  30

Ala Trp Leu Cys Cys Ser Pro Asn Arg Lys Asn Pro Leu Trp Pro Ser
        35                  40                  45

Val Pro Asp Pro Ala His Ser Ser Leu Gly Ser Trp Val Pro Thr Ile
    50                  55                  60

Met Glu Glu Asp Ala Phe Gln Leu Pro Gly Leu Gly Thr Pro Pro Ile
65                  70                  75                  80

Thr Lys Leu Thr Val Leu Glu Glu Asp Glu Lys Lys Pro Val Pro Trp
                85                  90                  95
```

Glu

<210> SEQ ID NO 16
<211> LENGTH: 92
<212> TYPE: PRT
<213> ORGANISM: Homo sapiens

<400> SEQUENCE: 16

Thr Thr Pro Lys Phe Ala Gln Gly Glu Ile Glu Ala Ile Val Val Pro
1 5 10 15

Val Cys Leu Ala Phe Leu Leu Thr Thr Leu Leu Gly Val Leu Phe Cys
20 25 30

Phe Asn Lys Arg Asp Leu Ile Lys Lys His Ile Trp Pro Asn Val Pro
35 40 45

Asp Pro Ser Lys Ser His Ile Ala Gln Trp Ser Pro His Thr Pro Pro
50 55 60

Arg His Asn Phe Asn Ser Lys Asp Gln Met Tyr Ser Asp Gly Asn Phe
65 70 75 80

Thr Asp Val Ser Val Val Glu Ile Glu Ala Asn Asp
85 90

<210> SEQ ID NO 17
<211> LENGTH: 105
<212> TYPE: PRT
<213> ORGANISM: Homo sapiens

<400> SEQUENCE: 17

Ser Asp Pro Thr Arg Val Glu Thr Ala Thr Glu Thr Ala Trp Ile Ser
1 5 10 15

Leu Val Thr Ala Leu His Leu Val Leu Gly Leu Ser Ala Val Leu Gly
20 25 30

Leu Leu Leu Leu Arg Trp Gln Phe Pro Ala His Tyr Arg Arg Leu Arg
35 40 45

His Ala Leu Trp Pro Ser Leu Pro Asp Leu His Arg Val Leu Gly Gln
50 55 60

Tyr Leu Arg Asp Thr Ala Ala Leu Ser Pro Pro Lys Ala Thr Val Ser
65 70 75 80

Asp Thr Cys Glu Glu Val Glu Pro Ser Leu Leu Glu Ile Leu Pro Lys
85 90 95

Ser Ser Glu Arg Thr Pro Leu Pro Leu
100 105

<210> SEQ ID NO 18
<211> LENGTH: 104
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 18

Ser Asp Pro Thr Arg Val Glu Thr Ala Thr Glu Thr Trp Ile Ser Leu
1 5 10 15

Val Thr Ala Leu His Leu Val Leu Gly Leu Ser Ala Val Leu Gly Leu
20 25 30

Leu Leu Leu Arg Trp Gln Phe Pro Ala His Tyr Arg Arg Leu Arg His
35 40 45

Ala Leu Trp Pro Ser Leu Pro Asp Leu His Arg Val Leu Gly Gln Tyr

```
    50                  55                  60

Leu Arg Asp Thr Ala Ala Leu Ser Pro Pro Lys Ala Thr Val Ser Asp
65                  70                  75                  80

Thr Cys Glu Glu Val Glu Pro Ser Leu Leu Glu Ile Leu Pro Lys Ser
                85                  90                  95

Ser Glu Arg Thr Pro Leu Pro Leu
            100


<210> SEQ ID NO 19
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Ser Asp Pro Thr Arg Val Glu Thr Ala Thr Glu Thr Ile Ser Leu Val
1               5                   10                  15

Thr Ala Leu His Leu Val Leu Gly Leu Ser Ala Val Leu Gly Leu Leu
            20                  25                  30

Leu Leu Arg Trp Gln Phe Pro Ala His Tyr Arg Arg Leu Arg His Ala
        35                  40                  45

Leu Trp Pro Ser Leu Pro Asp Leu His Arg Val Leu Gly Gln Tyr Leu
    50                  55                  60

Arg Asp Thr Ala Ala Leu Ser Pro Pro Lys Ala Thr Val Ser Asp Thr
65                  70                  75                  80

Cys Glu Glu Val Glu Pro Ser Leu Leu Glu Ile Leu Pro Lys Ser Ser
                85                  90                  95

Glu Arg Thr Pro Leu Pro Leu
            100


<210> SEQ ID NO 20
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Ser Asp Pro Thr Arg Val Glu Thr Ala Thr Glu Thr Leu Ile Ser Leu
1               5                   10                  15

Val Thr Ala Leu His Leu Val Leu Gly Leu Ser Ala Val Leu Gly Leu
            20                  25                  30

Leu Leu Leu Arg Trp Gln Phe Pro Ala His Tyr Arg Arg Leu Arg His
        35                  40                  45

Ala Leu Trp Pro Ser Leu Pro Asp Leu His Arg Val Leu Gly Gln Tyr
    50                  55                  60

Leu Arg Asp Thr Ala Ala Leu Ser Pro Pro Lys Ala Thr Val Ser Asp
65                  70                  75                  80

Thr Cys Glu Glu Val Glu Pro Ser Leu Leu Glu Ile Leu Pro Lys Ser
                85                  90                  95

Ser Glu Arg Thr Pro Leu Pro Leu
            100


<210> SEQ ID NO 21
<211> LENGTH: 102
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 21

Ser Asp Pro Thr Arg Val Glu Thr Ala Thr Glu Thr Ser Leu Val Thr
1               5                   10                  15

Ala Leu His Leu Val Leu Gly Leu Ser Ala Val Leu Gly Leu Leu Leu
            20                  25                  30

Leu Arg Trp Gln Phe Pro Ala His Tyr Arg Arg Leu Arg His Ala Leu
        35                  40                  45

Trp Pro Ser Leu Pro Asp Leu His Arg Val Leu Gly Gln Tyr Leu Arg
    50                  55                  60

Asp Thr Ala Ala Leu Ser Pro Pro Lys Ala Thr Val Ser Asp Thr Cys
65                  70                  75                  80

Glu Glu Val Glu Pro Ser Leu Leu Glu Ile Leu Pro Lys Ser Ser Glu
                85                  90                  95

Arg Thr Pro Leu Pro Leu
            100


<210> SEQ ID NO 22
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Ser Asp Pro Thr Arg Val Glu Thr Ala Thr Glu Thr Leu Val Thr Ala
1               5                   10                  15

Leu His Leu Val Leu Gly Leu Ser Ala Val Leu Gly Leu Leu Leu Leu
            20                  25                  30

Arg Trp Gln Phe Pro Ala His Tyr Arg Arg Leu Arg His Ala Leu Trp
        35                  40                  45

Pro Ser Leu Pro Asp Leu His Arg Val Leu Gly Gln Tyr Leu Arg Asp
    50                  55                  60

Thr Ala Ala Leu Ser Pro Pro Lys Ala Thr Val Ser Asp Thr Cys Glu
65                  70                  75                  80

Glu Val Glu Pro Ser Leu Leu Glu Ile Leu Pro Lys Ser Ser Glu Arg
                85                  90                  95

Thr Pro Leu Pro Leu
            100


<210> SEQ ID NO 23
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Ser Asp Pro Thr Arg Val Glu Thr Ala Thr Glu Thr Ile Leu Val Thr
1               5                   10                  15

Ala Leu His Leu Val Leu Gly Leu Ser Ala Val Leu Gly Leu Leu Leu
            20                  25                  30

Leu Arg Trp Gln Phe Pro Ala His Tyr Arg Arg Leu Arg His Ala Leu
        35                  40                  45
```

```
Trp Pro Ser Leu Pro Asp Leu His Arg Val Leu Gly Gln Tyr Leu Arg
    50                  55                  60

Asp Thr Ala Ala Leu Ser Pro Pro Lys Ala Thr Val Ser Asp Thr Cys
65                  70                  75                  80

Glu Glu Val Glu Pro Ser Leu Leu Glu Ile Leu Pro Lys Ser Ser Glu
                85                  90                  95

Arg Thr Pro Leu Pro Leu
            100


<210> SEQ ID NO 24
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Ser Asp Pro Thr Arg Val Glu Thr Ala Thr Glu Thr Val Thr Ala Leu
1               5                   10                  15

His Leu Val Leu Gly Leu Ser Ala Val Leu Gly Leu Leu Leu Leu Arg
            20                  25                  30

Trp Gln Phe Pro Ala His Tyr Arg Arg Leu Arg His Ala Leu Trp Pro
        35                  40                  45

Ser Leu Pro Asp Leu His Arg Val Leu Gly Gln Tyr Leu Arg Asp Thr
    50                  55                  60

Ala Ala Leu Ser Pro Pro Lys Ala Thr Val Ser Asp Thr Cys Glu Glu
65                  70                  75                  80

Val Glu Pro Ser Leu Leu Glu Ile Leu Pro Lys Ser Ser Glu Arg Thr
                85                  90                  95

Pro Leu Pro Leu
            100


<210> SEQ ID NO 25
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Ser Asp Pro Thr Arg Val Glu Thr Ala Thr Glu Thr Thr Ala Leu His
1               5                   10                  15

Leu Val Leu Gly Leu Ser Ala Val Leu Gly Leu Leu Leu Leu Arg Trp
            20                  25                  30

Gln Phe Pro Ala His Tyr Arg Arg Leu Arg His Ala Leu Trp Pro Ser
        35                  40                  45

Leu Pro Asp Leu His Arg Val Leu Gly Gln Tyr Leu Arg Asp Thr Ala
    50                  55                  60

Ala Leu Ser Pro Pro Lys Ala Thr Val Ser Asp Thr Cys Glu Glu Val
65                  70                  75                  80

Glu Pro Ser Leu Leu Glu Ile Leu Pro Lys Ser Ser Glu Arg Thr Pro
                85                  90                  95

Leu Pro Leu


<210> SEQ ID NO 26
<211> LENGTH: 98
```

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 26

```
Ser Asp Pro Thr Arg Val Glu Thr Ala Thr Glu Thr Ala Leu His Leu
1               5                   10                  15

Val Leu Gly Leu Ser Ala Val Leu Gly Leu Leu Leu Leu Arg Trp Gln
            20                  25                  30

Phe Pro Ala His Tyr Arg Arg Leu Arg His Ala Leu Trp Pro Ser Leu
        35                  40                  45

Pro Asp Leu His Arg Val Leu Gly Gln Tyr Leu Arg Asp Thr Ala Ala
    50                  55                  60

Leu Ser Pro Pro Lys Ala Thr Val Ser Asp Thr Cys Glu Glu Val Glu
65                  70                  75                  80

Pro Ser Leu Leu Glu Ile Leu Pro Lys Ser Ser Glu Arg Thr Pro Leu
                85                  90                  95

Pro Leu
```

<210> SEQ ID NO 27
<211> LENGTH: 97
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 27

```
Ser Asp Pro Thr Arg Val Glu Thr Ala Thr Glu Thr Leu His Leu Val
1               5                   10                  15

Leu Gly Leu Ser Ala Val Leu Gly Leu Leu Leu Leu Arg Trp Gln Phe
            20                  25                  30

Pro Ala His Tyr Arg Arg Leu Arg His Ala Leu Trp Pro Ser Leu Pro
        35                  40                  45

Asp Leu His Arg Val Leu Gly Gln Tyr Leu Arg Asp Thr Ala Ala Leu
    50                  55                  60

Ser Pro Pro Lys Ala Thr Val Ser Asp Thr Cys Glu Glu Val Glu Pro
65                  70                  75                  80

Ser Leu Leu Glu Ile Leu Pro Lys Ser Ser Glu Arg Thr Pro Leu Pro
                85                  90                  95

Leu
```

<210> SEQ ID NO 28
<211> LENGTH: 96
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 28

```
Ser Asp Pro Thr Arg Val Glu Thr Ala Thr Glu Thr His Leu Val Leu
1               5                   10                  15

Gly Leu Ser Ala Val Leu Gly Leu Leu Leu Leu Arg Trp Gln Phe Pro
            20                  25                  30

Ala His Tyr Arg Arg Leu Arg His Ala Leu Trp Pro Ser Leu Pro Asp
        35                  40                  45
```

-continued

```
Leu His Arg Val Leu Gly Gln Tyr Leu Arg Asp Thr Ala Ala Leu Ser
    50                  55                  60

Pro Pro Lys Ala Thr Val Ser Asp Thr Cys Glu Glu Val Glu Pro Ser
65                  70                  75                  80

Leu Leu Glu Ile Leu Pro Lys Ser Ser Glu Arg Thr Pro Leu Pro Leu
                85                  90                  95
```

<210> SEQ ID NO 29
<211> LENGTH: 95
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 29

```
Ser Asp Pro Thr Arg Val Glu Thr Ala Thr Glu Thr Leu Val Leu Gly
1               5                   10                  15

Leu Ser Ala Val Leu Gly Leu Leu Leu Leu Arg Trp Gln Phe Pro Ala
            20                  25                  30

His Tyr Arg Arg Leu Arg His Ala Leu Trp Pro Ser Leu Pro Asp Leu
        35                  40                  45

His Arg Val Leu Gly Gln Tyr Leu Arg Asp Thr Ala Ala Leu Ser Pro
    50                  55                  60

Pro Lys Ala Thr Val Ser Asp Thr Cys Glu Glu Val Glu Pro Ser Leu
65                  70                  75                  80

Leu Glu Ile Leu Pro Lys Ser Ser Glu Arg Thr Pro Leu Pro Leu
                85                  90                  95
```

<210> SEQ ID NO 30
<211> LENGTH: 94
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 30

```
Ser Asp Pro Thr Arg Val Glu Thr Ala Thr Glu Thr Val Leu Gly Leu
1               5                   10                  15

Ser Ala Val Leu Gly Leu Leu Leu Leu Arg Trp Gln Phe Pro Ala His
            20                  25                  30

Tyr Arg Arg Leu Arg His Ala Leu Trp Pro Ser Leu Pro Asp Leu His
        35                  40                  45

Arg Val Leu Gly Gln Tyr Leu Arg Asp Thr Ala Ala Leu Ser Pro Pro
    50                  55                  60

Lys Ala Thr Val Ser Asp Thr Cys Glu Glu Val Glu Pro Ser Leu Leu
65                  70                  75                  80

Glu Ile Leu Pro Lys Ser Ser Glu Arg Thr Pro Leu Pro Leu
                85                  90
```

<210> SEQ ID NO 31
<211> LENGTH: 93
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 31

```
Ser Asp Pro Thr Arg Val Glu Thr Ala Thr Glu Thr Leu Gly Leu Ser
```

```
1               5                   10                  15

Ala Val Leu Gly Leu Leu Leu Leu Arg Trp Gln Phe Pro Ala His Tyr
            20                  25                  30

Arg Arg Leu Arg His Ala Leu Trp Pro Ser Leu Pro Asp Leu His Arg
        35                  40                  45

Val Leu Gly Gln Tyr Leu Arg Asp Thr Ala Ala Leu Ser Pro Pro Lys
    50                  55                  60

Ala Thr Val Ser Asp Thr Cys Glu Glu Val Glu Pro Ser Leu Leu Glu
65                  70                  75                  80

Ile Leu Pro Lys Ser Ser Glu Arg Thr Pro Leu Pro Leu
                85                  90


<210> SEQ ID NO 32
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Ser Asp Pro Thr Arg Val Glu Thr Ala Thr Glu Thr Gly Leu Ser Ala
1               5                   10                  15

Val Leu Gly Leu Leu Leu Leu Arg Trp Gln Phe Pro Ala His Tyr Arg
            20                  25                  30

Arg Leu Arg His Ala Leu Trp Pro Ser Leu Pro Asp Leu His Arg Val
        35                  40                  45

Leu Gly Gln Tyr Leu Arg Asp Thr Ala Ala Leu Ser Pro Pro Lys Ala
    50                  55                  60

Thr Val Ser Asp Thr Cys Glu Glu Val Glu Pro Ser Leu Leu Glu Ile
65                  70                  75                  80

Leu Pro Lys Ser Ser Glu Arg Thr Pro Leu Pro Leu
                85                  90


<210> SEQ ID NO 33
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Ser Asp Pro Thr Arg Val Glu Thr Ala Thr Glu Thr Leu Ser Ala Val
1               5                   10                  15

Leu Gly Leu Leu Leu Leu Arg Trp Gln Phe Pro Ala His Tyr Arg Arg
            20                  25                  30

Leu Arg His Ala Leu Trp Pro Ser Leu Pro Asp Leu His Arg Val Leu
        35                  40                  45

Gly Gln Tyr Leu Arg Asp Thr Ala Ala Leu Ser Pro Pro Lys Ala Thr
    50                  55                  60

Val Ser Asp Thr Cys Glu Glu Val Glu Pro Ser Leu Leu Glu Ile Leu
65                  70                  75                  80

Pro Lys Ser Ser Glu Arg Thr Pro Leu Pro Leu
                85                  90


<210> SEQ ID NO 34
<211> LENGTH: 90
<212> TYPE: PRT
```

<213> ORGANISM: Artificial Sequence
<220> FEATURE:
<223> OTHER INFORMATION: Description of Artificial Sequence: Synthetic
polypeptide

<400> SEQUENCE: 34

Ser Asp Pro Thr Arg Val Glu Thr Ala Thr Glu Thr Ser Ala Val Leu
1 5 10 15

Gly Leu Leu Leu Leu Arg Trp Gln Phe Pro Ala His Tyr Arg Arg Leu
20 25 30

Arg His Ala Leu Trp Pro Ser Leu Pro Asp Leu His Arg Val Leu Gly
35 40 45

Gln Tyr Leu Arg Asp Thr Ala Ala Leu Ser Pro Pro Lys Ala Thr Val
50 55 60

Ser Asp Thr Cys Glu Glu Val Glu Pro Ser Leu Leu Glu Ile Leu Pro
65 70 75 80

Lys Ser Ser Glu Arg Thr Pro Leu Pro Leu
85 90

<210> SEQ ID NO 35
<211> LENGTH: 89
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 35

Ser Asp Pro Thr Arg Val Glu Thr Ala Thr Glu Thr Ala Val Leu Gly
1 5 10 15

Leu Leu Leu Leu Arg Trp Gln Phe Pro Ala His Tyr Arg Arg Leu Arg
20 25 30

His Ala Leu Trp Pro Ser Leu Pro Asp Leu His Arg Val Leu Gly Gln
35 40 45

Tyr Leu Arg Asp Thr Ala Ala Leu Ser Pro Pro Lys Ala Thr Val Ser
50 55 60

Asp Thr Cys Glu Glu Val Glu Pro Ser Leu Leu Glu Ile Leu Pro Lys
65 70 75 80

Ser Ser Glu Arg Thr Pro Leu Pro Leu
85

<210> SEQ ID NO 36
<211> LENGTH: 88
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 36

Ser Asp Pro Thr Arg Val Glu Thr Ala Thr Glu Thr Val Leu Gly Leu
1 5 10 15

Leu Leu Leu Arg Trp Gln Phe Pro Ala His Tyr Arg Arg Leu Arg His
20 25 30

Ala Leu Trp Pro Ser Leu Pro Asp Leu His Arg Val Leu Gly Gln Tyr
35 40 45

Leu Arg Asp Thr Ala Ala Leu Ser Pro Pro Lys Ala Thr Val Ser Asp
50 55 60

Thr Cys Glu Glu Val Glu Pro Ser Leu Leu Glu Ile Leu Pro Lys Ser
65 70 75 80

```
Ser Glu Arg Thr Pro Leu Pro Leu
                85


<210> SEQ ID NO 37
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Ser Asp Pro Thr Arg Val Glu Thr Ala Thr Glu Thr Leu Gly Leu Leu
1               5                   10                  15

Leu Leu Arg Trp Gln Phe Pro Ala His Tyr Arg Arg Leu Arg His Ala
            20                  25                  30

Leu Trp Pro Ser Leu Pro Asp Leu His Arg Val Leu Gly Gln Tyr Leu
        35                  40                  45

Arg Asp Thr Ala Ala Leu Ser Pro Pro Lys Ala Thr Val Ser Asp Thr
    50                  55                  60

Cys Glu Glu Val Glu Pro Ser Leu Leu Glu Ile Leu Pro Lys Ser Ser
65                  70                  75                  80

Glu Arg Thr Pro Leu Pro Leu
                85


<210> SEQ ID NO 38
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Ser Asp Pro Thr Arg Val Glu Thr Ala Thr Glu Thr Ala Trp Leu Ile
1               5                   10                  15

Ser Leu Val Thr Ala Leu His Leu Val Leu Gly Leu Ser Ala Val Leu
            20                  25                  30

Gly Leu Leu Leu Leu Arg Trp Gln Phe Pro Ala His Tyr Arg Arg Leu
        35                  40                  45

Arg His Ala Leu Trp Pro Ser Leu Pro Asp Leu His Arg Val Leu Gly
    50                  55                  60

Gln Tyr Leu Arg Asp Thr Ala Ala Leu Ser Pro Pro Lys Ala Thr Val
65                  70                  75                  80

Ser Asp Thr Cys Glu Glu Val Glu Pro Ser Leu Leu Glu Ile Leu Pro
                85                  90                  95

Lys Ser Ser Glu Arg Thr Pro Leu Pro Leu
            100                 105


<210> SEQ ID NO 39
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Ser Asp Pro Thr Arg Val Glu Thr Ala Thr Glu Thr Ala Trp Val Leu
1               5                   10                  15
```

```
Ile Ser Leu Val Thr Ala Leu His Leu Val Leu Gly Leu Ser Ala Val
            20                  25                  30

Leu Gly Leu Leu Leu Leu Arg Trp Gln Phe Pro Ala His Tyr Arg Arg
        35                  40                  45

Leu Arg His Ala Leu Trp Pro Ser Leu Pro Asp Leu His Arg Val Leu
    50                  55                  60

Gly Gln Tyr Leu Arg Asp Thr Ala Ala Leu Ser Pro Pro Lys Ala Thr
65                  70                  75                  80

Val Ser Asp Thr Cys Glu Glu Val Glu Pro Ser Leu Leu Glu Ile Leu
                85                  90                  95

Pro Lys Ser Ser Glu Arg Thr Pro Leu Pro Leu
            100                 105


<210> SEQ ID NO 40
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Ser Asp Pro Thr Arg Val Glu Thr Ala Thr Glu Thr Ala Trp Leu Val
1               5                   10                  15

Leu Ile Ser Leu Val Thr Ala Leu His Leu Val Leu Gly Leu Ser Ala
            20                  25                  30

Val Leu Gly Leu Leu Leu Leu Arg Trp Gln Phe Pro Ala His Tyr Arg
        35                  40                  45

Arg Leu Arg His Ala Leu Trp Pro Ser Leu Pro Asp Leu His Arg Val
    50                  55                  60

Leu Gly Gln Tyr Leu Arg Asp Thr Ala Ala Leu Ser Pro Pro Lys Ala
65                  70                  75                  80

Thr Val Ser Asp Thr Cys Glu Glu Val Glu Pro Ser Leu Leu Glu Ile
                85                  90                  95

Leu Pro Lys Ser Ser Glu Arg Thr Pro Leu Pro Leu
            100                 105


<210> SEQ ID NO 41
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Ser Asp Pro Thr Arg Val Glu Thr Ala Thr Glu Thr Ala Trp Ile Leu
1               5                   10                  15

Val Leu Ile Ser Leu Val Thr Ala Leu His Leu Val Leu Gly Leu Ser
            20                  25                  30

Ala Val Leu Gly Leu Leu Leu Leu Arg Trp Gln Phe Pro Ala His Tyr
        35                  40                  45

Arg Arg Leu Arg His Ala Leu Trp Pro Ser Leu Pro Asp Leu His Arg
    50                  55                  60

Val Leu Gly Gln Tyr Leu Arg Asp Thr Ala Ala Leu Ser Pro Pro Lys
65                  70                  75                  80

Ala Thr Val Ser Asp Thr Cys Glu Glu Val Glu Pro Ser Leu Leu Glu
                85                  90                  95
```

-continued

```
Ile Leu Pro Lys Ser Ser Glu Arg Thr Pro Leu Pro Leu
            100                 105


<210> SEQ ID NO 42
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Ser Asp Pro Thr Arg Val Glu Thr Ala Thr Glu Thr Ala Trp Leu Ile
1               5                   10                  15

Leu Val Leu Ile Ser Leu Val Thr Ala Leu His Leu Val Leu Gly Leu
            20                  25                  30

Ser Ala Val Leu Gly Leu Leu Leu Leu Arg Trp Gln Phe Pro Ala His
        35                  40                  45

Tyr Arg Arg Leu Arg His Ala Leu Trp Pro Ser Leu Pro Asp Leu His
    50                  55                  60

Arg Val Leu Gly Gln Tyr Leu Arg Asp Thr Ala Ala Leu Ser Pro Pro
65                  70                  75                  80

Lys Ala Thr Val Ser Asp Thr Cys Glu Glu Val Glu Pro Ser Leu Leu
                85                  90                  95

Glu Ile Leu Pro Lys Ser Ser Glu Arg Thr Pro Leu Pro Leu
            100                 105                 110


<210> SEQ ID NO 43
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Ser Asp Pro Thr Arg Val Glu Thr Ala Thr Glu Thr Ala Trp Leu Leu
1               5                   10                  15

Ile Leu Val Leu Ile Ser Leu Val Thr Ala Leu His Leu Val Leu Gly
            20                  25                  30

Leu Ser Ala Val Leu Gly Leu Leu Leu Leu Arg Trp Gln Phe Pro Ala
        35                  40                  45

His Tyr Arg Arg Leu Arg His Ala Leu Trp Pro Ser Leu Pro Asp Leu
    50                  55                  60

His Arg Val Leu Gly Gln Tyr Leu Arg Asp Thr Ala Ala Leu Ser Pro
65                  70                  75                  80

Pro Lys Ala Thr Val Ser Asp Thr Cys Glu Glu Val Glu Pro Ser Leu
                85                  90                  95

Leu Glu Ile Leu Pro Lys Ser Ser Glu Arg Thr Pro Leu Pro Leu
            100                 105                 110


<210> SEQ ID NO 44
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Ser Asp Pro Thr Arg Val Glu Thr Ala Thr Glu Thr Ala Trp Val Leu
```

-continued

```
1               5                   10                  15

Leu Ile Leu Val Leu Ile Ser Leu Val Thr Ala Leu His Leu Val Leu
            20                  25                  30

Gly Leu Ser Ala Val Leu Gly Leu Leu Leu Leu Arg Trp Gln Phe Pro
        35                  40                  45

Ala His Tyr Arg Arg Leu Arg His Ala Leu Trp Pro Ser Leu Pro Asp
    50                  55                  60

Leu His Arg Val Leu Gly Gln Tyr Leu Arg Asp Thr Ala Ala Leu Ser
65                  70                  75                  80

Pro Pro Lys Ala Thr Val Ser Asp Thr Cys Glu Glu Val Glu Pro Ser
                85                  90                  95

Leu Leu Glu Ile Leu Pro Lys Ser Ser Glu Arg Thr Pro Leu Pro Leu
            100                 105                 110


<210> SEQ ID NO 45
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Ser Asp Pro Thr Arg Val Glu Thr Ala Thr Glu Thr Ala Trp Leu Val
1               5                   10                  15

Leu Leu Ile Leu Val Leu Ile Ser Leu Val Thr Ala Leu His Leu Val
            20                  25                  30

Leu Gly Leu Ser Ala Val Leu Gly Leu Leu Leu Leu Arg Trp Gln Phe
        35                  40                  45

Pro Ala His Tyr Arg Arg Leu Arg His Ala Leu Trp Pro Ser Leu Pro
    50                  55                  60

Asp Leu His Arg Val Leu Gly Gln Tyr Leu Arg Asp Thr Ala Ala Leu
65                  70                  75                  80

Ser Pro Pro Lys Ala Thr Val Ser Asp Thr Cys Glu Glu Val Glu Pro
                85                  90                  95

Ser Leu Leu Glu Ile Leu Pro Lys Ser Ser Glu Arg Thr Pro Leu Pro
            100                 105                 110

Leu


<210> SEQ ID NO 46
<211> LENGTH: 144
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Ala Arg Asp Glu Val Glu Gly Phe Leu Gln Asp Thr Phe Pro Gln Gln
1               5                   10                  15

Leu Glu Glu Ser Glu Lys Gln Arg Leu Gly Gly Asp Val Gln Ser Pro
            20                  25                  30

Asn Cys Pro Ser Glu Asp Val Val Ile Thr Pro Glu Ser Phe Gly Arg
        35                  40                  45

Asp Ser Ser Leu Thr Cys Leu Ala Gly Asn Val Ser Ala Cys Asp Ala
    50                  55                  60

Pro Ile Leu Ser Ser Ser Arg Ser Leu Asp Cys Arg Glu Ser Gly Lys
65                  70                  75                  80
```

Asn Gly Pro His Val Tyr Gln Asp Leu Leu Leu Ser Leu Gly Thr Thr
85 90 95

Asn Ser Thr Leu Pro Pro Pro Phe Ser Leu Gln Ser Gly Ile Leu Thr
100 105 110

Leu Asn Pro Val Ala Gln Gly Gln Pro Ile Leu Thr Ser Leu Gly Ser
115 120 125

Asn Gln Glu Glu Ala Tyr Val Thr Met Ser Ser Phe Tyr Gln Asn Gln
130 135 140

<210> SEQ ID NO 47
<211> LENGTH: 219
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 47

Val Thr Gln Leu Leu Leu Gln Gln Asp Lys Val Pro Glu Pro Ala Ser
1 5 10 15

Leu Ser Ser Asn His Ser Leu Thr Ser Cys Phe Thr Asn Gln Gly Tyr
20 25 30

Phe Phe Phe His Leu Pro Asp Ala Leu Glu Ile Glu Ala Cys Gln Val
35 40 45

Tyr Phe Thr Tyr Asp Pro Tyr Ser Glu Glu Asp Pro Asp Glu Gly Val
50 55 60

Ala Gly Ala Pro Thr Gly Ser Ser Pro Gln Pro Leu Gln Pro Leu Ser
65 70 75 80

Gly Glu Asp Asp Ala Tyr Cys Thr Phe Pro Ser Arg Asp Asp Leu Leu
85 90 95

Leu Phe Ser Pro Ser Leu Leu Gly Gly Pro Ser Pro Pro Ser Thr Ala
100 105 110

Pro Gly Gly Ser Gly Ala Gly Glu Glu Arg Met Pro Pro Ser Leu Gln
115 120 125

Glu Arg Val Pro Arg Asp Trp Asp Pro Gln Pro Leu Gly Pro Pro Thr
130 135 140

Pro Gly Val Pro Asp Leu Val Asp Phe Gln Pro Pro Pro Glu Leu Val
145 150 155 160

Leu Arg Glu Ala Gly Glu Glu Val Pro Asp Ala Gly Pro Arg Glu Gly
165 170 175

Val Ser Phe Pro Trp Ser Arg Pro Pro Gly Gln Gly Glu Phe Arg Ala
180 185 190

Leu Asn Ala Arg Leu Pro Leu Asn Thr Asp Ala Tyr Leu Ser Leu Gln
195 200 205

Glu Leu Gln Gly Gln Asp Pro Thr His Leu Val
210 215

<210> SEQ ID NO 48
<211> LENGTH: 50
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 48

Ile Ser Thr Ile Ala Thr Val Glu Glu Thr Asn Gln Thr Asp Glu Asp
1 5 10 15

```
His Lys Lys Tyr Ser Ser Gln Thr Ser Gln Asp Ser Gly Asn Tyr Ser
            20                  25                  30

Asn Glu Asp Glu Ser Glu Ser Lys Thr Ser Glu Glu Leu Gln Gln Asp
        35                  40                  45

Phe Val
    50


<210> SEQ ID NO 49
<211> LENGTH: 206
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Lys Lys Lys Val Trp Asp Tyr Asn Tyr Asp Asp Glu Ser Asp Ser Asp
1               5                   10                  15

Thr Glu Ala Ala Pro Arg Thr Ser Gly Gly Gly Tyr Thr Met His Gly
            20                  25                  30

Leu Thr Val Arg Pro Leu Gly Gln Ala Ser Ala Thr Ser Thr Glu Ser
        35                  40                  45

Gln Leu Ile Asp Pro Glu Ser Glu Glu Glu Pro Asp Leu Pro Glu Val
    50                  55                  60

Asp Val Glu Leu Pro Thr Met Pro Lys Asp Ser Pro Gln Gln Leu Glu
65                  70                  75                  80

Leu Leu Ser Gly Pro Cys Glu Arg Arg Lys Ser Pro Leu Gln Asp Pro
                85                  90                  95

Phe Pro Glu Glu Asp Tyr Ser Ser Thr Glu Gly Ser Gly Gly Arg Ile
            100                 105                 110

Thr Phe Asn Val Asp Leu Asn Ser Val Phe Leu Arg Val Leu Asp Asp
        115                 120                 125

Glu Asp Ser Asp Asp Leu Glu Ala Pro Leu Met Leu Ser Ser His Leu
    130                 135                 140

Glu Glu Met Val Asp Pro Glu Asp Pro Asp Asn Val Gln Ser Asn His
145                 150                 155                 160

Leu Leu Ala Ser Gly Glu Gly Thr Gln Pro Thr Phe Pro Ser Pro Ser
                165                 170                 175

Ser Glu Gly Leu Trp Ser Glu Asp Ala Pro Ser Asp Gln Ser Asp Thr
            180                 185                 190

Ser Glu Ser Asp Val Asp Leu Gly Asp Gly Tyr Ile Met Arg
        195                 200                 205


<210> SEQ ID NO 50
<211> LENGTH: 256
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Ile Ser Thr Ile Ala Thr Val Glu Glu Thr Asn Gln Thr Asp Glu Asp
1               5                   10                  15

His Lys Lys Tyr Ser Ser Gln Thr Ser Gln Asp Ser Gly Asn Tyr Ser
            20                  25                  30

Asn Glu Asp Glu Ser Glu Ser Lys Thr Ser Glu Glu Leu Gln Gln Asp
        35                  40                  45
```

```
Phe Val Lys Lys Lys Val Trp Asp Tyr Asn Tyr Asp Asp Glu Ser Asp
    50                  55                  60

Ser Asp Thr Glu Ala Ala Pro Arg Thr Ser Gly Gly Gly Tyr Thr Met
65                  70                  75                  80

His Gly Leu Thr Val Arg Pro Leu Gly Gln Ala Ser Ala Thr Ser Thr
                85                  90                  95

Glu Ser Gln Leu Ile Asp Pro Glu Ser Glu Glu Glu Pro Asp Leu Pro
            100                 105                 110

Glu Val Asp Val Glu Leu Pro Thr Met Pro Lys Asp Ser Pro Gln Gln
        115                 120                 125

Leu Glu Leu Leu Ser Gly Pro Cys Glu Arg Arg Lys Ser Pro Leu Gln
    130                 135                 140

Asp Pro Phe Pro Glu Glu Asp Tyr Ser Ser Thr Glu Gly Ser Gly Gly
145                 150                 155                 160

Arg Ile Thr Phe Asn Val Asp Leu Asn Ser Val Phe Leu Arg Val Leu
                165                 170                 175

Asp Asp Glu Asp Ser Asp Asp Leu Glu Ala Pro Leu Met Leu Ser Ser
            180                 185                 190

His Leu Glu Glu Met Val Asp Pro Glu Asp Pro Asp Asn Val Gln Ser
        195                 200                 205

Asn His Leu Leu Ala Ser Gly Glu Gly Thr Gln Pro Thr Phe Pro Ser
    210                 215                 220

Pro Ser Ser Glu Gly Leu Trp Ser Glu Asp Ala Pro Ser Asp Gln Ser
225                 230                 235                 240

Asp Thr Ser Glu Ser Asp Val Asp Leu Gly Asp Gly Tyr Ile Met Arg
                245                 250                 255


<210> SEQ ID NO 51
<211> LENGTH: 221
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Arg Gly Val Arg Pro Thr Pro Arg Val Arg Ala Pro Ala Thr Gln Gln
1               5                   10                  15

Thr Arg Trp Lys Lys Asp Leu Ala Glu Asp Glu Glu Glu Glu Asp Glu
            20                  25                  30

Glu Asp Thr Glu Asp Gly Val Ser Phe Gln Pro Tyr Ile Glu Pro Pro
        35                  40                  45

Ser Phe Leu Gly Gln Glu His Gln Ala Pro Gly His Ser Glu Ala Gly
    50                  55                  60

Gly Val Asp Ser Gly Arg Pro Arg Ala Pro Leu Val Pro Ser Glu Gly
65                  70                  75                  80

Ser Ser Ala Trp Asp Ser Ser Asp Arg Ser Trp Ala Ser Thr Val Asp
                85                  90                  95

Ser Ser Trp Asp Arg Ala Gly Ser Ser Gly Tyr Leu Ala Glu Lys Gly
            100                 105                 110

Pro Gly Gln Gly Pro Gly Gly Asp Gly His Gln Glu Ser Leu Pro Pro
        115                 120                 125

Pro Glu Phe Ser Lys Asp Ser Gly Phe Leu Glu Glu Leu Pro Glu Asp
    130                 135                 140

Asn Leu Ser Ser Trp Ala Thr Trp Gly Thr Leu Pro Pro Glu Pro Asn
```

```
145                 150                 155                 160

Leu Val Pro Gly Gly Pro Pro Val Ser Leu Gln Thr Leu Thr Phe Cys
                165                 170                 175

Trp Glu Ser Ser Pro Glu Glu Glu Glu Glu Ala Arg Glu Ser Glu Ile
            180                 185                 190

Glu Asp Ser Asp Ala Gly Ser Trp Gly Ala Glu Ser Thr Gln Arg Thr
        195                 200                 205

Glu Asp Arg Gly Arg Thr Leu Gly His Tyr Met Ala Arg
    210                 215                 220


<210> SEQ ID NO 52
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Ile Pro Pro Lys Gly Gly Ala Leu Gly Glu Gly Pro Gly Ala Ser Pro
1               5                   10                  15

Cys Asn Gln His Ser Pro Tyr Trp Ala Pro Pro Cys Tyr Thr Leu Lys
            20                  25                  30

Pro Glu Thr
        35


<210> SEQ ID NO 53
<211> LENGTH: 166
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Thr Ala Leu Leu Thr Cys Gly Pro Ala Arg Pro Trp Lys Ser Val Ala
1               5                   10                  15

Leu Glu Glu Glu Gln Glu Gly Pro Gly Thr Arg Leu Pro Gly Asn Leu
            20                  25                  30

Ser Ser Glu Asp Val Leu Pro Ala Gly Cys Thr Glu Trp Arg Val Gln
        35                  40                  45

Thr Leu Ala Tyr Leu Pro Gln Glu Asp Trp Ala Pro Thr Ser Leu Thr
    50                  55                  60

Arg Pro Ala Pro Pro Asp Ser Glu Gly Ser Arg Ser Ser Ser Ser Ser
65                  70                  75                  80

Ser Ser Ser Asn Asn Asn Asn Tyr Cys Ala Leu Gly Cys Tyr Gly Gly
                85                  90                  95

Trp His Leu Ser Ala Leu Pro Gly Asn Thr Gln Ser Ser Gly Pro Ile
            100                 105                 110

Pro Ala Leu Ala Cys Gly Leu Ser Cys Asp His Gln Gly Leu Glu Thr
        115                 120                 125

Gln Gln Gly Val Ala Trp Val Leu Ala Gly His Cys Gln Arg Pro Gly
    130                 135                 140

Leu His Glu Asp Leu Gln Gly Met Leu Leu Pro Ser Val Leu Ser Lys
145                 150                 155                 160

Ala Arg Ser Trp Thr Phe
                165
```

-continued

<210> SEQ ID NO 54
<211> LENGTH: 217
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 54

```
Pro Arg Ser Pro Ala Lys Arg Leu Gln Leu Thr Glu Leu Gln Glu Pro
1               5                   10                  15

Ala Glu Leu Val Glu Ser Asp Gly Val Pro Lys Pro Ser Phe Trp Pro
            20                  25                  30

Thr Ala Gln Asn Ser Gly Gly Ser Ala Tyr Ser Glu Glu Arg Asp Arg
        35                  40                  45

Pro Tyr Gly Leu Val Ser Ile Asp Thr Val Thr Val Leu Asp Ala Glu
    50                  55                  60

Gly Pro Cys Thr Trp Pro Cys Ser Cys Glu Asp Asp Gly Tyr Pro Ala
65                  70                  75                  80

Leu Asp Leu Asp Ala Gly Leu Glu Pro Ser Pro Gly Leu Glu Asp Pro
                85                  90                  95

Leu Leu Asp Ala Gly Thr Thr Val Leu Ser Cys Gly Cys Val Ser Ala
            100                 105                 110

Gly Ser Pro Gly Leu Gly Gly Pro Leu Gly Ser Leu Leu Asp Arg Leu
        115                 120                 125

Lys Pro Pro Leu Ala Asp Gly Glu Asp Trp Ala Gly Gly Leu Pro Trp
    130                 135                 140

Gly Gly Arg Ser Pro Gly Gly Val Ser Glu Ser Glu Ala Gly Ser Pro
145                 150                 155                 160

Leu Ala Gly Leu Asp Met Asp Thr Phe Asp Ser Gly Phe Val Gly Ser
                165                 170                 175

Asp Cys Ser Ser Pro Val Glu Cys Asp Phe Thr Ser Pro Gly Asp Glu
            180                 185                 190

Gly Pro Pro Arg Ser Tyr Leu Arg Gln Trp Val Val Ile Pro Pro Pro
        195                 200                 205

Leu Ser Ser Pro Gly Pro Gln Ala Ser
    210                 215
```

<210> SEQ ID NO 55
<211> LENGTH: 286
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 55

```
Pro Asp Glu Lys Thr Glu Glu Ser Asp Thr Asp Arg Leu Leu Ser Ser
1               5                   10                  15

Asp His Glu Lys Ser His Ser Asn Leu Gly Val Lys Asp Gly Asp Ser
            20                  25                  30

Gly Arg Thr Ser Cys Cys Glu Pro Asp Ile Leu Glu Thr Asp Phe Asn
        35                  40                  45

Ala Asn Asp Ile His Glu Gly Thr Ser Glu Val Ala Gln Pro Gln Arg
    50                  55                  60

Leu Lys Gly Glu Ala Asp Leu Leu Cys Leu Asp Gln Lys Asn Gln Asn
65                  70                  75                  80

Asn Ser Pro Tyr His Asp Ala Cys Pro Ala Thr Gln Gln Pro Ser Val
```

```
                85                  90                  95

Ile Gln Ala Glu Lys Asn Lys Pro Gln Pro Leu Pro Thr Glu Gly Ala
            100                 105                 110

Glu Ser Thr His Gln Ala Ala His Ile Gln Leu Ser Asn Pro Ser Ser
        115                 120                 125

Leu Ser Asn Ile Asp Phe Tyr Ala Gln Val Ser Asp Ile Thr Pro Ala
    130                 135                 140

Gly Ser Val Val Leu Ser Pro Gly Gln Lys Asn Lys Ala Gly Met Ser
145                 150                 155                 160

Gln Cys Asp Met His Pro Glu Met Val Ser Leu Cys Gln Glu Asn Phe
                165                 170                 175

Leu Met Asp Asn Ala Tyr Phe Cys Glu Ala Asp Ala Lys Lys Cys Ile
            180                 185                 190

Pro Val Ala Pro His Ile Lys Val Glu Ser His Ile Gln Pro Ser Leu
        195                 200                 205

Asn Gln Glu Asp Ile Tyr Ile Thr Thr Glu Ser Leu Thr Thr Ala Ala
    210                 215                 220

Gly Arg Pro Gly Thr Gly Glu His Val Pro Gly Ser Glu Met Pro Val
225                 230                 235                 240

Pro Asp Tyr Thr Ser Ile His Ile Val Gln Ser Pro Gln Gly Leu Ile
                245                 250                 255

Leu Asn Ala Thr Ala Leu Pro Leu Pro Asp Lys Glu Phe Leu Ser Ser
            260                 265                 270

Cys Gly Tyr Val Ser Thr Asp Gln Leu Asn Lys Ile Met Pro
        275                 280                 285


<210> SEQ ID NO 56
<211> LENGTH: 170
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Trp Gly Thr Met Gln Ala Val Glu Pro Gly Thr Asp Asp Glu Gly Pro
1               5                   10                  15

Leu Leu Glu Pro Val Gly Ser Glu His Ala Gln Asp Thr Tyr Leu Val
            20                  25                  30

Leu Asp Lys Trp Leu Leu Pro Arg Asn Pro Pro Ser Glu Asp Leu Pro
        35                  40                  45

Gly Pro Gly Gly Ser Val Asp Ile Val Ala Met Asp Glu Gly Ser Glu
    50                  55                  60

Ala Ser Ser Cys Ser Ser Ala Leu Ala Ser Lys Pro Ser Pro Glu Gly
65                  70                  75                  80

Ala Ser Ala Ala Ser Phe Glu Tyr Thr Ile Leu Asp Pro Ser Ser Gln
                85                  90                  95

Leu Leu Arg Pro Trp Thr Leu Cys Pro Glu Leu Pro Pro Thr Pro Pro
            100                 105                 110

His Leu Lys Tyr Leu Tyr Leu Val Val Ser Asp Ser Gly Ile Ser Thr
        115                 120                 125

Asp Tyr Ser Ser Gly Asp Ser Gln Gly Ala Gln Gly Gly Leu Ser Asp
    130                 135                 140

Gly Pro Tyr Ser Asn Pro Tyr Glu Asn Ser Leu Ile Pro Ala Ala Glu
145                 150                 155                 160
```

-continued

Pro Leu Pro Pro Ser Tyr Val Ala Cys Ser
165 170

<210> SEQ ID NO 57
<211> LENGTH: 203
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 57

Ala Val Gln Leu Leu Leu Leu Gln Lys Asp Ser Ala Pro Leu Pro Ser
1 5 10 15

Pro Ser Gly His Ser Gln Ala Ser Cys Phe Thr Asn Gln Gly Tyr Phe
20 25 30

Phe Phe His Leu Pro Asn Ala Leu Glu Ile Glu Ser Cys Gln Val Tyr
35 40 45

Phe Thr Tyr Asp Pro Cys Val Glu Glu Glu Val Glu Glu Asp Gly Ser
50 55 60

Arg Leu Pro Glu Gly Ser Pro His Pro Pro Leu Leu Pro Leu Ala Gly
65 70 75 80

Glu Gln Asp Asp Tyr Cys Ala Phe Pro Pro Arg Asp Asp Leu Leu Leu
85 90 95

Phe Ser Pro Ser Leu Ser Thr Pro Asn Thr Ala Tyr Gly Gly Ser Arg
100 105 110

Ala Pro Glu Glu Arg Ser Pro Leu Ser Leu His Glu Gly Leu Pro Ser
115 120 125

Leu Ala Ser Arg Asp Leu Met Gly Leu Gln Arg Pro Leu Glu Arg Met
130 135 140

Pro Glu Gly Asp Gly Glu Gly Leu Ser Ala Asn Ser Ser Gly Glu Gln
145 150 155 160

Ala Ser Val Pro Glu Gly Asn Leu His Gly Gln Asp Gln Asp Arg Gly
165 170 175

Gln Gly Pro Ile Leu Thr Leu Asn Thr Asp Ala Tyr Leu Ser Leu Gln
180 185 190

Glu Leu Gln Ala Gln Asp Ser Val His Leu Ile
195 200

<210> SEQ ID NO 58
<211> LENGTH: 144
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 58

Ala Arg Asp Glu Val Glu Ser Phe Leu Pro Asn Asp Leu Pro Ala Gln
1 5 10 15

Pro Glu Glu Leu Glu Thr Gln Gly His Arg Ala Ala Val His Ser Ala
20 25 30

Asn Arg Ser Pro Glu Thr Ser Val Ser Pro Pro Glu Thr Val Arg Arg
35 40 45

Glu Ser Pro Leu Arg Cys Leu Ala Arg Asn Leu Ser Thr Cys Asn Ala
50 55 60

Pro Pro Leu Leu Ser Ser Arg Ser Pro Asp Tyr Arg Asp Gly Asp Arg
65 70 75 80

```
Asn Arg Pro Pro Val Tyr Gln Asp Leu Leu Pro Asn Ser Gly Asn Thr
                85                  90                  95

Asn Val Pro Val Pro Val Pro Gln Pro Leu Pro Phe Gln Ser Gly Ile
            100                 105                 110

Leu Ile Pro Val Ser Gln Arg Gln Pro Ile Ser Thr Ser Ser Val Leu
        115                 120                 125

Asn Gln Glu Glu Ala Tyr Val Thr Met Ser Ser Phe Tyr Gln Asn Lys
    130                 135                 140


<210> SEQ ID NO 59
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Val Ile Gln Gly Asp Glu Arg Met His Leu Pro Ser Pro Thr Asp Ser
1               5                   10                  15

Asn Phe Tyr Arg Ala Leu Met Asp Glu Glu Asp Met Asp Asp Val Val
            20                  25                  30

Asp Ala Asp Glu Tyr Leu Ile Pro Gln Gln Gly Phe Phe Ser Ser Pro
        35                  40                  45

Ser Thr Ser Arg Thr Pro Leu Leu Ser Ser Leu Ser Ala Thr Ser Asn
    50                  55                  60

Asn Ser Thr Val Ala Cys Ile Asp Arg Asn Gly Leu Gln Ser Cys Pro
65                  70                  75                  80

Ile Lys Glu Asp Ser Phe Leu Gln Arg Tyr Ser Ser Asp Pro Thr Gly
                85                  90                  95

Ala Leu Thr Glu Asp Ser Ile Asp Asp Thr Phe Leu Pro Val Pro Glu
            100                 105                 110

Tyr Ile Asn Gln Ser Val Pro Lys Arg Pro Ala Gly Ser Val Gln Asn
        115                 120                 125

Pro Val Tyr His Asn Gln Pro Leu Asn Pro Ala Pro Ser Arg Asp Pro
    130                 135                 140

His Tyr Gln Asp Pro His Ser Thr Ala Val Gly Asn Pro Glu Tyr Leu
145                 150                 155                 160

Asn Thr Val Gln Pro Thr Cys Val Asn Ser Thr Phe Asp Ser Pro Ala
                165                 170                 175

His Trp Ala Gln Lys Gly Ser His Gln Ile Ser Leu Asp Asn Pro Asp
            180                 185                 190

Tyr Gln Gln Asp Phe Phe Pro Lys Glu Ala Lys Pro Asn Gly Ile Phe
        195                 200                 205

Lys Gly Ser Thr Ala Glu Asn Ala Glu Tyr Leu Arg Val Ala Pro Gln
    210                 215                 220

Ser Ser Glu Phe Ile Gly Ala
225                 230


<210> SEQ ID NO 60
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60
```

-continued

```
Val Ile Gln Gly Asp Glu Arg Met His Leu Pro Ser Pro Thr Asp Ser
1               5                   10                  15

Asn Phe Phe Arg Ala Leu Met Asp Glu Glu Asp Met Asp Asp Val Val
            20                  25                  30

Asp Ala Asp Glu Tyr Leu Ile Pro Gln Gln Gly Phe Phe Ser Ser Pro
        35                  40                  45

Ser Thr Ser Arg Thr Pro Leu Leu Ser Ser Leu Ser Ala Thr Ser Asn
    50                  55                  60

Asn Ser Thr Val Ala Cys Ile Asp Arg Asn Gly Leu Gln Ser Cys Pro
65                  70                  75                  80

Ile Lys Glu Asp Ser Phe Leu Gln Arg Ile Asp Asp Thr Phe Leu Pro
                85                  90                  95

Val Pro Glu Tyr Ile Asn Gln Ser Val Pro Lys Arg Pro Ala Gly Ser
            100                 105                 110

Val Gln Asn Pro Val Tyr His Asn Gln Pro Leu Asn Pro Ala Pro Ser
        115                 120                 125

Arg Asp Pro His Tyr Gln Asp Pro His Ser Thr Ala Val Gly Asn Pro
    130                 135                 140

Glu Tyr Leu Asn Thr Val Gln Pro Thr Cys Val Asn Ser Thr Phe Asp
145                 150                 155                 160

Ser Pro Ala His Trp Ala Gln Lys Gly Ser His Gln Ile Ser Leu Asp
                165                 170                 175

Asn Pro Asp Tyr Gln Gln Asp Phe Phe Pro Lys Glu Ala Lys Pro Asn
            180                 185                 190

Gly Ile Phe Lys Gly Ser Thr Ala Glu Asn Ala Glu Tyr Leu Arg Val
        195                 200                 205

Ala Pro Gln Ser Ser Glu Phe Ile Gly Ala
    210                 215
```

<210> SEQ ID NO 61
<211> LENGTH: 54
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 61

```
Val Ile Gln Gly Asp Glu Arg Met His Leu Pro Ser Pro Thr Asp Ser
1               5                   10                  15

Asn Phe Phe Arg Ala Leu Met Asp Glu Glu Asp Met Asp Asp Val Val
            20                  25                  30

Asp Ala Asp Glu Tyr Leu Ile Pro Gln Gln Gly Phe Phe Ser Ser Pro
        35                  40                  45

Ser Thr Ser Arg Thr Pro
    50
```

<210> SEQ ID NO 62
<211> LENGTH: 54
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 62

```
Asn Asn Ser Thr Val Ala Cys Ile Asp Arg Asn Gly Leu Gln Ser Cys
1               5                   10                  15
```

```
Pro Ile Lys Glu Asp Ser Phe Leu Gln Arg Ile Asp Asp Thr Phe Leu
            20                  25                  30

Pro Val Pro Glu Tyr Ile Asn Gln Ser Val Pro Lys Arg Pro Ala Gly
        35                  40                  45

Ser Val Gln Asn Pro Val
    50


<210> SEQ ID NO 63
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Lys Glu Asp Ser Phe Leu Gln Arg Ile Asp Asp Thr Phe Leu Pro Val
1               5                   10                  15

Pro Glu Phe Ile Asn Gln Ser Val Pro Lys Arg Pro Ala Gly Ser Val
            20                  25                  30

Gln Asn Pro Val Tyr His Asn Gln Pro Leu Asn Pro Ala Pro Ser Arg
        35                  40                  45

Asp Pro His Phe Gln Asp
    50


<210> SEQ ID NO 64
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Val Pro Glu Phe Ile Asn Gln Ser Val Pro Lys Arg Pro Ala Gly Ser
1               5                   10                  15

Val Gln Asn Pro Val Phe His Asn Gln Pro Leu Asn Pro Ala Pro Ser
            20                  25                  30

Arg Asp Pro His Tyr Gln Asp Pro His Ser Thr Ala Val Gly Asn Pro
        35                  40                  45

Glu Tyr Leu Asn Thr Val
    50


<210> SEQ ID NO 65
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Pro Glu Tyr Leu Asn Thr Val Gln Pro Thr Cys Val Asn Ser Thr Phe
1               5                   10                  15

Asp Ser Pro Ala His Trp Ala Gln Lys Gly Ser His Gln Ile Ser Leu
            20                  25                  30

Asp Asn Pro Asp Tyr Gln Gln Asp Phe Phe Pro Lys Glu Ala Lys Pro
        35                  40                  45

Asn Gly Ile Phe Lys Gly
    50
```

-continued

```
<210> SEQ ID NO 66
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Trp Ala Gln Lys Gly Ser His Gln Ile Ser Leu Asp Asn Pro Asp Phe
1               5                   10                  15

Gln Gln Asp Phe Phe Pro Lys Glu Ala Lys Pro Asn Gly Ile Phe Lys
            20                  25                  30

Gly Ser Thr Ala Glu Asn Ala Glu Tyr Leu Arg Val Ala Pro Gln Ser
        35                  40                  45

Ser Glu Phe Ile Gly Ala
    50


<210> SEQ ID NO 67
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Ser Asp Pro Lys Pro Glu Asn Pro Ala Cys Pro Trp Thr Val Leu Pro
1               5                   10                  15

Ala Gly Asp Leu Pro Thr His Asp Gly Tyr Leu Pro Ser Asn Ile Asp
            20                  25                  30

Asp Leu Pro Ser His Glu Ala Pro Leu Ala Asp Ser Leu Glu Glu Leu
        35                  40                  45

Glu Pro Gln
    50


<210> SEQ ID NO 68
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Ala Cys Asp Ala Pro Ile Leu Ser Ser Ser Arg Ser Leu Asp Cys Arg
1               5                   10                  15

Glu Ser Gly Lys Asn Gly Pro His Val Tyr Gln Asp Leu Leu Leu Ser
            20                  25                  30

Leu Gly Thr Thr Asn Ser Thr Leu Pro
        35                  40


<210> SEQ ID NO 69
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Gly Ile Leu Thr Leu Asn Pro Val Ala Gln Gly Gln Pro Ile Leu Thr
1               5                   10                  15
```

```
Ser Leu Gly Ser Asn Gln Glu Glu Ala Tyr Val Thr Met Ser Ser Phe
            20                  25                  30

Tyr Gln Asn Gln
        35


<210> SEQ ID NO 70
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Ala Cys Asp Ala Pro Ile Leu Ser Ser Ser Arg Ser Leu Asp Cys Arg
1               5                   10                  15

Glu Ser Gly Lys Asn Gly Pro His Val Tyr Gln Asp Leu Leu Leu Ser
            20                  25                  30

Leu Gly Thr Thr Asn Ser Thr Leu Pro Gln Gly Gln Pro Ile Leu Thr
        35                  40                  45

Ser Leu Gly Ser Asn Gln Glu Glu Ala Tyr Val Thr Met Ser Ser Phe
    50                  55                  60

Tyr Gln Asn Gln
65


<210> SEQ ID NO 71
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Gly Ile Leu Thr Leu Asn Pro Val Ala Gln Gly Gln Pro Ile Leu Thr
1               5                   10                  15

Ser Leu Gly Ser Asn Gln Glu Glu Ala Tyr Val Thr Met Ser Ser Phe
            20                  25                  30

Phe Gln Asn Gln
        35


<210> SEQ ID NO 72
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Ala Cys Asp Ala Pro Ile Leu Ser Ser Ser Arg Ser Leu Asp Cys Arg
1               5                   10                  15

Glu Ser Gly Lys Asn Gly Pro His Val Tyr Gln Asp Leu Leu Leu Ser
            20                  25                  30

Leu Gly Thr Thr Asn Ser Thr Leu Pro Gln Gly Gln Pro Ile Leu Thr
        35                  40                  45

Ser Leu Gly Ser Asn Gln Glu Glu Ala Tyr Val Thr Met Ser Ser Phe
    50                  55                  60

Phe Gln Asn Gln
65
```

<210> SEQ ID NO 73
<211> LENGTH: 75
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 73

Asp Glu Gly Val Ala Gly Ala Pro Thr Gly Ser Ser Pro Gln Pro Leu
1 5 10 15

Gln Pro Leu Ser Gly Glu Asp Asp Ala Tyr Cys Thr Phe Pro Ser Arg
20 25 30

Asp Asp Leu Leu Leu Phe Ser Pro Ser Gly Gln Gly Glu Phe Arg Ala
35 40 45

Leu Asn Ala Arg Leu Pro Leu Asn Thr Asp Ala Tyr Leu Ser Leu Gln
50 55 60

Glu Leu Gln Gly Gln Asp Pro Thr His Leu Val
65 70 75

<210> SEQ ID NO 74
<211> LENGTH: 34
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 74

Gly Gln Gly Glu Phe Arg Ala Leu Asn Ala Arg Leu Pro Leu Asn Thr
1 5 10 15

Asp Ala Tyr Leu Ser Leu Gln Glu Leu Gln Gly Gln Asp Pro Thr His
20 25 30

Leu Val

<210> SEQ ID NO 75
<211> LENGTH: 82
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 75

Gln Gln Asp Lys Val Pro Glu Pro Ala Ser Leu Ser Ser Asn His Ser
1 5 10 15

Leu Thr Ser Cys Phe Thr Asn Gln Gly Tyr Phe Phe Phe His Leu Pro
20 25 30

Asp Ala Leu Glu Ile Glu Ala Cys Gln Asp Glu Gly Val Ala Gly Ala
35 40 45

Pro Thr Gly Ser Ser Pro Gln Pro Leu Gln Pro Leu Ser Gly Glu Asp
50 55 60

Asp Ala Tyr Cys Thr Phe Pro Ser Arg Asp Asp Leu Leu Leu Phe Ser
65 70 75 80

Pro Ser

<210> SEQ ID NO 76
<211> LENGTH: 75
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 76

Gln Gln Asp Lys Val Pro Glu Pro Ala Ser Leu Ser Ser Asn His Ser
1 5 10 15

Leu Thr Ser Cys Phe Thr Asn Gln Gly Tyr Phe Phe Phe His Leu Pro
20 25 30

Asp Ala Leu Glu Ile Glu Ala Cys Gln Gly Gln Gly Glu Phe Arg Ala
35 40 45

Leu Asn Ala Arg Leu Pro Leu Asn Thr Asp Ala Tyr Leu Ser Leu Gln
50 55 60

Glu Leu Gln Gly Gln Asp Pro Thr His Leu Val
65 70 75

<210> SEQ ID NO 77
<211> LENGTH: 75
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 77

Asp Glu Gly Val Ala Gly Ala Pro Thr Gly Ser Ser Pro Gln Pro Leu
1 5 10 15

Gln Pro Leu Ser Gly Glu Asp Asp Ala Tyr Cys Thr Phe Pro Ser Arg
20 25 30

Asp Asp Leu Leu Leu Phe Ser Pro Ser Gly Gln Gly Glu Phe Arg Ala
35 40 45

Leu Asn Ala Arg Leu Pro Leu Asn Thr Asp Ala Tyr Leu Ser Leu Gln
50 55 60

Glu Leu Gln Gly Gln Asp Pro Thr His Leu Val
65 70 75

<210> SEQ ID NO 78
<211> LENGTH: 116
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 78

Gln Gln Asp Lys Val Pro Glu Pro Ala Ser Leu Ser Ser Asn His Ser
1 5 10 15

Leu Thr Ser Cys Phe Thr Asn Gln Gly Tyr Phe Phe Phe His Leu Pro
20 25 30

Asp Ala Leu Glu Ile Glu Ala Cys Gln Asp Glu Gly Val Ala Gly Ala
35 40 45

Pro Thr Gly Ser Ser Pro Gln Pro Leu Gln Pro Leu Ser Gly Glu Asp
50 55 60

Asp Ala Tyr Cys Thr Phe Pro Ser Arg Asp Asp Leu Leu Leu Phe Ser
65 70 75 80

Pro Ser Gly Gln Gly Glu Phe Arg Ala Leu Asn Ala Arg Leu Pro Leu
85 90 95

Asn Thr Asp Ala Tyr Leu Ser Leu Gln Glu Leu Gln Gly Gln Asp Pro
100 105 110

Thr His Leu Val
115

<210> SEQ ID NO 79
<211> LENGTH: 43
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 79

```
Lys Lys Lys Val Trp Asp Tyr Asn Tyr Asp Asp Glu Ser Asp Ser Asp
1               5                   10                  15

Thr Glu Ala Ala Pro Arg Thr Ser Gly Gly Gly Tyr Thr Met His Gly
            20                  25                  30

Leu Thr Val Arg Pro Leu Gly Gln Ala Ser Ala
        35                  40
```

<210> SEQ ID NO 80
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 80

```
Glu Gly Leu Trp Ser Glu Asp Ala Pro Ser Asp Gln Ser Asp Thr Ser
1               5                   10                  15

Glu Ser Asp Val Asp Leu Gly Asp Gly Tyr Ile Met Arg
            20                  25
```

<210> SEQ ID NO 81
<211> LENGTH: 72
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 81

```
Lys Lys Lys Val Trp Asp Tyr Asn Tyr Asp Asp Glu Ser Asp Ser Asp
1               5                   10                  15

Thr Glu Ala Ala Pro Arg Thr Ser Gly Gly Gly Tyr Thr Met His Gly
            20                  25                  30

Leu Thr Val Arg Pro Leu Gly Gln Ala Ser Ala Glu Gly Leu Trp Ser
        35                  40                  45

Glu Asp Ala Pro Ser Asp Gln Ser Asp Thr Ser Glu Ser Asp Val Asp
    50                  55                  60

Leu Gly Asp Gly Tyr Ile Met Arg
65                  70
```

<210> SEQ ID NO 82
<211> LENGTH: 156
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 82

```
Ala Ser Glu Ser Pro Ala Asp Glu Glu Glu Gln Trp Ser Asp Asp Phe
1               5                   10                  15

Asp Ser Asp Tyr Glu Asn Pro Asp Glu His Ser Asp Ser Glu Met Tyr
```

```
            20                  25                  30

Val Met Pro Ala Glu Glu Asn Ala Asp Asp Ser Tyr Glu Pro Pro Pro
        35                  40                  45

Val Glu Gln Glu Thr Arg Pro Val His Pro Ala Leu Pro Phe Ala Arg
    50                  55                  60

Gly Glu Tyr Ile Asp Asn Arg Ser Ser Gln Arg His Ser Pro Pro Phe
65                  70                  75                  80

Ser Lys Thr Leu Pro Ser Lys Pro Ser Trp Pro Ser Glu Lys Ala Arg
                85                  90                  95

Leu Thr Ser Thr Leu Pro Ala Leu Thr Ala Leu Gln Lys Pro Gln Val
            100                 105                 110

Pro Pro Lys Pro Lys Gly Leu Leu Glu Asp Glu Ala Asp Tyr Val Val
        115                 120                 125

Pro Val Glu Asp Asn Asp Glu Asn Tyr Ile His Pro Thr Glu Ser Ser
    130                 135                 140

Ser Pro Pro Pro Glu Lys Ala Pro Met Val Asn Arg
145                 150                 155


<210> SEQ ID NO 83
<211> LENGTH: 156
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Ala Ser Glu Ser Pro Ala Asp Glu Glu Glu Gln Trp Ser Asp Asp Phe
1               5                   10                  15

Asp Ser Asp Phe Glu Asn Pro Asp Glu His Ser Asp Ser Glu Met Tyr
            20                  25                  30

Val Met Pro Ala Glu Glu Asn Ala Asp Asp Ser Tyr Glu Pro Pro Pro
        35                  40                  45

Val Glu Gln Glu Thr Arg Pro Val His Pro Ala Leu Pro Phe Ala Arg
    50                  55                  60

Gly Glu Tyr Ile Asp Asn Arg Ser Ser Gln Arg His Ser Pro Pro Phe
65                  70                  75                  80

Ser Lys Thr Leu Pro Ser Lys Pro Ser Trp Pro Ser Glu Lys Ala Arg
                85                  90                  95

Leu Thr Ser Thr Leu Pro Ala Leu Thr Ala Leu Gln Lys Pro Gln Val
            100                 105                 110

Pro Pro Lys Pro Lys Gly Leu Leu Glu Asp Glu Ala Asp Tyr Val Val
        115                 120                 125

Pro Val Glu Asp Asn Asp Glu Asn Tyr Ile His Pro Thr Glu Ser Ser
    130                 135                 140

Ser Pro Pro Pro Glu Lys Ala Pro Met Val Asn Arg
145                 150                 155


<210> SEQ ID NO 84
<211> LENGTH: 156
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Ala Ser Glu Ser Pro Ala Asp Glu Glu Glu Gln Trp Ser Asp Asp Phe
```

```
1               5                   10                  15

Asp Ser Asp Phe Glu Asn Pro Asp Glu His Ser Asp Ser Glu Met Tyr
            20                  25                  30

Val Met Pro Ala Glu Glu Asn Ala Asp Asp Ser Phe Glu Pro Pro Pro
        35                  40                  45

Val Glu Gln Glu Thr Arg Pro Val His Pro Ala Leu Pro Phe Ala Arg
    50                  55                  60

Gly Glu Tyr Ile Asp Asn Arg Ser Ser Gln Arg His Ser Pro Pro Phe
65                  70                  75                  80

Ser Lys Thr Leu Pro Ser Lys Pro Ser Trp Pro Ser Glu Lys Ala Arg
                85                  90                  95

Leu Thr Ser Thr Leu Pro Ala Leu Thr Ala Leu Gln Lys Pro Gln Val
            100                 105                 110

Pro Pro Lys Pro Lys Gly Leu Leu Glu Asp Glu Ala Asp Tyr Val Val
        115                 120                 125

Pro Val Glu Asp Asn Asp Glu Asn Tyr Ile His Pro Thr Glu Ser Ser
    130                 135                 140

Ser Pro Pro Pro Glu Lys Ala Pro Met Val Asn Arg
145                 150                 155


<210> SEQ ID NO 85
<211> LENGTH: 170
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Trp Gly Thr Met Gln Ala Val Glu Pro Gly Thr Asp Asp Glu Gly Pro
1               5                   10                  15

Leu Leu Glu Pro Val Gly Ser Glu His Ala Gln Asp Thr Tyr Leu Val
            20                  25                  30

Leu Asp Lys Trp Leu Leu Pro Arg Asn Pro Pro Ser Glu Asp Leu Pro
        35                  40                  45

Gly Pro Gly Gly Ser Val Asp Ile Val Ala Met Asp Glu Gly Ser Glu
    50                  55                  60

Ala Ser Ser Cys Ser Ser Ala Leu Ala Ser Lys Pro Ser Pro Glu Gly
65                  70                  75                  80

Ala Ser Ala Ala Ser Phe Glu Tyr Thr Ile Leu Asp Pro Ser Ser Gln
                85                  90                  95

Leu Leu Arg Pro Trp Thr Leu Cys Pro Glu Leu Pro Pro Thr Pro Pro
            100                 105                 110

His Leu Lys Tyr Leu Tyr Leu Val Val Ser Asp Ser Gly Ile Ser Thr
        115                 120                 125

Asp Tyr Ser Ser Gly Asp Ser Gln Gly Ala Gln Gly Gly Leu Ser Asp
    130                 135                 140

Gly Pro Tyr Ser Asn Pro Tyr Glu Asn Ser Leu Ile Pro Ala Ala Glu
145                 150                 155                 160

Pro Leu Pro Pro Ser Tyr Val Ala Cys Ser
                165                 170


<210> SEQ ID NO 86
<211> LENGTH: 149
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 86

Val Thr Pro Val Phe Arg His Pro Pro Cys Ser Asn Trp Pro Gln Arg
1 5 10 15

Glu Lys Gly Ile Gln Gly His Gln Ala Ser Glu Lys Asp Met Met His
20 25 30

Ser Ala Ser Ser Pro Pro Pro Pro Arg Ala Leu Gln Ala Glu Ser Arg
35 40 45

Gln Leu Val Asp Leu Tyr Lys Val Leu Glu Ser Arg Gly Ser Asp Pro
50 55 60

Lys Pro Glu Asn Pro Ala Cys Pro Trp Thr Val Leu Pro Ala Gly Asp
65 70 75 80

Leu Pro Thr His Asp Gly Tyr Leu Pro Ser Asn Ile Asp Asp Leu Pro
85 90 95

Ser His Glu Ala Pro Leu Ala Asp Ser Leu Glu Glu Leu Glu Pro Gln
100 105 110

His Ile Ser Leu Ser Val Phe Pro Ser Ser Ser Leu His Pro Leu Thr
115 120 125

Phe Ser Cys Gly Asp Lys Leu Thr Leu Asp Gln Leu Lys Met Arg Cys
130 135 140

Asp Ser Leu Met Leu
145

<210> SEQ ID NO 87
<211> LENGTH: 40
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 87

Trp Asp Lys Gly Glu Arg Thr Glu Pro Leu Glu Lys Thr Glu Leu Pro
1 5 10 15

Glu Gly Ala Pro Glu Leu Ala Leu Asp Thr Glu Leu Ser Leu Glu Asp
20 25 30

Gly Asp Arg Cys Lys Ala Lys Met
35 40

<210> SEQ ID NO 88
<211> LENGTH: 275
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 88

Val Ser Pro Glu Leu Lys Asn Leu Asp Leu His Gly Ser Thr Asp Ser
1 5 10 15

Gly Phe Gly Ser Thr Lys Pro Ser Leu Gln Thr Glu Glu Pro Gln Phe
20 25 30

Leu Leu Pro Asp Pro His Pro Gln Ala Asp Arg Thr Leu Gly Asn Arg
35 40 45

Glu Pro Pro Val Leu Gly Asp Ser Cys Ser Ser Gly Ser Ser Asn Ser
50 55 60

Thr Asp Ser Gly Ile Cys Leu Gln Glu Pro Ser Leu Ser Pro Ser Thr

```
65                  70                  75                  80

Gly Pro Thr Trp Glu Gln Gln Val Gly Ser Asn Ser Arg Gly Gln Asp
                85                  90                  95

Asp Ser Gly Ile Asp Leu Val Gln Asn Ser Glu Gly Arg Ala Gly Asp
            100                 105                 110

Thr Gln Gly Gly Ser Ala Leu Gly His His Ser Pro Pro Glu Pro Glu
        115                 120                 125

Val Pro Gly Glu Glu Asp Pro Ala Ala Val Ala Phe Gln Gly Tyr Leu
    130                 135                 140

Arg Gln Thr Arg Cys Ala Glu Glu Lys Ala Thr Lys Thr Gly Cys Leu
145                 150                 155                 160

Glu Glu Glu Ser Pro Leu Thr Asp Gly Leu Gly Pro Lys Phe Gly Arg
                165                 170                 175

Cys Leu Val Asp Glu Ala Gly Leu His Pro Pro Ala Leu Ala Lys Gly
            180                 185                 190

Tyr Leu Lys Gln Asp Pro Leu Glu Met Thr Leu Ala Ser Ser Gly Ala
        195                 200                 205

Pro Thr Gly Gln Trp Asn Gln Pro Thr Glu Glu Trp Ser Leu Leu Ala
    210                 215                 220

Leu Ser Ser Cys Ser Asp Leu Gly Ile Ser Asp Trp Ser Phe Ala His
225                 230                 235                 240

Asp Leu Ala Pro Leu Gly Cys Val Ala Ala Pro Gly Gly Leu Leu Gly
                245                 250                 255

Ser Phe Asn Ser Asp Leu Val Thr Leu Pro Leu Ile Ser Ser Leu Gln
            260                 265                 270

Ser Ser Glu
        275


<210> SEQ ID NO 89
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Met Ala Leu Pro Val Thr Ala Leu Leu Leu Pro Leu Ala Leu Leu Leu
1               5                   10                  15

His Ala Ala Arg Pro
            20


<210> SEQ ID NO 90
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Ser Asp Pro Thr Arg Val Glu Thr Ala Thr Glu Thr Ala Trp Ile Ser
1               5                   10                  15

Leu Val Thr Ala Leu His Leu Val Leu Gly Leu Ser Ala Val Leu Gly
            20                  25                  30

Leu Leu Leu Leu Arg Trp Gln Phe Pro Ala His Tyr Arg Arg Leu Arg
        35                  40                  45

His Ala Leu Trp Pro Ser Leu Pro Asp Leu His Arg Val Leu Gly Gln
```

```
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Ala Arg Asp Glu Val Glu Gly
            100                 105                 110

Phe Leu Gln Asp Thr Phe Pro Gln Gln Leu Glu Glu Ser Glu Lys Gln
        115                 120                 125

Arg Leu Gly Gly Asp Val Gln Ser Pro Asn Cys Pro Ser Glu Asp Val
    130                 135                 140

Val Ile Thr Pro Glu Ser Phe Gly Arg Asp Ser Ser Leu Thr Cys Leu
145                 150                 155                 160

Ala Gly Asn Val Ser Ala Cys Asp Ala Pro Ile Leu Ser Ser Ser Arg
                165                 170                 175

Ser Leu Asp Cys Arg Glu Ser Gly Lys Asn Gly Pro His Val Tyr Gln
            180                 185                 190

Asp Leu Leu Leu Ser Leu Gly Thr Thr Asn Ser Thr Leu Pro Pro Pro
        195                 200                 205

Phe Ser Leu Gln Ser Gly Ile Leu Thr Leu Asn Pro Val Ala Gln Gly
    210                 215                 220

Gln Pro Ile Leu Thr Ser Leu Gly Ser Asn Gln Glu Glu Ala Tyr Val
225                 230                 235                 240

Thr Met Ser Ser Phe Tyr Gln Asn Gln
                245


<210> SEQ ID NO 91
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Ser Asp Pro Thr Arg Val Glu Thr Ala Thr Glu Thr Ala Trp Ile Ser
1               5                   10                  15

Leu Val Thr Ala Leu Leu Leu Val Leu Gly Leu Asn Ala Val Leu Gly
            20                  25                  30

Leu Leu Leu Leu Arg Trp Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Ala Arg Asp Glu Val Glu Gly
            100                 105                 110

Phe Leu Gln Asp Thr Phe Pro Gln Gln Leu Glu Glu Ser Glu Lys Gln
        115                 120                 125

Arg Leu Gly Gly Asp Val Gln Ser Pro Asn Cys Pro Ser Glu Asp Val
    130                 135                 140

Val Ile Thr Pro Glu Ser Phe Gly Arg Asp Ser Ser Leu Thr Cys Leu
145                 150                 155                 160
```

-continued

```
Ala Gly Asn Val Ser Ala Cys Asp Ala Pro Ile Leu Ser Ser Ser Arg
                165                 170                 175

Ser Leu Asp Cys Arg Glu Ser Gly Lys Asn Gly Pro His Val Tyr Gln
            180                 185                 190

Asp Leu Leu Leu Ser Leu Gly Thr Thr Asn Ser Thr Leu Pro Pro Pro
        195                 200                 205

Phe Ser Leu Gln Ser Gly Ile Leu Thr Leu Asn Pro Val Ala Gln Gly
    210                 215                 220

Gln Pro Ile Leu Thr Ser Leu Gly Ser Asn Gln Glu Glu Ala Tyr Val
225                 230                 235                 240

Thr Met Ser Ser Phe Tyr Gln Asn Gln
                245


<210> SEQ ID NO 92
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Ser Asp Pro Thr Arg Val Glu Thr Ala Thr Glu Thr Ala Trp Ile Ser
1               5                   10                  15

Leu Val Thr Ala Leu His Leu Val Leu Gly Leu Asn Ala Val Leu Gly
            20                  25                  30

Leu Leu Leu Leu Arg Trp Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Ala Arg Asp Glu Val Glu Gly
            100                 105                 110

Phe Leu Gln Asp Thr Phe Pro Gln Gln Leu Glu Glu Ser Glu Lys Gln
        115                 120                 125

Arg Leu Gly Gly Asp Val Gln Ser Pro Asn Cys Pro Ser Glu Asp Val
    130                 135                 140

Val Ile Thr Pro Glu Ser Phe Gly Arg Asp Ser Ser Leu Thr Cys Leu
145                 150                 155                 160

Ala Gly Asn Val Ser Ala Cys Asp Ala Pro Ile Leu Ser Ser Ser Arg
                165                 170                 175

Ser Leu Asp Cys Arg Glu Ser Gly Lys Asn Gly Pro His Val Tyr Gln
            180                 185                 190

Asp Leu Leu Leu Ser Leu Gly Thr Thr Asn Ser Thr Leu Pro Pro Pro
        195                 200                 205

Phe Ser Leu Gln Ser Gly Ile Leu Thr Leu Asn Pro Val Ala Gln Gly
    210                 215                 220

Gln Pro Ile Leu Thr Ser Leu Gly Ser Asn Gln Glu Glu Ala Tyr Val
225                 230                 235                 240

Thr Met Ser Ser Phe Tyr Gln Asn Gln
                245


<210> SEQ ID NO 93
```

-continued

<211> LENGTH: 249
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 93

```
Ser Asp Pro Thr Arg Val Glu Thr Ala Thr Glu Thr Ala Trp Ile Ser
1               5                   10                  15

Leu Val Thr Ala Leu Leu Leu Val Leu Gly Leu Ser Ala Val Leu Gly
            20                  25                  30

Leu Leu Leu Leu Arg Lys Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Ala Arg Asp Glu Val Glu Gly
            100                 105                 110

Phe Leu Gln Asp Thr Phe Pro Gln Gln Leu Glu Glu Ser Glu Lys Gln
        115                 120                 125

Arg Leu Gly Gly Asp Val Gln Ser Pro Asn Cys Pro Ser Glu Asp Val
    130                 135                 140

Val Ile Thr Pro Glu Ser Phe Gly Arg Asp Ser Ser Leu Thr Cys Leu
145                 150                 155                 160

Ala Gly Asn Val Ser Ala Cys Asp Ala Pro Ile Leu Ser Ser Ser Arg
                165                 170                 175

Ser Leu Asp Cys Arg Glu Ser Gly Lys Asn Gly Pro His Val Tyr Gln
            180                 185                 190

Asp Leu Leu Leu Ser Leu Gly Thr Thr Asn Ser Thr Leu Pro Pro Pro
        195                 200                 205

Phe Ser Leu Gln Ser Gly Ile Leu Thr Leu Asn Pro Val Ala Gln Gly
    210                 215                 220

Gln Pro Ile Leu Thr Ser Leu Gly Ser Asn Gln Glu Glu Ala Tyr Val
225                 230                 235                 240

Thr Met Ser Ser Phe Tyr Gln Asn Gln
                245
```

<210> SEQ ID NO 94
<211> LENGTH: 249
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 94

```
Ser Asp Pro Thr Arg Val Glu Thr Ala Thr Glu Thr Ala Trp Ile Ser
1               5                   10                  15

Leu Val Thr Ala Leu His Leu Val Leu Gly Leu Ser Ala Val Leu Gly
            20                  25                  30

Leu Leu Leu Leu Arg Lys Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60
```

```
Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Ala Arg Asp Glu Val Glu Gly
            100                 105                 110

Phe Leu Gln Asp Thr Phe Pro Gln Gln Leu Glu Glu Ser Glu Lys Gln
        115                 120                 125

Arg Leu Gly Gly Asp Val Gln Ser Pro Asn Cys Pro Ser Glu Asp Val
    130                 135                 140

Val Ile Thr Pro Glu Ser Phe Gly Arg Asp Ser Ser Leu Thr Cys Leu
145                 150                 155                 160

Ala Gly Asn Val Ser Ala Cys Asp Ala Pro Ile Leu Ser Ser Ser Arg
                165                 170                 175

Ser Leu Asp Cys Arg Glu Ser Gly Lys Asn Gly Pro His Val Tyr Gln
            180                 185                 190

Asp Leu Leu Leu Ser Leu Gly Thr Thr Asn Ser Thr Leu Pro Pro Pro
        195                 200                 205

Phe Ser Leu Gln Ser Gly Ile Leu Thr Leu Asn Pro Val Ala Gln Gly
    210                 215                 220

Gln Pro Ile Leu Thr Ser Leu Gly Ser Asn Gln Glu Glu Ala Tyr Val
225                 230                 235                 240

Thr Met Ser Ser Phe Tyr Gln Asn Gln
                245


<210> SEQ ID NO 95
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Ser Asp Pro Thr Arg Val Glu Thr Ala Thr Glu Thr Ala Trp Ile Ser
1               5                   10                  15

Leu Val Thr Ala Leu Leu Leu Val Leu Gly Leu Asn Ala Val Leu Gly
            20                  25                  30

Leu Leu Leu Leu Arg Lys Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Ala Arg Asp Glu Val Glu Gly
            100                 105                 110

Phe Leu Gln Asp Thr Phe Pro Gln Gln Leu Glu Glu Ser Glu Lys Gln
        115                 120                 125

Arg Leu Gly Gly Asp Val Gln Ser Pro Asn Cys Pro Ser Glu Asp Val
    130                 135                 140

Val Ile Thr Pro Glu Ser Phe Gly Arg Asp Ser Ser Leu Thr Cys Leu
145                 150                 155                 160

Ala Gly Asn Val Ser Ala Cys Asp Ala Pro Ile Leu Ser Ser Ser Arg
```

-continued

```
                165                 170                 175

Ser Leu Asp Cys Arg Glu Ser Gly Lys Asn Gly Pro His Val Tyr Gln
            180                 185                 190

Asp Leu Leu Leu Ser Leu Gly Thr Thr Asn Ser Thr Leu Pro Pro Pro
        195                 200                 205

Phe Ser Leu Gln Ser Gly Ile Leu Thr Leu Asn Pro Val Ala Gln Gly
    210                 215                 220

Gln Pro Ile Leu Thr Ser Leu Gly Ser Asn Gln Glu Glu Ala Tyr Val
225                 230                 235                 240

Thr Met Ser Ser Phe Tyr Gln Asn Gln
                245


<210> SEQ ID NO 96
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Ser Asp Pro Thr Arg Val Glu Thr Ala Thr Glu Thr Ala Trp Ile Ser
1               5                   10                  15

Leu Val Thr Ala Leu His Leu Val Leu Gly Leu Asn Ala Val Leu Gly
            20                  25                  30

Leu Leu Leu Leu Arg Lys Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Ala Arg Asp Glu Val Glu Gly
            100                 105                 110

Phe Leu Gln Asp Thr Phe Pro Gln Gln Leu Glu Glu Ser Glu Lys Gln
        115                 120                 125

Arg Leu Gly Gly Asp Val Gln Ser Pro Asn Cys Pro Ser Glu Asp Val
    130                 135                 140

Val Ile Thr Pro Glu Ser Phe Gly Arg Asp Ser Ser Leu Thr Cys Leu
145                 150                 155                 160

Ala Gly Asn Val Ser Ala Cys Asp Ala Pro Ile Leu Ser Ser Ser Arg
                165                 170                 175

Ser Leu Asp Cys Arg Glu Ser Gly Lys Asn Gly Pro His Val Tyr Gln
            180                 185                 190

Asp Leu Leu Leu Ser Leu Gly Thr Thr Asn Ser Thr Leu Pro Pro Pro
        195                 200                 205

Phe Ser Leu Gln Ser Gly Ile Leu Thr Leu Asn Pro Val Ala Gln Gly
    210                 215                 220

Gln Pro Ile Leu Thr Ser Leu Gly Ser Asn Gln Glu Glu Ala Tyr Val
225                 230                 235                 240

Thr Met Ser Ser Phe Tyr Gln Asn Gln
                245


<210> SEQ ID NO 97
<211> LENGTH: 249
```

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 97

```
Ser Asp Pro Thr Arg Val Glu Thr Ala Thr Glu Thr Ala Trp Ile Ser
1               5                   10                  15

Leu Val Thr Ala Leu Leu Leu Val Leu Gly Leu Ser Ala Val Leu Asn
            20                  25                  30

Leu Leu Leu Leu Arg Trp Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Ala Arg Asp Glu Val Glu Gly
            100                 105                 110

Phe Leu Gln Asp Thr Phe Pro Gln Gln Leu Glu Glu Ser Glu Lys Gln
        115                 120                 125

Arg Leu Gly Gly Asp Val Gln Ser Pro Asn Cys Pro Ser Glu Asp Val
    130                 135                 140

Val Ile Thr Pro Glu Ser Phe Gly Arg Asp Ser Ser Leu Thr Cys Leu
145                 150                 155                 160

Ala Gly Asn Val Ser Ala Cys Asp Ala Pro Ile Leu Ser Ser Ser Arg
                165                 170                 175

Ser Leu Asp Cys Arg Glu Ser Gly Lys Asn Gly Pro His Val Tyr Gln
            180                 185                 190

Asp Leu Leu Leu Ser Leu Gly Thr Thr Asn Ser Thr Leu Pro Pro Pro
        195                 200                 205

Phe Ser Leu Gln Ser Gly Ile Leu Thr Leu Asn Pro Val Ala Gln Gly
    210                 215                 220

Gln Pro Ile Leu Thr Ser Leu Gly Ser Asn Gln Glu Glu Ala Tyr Val
225                 230                 235                 240

Thr Met Ser Ser Phe Tyr Gln Asn Gln
                245
```

<210> SEQ ID NO 98
<211> LENGTH: 249
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 98

```
Ser Asp Pro Thr Arg Val Glu Thr Ala Thr Glu Thr Ala Trp Ile Ser
1               5                   10                  15

Leu Val Thr Ala Leu Leu Leu Val Leu Gly Leu Asn Ala Val Leu Gly
            20                  25                  30

Leu Leu Leu Leu Arg Trp Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60
```

-continued

```
Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Ala Arg Asp Glu Val Glu Gly
            100                 105                 110

Phe Leu Gln Asp Thr Phe Pro Gln Gln Leu Glu Glu Ser Glu Lys Gln
        115                 120                 125

Arg Leu Gly Gly Asp Val Gln Ser Pro Asn Cys Pro Ser Glu Asp Val
    130                 135                 140

Val Ile Thr Pro Glu Ser Phe Gly Arg Asp Ser Ser Leu Thr Cys Leu
145                 150                 155                 160

Ala Gly Asn Val Ser Ala Cys Asp Ala Pro Ile Leu Ser Ser Ser Arg
                165                 170                 175

Ser Leu Asp Cys Arg Glu Ser Gly Lys Asn Gly Pro His Val Tyr Gln
            180                 185                 190

Asp Leu Leu Leu Ser Leu Gly Thr Thr Asn Ser Thr Leu Pro Pro Pro
        195                 200                 205

Phe Ser Leu Gln Ser Gly Ile Leu Thr Leu Asn Pro Val Ala Gln Gly
    210                 215                 220

Gln Pro Ile Leu Thr Ser Leu Gly Ser Asn Gln Glu Glu Ala Tyr Val
225                 230                 235                 240

Thr Met Ser Ser Phe Tyr Gln Asn Gln
                245


<210> SEQ ID NO 99
<211> LENGTH: 182
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Ser Asp Pro Thr Arg Val Glu Thr Ala Thr Glu Thr Ala Trp Ile Ser
1               5                   10                  15

Leu Val Thr Ala Leu His Leu Val Leu Gly Leu Asn Ala Val Leu Gly
            20                  25                  30

Leu Leu Leu Leu Arg Lys Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Leu Glu Asp Glu Gly Val Ala
            100                 105                 110

Gly Ala Pro Thr Gly Ser Ser Pro Gln Pro Leu Gln Pro Leu Ser Gly
        115                 120                 125

Glu Asp Asp Ala Tyr Cys Thr Phe Pro Ser Arg Asp Asp Leu Leu Leu
    130                 135                 140

Phe Ser Pro Ser Gly Gln Gly Glu Phe Arg Ala Leu Asn Ala Arg Leu
145                 150                 155                 160

Pro Leu Asn Thr Asp Ala Tyr Leu Ser Leu Gln Glu Leu Gln Gly Gln
                165                 170                 175
```

Asp Pro Thr His Leu Val
            180

<210> SEQ ID NO 100
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Ser Asp Pro Thr Arg Val Glu Thr Ala Thr Glu Thr Ala Trp Ile Ser
1               5                   10                  15

Leu Val Thr Ala Leu Leu Leu Val Leu Gly Leu Asn Ala Val Leu Gly
            20                  25                  30

Leu Leu Leu Leu Arg Lys Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Leu Glu Gln Gln Asp Lys Val
            100                 105                 110

Pro Glu Pro Ala Ser Leu Ser Ser Asn His Ser Leu Thr Ser Cys Phe
        115                 120                 125

Thr Asn Gln Gly Tyr Phe Phe Phe His Leu Pro Asp Ala Leu Glu Ile
    130                 135                 140

Glu Ala Cys Gln Asp Glu Gly Val Ala Gly Ala Pro Thr Gly Ser Ser
145                 150                 155                 160

Pro Gln Pro Leu Gln Pro Leu Ser Gly Glu Asp Asp Ala Tyr Cys Thr
                165                 170                 175

Phe Pro Ser Arg Asp Asp Leu Leu Leu Phe Ser Pro Ser Gly Gln Gly
            180                 185                 190

Glu Phe Arg Ala Leu Asn Ala Arg Leu Pro Leu Asn Thr Asp Ala Tyr
        195                 200                 205

Leu Ser Leu Gln Glu Leu Gln Gly Gln Asp Pro Thr His Leu Val
    210                 215                 220

<210> SEQ ID NO 101
<211> LENGTH: 69
<212> TYPE: PRT
<213> ORGANISM: Homo sapiens

<400> SEQUENCE: 101

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr Cys
65

<210> SEQ ID NO 102
<211> LENGTH: 42
<212> TYPE: PRT
<213> ORGANISM: Homo sapiens

<400> SEQUENCE: 102

Lys Arg Gly Arg Lys Lys Leu Leu Tyr Ile Phe Lys Gln Pro Phe Met
1 5 10 15

Arg Pro Val Gln Thr Thr Gln Glu Glu Asp Gly Cys Ser Cys Arg Phe
20 25 30

Pro Glu Glu Glu Glu Gly Gly Cys Glu Leu
35 40

<210> SEQ ID NO 103
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 103

Arg Val Lys Phe Ser Arg Ser Ala Asp Ala Pro Ala Tyr Gln Gln Gly
1 5 10 15

Gln Asn Gln Leu Tyr Asn Glu Leu Asn Leu Gly Arg Arg Glu Glu Tyr
20 25 30

Asp Val Leu Asp Lys Arg Arg Gly Arg Asp Pro Glu Met Gly Gly Lys
35 40 45

Pro Arg Arg Lys Asn Pro Gln Glu Gly Leu Tyr Asn Glu Leu Gln Lys
50 55 60

Asp Lys Met Ala Glu Ala Tyr Ser Glu Ile Gly Met Lys Gly Glu Arg
65 70 75 80

Arg Arg Gly Lys Gly His Asp Gly Leu Tyr Gln Gly Leu Ser Thr Ala
85 90 95

Thr Lys Asp Thr Tyr Asp Ala Leu His Met Gln Ala Leu Pro Pro Arg
100 105 110

<210> SEQ ID NO 104
<211> LENGTH: 233
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 104

Met Ser Glu Leu Ile Lys Glu Asn Met His Met Lys Leu Tyr Met Glu
1 5 10 15

Gly Thr Val Asp Asn His His Phe Lys Cys Thr Ser Glu Gly Glu Gly
20 25 30

Lys Pro Tyr Glu Gly Thr Gln Thr Met Arg Ile Lys Val Val Glu Gly
35 40 45

Gly Pro Leu Pro Phe Ala Phe Asp Ile Leu Ala Thr Ser Phe Leu Tyr
50 55 60

Gly Ser Lys Thr Phe Ile Asn His Thr Gln Gly Ile Pro Asp Phe Phe
65 70 75 80

Lys Gln Ser Phe Pro Glu Gly Phe Thr Trp Glu Arg Val Thr Thr Tyr
85 90 95

-continued

```
Glu Asp Gly Gly Val Leu Thr Ala Thr Gln Asp Thr Ser Leu Gln Asp
            100                 105                 110

Gly Cys Leu Ile Tyr Asn Val Lys Ile Arg Gly Val Asn Phe Thr Ser
        115                 120                 125

Asn Gly Pro Val Met Gln Lys Lys Thr Leu Gly Trp Glu Ala Phe Thr
    130                 135                 140

Glu Thr Leu Tyr Pro Ala Asp Gly Gly Leu Glu Gly Arg Asn Asp Met
145                 150                 155                 160

Ala Leu Lys Leu Val Gly Gly Ser His Leu Ile Ala Asn Ile Lys Thr
                165                 170                 175

Thr Tyr Arg Ser Lys Lys Pro Ala Lys Asn Leu Lys Met Pro Gly Val
            180                 185                 190

Tyr Tyr Val Asp Tyr Arg Leu Glu Arg Ile Lys Glu Ala Asn Asn Glu
        195                 200                 205

Thr Tyr Val Glu Gln His Glu Val Ala Val Ala Arg Tyr Cys Asp Leu
    210                 215                 220

Pro Ser Lys Leu Gly His Lys Leu Asn
225                 230


<210> SEQ ID NO 105
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Gly Ser Gly Ala Thr Asn Phe Ser Leu Leu Lys Gln Ala Gly Asp Val
1               5                   10                  15

Glu Glu Asn Pro Gly Pro
            20


<210> SEQ ID NO 106
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Val Thr Gln Leu Leu Leu Gln Gln Asp Lys Val Pro Glu Pro Ala Ser
1               5                   10                  15

Leu Ser Ser Asn His Ser Leu Thr Ser Cys Phe Thr Asn Gln Gly Tyr
            20                  25                  30

Phe Phe Phe His Leu Pro Asp Ala Leu Glu Ile Glu Ala Cys Gln Val
        35                  40                  45

Ser Phe Thr Ser Asp Pro Ser Ser Glu Glu Asp Pro Asp Glu Gly Val
    50                  55                  60

Ala Gly Ala Pro Thr Gly Ser Ser Pro Gln Pro Leu Gln Pro Leu Ser
65                  70                  75                  80

Gly Glu Asp Asp Ala Tyr Cys Thr Phe Pro Ser Arg Asp Asp Leu Leu
                85                  90                  95

Leu Phe Ser Pro Ser Leu Leu Gly Gly Pro Ser Pro Pro Ser Thr Ala
            100                 105                 110

Pro Gly Gly Ser Gly Ala Gly Glu Glu Arg Met Pro Pro Ser Leu Gln
        115                 120                 125
```

-continued

```
Glu Arg Val Pro Arg Asp Trp Asp Pro Gln Pro Leu Gly Pro Pro Thr
    130                 135                 140

Pro Gly Val Pro Asp Leu Val Asp Phe Gln Pro Pro Pro Glu Leu Val
145                 150                 155                 160

Leu Arg Glu Ala Gly Glu Glu Val Pro Asp Ala Gly Pro Arg Glu Gly
                165                 170                 175

Val Ser Phe Pro Trp Ser Arg Pro Pro Gly Gln Gly Glu Phe Arg Ala
            180                 185                 190

Leu Asn Ala Arg Leu Pro Leu Asn Thr Asp Ala Tyr Leu Ser Leu Gln
        195                 200                 205

Glu Leu Gln Gly Gln Asp Pro Thr His Leu Val
    210                 215


<210> SEQ ID NO 107
<211> LENGTH: 275
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Met Ala Leu Pro Val Thr Ala Leu Leu Leu Pro Leu Ala Leu Leu Leu
1               5                   10                  15

His Ala Ala Arg Pro Ser Asp Pro Thr Arg Val Glu Thr Ala Thr Glu
            20                  25                  30

Thr Ala Trp Ile Ser Leu Val Thr Ala Leu His Leu Val Leu Gly Leu
        35                  40                  45

Asn Ala Val Leu Gly Leu Leu Leu Leu Arg Lys Gln Phe Pro Ala His
    50                  55                  60

Tyr Arg Arg Leu Arg His Ala Leu Trp Pro Ser Leu Pro Asp Leu His
65                  70                  75                  80

Arg Val Leu Gly Gln Tyr Leu Arg Asp Thr Ala Ala Leu Ser Pro Pro
                85                  90                  95

Lys Ala Thr Val Ser Asp Thr Cys Glu Glu Val Glu Pro Ser Leu Leu
            100                 105                 110

Glu Ile Leu Pro Lys Ser Ser Glu Arg Thr Pro Leu Pro Leu Val Thr
        115                 120                 125

Pro Val Phe Arg His Pro Pro Cys Ser Asn Trp Pro Gln Arg Glu Lys
    130                 135                 140

Gly Ile Gln Gly His Gln Ala Ser Glu Lys Asp Met Met His Ser Ala
145                 150                 155                 160

Ser Ser Pro Pro Pro Pro Arg Ala Leu Gln Ala Glu Ser Arg Gln Leu
                165                 170                 175

Val Asp Leu Tyr Lys Val Leu Glu Ser Arg Gly Ser Asp Pro Lys Pro
            180                 185                 190

Glu Asn Pro Ala Cys Pro Trp Thr Val Leu Pro Ala Gly Asp Leu Pro
        195                 200                 205

Thr His Asp Gly Tyr Leu Pro Ser Asn Ile Asp Asp Leu Pro Ser His
    210                 215                 220

Glu Ala Pro Leu Ala Asp Ser Leu Glu Glu Leu Glu Pro Gln His Ile
225                 230                 235                 240

Ser Leu Ser Val Phe Pro Ser Ser Ser Leu His Pro Leu Thr Phe Ser
                245                 250                 255

Cys Gly Asp Lys Leu Thr Leu Asp Gln Leu Lys Met Arg Cys Asp Ser
            260                 265                 270
```

Leu Met Leu
275

<210> SEQ ID NO 108
<211> LENGTH: 275
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 108

Met Ala Leu Pro Val Thr Ala Leu Leu Leu Pro Leu Ala Leu Leu Leu
1 5 10 15

His Ala Ala Arg Pro Ser Asp Pro Thr Arg Val Glu Thr Ala Thr Glu
20 25 30

Thr Ala Trp Ile Ser Leu Val Thr Ala Leu Leu Leu Val Leu Gly Leu
35 40 45

Asn Ala Val Leu Gly Leu Leu Leu Leu Arg Lys Gln Phe Pro Ala His
50 55 60

Tyr Arg Arg Leu Arg His Ala Leu Trp Pro Ser Leu Pro Asp Leu His
65 70 75 80

Arg Val Leu Gly Gln Tyr Leu Arg Asp Thr Ala Ala Leu Ser Pro Pro
85 90 95

Lys Ala Thr Val Ser Asp Thr Cys Glu Glu Val Glu Pro Ser Leu Leu
100 105 110

Glu Ile Leu Pro Lys Ser Ser Glu Arg Thr Pro Leu Pro Leu Val Thr
115 120 125

Pro Val Phe Arg His Pro Pro Cys Ser Asn Trp Pro Gln Arg Glu Lys
130 135 140

Gly Ile Gln Gly His Gln Ala Ser Glu Lys Asp Met Met His Ser Ala
145 150 155 160

Ser Ser Pro Pro Pro Pro Arg Ala Leu Gln Ala Glu Ser Arg Gln Leu
165 170 175

Val Asp Leu Tyr Lys Val Leu Glu Ser Arg Gly Ser Asp Pro Lys Pro
180 185 190

Glu Asn Pro Ala Cys Pro Trp Thr Val Leu Pro Ala Gly Asp Leu Pro
195 200 205

Thr His Asp Gly Tyr Leu Pro Ser Asn Ile Asp Asp Leu Pro Ser His
210 215 220

Glu Ala Pro Leu Ala Asp Ser Leu Glu Glu Leu Glu Pro Gln His Ile
225 230 235 240

Ser Leu Ser Val Phe Pro Ser Ser Ser Leu His Pro Leu Thr Phe Ser
245 250 255

Cys Gly Asp Lys Leu Thr Leu Asp Gln Leu Lys Met Arg Cys Asp Ser
260 265 270

Leu Met Leu
275

<210> SEQ ID NO 109
<211> LENGTH: 177
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 109

```
Met Ala Leu Pro Val Thr Ala Leu Leu Leu Pro Leu Ala Leu Leu Leu
1               5                   10                  15

His Ala Ala Arg Pro Ser Asp Pro Thr Arg Val Glu Thr Ala Thr Glu
            20                  25                  30

Thr Ala Trp Ile Ser Leu Val Thr Ala Leu His Leu Val Leu Gly Leu
        35                  40                  45

Asn Ala Val Leu Gly Leu Leu Leu Leu Arg Lys Gln Phe Pro Ala His
    50                  55                  60

Tyr Arg Arg Leu Arg His Ala Leu Trp Pro Ser Leu Pro Asp Leu His
65                  70                  75                  80

Arg Val Leu Gly Gln Tyr Leu Arg Asp Thr Ala Ala Leu Ser Pro Pro
                85                  90                  95

Lys Ala Thr Val Ser Asp Thr Cys Glu Glu Val Glu Pro Ser Leu Leu
            100                 105                 110

Glu Ile Leu Pro Lys Ser Ser Glu Arg Thr Pro Leu Pro Leu Ser Asp
        115                 120                 125

Pro Lys Pro Glu Asn Pro Ala Cys Pro Trp Thr Val Leu Pro Ala Gly
    130                 135                 140

Asp Leu Pro Thr His Asp Gly Tyr Leu Pro Ser Asn Ile Asp Asp Leu
145                 150                 155                 160

Pro Ser His Glu Ala Pro Leu Ala Asp Ser Leu Glu Glu Leu Glu Pro
                165                 170                 175

Gln
```

<210> SEQ ID NO 110
<211> LENGTH: 177
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 110

```
Met Ala Leu Pro Val Thr Ala Leu Leu Leu Pro Leu Ala Leu Leu Leu
1               5                   10                  15

His Ala Ala Arg Pro Ser Asp Pro Thr Arg Val Glu Thr Ala Thr Glu
            20                  25                  30

Thr Ala Trp Ile Ser Leu Val Thr Ala Leu Leu Leu Val Leu Gly Leu
        35                  40                  45

Asn Ala Val Leu Gly Leu Leu Leu Leu Arg Lys Gln Phe Pro Ala His
    50                  55                  60

Tyr Arg Arg Leu Arg His Ala Leu Trp Pro Ser Leu Pro Asp Leu His
65                  70                  75                  80

Arg Val Leu Gly Gln Tyr Leu Arg Asp Thr Ala Ala Leu Ser Pro Pro
                85                  90                  95

Lys Ala Thr Val Ser Asp Thr Cys Glu Glu Val Glu Pro Ser Leu Leu
            100                 105                 110

Glu Ile Leu Pro Lys Ser Ser Glu Arg Thr Pro Leu Pro Leu Ser Asp
        115                 120                 125

Pro Lys Pro Glu Asn Pro Ala Cys Pro Trp Thr Val Leu Pro Ala Gly
    130                 135                 140

Asp Leu Pro Thr His Asp Gly Tyr Leu Pro Ser Asn Ile Asp Asp Leu
145                 150                 155                 160

Pro Ser His Glu Ala Pro Leu Ala Asp Ser Leu Glu Glu Leu Glu Pro
                165                 170                 175
```

Gln

<210> SEQ ID NO 111
<211> LENGTH: 345
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

```
Met Ala Leu Pro Val Thr Ala Leu Leu Leu Pro Leu Ala Leu Leu Leu
1               5                   10                  15

His Ala Ala Arg Pro Ser Asp Pro Thr Arg Val Glu Thr Ala Thr Glu
            20                  25                  30

Thr Ala Trp Ile Ser Leu Val Thr Ala Leu His Leu Val Leu Gly Leu
        35                  40                  45

Asn Ala Val Leu Gly Leu Leu Leu Leu Arg Lys Gln Phe Pro Ala His
    50                  55                  60

Tyr Arg Arg Leu Arg His Ala Leu Trp Pro Ser Leu Pro Asp Leu His
65                  70                  75                  80

Arg Val Leu Gly Gln Tyr Leu Arg Asp Thr Ala Ala Leu Ser Pro Pro
                85                  90                  95

Lys Ala Thr Val Ser Asp Thr Cys Glu Glu Val Glu Pro Ser Leu Leu
            100                 105                 110

Glu Ile Leu Pro Lys Ser Ser Glu Arg Thr Pro Leu Pro Leu Val Thr
        115                 120                 125

Gln Leu Leu Leu Gln Gln Asp Lys Val Pro Glu Pro Ala Ser Leu Ser
    130                 135                 140

Ser Asn His Ser Leu Thr Ser Cys Phe Thr Asn Gln Gly Tyr Phe Phe
145                 150                 155                 160

Phe His Leu Pro Asp Ala Leu Glu Ile Glu Ala Cys Gln Val Tyr Phe
                165                 170                 175

Thr Tyr Asp Pro Tyr Ser Glu Glu Asp Pro Asp Glu Gly Val Ala Gly
            180                 185                 190

Ala Pro Thr Gly Ser Ser Pro Gln Pro Leu Gln Pro Leu Ser Gly Glu
        195                 200                 205

Asp Asp Ala Tyr Cys Thr Phe Pro Ser Arg Asp Asp Leu Leu Leu Phe
    210                 215                 220

Ser Pro Ser Leu Leu Gly Gly Pro Ser Pro Pro Ser Thr Ala Pro Gly
225                 230                 235                 240

Gly Ser Gly Ala Gly Glu Glu Arg Met Pro Pro Ser Leu Gln Glu Arg
                245                 250                 255

Val Pro Arg Asp Trp Asp Pro Gln Pro Leu Gly Pro Pro Thr Pro Gly
            260                 265                 270

Val Pro Asp Leu Val Asp Phe Gln Pro Pro Pro Glu Leu Val Leu Arg
        275                 280                 285

Glu Ala Gly Glu Glu Val Pro Asp Ala Gly Pro Arg Glu Gly Val Ser
    290                 295                 300

Phe Pro Trp Ser Arg Pro Pro Gly Gln Gly Glu Phe Arg Ala Leu Asn
305                 310                 315                 320

Ala Arg Leu Pro Leu Asn Thr Asp Ala Tyr Leu Ser Leu Gln Glu Leu
                325                 330                 335

Gln Gly Gln Asp Pro Thr His Leu Val
            340                 345
```

<210> SEQ ID NO 112
<211> LENGTH: 345
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 112

```
Met Ala Leu Pro Val Thr Ala Leu Leu Leu Pro Leu Ala Leu Leu Leu
1               5                   10                  15

His Ala Ala Arg Pro Ser Asp Pro Thr Arg Val Glu Thr Ala Thr Glu
            20                  25                  30

Thr Ala Trp Ile Ser Leu Val Thr Ala Leu Leu Leu Val Leu Gly Leu
        35                  40                  45

Asn Ala Val Leu Gly Leu Leu Leu Leu Arg Lys Gln Phe Pro Ala His
    50                  55                  60

Tyr Arg Arg Leu Arg His Ala Leu Trp Pro Ser Leu Pro Asp Leu His
65                  70                  75                  80

Arg Val Leu Gly Gln Tyr Leu Arg Asp Thr Ala Ala Leu Ser Pro Pro
                85                  90                  95

Lys Ala Thr Val Ser Asp Thr Cys Glu Glu Val Glu Pro Ser Leu Leu
            100                 105                 110

Glu Ile Leu Pro Lys Ser Ser Glu Arg Thr Pro Leu Pro Leu Val Thr
        115                 120                 125

Gln Leu Leu Leu Gln Gln Asp Lys Val Pro Glu Pro Ala Ser Leu Ser
    130                 135                 140

Ser Asn His Ser Leu Thr Ser Cys Phe Thr Asn Gln Gly Tyr Phe Phe
145                 150                 155                 160

Phe His Leu Pro Asp Ala Leu Glu Ile Glu Ala Cys Gln Val Tyr Phe
                165                 170                 175

Thr Tyr Asp Pro Tyr Ser Glu Glu Asp Pro Asp Glu Gly Val Ala Gly
            180                 185                 190

Ala Pro Thr Gly Ser Ser Pro Gln Pro Leu Gln Pro Leu Ser Gly Glu
        195                 200                 205

Asp Asp Ala Tyr Cys Thr Phe Pro Ser Arg Asp Asp Leu Leu Leu Phe
    210                 215                 220

Ser Pro Ser Leu Leu Gly Gly Pro Ser Pro Pro Ser Thr Ala Pro Gly
225                 230                 235                 240

Gly Ser Gly Ala Gly Glu Glu Arg Met Pro Pro Ser Leu Gln Glu Arg
                245                 250                 255

Val Pro Arg Asp Trp Asp Pro Gln Pro Leu Gly Pro Pro Thr Pro Gly
            260                 265                 270

Val Pro Asp Leu Val Asp Phe Gln Pro Pro Pro Glu Leu Val Leu Arg
        275                 280                 285

Glu Ala Gly Glu Glu Val Pro Asp Ala Gly Pro Arg Glu Gly Val Ser
    290                 295                 300

Phe Pro Trp Ser Arg Pro Pro Gly Gln Gly Glu Phe Arg Ala Leu Asn
305                 310                 315                 320

Ala Arg Leu Pro Leu Asn Thr Asp Ala Tyr Leu Ser Leu Gln Glu Leu
                325                 330                 335

Gln Gly Gln Asp Pro Thr His Leu Val
            340                 345
```

<210> SEQ ID NO 113
<211> LENGTH: 201
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 113

```
Met Ala Leu Pro Val Thr Ala Leu Leu Leu Pro Leu Ala Leu Leu Leu
1               5                   10                  15

His Ala Ala Arg Pro Ser Asp Pro Thr Arg Val Glu Thr Ala Thr Glu
            20                  25                  30

Thr Ala Trp Ile Ser Leu Val Thr Ala Leu His Leu Val Leu Gly Leu
        35                  40                  45

Asn Ala Val Leu Gly Leu Leu Leu Leu Arg Lys Gln Phe Pro Ala His
    50                  55                  60

Tyr Arg Arg Leu Arg His Ala Leu Trp Pro Ser Leu Pro Asp Leu His
65                  70                  75                  80

Arg Val Leu Gly Gln Tyr Leu Arg Asp Thr Ala Ala Leu Ser Pro Pro
                85                  90                  95

Lys Ala Thr Val Ser Asp Thr Cys Glu Glu Val Glu Pro Ser Leu Leu
            100                 105                 110

Glu Ile Leu Pro Lys Ser Ser Glu Arg Thr Pro Leu Pro Leu Asp Glu
        115                 120                 125

Gly Val Ala Gly Ala Pro Thr Gly Ser Ser Pro Gln Pro Leu Gln Pro
    130                 135                 140

Leu Ser Gly Glu Asp Asp Ala Tyr Cys Thr Phe Pro Ser Arg Asp Asp
145                 150                 155                 160

Leu Leu Leu Phe Ser Pro Ser Gly Gln Gly Glu Phe Arg Ala Leu Asn
                165                 170                 175

Ala Arg Leu Pro Leu Asn Thr Asp Ala Tyr Leu Ser Leu Gln Glu Leu
            180                 185                 190

Gln Gly Gln Asp Pro Thr His Leu Val
        195                 200
```

<210> SEQ ID NO 114
<211> LENGTH: 201
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 114

```
Met Ala Leu Pro Val Thr Ala Leu Leu Leu Pro Leu Ala Leu Leu Leu
1               5                   10                  15

His Ala Ala Arg Pro Ser Asp Pro Thr Arg Val Glu Thr Ala Thr Glu
            20                  25                  30

Thr Ala Trp Ile Ser Leu Val Thr Ala Leu Leu Leu Val Leu Gly Leu
        35                  40                  45

Asn Ala Val Leu Gly Leu Leu Leu Leu Arg Lys Gln Phe Pro Ala His
    50                  55                  60

Tyr Arg Arg Leu Arg His Ala Leu Trp Pro Ser Leu Pro Asp Leu His
65                  70                  75                  80

Arg Val Leu Gly Gln Tyr Leu Arg Asp Thr Ala Ala Leu Ser Pro Pro
                85                  90                  95

Lys Ala Thr Val Ser Asp Thr Cys Glu Glu Val Glu Pro Ser Leu Leu
```

```
            100                 105                 110

Glu Ile Leu Pro Lys Ser Ser Glu Arg Thr Pro Leu Pro Leu Asp Glu
        115                 120                 125

Gly Val Ala Gly Ala Pro Thr Gly Ser Ser Pro Gln Pro Leu Gln Pro
    130                 135                 140

Leu Ser Gly Glu Asp Asp Ala Tyr Cys Thr Phe Pro Ser Arg Asp Asp
145                 150                 155                 160

Leu Leu Leu Phe Ser Pro Ser Gly Gln Gly Glu Phe Arg Ala Leu Asn
                165                 170                 175

Ala Arg Leu Pro Leu Asn Thr Asp Ala Tyr Leu Ser Leu Gln Glu Leu
            180                 185                 190

Gln Gly Gln Asp Pro Thr His Leu Val
        195                 200


<210> SEQ ID NO 115
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Met Ala Leu Pro Val Thr Ala Leu Leu Leu Pro Leu Ala Leu Leu Leu
1               5                   10                  15

His Ala Ala Arg Pro Ser Asp Pro Thr Arg Val Glu Thr Ala Thr Glu
            20                  25                  30

Thr Ala Trp Ile Ser Leu Val Thr Ala Leu His Leu Val Leu Gly Leu
        35                  40                  45

Asn Ala Val Leu Gly Leu Leu Leu Leu Arg Lys Gln Phe Pro Ala His
    50                  55                  60

Tyr Arg Arg Leu Arg His Ala Leu Trp Pro Ser Leu Pro Asp Leu His
65                  70                  75                  80

Arg Val Leu Gly Gln Tyr Leu Arg Asp Thr Ala Ala Leu Ser Pro Pro
                85                  90                  95

Lys Ala Thr Val Ser Asp Thr Cys Glu Glu Val Glu Pro Ser Leu Leu
            100                 105                 110

Glu Ile Leu Pro Lys Ser Ser Glu Arg Thr Pro Leu Pro Leu Gln Gln
        115                 120                 125

Asp Lys Val Pro Glu Pro Ala Ser Leu Ser Ser Asn His Ser Leu Thr
    130                 135                 140

Ser Cys Phe Thr Asn Gln Gly Tyr Phe Phe Phe His Leu Pro Asp Ala
145                 150                 155                 160

Leu Glu Ile Glu Ala Cys Gln Asp Glu Gly Val Ala Gly Ala Pro Thr
                165                 170                 175

Gly Ser Ser Pro Gln Pro Leu Gln Pro Leu Ser Gly Glu Asp Asp Ala
            180                 185                 190

Tyr Cys Thr Phe Pro Ser Arg Asp Asp Leu Leu Leu Phe Ser Pro Ser
        195                 200                 205

Gly Gln Gly Glu Phe Arg Ala Leu Asn Ala Arg Leu Pro Leu Asn Thr
    210                 215                 220

Asp Ala Tyr Leu Ser Leu Gln Glu Leu Gln Gly Gln Asp Pro Thr His
225                 230                 235                 240

Leu Val
```

<210> SEQ ID NO 116
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

```
Met Ala Leu Pro Val Thr Ala Leu Leu Leu Pro Leu Ala Leu Leu Leu
1               5                   10                  15

His Ala Ala Arg Pro Ser Asp Pro Thr Arg Val Glu Thr Ala Thr Glu
            20                  25                  30

Thr Ala Trp Ile Ser Leu Val Thr Ala Leu Leu Leu Val Leu Gly Leu
        35                  40                  45

Asn Ala Val Leu Gly Leu Leu Leu Leu Arg Lys Gln Phe Pro Ala His
    50                  55                  60

Tyr Arg Arg Leu Arg His Ala Leu Trp Pro Ser Leu Pro Asp Leu His
65                  70                  75                  80

Arg Val Leu Gly Gln Tyr Leu Arg Asp Thr Ala Ala Leu Ser Pro Pro
                85                  90                  95

Lys Ala Thr Val Ser Asp Thr Cys Glu Glu Val Glu Pro Ser Leu Leu
            100                 105                 110

Glu Ile Leu Pro Lys Ser Ser Glu Arg Thr Pro Leu Pro Leu Gln Gln
        115                 120                 125

Asp Lys Val Pro Glu Pro Ala Ser Leu Ser Ser Asn His Ser Leu Thr
    130                 135                 140

Ser Cys Phe Thr Asn Gln Gly Tyr Phe Phe Phe His Leu Pro Asp Ala
145                 150                 155                 160

Leu Glu Ile Glu Ala Cys Gln Asp Glu Gly Val Ala Gly Ala Pro Thr
                165                 170                 175

Gly Ser Ser Pro Gln Pro Leu Gln Pro Leu Ser Gly Glu Asp Asp Ala
            180                 185                 190

Tyr Cys Thr Phe Pro Ser Arg Asp Asp Leu Leu Leu Phe Ser Pro Ser
        195                 200                 205

Gly Gln Gly Glu Phe Arg Ala Leu Asn Ala Arg Leu Pro Leu Asn Thr
    210                 215                 220

Asp Ala Tyr Leu Ser Leu Gln Glu Leu Gln Gly Gln Asp Pro Thr His
225                 230                 235                 240

Leu Val
```

<210> SEQ ID NO 117
<211> LENGTH: 321
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

```
Met Ala Leu Pro Val Thr Ala Leu Leu Leu Pro Leu Ala Leu Leu Leu
1               5                   10                  15

His Ala Ala Arg Pro Ser Asp Pro Thr Arg Val Glu Thr Ala Thr Glu
            20                  25                  30

Thr Ala Trp Ile Ser Leu Val Thr Ala Leu His Leu Val Leu Gly Leu
        35                  40                  45

Asn Ala Val Leu Gly Leu Leu Leu Leu Arg Lys Gln Phe Pro Ala His
    50                  55                  60
```

Tyr Arg Arg Leu Arg His Ala Leu Trp Pro Ser Leu Pro Asp Leu His
65 70 75 80

Arg Val Leu Gly Gln Tyr Leu Arg Asp Thr Ala Ala Leu Ser Pro Pro
85 90 95

Lys Ala Thr Val Ser Asp Thr Cys Glu Glu Val Glu Pro Ser Leu Leu
100 105 110

Glu Ile Leu Pro Lys Ser Ser Glu Arg Thr Pro Leu Pro Leu Ala Arg
115 120 125

Asp Glu Val Glu Gly Phe Leu Gln Asp Thr Phe Pro Gln Gln Leu Glu
130 135 140

Glu Ser Glu Lys Gln Arg Leu Gly Gly Asp Val Gln Ser Pro Asn Cys
145 150 155 160

Pro Ser Glu Asp Val Val Ile Thr Pro Glu Ser Phe Gly Arg Asp Ser
165 170 175

Ser Leu Thr Cys Leu Ala Gly Asn Val Ser Ala Cys Asp Ala Pro Ile
180 185 190

Leu Ser Ser Ser Arg Ser Leu Asp Cys Arg Glu Ser Gly Lys Asn Gly
195 200 205

Pro His Val Tyr Gln Asp Leu Leu Leu Ser Leu Gly Thr Thr Asn Ser
210 215 220

Thr Leu Pro Pro Pro Phe Ser Leu Gln Ser Gly Ile Leu Thr Leu Asn
225 230 235 240

Pro Val Ala Gln Gly Gln Pro Ile Leu Thr Ser Leu Gly Ser Asn Gln
245 250 255

Glu Glu Ala Tyr Val Thr Met Ser Ser Phe Tyr Gln Asn Gln Ser Asp
260 265 270

Pro Lys Pro Glu Asn Pro Ala Cys Pro Trp Thr Val Leu Pro Ala Gly
275 280 285

Asp Leu Pro Thr His Asp Gly Tyr Leu Pro Ser Asn Ile Asp Asp Leu
290 295 300

Pro Ser His Glu Ala Pro Leu Ala Asp Ser Leu Glu Glu Leu Glu Pro
305 310 315 320

Gln

<210> SEQ ID NO 118
<211> LENGTH: 321
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 118

Met Ala Leu Pro Val Thr Ala Leu Leu Leu Pro Leu Ala Leu Leu Leu
1 5 10 15

His Ala Ala Arg Pro Ser Asp Pro Thr Arg Val Glu Thr Ala Thr Glu
20 25 30

Thr Ala Trp Ile Ser Leu Val Thr Ala Leu Leu Leu Val Leu Gly Leu
35 40 45

Asn Ala Val Leu Gly Leu Leu Leu Leu Arg Lys Gln Phe Pro Ala His
50 55 60

Tyr Arg Arg Leu Arg His Ala Leu Trp Pro Ser Leu Pro Asp Leu His
65 70 75 80

Arg Val Leu Gly Gln Tyr Leu Arg Asp Thr Ala Ala Leu Ser Pro Pro
85 90 95

```
Lys Ala Thr Val Ser Asp Thr Cys Glu Glu Val Glu Pro Ser Leu Leu
            100                 105                 110

Glu Ile Leu Pro Lys Ser Ser Glu Arg Thr Pro Leu Pro Leu Ala Arg
        115                 120                 125

Asp Glu Val Glu Gly Phe Leu Gln Asp Thr Phe Pro Gln Gln Leu Glu
    130                 135                 140

Glu Ser Glu Lys Gln Arg Leu Gly Gly Asp Val Gln Ser Pro Asn Cys
145                 150                 155                 160

Pro Ser Glu Asp Val Val Ile Thr Pro Glu Ser Phe Gly Arg Asp Ser
                165                 170                 175

Ser Leu Thr Cys Leu Ala Gly Asn Val Ser Ala Cys Asp Ala Pro Ile
            180                 185                 190

Leu Ser Ser Ser Arg Ser Leu Asp Cys Arg Glu Ser Gly Lys Asn Gly
        195                 200                 205

Pro His Val Tyr Gln Asp Leu Leu Leu Ser Leu Gly Thr Thr Asn Ser
    210                 215                 220

Thr Leu Pro Pro Pro Phe Ser Leu Gln Ser Gly Ile Leu Thr Leu Asn
225                 230                 235                 240

Pro Val Ala Gln Gly Gln Pro Ile Leu Thr Ser Leu Gly Ser Asn Gln
                245                 250                 255

Glu Glu Ala Tyr Val Thr Met Ser Ser Phe Tyr Gln Asn Gln Ser Asp
            260                 265                 270

Pro Lys Pro Glu Asn Pro Ala Cys Pro Trp Thr Val Leu Pro Ala Gly
        275                 280                 285

Asp Leu Pro Thr His Asp Gly Tyr Leu Pro Ser Asn Ile Asp Asp Leu
    290                 295                 300

Pro Ser His Glu Ala Pro Leu Ala Asp Ser Leu Glu Glu Leu Glu Pro
305                 310                 315                 320

Gln
```

```
<210> SEQ ID NO 119
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Ser Asp Pro Thr Arg Val Glu Thr Ala Thr Glu Thr Ala Trp Ile Ser
1               5                   10                  15

Leu Val Thr Ala Leu His Leu Val Leu Gly Leu Ser Ala Val Leu Gly
            20                  25                  30

Leu Leu Leu Leu Arg Trp Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Leu Glu Ala Arg Asp Glu Val
            100                 105                 110

Glu Gly Phe Leu Gln Asp Thr Phe Pro Gln Gln Leu Glu Glu Ser Glu
        115                 120                 125
```

Lys Gln Arg Leu Gly Gly Asp Val Gln Ser Pro Asn Cys Pro Ser Glu
    130                 135                 140

Asp Val Val Ile Thr Pro Glu Ser Phe Gly Arg Asp Ser Ser Leu Thr
145                 150                 155                 160

Cys Leu Ala Gly Asn Val Ser Ala Cys Asp Ala Pro Ile Leu Ser Ser
                165                 170                 175

Ser Arg Ser Leu Asp Cys Arg Glu Ser Gly Lys Asn Gly Pro His Val
            180                 185                 190

Tyr Gln Asp Leu Leu Leu Ser Leu Gly Thr Thr Asn Ser Thr Leu Pro
        195                 200                 205

Pro Pro Phe Ser Leu Gln Ser Gly Ile Leu Thr Leu Asn Pro Val Ala
    210                 215                 220

Gln Gly Gln Pro Ile Leu Thr Ser Leu Gly Ser Asn Gln Glu Glu Ala
225                 230                 235                 240

Tyr Val Thr Met Ser Ser Phe Tyr Gln Asn Gln
                245                 250

<210> SEQ ID NO 120
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Ser Asp Pro Thr Arg Val Glu Thr Ala Thr Glu Thr Ala Trp Ile Ser
1               5                   10                  15

Leu Val Thr Ala Leu Leu Leu Val Leu Gly Leu Asn Ala Val Leu Gly
            20                  25                  30

Leu Leu Leu Leu Arg Trp Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Leu Glu Ala Arg Asp Glu Val
            100                 105                 110

Glu Gly Phe Leu Gln Asp Thr Phe Pro Gln Gln Leu Glu Glu Ser Glu
        115                 120                 125

Lys Gln Arg Leu Gly Gly Asp Val Gln Ser Pro Asn Cys Pro Ser Glu
    130                 135                 140

Asp Val Val Ile Thr Pro Glu Ser Phe Gly Arg Asp Ser Ser Leu Thr
145                 150                 155                 160

Cys Leu Ala Gly Asn Val Ser Ala Cys Asp Ala Pro Ile Leu Ser Ser
                165                 170                 175

Ser Arg Ser Leu Asp Cys Arg Glu Ser Gly Lys Asn Gly Pro His Val
            180                 185                 190

Tyr Gln Asp Leu Leu Leu Ser Leu Gly Thr Thr Asn Ser Thr Leu Pro
        195                 200                 205

Pro Pro Phe Ser Leu Gln Ser Gly Ile Leu Thr Leu Asn Pro Val Ala
    210                 215                 220

Gln Gly Gln Pro Ile Leu Thr Ser Leu Gly Ser Asn Gln Glu Glu Ala

```
225                 230                 235                 240

Tyr Val Thr Met Ser Ser Phe Tyr Gln Asn Gln
                245                 250


<210> SEQ ID NO 121
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Ser Asp Pro Thr Arg Val Glu Thr Ala Thr Glu Thr Ala Trp Ile Ser
1               5                   10                  15

Leu Val Thr Ala Leu His Leu Val Leu Gly Leu Asn Ala Val Leu Gly
            20                  25                  30

Leu Leu Leu Leu Arg Trp Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Leu Glu Ala Arg Asp Glu Val
            100                 105                 110

Glu Gly Phe Leu Gln Asp Thr Phe Pro Gln Gln Leu Glu Glu Ser Glu
        115                 120                 125

Lys Gln Arg Leu Gly Gly Asp Val Gln Ser Pro Asn Cys Pro Ser Glu
    130                 135                 140

Asp Val Val Ile Thr Pro Glu Ser Phe Gly Arg Asp Ser Ser Leu Thr
145                 150                 155                 160

Cys Leu Ala Gly Asn Val Ser Ala Cys Asp Ala Pro Ile Leu Ser Ser
                165                 170                 175

Ser Arg Ser Leu Asp Cys Arg Glu Ser Gly Lys Asn Gly Pro His Val
            180                 185                 190

Tyr Gln Asp Leu Leu Leu Ser Leu Gly Thr Thr Asn Ser Thr Leu Pro
        195                 200                 205

Pro Pro Phe Ser Leu Gln Ser Gly Ile Leu Thr Leu Asn Pro Val Ala
    210                 215                 220

Gln Gly Gln Pro Ile Leu Thr Ser Leu Gly Ser Asn Gln Glu Glu Ala
225                 230                 235                 240

Tyr Val Thr Met Ser Ser Phe Tyr Gln Asn Gln
                245                 250


<210> SEQ ID NO 122
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Ser Asp Pro Thr Arg Val Glu Thr Ala Thr Glu Thr Ala Trp Ile Ser
1               5                   10                  15

Leu Val Thr Ala Leu Leu Leu Val Leu Gly Leu Ser Ala Val Leu Gly
```

20 25 30

Leu Leu Leu Leu Arg Lys Gln Phe Pro Ala His Tyr Arg Arg Leu Arg
35 40 45

His Ala Leu Trp Pro Ser Leu Pro Asp Leu His Arg Val Leu Gly Gln
50 55 60

Tyr Leu Arg Asp Thr Ala Ala Leu Ser Pro Pro Lys Ala Thr Val Ser
65 70 75 80

Asp Thr Cys Glu Glu Val Glu Pro Ser Leu Leu Glu Ile Leu Pro Lys
85 90 95

Ser Ser Glu Arg Thr Pro Leu Pro Leu Leu Glu Ala Arg Asp Glu Val
100 105 110

Glu Gly Phe Leu Gln Asp Thr Phe Pro Gln Gln Leu Glu Glu Ser Glu
115 120 125

Lys Gln Arg Leu Gly Gly Asp Val Gln Ser Pro Asn Cys Pro Ser Glu
130 135 140

Asp Val Val Ile Thr Pro Glu Ser Phe Gly Arg Asp Ser Ser Leu Thr
145 150 155 160

Cys Leu Ala Gly Asn Val Ser Ala Cys Asp Ala Pro Ile Leu Ser Ser
165 170 175

Ser Arg Ser Leu Asp Cys Arg Glu Ser Gly Lys Asn Gly Pro His Val
180 185 190

Tyr Gln Asp Leu Leu Leu Ser Leu Gly Thr Thr Asn Ser Thr Leu Pro
195 200 205

Pro Pro Phe Ser Leu Gln Ser Gly Ile Leu Thr Leu Asn Pro Val Ala
210 215 220

Gln Gly Gln Pro Ile Leu Thr Ser Leu Gly Ser Asn Gln Glu Glu Ala
225 230 235 240

Tyr Val Thr Met Ser Ser Phe Tyr Gln Asn Gln
245 250

<210> SEQ ID NO 123
<211> LENGTH: 251
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 123

Ser Asp Pro Thr Arg Val Glu Thr Ala Thr Glu Thr Ala Trp Ile Ser
1 5 10 15

Leu Val Thr Ala Leu His Leu Val Leu Gly Leu Ser Ala Val Leu Gly
20 25 30

Leu Leu Leu Leu Arg Lys Gln Phe Pro Ala His Tyr Arg Arg Leu Arg
35 40 45

His Ala Leu Trp Pro Ser Leu Pro Asp Leu His Arg Val Leu Gly Gln
50 55 60

Tyr Leu Arg Asp Thr Ala Ala Leu Ser Pro Pro Lys Ala Thr Val Ser
65 70 75 80

Asp Thr Cys Glu Glu Val Glu Pro Ser Leu Leu Glu Ile Leu Pro Lys
85 90 95

Ser Ser Glu Arg Thr Pro Leu Pro Leu Leu Glu Ala Arg Asp Glu Val
100 105 110

Glu Gly Phe Leu Gln Asp Thr Phe Pro Gln Gln Leu Glu Glu Ser Glu
115 120 125

```
Lys Gln Arg Leu Gly Gly Asp Val Gln Ser Pro Asn Cys Pro Ser Glu
    130                 135                 140

Asp Val Val Ile Thr Pro Glu Ser Phe Gly Arg Asp Ser Ser Leu Thr
145                 150                 155                 160

Cys Leu Ala Gly Asn Val Ser Ala Cys Asp Ala Pro Ile Leu Ser Ser
                165                 170                 175

Ser Arg Ser Leu Asp Cys Arg Glu Ser Gly Lys Asn Gly Pro His Val
            180                 185                 190

Tyr Gln Asp Leu Leu Leu Ser Leu Gly Thr Thr Asn Ser Thr Leu Pro
        195                 200                 205

Pro Pro Phe Ser Leu Gln Ser Gly Ile Leu Thr Leu Asn Pro Val Ala
    210                 215                 220

Gln Gly Gln Pro Ile Leu Thr Ser Leu Gly Ser Asn Gln Glu Glu Ala
225                 230                 235                 240

Tyr Val Thr Met Ser Ser Phe Tyr Gln Asn Gln
                245                 250


<210> SEQ ID NO 124
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Ser Asp Pro Thr Arg Val Glu Thr Ala Thr Glu Thr Ala Trp Ile Ser
1               5                   10                  15

Leu Val Thr Ala Leu Leu Leu Val Leu Gly Leu Asn Ala Val Leu Gly
            20                  25                  30

Leu Leu Leu Leu Arg Lys Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Leu Glu Ala Arg Asp Glu Val
            100                 105                 110

Glu Gly Phe Leu Gln Asp Thr Phe Pro Gln Gln Leu Glu Glu Ser Glu
        115                 120                 125

Lys Gln Arg Leu Gly Gly Asp Val Gln Ser Pro Asn Cys Pro Ser Glu
    130                 135                 140

Asp Val Val Ile Thr Pro Glu Ser Phe Gly Arg Asp Ser Ser Leu Thr
145                 150                 155                 160

Cys Leu Ala Gly Asn Val Ser Ala Cys Asp Ala Pro Ile Leu Ser Ser
                165                 170                 175

Ser Arg Ser Leu Asp Cys Arg Glu Ser Gly Lys Asn Gly Pro His Val
            180                 185                 190

Tyr Gln Asp Leu Leu Leu Ser Leu Gly Thr Thr Asn Ser Thr Leu Pro
        195                 200                 205

Pro Pro Phe Ser Leu Gln Ser Gly Ile Leu Thr Leu Asn Pro Val Ala
    210                 215                 220

Gln Gly Gln Pro Ile Leu Thr Ser Leu Gly Ser Asn Gln Glu Glu Ala
225                 230                 235                 240
```

Tyr Val Thr Met Ser Ser Phe Tyr Gln Asn Gln
245 250

<210> SEQ ID NO 125
<211> LENGTH: 251
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 125

Ser Asp Pro Thr Arg Val Glu Thr Ala Thr Glu Thr Ala Trp Ile Ser
1 5 10 15

Leu Val Thr Ala Leu His Leu Val Leu Gly Leu Asn Ala Val Leu Gly
20 25 30

Leu Leu Leu Leu Arg Lys Gln Phe Pro Ala His Tyr Arg Arg Leu Arg
35 40 45

His Ala Leu Trp Pro Ser Leu Pro Asp Leu His Arg Val Leu Gly Gln
50 55 60

Tyr Leu Arg Asp Thr Ala Ala Leu Ser Pro Pro Lys Ala Thr Val Ser
65 70 75 80

Asp Thr Cys Glu Glu Val Glu Pro Ser Leu Leu Glu Ile Leu Pro Lys
85 90 95

Ser Ser Glu Arg Thr Pro Leu Pro Leu Leu Glu Ala Arg Asp Glu Val
100 105 110

Glu Gly Phe Leu Gln Asp Thr Phe Pro Gln Gln Leu Glu Glu Ser Glu
115 120 125

Lys Gln Arg Leu Gly Gly Asp Val Gln Ser Pro Asn Cys Pro Ser Glu
130 135 140

Asp Val Val Ile Thr Pro Glu Ser Phe Gly Arg Asp Ser Ser Leu Thr
145 150 155 160

Cys Leu Ala Gly Asn Val Ser Ala Cys Asp Ala Pro Ile Leu Ser Ser
165 170 175

Ser Arg Ser Leu Asp Cys Arg Glu Ser Gly Lys Asn Gly Pro His Val
180 185 190

Tyr Gln Asp Leu Leu Leu Ser Leu Gly Thr Thr Asn Ser Thr Leu Pro
195 200 205

Pro Pro Phe Ser Leu Gln Ser Gly Ile Leu Thr Leu Asn Pro Val Ala
210 215 220

Gln Gly Gln Pro Ile Leu Thr Ser Leu Gly Ser Asn Gln Glu Glu Ala
225 230 235 240

Tyr Val Thr Met Ser Ser Phe Tyr Gln Asn Gln
245 250

<210> SEQ ID NO 126
<211> LENGTH: 251
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 126

Ser Asp Pro Thr Arg Val Glu Thr Ala Thr Glu Thr Ala Trp Ile Ser
1 5 10 15

Leu Val Thr Ala Leu Leu Leu Val Leu Gly Leu Ser Ala Val Leu Asn
20 25 30

```
Leu Leu Leu Leu Arg Trp Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Leu Glu Ala Arg Asp Glu Val
            100                 105                 110

Glu Gly Phe Leu Gln Asp Thr Phe Pro Gln Gln Leu Glu Glu Ser Glu
        115                 120                 125

Lys Gln Arg Leu Gly Gly Asp Val Gln Ser Pro Asn Cys Pro Ser Glu
    130                 135                 140

Asp Val Val Ile Thr Pro Glu Ser Phe Gly Arg Asp Ser Ser Leu Thr
145                 150                 155                 160

Cys Leu Ala Gly Asn Val Ser Ala Cys Asp Ala Pro Ile Leu Ser Ser
                165                 170                 175

Ser Arg Ser Leu Asp Cys Arg Glu Ser Gly Lys Asn Gly Pro His Val
            180                 185                 190

Tyr Gln Asp Leu Leu Leu Ser Leu Gly Thr Thr Asn Ser Thr Leu Pro
        195                 200                 205

Pro Pro Phe Ser Leu Gln Ser Gly Ile Leu Thr Leu Asn Pro Val Ala
    210                 215                 220

Gln Gly Gln Pro Ile Leu Thr Ser Leu Gly Ser Asn Gln Glu Glu Ala
225                 230                 235                 240

Tyr Val Thr Met Ser Ser Phe Tyr Gln Asn Gln
                245                 250


<210> SEQ ID NO 127
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Ser Asp Pro Thr Arg Val Glu Thr Ala Thr Glu Thr Ala Trp Ile Ser
1               5                   10                  15

Leu Val Thr Ala Leu Leu Leu Val Leu Gly Leu Asn Ala Val Leu Gly
            20                  25                  30

Leu Leu Leu Leu Arg Trp Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Leu Glu Ala Arg Asp Glu Val
            100                 105                 110

Glu Gly Phe Leu Gln Asp Thr Phe Pro Gln Gln Leu Glu Glu Ser Glu
        115                 120                 125

Lys Gln Arg Leu Gly Gly Asp Val Gln Ser Pro Asn Cys Pro Ser Glu
```

```
    130                 135                 140

Asp Val Val Ile Thr Pro Glu Ser Phe Gly Arg Asp Ser Ser Leu Thr
145                 150                 155                 160

Cys Leu Ala Gly Asn Val Ser Ala Cys Asp Ala Pro Ile Leu Ser Ser
                165                 170                 175

Ser Arg Ser Leu Asp Cys Arg Glu Ser Gly Lys Asn Gly Pro His Val
            180                 185                 190

Tyr Gln Asp Leu Leu Leu Ser Leu Gly Thr Thr Asn Ser Thr Leu Pro
        195                 200                 205

Pro Pro Phe Ser Leu Gln Ser Gly Ile Leu Thr Leu Asn Pro Val Ala
    210                 215                 220

Gln Gly Gln Pro Ile Leu Thr Ser Leu Gly Ser Asn Gln Glu Glu Ala
225                 230                 235                 240

Tyr Val Thr Met Ser Ser Phe Tyr Gln Asn Gln
                245                 250


<210> SEQ ID NO 128
<211> LENGTH: 326
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Ser Asp Pro Thr Arg Val Glu Thr Ala Thr Glu Thr Ala Trp Ile Ser
1               5                   10                  15

Leu Val Thr Ala Leu His Leu Val Leu Gly Leu Asn Ala Val Leu Gly
            20                  25                  30

Leu Leu Leu Leu Arg Lys Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Leu Glu Val Thr Gln Leu Leu
            100                 105                 110

Leu Gln Gln Asp Lys Val Pro Glu Pro Ala Ser Leu Ser Ser Asn His
        115                 120                 125

Ser Leu Thr Ser Cys Phe Thr Asn Gln Gly Tyr Phe Phe Phe His Leu
    130                 135                 140

Pro Asp Ala Leu Glu Ile Glu Ala Cys Gln Val Tyr Phe Thr Tyr Asp
145                 150                 155                 160

Pro Tyr Ser Glu Glu Asp Pro Asp Glu Gly Val Ala Gly Ala Pro Thr
                165                 170                 175

Gly Ser Ser Pro Gln Pro Leu Gln Pro Leu Ser Gly Glu Asp Asp Ala
            180                 185                 190

Tyr Cys Thr Phe Pro Ser Arg Asp Asp Leu Leu Leu Phe Ser Pro Ser
        195                 200                 205

Leu Leu Gly Gly Pro Ser Pro Pro Ser Thr Ala Pro Gly Gly Ser Gly
    210                 215                 220

Ala Gly Glu Glu Arg Met Pro Pro Ser Leu Gln Glu Arg Val Pro Arg
225                 230                 235                 240
```

```
Asp Trp Asp Pro Gln Pro Leu Gly Pro Pro Thr Pro Gly Val Pro Asp
                245                 250                 255

Leu Val Asp Phe Gln Pro Pro Pro Glu Leu Val Leu Arg Glu Ala Gly
            260                 265                 270

Glu Glu Val Pro Asp Ala Gly Pro Arg Glu Gly Val Ser Phe Pro Trp
        275                 280                 285

Ser Arg Pro Pro Gly Gln Gly Glu Phe Arg Ala Leu Asn Ala Arg Leu
    290                 295                 300

Pro Leu Asn Thr Asp Ala Tyr Leu Ser Leu Gln Glu Leu Gln Gly Gln
305                 310                 315                 320

Asp Pro Thr His Leu Val
                325


<210> SEQ ID NO 129
<211> LENGTH: 256
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Ser Asp Pro Thr Arg Val Glu Thr Ala Thr Glu Thr Ala Trp Ile Ser
1               5                   10                  15

Leu Val Thr Ala Leu His Leu Val Leu Gly Leu Asn Ala Val Leu Gly
            20                  25                  30

Leu Leu Leu Leu Arg Lys Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Leu Glu Val Thr Pro Val Phe
            100                 105                 110

Arg His Pro Pro Cys Ser Asn Trp Pro Gln Arg Glu Lys Gly Ile Gln
        115                 120                 125

Gly His Gln Ala Ser Glu Lys Asp Met Met His Ser Ala Ser Ser Pro
    130                 135                 140

Pro Pro Pro Arg Ala Leu Gln Ala Glu Ser Arg Gln Leu Val Asp Leu
145                 150                 155                 160

Tyr Lys Val Leu Glu Ser Arg Gly Ser Asp Pro Lys Pro Glu Asn Pro
                165                 170                 175

Ala Cys Pro Trp Thr Val Leu Pro Ala Gly Asp Leu Pro Thr His Asp
            180                 185                 190

Gly Tyr Leu Pro Ser Asn Ile Asp Asp Leu Pro Ser His Glu Ala Pro
        195                 200                 205

Leu Ala Asp Ser Leu Glu Glu Leu Glu Pro Gln His Ile Ser Leu Ser
    210                 215                 220

Val Phe Pro Ser Ser Ser Leu His Pro Leu Thr Phe Ser Cys Gly Asp
225                 230                 235                 240

Lys Leu Thr Leu Asp Gln Leu Lys Met Arg Cys Asp Ser Leu Met Leu
                245                 250                 255


<210> SEQ ID NO 130
```

<211> LENGTH: 326
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 130

```
Ser Asp Pro Thr Arg Val Glu Thr Ala Thr Glu Thr Ala Trp Ile Ser
1               5                   10                  15

Leu Val Thr Ala Leu Leu Leu Val Leu Gly Leu Asn Ala Val Leu Gly
            20                  25                  30

Leu Leu Leu Leu Arg Lys Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Leu Glu Val Thr Gln Leu Leu
            100                 105                 110

Leu Gln Gln Asp Lys Val Pro Glu Pro Ala Ser Leu Ser Ser Asn His
        115                 120                 125

Ser Leu Thr Ser Cys Phe Thr Asn Gln Gly Tyr Phe Phe Phe His Leu
    130                 135                 140

Pro Asp Ala Leu Glu Ile Glu Ala Cys Gln Val Tyr Phe Thr Tyr Asp
145                 150                 155                 160

Pro Tyr Ser Glu Glu Asp Pro Asp Glu Gly Val Ala Gly Ala Pro Thr
                165                 170                 175

Gly Ser Ser Pro Gln Pro Leu Gln Pro Leu Ser Gly Glu Asp Asp Ala
            180                 185                 190

Tyr Cys Thr Phe Pro Ser Arg Asp Asp Leu Leu Leu Phe Ser Pro Ser
        195                 200                 205

Leu Leu Gly Gly Pro Ser Pro Pro Ser Thr Ala Pro Gly Gly Ser Gly
    210                 215                 220

Ala Gly Glu Glu Arg Met Pro Pro Ser Leu Gln Glu Arg Val Pro Arg
225                 230                 235                 240

Asp Trp Asp Pro Gln Pro Leu Gly Pro Pro Thr Pro Gly Val Pro Asp
                245                 250                 255

Leu Val Asp Phe Gln Pro Pro Pro Glu Leu Val Leu Arg Glu Ala Gly
            260                 265                 270

Glu Glu Val Pro Asp Ala Gly Pro Arg Glu Gly Val Ser Phe Pro Trp
        275                 280                 285

Ser Arg Pro Pro Gly Gln Gly Glu Phe Arg Ala Leu Asn Ala Arg Leu
    290                 295                 300

Pro Leu Asn Thr Asp Ala Tyr Leu Ser Leu Gln Glu Leu Gln Gly Gln
305                 310                 315                 320

Asp Pro Thr His Leu Val
                325
```

<210> SEQ ID NO 131
<211> LENGTH: 256
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 131

Ser Asp Pro Thr Arg Val Glu Thr Ala Thr Glu Thr Ala Trp Ile Ser
1               5                   10                  15

Leu Val Thr Ala Leu Leu Leu Val Leu Gly Leu Asn Ala Val Leu Gly
            20                  25                  30

Leu Leu Leu Leu Arg Lys Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Leu Glu Val Thr Pro Val Phe
            100                 105                 110

Arg His Pro Pro Cys Ser Asn Trp Pro Gln Arg Glu Lys Gly Ile Gln
        115                 120                 125

Gly His Gln Ala Ser Glu Lys Asp Met Met His Ser Ala Ser Ser Pro
    130                 135                 140

Pro Pro Pro Arg Ala Leu Gln Ala Glu Ser Arg Gln Leu Val Asp Leu
145                 150                 155                 160

Tyr Lys Val Leu Glu Ser Arg Gly Ser Asp Pro Lys Pro Glu Asn Pro
                165                 170                 175

Ala Cys Pro Trp Thr Val Leu Pro Ala Gly Asp Leu Pro Thr His Asp
            180                 185                 190

Gly Tyr Leu Pro Ser Asn Ile Asp Asp Leu Pro Ser His Glu Ala Pro
        195                 200                 205

Leu Ala Asp Ser Leu Glu Glu Leu Glu Pro Gln His Ile Ser Leu Ser
    210                 215                 220

Val Phe Pro Ser Ser Ser Leu His Pro Leu Thr Phe Ser Cys Gly Asp
225                 230                 235                 240

Lys Leu Thr Leu Asp Gln Leu Lys Met Arg Cys Asp Ser Leu Met Leu
                245                 250                 255

<210> SEQ ID NO 132
<211> LENGTH: 158
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 132

Ser Asp Pro Thr Arg Val Glu Thr Ala Thr Glu Thr Ala Trp Ile Ser
1               5                   10                  15

Leu Val Thr Ala Leu His Leu Val Leu Gly Leu Asn Ala Val Leu Gly
            20                  25                  30

Leu Leu Leu Leu Arg Lys Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys

-continued

```
                85                  90                  95

Ser Ser Glu Arg Thr Pro Leu Pro Leu Leu Glu Ser Asp Pro Lys Pro
            100                 105                 110

Glu Asn Pro Ala Cys Pro Trp Thr Val Leu Pro Ala Gly Asp Leu Pro
        115                 120                 125

Thr His Asp Gly Tyr Leu Pro Ser Asn Ile Asp Asp Leu Pro Ser His
    130                 135                 140

Glu Ala Pro Leu Ala Asp Ser Leu Glu Glu Leu Glu Pro Gln
145                 150                 155


<210> SEQ ID NO 133
<211> LENGTH: 158
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Ser Asp Pro Thr Arg Val Glu Thr Ala Thr Glu Thr Ala Trp Ile Ser
1               5                   10                  15

Leu Val Thr Ala Leu Leu Leu Val Leu Gly Leu Asn Ala Val Leu Gly
            20                  25                  30

Leu Leu Leu Leu Arg Lys Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Leu Glu Ser Asp Pro Lys Pro
            100                 105                 110

Glu Asn Pro Ala Cys Pro Trp Thr Val Leu Pro Ala Gly Asp Leu Pro
        115                 120                 125

Thr His Asp Gly Tyr Leu Pro Ser Asn Ile Asp Asp Leu Pro Ser His
    130                 135                 140

Glu Ala Pro Leu Ala Asp Ser Leu Glu Glu Leu Glu Pro Gln
145                 150                 155


<210> SEQ ID NO 134
<211> LENGTH: 304
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Ser Asp Pro Thr Arg Val Glu Thr Ala Thr Glu Thr Ala Trp Ile Ser
1               5                   10                  15

Leu Val Thr Ala Leu His Leu Val Leu Gly Leu Asn Ala Val Leu Gly
            20                  25                  30

Leu Leu Leu Leu Arg Lys Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
```

```
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Leu Glu Ala Arg Asp Glu Val
            100                 105                 110

Glu Gly Phe Leu Gln Asp Thr Phe Pro Gln Gln Leu Glu Glu Ser Glu
        115                 120                 125

Lys Gln Arg Leu Gly Gly Asp Val Gln Ser Pro Asn Cys Pro Ser Glu
    130                 135                 140

Asp Val Val Ile Thr Pro Glu Ser Phe Gly Arg Asp Ser Ser Leu Thr
145                 150                 155                 160

Cys Leu Ala Gly Asn Val Ser Ala Cys Asp Ala Pro Ile Leu Ser Ser
                165                 170                 175

Ser Arg Ser Leu Asp Cys Arg Glu Ser Gly Lys Asn Gly Pro His Val
            180                 185                 190

Tyr Gln Asp Leu Leu Leu Ser Leu Gly Thr Thr Asn Ser Thr Leu Pro
        195                 200                 205

Pro Pro Phe Ser Leu Gln Ser Gly Ile Leu Thr Leu Asn Pro Val Ala
    210                 215                 220

Gln Gly Gln Pro Ile Leu Thr Ser Leu Gly Ser Asn Gln Glu Glu Ala
225                 230                 235                 240

Tyr Val Thr Met Ser Ser Phe Tyr Gln Asn Gln Ser Arg Ser Asp Pro
                245                 250                 255

Lys Pro Glu Asn Pro Ala Cys Pro Trp Thr Val Leu Pro Ala Gly Asp
            260                 265                 270

Leu Pro Thr His Asp Gly Tyr Leu Pro Ser Asn Ile Asp Asp Leu Pro
        275                 280                 285

Ser His Glu Ala Pro Leu Ala Asp Ser Leu Glu Glu Leu Glu Pro Gln
    290                 295                 300


<210> SEQ ID NO 135
<211> LENGTH: 304
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Ser Asp Pro Thr Arg Val Glu Thr Ala Thr Glu Thr Ala Trp Ile Ser
1               5                   10                  15

Leu Val Thr Ala Leu Leu Leu Val Leu Gly Leu Asn Ala Val Leu Gly
            20                  25                  30

Leu Leu Leu Leu Arg Lys Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Leu Glu Ala Arg Asp Glu Val
            100                 105                 110

Glu Gly Phe Leu Gln Asp Thr Phe Pro Gln Gln Leu Glu Glu Ser Glu
        115                 120                 125
```

```
Lys Gln Arg Leu Gly Gly Asp Val Gln Ser Pro Asn Cys Pro Ser Glu
    130                 135                 140

Asp Val Val Ile Thr Pro Glu Ser Phe Gly Arg Asp Ser Ser Leu Thr
145                 150                 155                 160

Cys Leu Ala Gly Asn Val Ser Ala Cys Asp Ala Pro Ile Leu Ser Ser
                165                 170                 175

Ser Arg Ser Leu Asp Cys Arg Glu Ser Gly Lys Asn Gly Pro His Val
            180                 185                 190

Tyr Gln Asp Leu Leu Leu Ser Leu Gly Thr Thr Asn Ser Thr Leu Pro
        195                 200                 205

Pro Pro Phe Ser Leu Gln Ser Gly Ile Leu Thr Leu Asn Pro Val Ala
    210                 215                 220

Gln Gly Gln Pro Ile Leu Thr Ser Leu Gly Ser Asn Gln Glu Glu Ala
225                 230                 235                 240

Tyr Val Thr Met Ser Ser Phe Tyr Gln Asn Gln Ser Arg Ser Asp Pro
                245                 250                 255

Lys Pro Glu Asn Pro Ala Cys Pro Trp Thr Val Leu Pro Ala Gly Asp
            260                 265                 270

Leu Pro Thr His Asp Gly Tyr Leu Pro Ser Asn Ile Asp Asp Leu Pro
        275                 280                 285

Ser His Glu Ala Pro Leu Ala Asp Ser Leu Glu Glu Leu Glu Pro Gln
    290                 295                 300


<210> SEQ ID NO 136
<211> LENGTH: 326
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Ser Asp Pro Thr Arg Val Glu Thr Ala Thr Glu Thr Ala Trp Ile Ser
1               5                   10                  15

Leu Val Thr Ala Leu His Leu Val Leu Gly Leu Asn Ala Val Leu Gly
            20                  25                  30

Leu Leu Leu Leu Arg Lys Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Leu Glu Val Thr Gln Leu Leu
            100                 105                 110

Leu Gln Gln Asp Lys Val Pro Glu Pro Ala Ser Leu Ser Ser Asn His
        115                 120                 125

Ser Leu Thr Ser Cys Phe Thr Asn Gln Gly Tyr Phe Phe Phe His Leu
    130                 135                 140

Pro Asp Ala Leu Glu Ile Glu Ala Cys Gln Val Ser Phe Thr Ser Asp
145                 150                 155                 160

Pro Ser Ser Glu Glu Asp Pro Asp Glu Gly Val Ala Gly Ala Pro Thr
                165                 170                 175

Gly Ser Ser Pro Gln Pro Leu Gln Pro Leu Ser Gly Glu Asp Asp Ala
            180                 185                 190
```

```
Tyr Cys Thr Phe Pro Ser Arg Asp Asp Leu Leu Leu Phe Ser Pro Ser
        195                 200                 205

Leu Leu Gly Gly Pro Ser Pro Pro Ser Thr Ala Pro Gly Gly Ser Gly
    210                 215                 220

Ala Gly Glu Glu Arg Met Pro Pro Ser Leu Gln Glu Arg Val Pro Arg
225                 230                 235                 240

Asp Trp Asp Pro Gln Pro Leu Gly Pro Pro Thr Pro Gly Val Pro Asp
                245                 250                 255

Leu Val Asp Phe Gln Pro Pro Pro Glu Leu Val Leu Arg Glu Ala Gly
            260                 265                 270

Glu Glu Val Pro Asp Ala Gly Pro Arg Glu Gly Val Ser Phe Pro Trp
        275                 280                 285

Ser Arg Pro Pro Gly Gln Gly Glu Phe Arg Ala Leu Asn Ala Arg Leu
    290                 295                 300

Pro Leu Asn Thr Asp Ala Tyr Leu Ser Leu Gln Glu Leu Gln Gly Gln
305                 310                 315                 320

Asp Pro Thr His Leu Val
                325


<210> SEQ ID NO 137
<211> LENGTH: 326
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Ser Asp Pro Thr Arg Val Glu Thr Ala Thr Glu Thr Ala Trp Ile Ser
1               5                   10                  15

Leu Val Thr Ala Leu Leu Leu Val Leu Gly Leu Asn Ala Val Leu Gly
            20                  25                  30

Leu Leu Leu Leu Arg Lys Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Leu Glu Val Thr Gln Leu Leu
            100                 105                 110

Leu Gln Gln Asp Lys Val Pro Glu Pro Ala Ser Leu Ser Ser Asn His
        115                 120                 125

Ser Leu Thr Ser Cys Phe Thr Asn Gln Gly Tyr Phe Phe Phe His Leu
    130                 135                 140

Pro Asp Ala Leu Glu Ile Glu Ala Cys Gln Val Ser Phe Thr Ser Asp
145                 150                 155                 160

Pro Ser Ser Glu Glu Asp Pro Asp Glu Gly Val Ala Gly Ala Pro Thr
                165                 170                 175

Gly Ser Ser Pro Gln Pro Leu Gln Pro Leu Ser Gly Glu Asp Asp Ala
            180                 185                 190

Tyr Cys Thr Phe Pro Ser Arg Asp Asp Leu Leu Leu Phe Ser Pro Ser
        195                 200                 205

Leu Leu Gly Gly Pro Ser Pro Pro Ser Thr Ala Pro Gly Gly Ser Gly
```

```
    210                 215                 220

Ala Gly Glu Glu Arg Met Pro Pro Ser Leu Gln Glu Arg Val Pro Arg
225                 230                 235                 240

Asp Trp Asp Pro Gln Pro Leu Gly Pro Pro Thr Pro Gly Val Pro Asp
                245                 250                 255

Leu Val Asp Phe Gln Pro Pro Pro Glu Leu Val Leu Arg Glu Ala Gly
            260                 265                 270

Glu Glu Val Pro Asp Ala Gly Pro Arg Glu Gly Val Ser Phe Pro Trp
        275                 280                 285

Ser Arg Pro Pro Gly Gln Gly Glu Phe Arg Ala Leu Asn Ala Arg Leu
    290                 295                 300

Pro Leu Asn Thr Asp Ala Tyr Leu Ser Leu Gln Glu Leu Gln Gly Gln
305                 310                 315                 320

Asp Pro Thr His Leu Val
                325


<210> SEQ ID NO 138
<211> LENGTH: 326
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Ser Asp Pro Thr Arg Val Glu Thr Ala Thr Glu Thr Ala Trp Ile Ser
1               5                   10                  15

Leu Val Thr Ala Leu His Leu Val Leu Gly Leu Asn Ala Val Leu Gly
            20                  25                  30

Leu Leu Leu Leu Arg Lys Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Leu Glu Val Thr Gln Leu Leu
            100                 105                 110

Leu Gln Gln Asp Lys Val Pro Glu Pro Ala Ser Leu Ser Ser Asn His
        115                 120                 125

Ser Leu Thr Ser Cys Phe Thr Asn Gln Gly Ser Phe Phe Phe His Leu
    130                 135                 140

Pro Asp Ala Leu Glu Ile Glu Ala Cys Gln Val Ser Phe Thr Ser Asp
145                 150                 155                 160

Pro Ser Ser Glu Glu Asp Pro Asp Glu Gly Val Ala Gly Ala Pro Thr
                165                 170                 175

Gly Ser Ser Pro Gln Pro Leu Gln Pro Leu Ser Gly Glu Asp Asp Ala
            180                 185                 190

Tyr Cys Thr Phe Pro Ser Arg Asp Asp Leu Leu Leu Phe Ser Pro Ser
        195                 200                 205

Leu Leu Gly Gly Pro Ser Pro Pro Ser Thr Ala Pro Gly Gly Ser Gly
    210                 215                 220

Ala Gly Glu Glu Arg Met Pro Pro Ser Leu Gln Glu Arg Val Pro Arg
225                 230                 235                 240
```

```
Asp Trp Asp Pro Gln Pro Leu Gly Pro Pro Thr Pro Gly Val Pro Asp
            245                 250                 255

Leu Val Asp Phe Gln Pro Pro Pro Glu Leu Val Leu Arg Glu Ala Gly
            260                 265                 270

Glu Glu Val Pro Asp Ala Gly Pro Arg Glu Gly Val Ser Phe Pro Trp
        275                 280                 285

Ser Arg Pro Pro Gly Gln Gly Glu Phe Arg Ala Leu Asn Ala Arg Leu
    290                 295                 300

Pro Leu Asn Thr Asp Ala Tyr Leu Ser Leu Gln Glu Leu Gln Gly Gln
305                 310                 315                 320

Asp Pro Thr His Leu Val
            325


<210> SEQ ID NO 139
<211> LENGTH: 326
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Ser Asp Pro Thr Arg Val Glu Thr Ala Thr Glu Thr Ala Trp Ile Ser
1               5                   10                  15

Leu Val Thr Ala Leu Leu Leu Val Leu Gly Leu Asn Ala Val Leu Gly
            20                  25                  30

Leu Leu Leu Leu Arg Lys Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Leu Glu Val Thr Gln Leu Leu
            100                 105                 110

Leu Gln Gln Asp Lys Val Pro Glu Pro Ala Ser Leu Ser Ser Asn His
        115                 120                 125

Ser Leu Thr Ser Cys Phe Thr Asn Gln Gly Ser Phe Phe Phe His Leu
    130                 135                 140

Pro Asp Ala Leu Glu Ile Glu Ala Cys Gln Val Ser Phe Thr Ser Asp
145                 150                 155                 160

Pro Ser Ser Glu Glu Asp Pro Asp Glu Gly Val Ala Gly Ala Pro Thr
                165                 170                 175

Gly Ser Ser Pro Gln Pro Leu Gln Pro Leu Ser Gly Glu Asp Asp Ala
            180                 185                 190

Tyr Cys Thr Phe Pro Ser Arg Asp Asp Leu Leu Leu Phe Ser Pro Ser
        195                 200                 205

Leu Leu Gly Gly Pro Ser Pro Pro Ser Thr Ala Pro Gly Gly Ser Gly
    210                 215                 220

Ala Gly Glu Glu Arg Met Pro Pro Ser Leu Gln Glu Arg Val Pro Arg
225                 230                 235                 240

Asp Trp Asp Pro Gln Pro Leu Gly Pro Pro Thr Pro Gly Val Pro Asp
                245                 250                 255

Leu Val Asp Phe Gln Pro Pro Pro Glu Leu Val Leu Arg Glu Ala Gly
            260                 265                 270
```

```
Glu Glu Val Pro Asp Ala Gly Pro Arg Glu Gly Val Ser Phe Pro Trp
        275                 280                 285

Ser Arg Pro Pro Gly Gln Gly Glu Phe Arg Ala Leu Asn Ala Arg Leu
    290                 295                 300

Pro Leu Asn Thr Asp Ala Tyr Leu Ser Leu Gln Glu Leu Gln Gly Gln
305                 310                 315                 320

Asp Pro Thr His Leu Val
                325


<210> SEQ ID NO 140
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Asp Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Asp Ile Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Glu Ile Val Leu Thr Gln Ser Pro Gly Thr Leu Ser Leu Ser
    130                 135                 140

Pro Gly Glu Arg Ala Thr Leu Ser Cys Arg Ala Ser Gln Ser Val Ser
145                 150                 155                 160

Ser Ser Tyr Leu Ala Trp Tyr Gln Gln Lys Pro Gly Gln Ala Pro Arg
                165                 170                 175

Leu Leu Met Tyr Asp Ala Ser Ile Arg Ala Thr Gly Ile Pro Asp Arg
            180                 185                 190

Phe Ser Gly Ser Gly Ser Gly Thr Asp Phe Thr Leu Thr Ile Ser Arg
        195                 200                 205

Leu Glu Pro Glu Asp Phe Ala Val Tyr Tyr Cys Gln Gln Tyr Gly Ser
    210                 215                 220

Trp Pro Leu Thr Phe Gly Gln Gly Thr Lys Val Glu Ile Lys
225                 230                 235


<210> SEQ ID NO 141
<211> LENGTH: 519
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141
```

```
Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Ser Tyr Ala Met Asn Trp Val Arg Gln Ala Pro Gly Lys
    50                  55                  60

Gly Leu Glu Trp Val Ser Ala Ile Ser Asp Ser Gly Gly Ser Thr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Tyr Trp Pro Met Asp Ile Trp Gly Gln
        115                 120                 125

Gly Thr Leu Val Thr Val Ser Ser Gly Gly Gly Gly Ser Gly Gly Gly
    130                 135                 140

Gly Ser Gly Gly Gly Gly Ser Glu Ile Val Leu Thr Gln Ser Pro Gly
145                 150                 155                 160

Thr Leu Ser Leu Ser Pro Gly Glu Arg Ala Thr Leu Ser Cys Arg Ala
                165                 170                 175

Ser Gln Ser Val Ser Ser Ser Tyr Leu Ala Trp Tyr Gln Gln Lys Pro
            180                 185                 190

Gly Gln Ala Pro Arg Leu Leu Met Tyr Asp Ala Ser Ile Arg Ala Thr
        195                 200                 205

Gly Ile Pro Asp Arg Phe Ser Gly Ser Gly Ser Gly Thr Asp Phe Thr
    210                 215                 220

Leu Thr Ile Ser Arg Leu Glu Pro Glu Asp Phe Ala Val Tyr Tyr Cys
225                 230                 235                 240

Gln Gln Tyr Gly Ser Trp Pro Leu Thr Phe Gly Gln Gly Thr Lys Val
                245                 250                 255

Glu Ile Lys Gly Ser Gly Gly Gly Gly Ser Cys Pro Tyr Ser Asn Pro
            260                 265                 270

Ser Leu Cys Ser Gly Gly Gly Gly Ser Cys Pro Tyr Ser Asn Pro Ser
        275                 280                 285

Leu Cys Ser Gly Gly Gly Gly Ser Thr Thr Thr Pro Ala Pro Arg Pro
    290                 295                 300

Pro Thr Pro Ala Pro Thr Ile Ala Ser Gln Pro Leu Ser Leu Arg Pro
305                 310                 315                 320

Glu Ala Cys Arg Pro Ala Ala Gly Gly Ala Val His Thr Arg Gly Leu
                325                 330                 335

Asp Phe Ala Cys Asp Ile Tyr Ile Trp Ala Pro Leu Ala Gly Thr Cys
            340                 345                 350

Gly Val Leu Leu Leu Ser Leu Val Ile Thr Leu Tyr Cys Lys Arg Gly
        355                 360                 365

Arg Lys Lys Leu Leu Tyr Ile Phe Lys Gln Pro Phe Met Arg Pro Val
    370                 375                 380

Gln Thr Thr Gln Glu Glu Asp Gly Cys Ser Cys Arg Phe Pro Glu Glu
385                 390                 395                 400

Glu Glu Gly Gly Cys Glu Leu Arg Val Lys Phe Ser Arg Ser Ala Asp
                405                 410                 415
```

-continued

```
Ala Pro Ala Tyr Gln Gln Gly Gln Asn Gln Leu Tyr Asn Glu Leu Asn
            420                 425                 430

Leu Gly Arg Arg Glu Glu Tyr Asp Val Leu Asp Lys Arg Arg Gly Arg
        435                 440                 445

Asp Pro Glu Met Gly Gly Lys Pro Arg Arg Lys Asn Pro Gln Glu Gly
    450                 455                 460

Leu Tyr Asn Glu Leu Gln Lys Asp Lys Met Ala Glu Ala Tyr Ser Glu
465                 470                 475                 480

Ile Gly Met Lys Gly Glu Arg Arg Arg Gly Lys Gly His Asp Gly Leu
                485                 490                 495

Tyr Gln Gly Leu Ser Thr Ala Thr Lys Asp Thr Tyr Asp Ala Leu His
            500                 505                 510

Met Gln Ala Leu Pro Pro Arg
        515
```

<210> SEQ ID NO 142
<211> LENGTH: 219
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 142

```
Val Thr Gln Leu Leu Leu Gln Gln Asp Lys Val Pro Glu Pro Ala Ser
1               5                   10                  15

Leu Ser Ser Asn His Ser Leu Thr Ser Cys Phe Thr Asn Gln Gly Ser
            20                  25                  30

Phe Phe Phe His Leu Pro Asp Ala Leu Glu Ile Glu Ala Cys Gln Val
        35                  40                  45

Ser Phe Thr Ser Asp Pro Ser Ser Glu Glu Asp Pro Asp Glu Gly Val
    50                  55                  60

Ala Gly Ala Pro Thr Gly Ser Ser Pro Gln Pro Leu Gln Pro Leu Ser
65                  70                  75                  80

Gly Glu Asp Asp Ala Tyr Cys Thr Phe Pro Ser Arg Asp Asp Leu Leu
                85                  90                  95

Leu Phe Ser Pro Ser Leu Leu Gly Gly Pro Ser Pro Pro Ser Thr Ala
            100                 105                 110

Pro Gly Gly Ser Gly Ala Gly Glu Glu Arg Met Pro Pro Ser Leu Gln
        115                 120                 125

Glu Arg Val Pro Arg Asp Trp Asp Pro Gln Pro Leu Gly Pro Pro Thr
    130                 135                 140

Pro Gly Val Pro Asp Leu Val Asp Phe Gln Pro Pro Pro Glu Leu Val
145                 150                 155                 160

Leu Arg Glu Ala Gly Glu Glu Val Pro Asp Ala Gly Pro Arg Glu Gly
                165                 170                 175

Val Ser Phe Pro Trp Ser Arg Pro Pro Gly Gln Gly Glu Phe Arg Ala
            180                 185                 190

Leu Asn Ala Arg Leu Pro Leu Asn Thr Asp Ala Tyr Leu Ser Leu Gln
        195                 200                 205

Glu Leu Gln Gly Gln Asp Pro Thr His Leu Val
    210                 215
```

<210> SEQ ID NO 143
<211> LENGTH: 182
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 143

Ser Asp Pro Thr Arg Val Glu Thr Ala Thr Glu Thr Ala Trp Ile Ser
1 5 10 15

Leu Val Thr Ala Leu Leu Leu Val Leu Gly Leu Asn Ala Val Leu Gly
20 25 30

Leu Leu Leu Leu Arg Lys Gln Phe Pro Ala His Tyr Arg Arg Leu Arg
35 40 45

His Ala Leu Trp Pro Ser Leu Pro Asp Leu His Arg Val Leu Gly Gln
50 55 60

Tyr Leu Arg Asp Thr Ala Ala Leu Ser Pro Pro Lys Ala Thr Val Ser
65 70 75 80

Asp Thr Cys Glu Glu Val Glu Pro Ser Leu Leu Glu Ile Leu Pro Lys
85 90 95

Ser Ser Glu Arg Thr Pro Leu Pro Leu Leu Glu Asp Glu Gly Val Ala
100 105 110

Gly Ala Pro Thr Gly Ser Ser Pro Gln Pro Leu Gln Pro Leu Ser Gly
115 120 125

Glu Asp Asp Ala Tyr Cys Thr Phe Pro Ser Arg Asp Asp Leu Leu Leu
130 135 140

Phe Ser Pro Ser Gly Gln Gly Glu Phe Arg Ala Leu Asn Ala Arg Leu
145 150 155 160

Pro Leu Asn Thr Asp Ala Tyr Leu Ser Leu Gln Glu Leu Gln Gly Gln
165 170 175

Asp Pro Thr His Leu Val
180

<210> SEQ ID NO 144
<211> LENGTH: 115
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 144

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Asn Trp Val Arg Gln Ala Pro Gly Lys Gly Leu Glu Trp Val
35 40 45

Ser Ala Ile Ser Asp Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Tyr Trp Pro Met Asp Ile Trp Gly Gln Gly Thr Leu Val Thr
100 105 110

Val Ser Ser
115

<210> SEQ ID NO 145

<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 145

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Trp Pro
                85                  90                  95

Leu Thr Phe Gly Gln Gly Thr Lys Val Glu Ile Lys
            100                 105
```

<210> SEQ ID NO 146
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 146

```
Ser Tyr Ala Met Asn
1               5
```

<210> SEQ ID NO 147
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 147

```
Gly Phe Thr Phe Ser Ser Tyr
1               5
```

<210> SEQ ID NO 148
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 148

```
Gly Phe Thr Phe Ser Ser Tyr Ala Met Asn
1               5                   10
```

<210> SEQ ID NO 149
<211> LENGTH: 17
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 149

Ala Ile Ser Asp Ser Gly Gly Ser Thr Tyr Tyr Ala Asp Ser Val Lys
1 5 10 15

Gly

<210> SEQ ID NO 150
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 150

Ser Asp Ser Gly Gly Ser
1 5

<210> SEQ ID NO 151
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 151

Tyr Trp Pro Met Asp Ile
1 5

<210> SEQ ID NO 152
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 152

Arg Ala Ser Gln Ser Val Ser Ser Ser Tyr Leu Ala
1 5 10

<210> SEQ ID NO 153
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 153

Asp Ala Ser Ile Arg Ala Thr
1 5

<210> SEQ ID NO 154
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 154

Gln Gln Tyr Gly Ser Trp Pro Leu Thr
1 5

<210> SEQ ID NO 155
<211> LENGTH: 115
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 155

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Pro Met Ser Trp Val Arg Gln Ala Pro Gly Lys Gly Leu Glu Trp Val
        35                  40                  45

Ser Ala Ile Gly Gly Ser Gly Gly Ser Leu Pro Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Asp Ile Trp Gly Gln Gly Thr Leu Val Thr
            100                 105                 110

Val Ser Ser
        115
```

<210> SEQ ID NO 156
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 156

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gln Ser Trp Pro
                85                  90                  95

Leu Thr Phe Gly Gln Gly Thr Lys Val Glu Ile Lys
            100                 105
```

<210> SEQ ID NO 157
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 157

```
Ser Tyr Pro Met Ser
```

1 5

<210> SEQ ID NO 158
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 158

Gly Phe Thr Phe Ser Ser Tyr
1 5

<210> SEQ ID NO 159
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 159

Gly Phe Thr Phe Ser Ser Tyr Pro Met Ser
1 5 10

<210> SEQ ID NO 160
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 160

Ala Ile Gly Gly Ser Gly Gly Ser Leu Pro Tyr Ala Asp Ser Val Lys
1 5 10 15

Gly

<210> SEQ ID NO 161
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 161

Gly Gly Ser Gly Gly Ser
1 5

<210> SEQ ID NO 162
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 162

Tyr Trp Pro Met Asp Ile
1 5

<210> SEQ ID NO 163
<211> LENGTH: 12
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 163

Arg Ala Ser Gln Ser Val Ser Ser Ser Tyr Leu Ala
1               5                   10


<210> SEQ ID NO 164
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Asp Ala Ser Ile Arg Ala Thr
1               5


<210> SEQ ID NO 165
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Gln Gln Tyr Gln Ser Trp Pro Leu Thr
1               5


<210> SEQ ID NO 166
<211> LENGTH: 498
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Asp Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Asp Ile Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Glu Ile Val Leu Thr Gln Ser Pro Gly Thr Leu Ser Leu Ser
    130                 135                 140

Pro Gly Glu Arg Ala Thr Leu Ser Cys Arg Ala Ser Gln Ser Val Ser
145                 150                 155                 160

Ser Ser Tyr Leu Ala Trp Tyr Gln Gln Lys Pro Gly Gln Ala Pro Arg
```

-continued

```
                165                 170                 175

Leu Leu Met Tyr Asp Ala Ser Ile Arg Ala Thr Gly Ile Pro Asp Arg
            180                 185                 190

Phe Ser Gly Ser Gly Ser Gly Thr Asp Phe Thr Leu Thr Ile Ser Arg
        195                 200                 205

Leu Glu Pro Glu Asp Phe Ala Val Tyr Tyr Cys Gln Gln Tyr Gly Ser
    210                 215                 220

Trp Pro Leu Thr Phe Gly Gln Gly Thr Lys Val Glu Ile Lys Gly Ser
225                 230                 235                 240

Gly Gly Gly Gly Ser Cys Pro Tyr Ser Asn Pro Ser Leu Cys Ser Gly
                245                 250                 255

Gly Gly Gly Ser Cys Pro Tyr Ser Asn Pro Ser Leu Cys Ser Gly Gly
            260                 265                 270

Gly Gly Ser Thr Thr Thr Pro Ala Pro Arg Pro Pro Thr Pro Ala Pro
        275                 280                 285

Thr Ile Ala Ser Gln Pro Leu Ser Leu Arg Pro Glu Ala Cys Arg Pro
    290                 295                 300

Ala Ala Gly Gly Ala Val His Thr Arg Gly Leu Asp Phe Ala Cys Asp
305                 310                 315                 320

Ile Tyr Ile Trp Ala Pro Leu Ala Gly Thr Cys Gly Val Leu Leu Leu
                325                 330                 335

Ser Leu Val Ile Thr Leu Tyr Cys Lys Arg Gly Arg Lys Lys Leu Leu
            340                 345                 350

Tyr Ile Phe Lys Gln Pro Phe Met Arg Pro Val Gln Thr Thr Gln Glu
        355                 360                 365

Glu Asp Gly Cys Ser Cys Arg Phe Pro Glu Glu Glu Glu Gly Gly Cys
    370                 375                 380

Glu Leu Arg Val Lys Phe Ser Arg Ser Ala Asp Ala Pro Ala Tyr Gln
385                 390                 395                 400

Gln Gly Gln Asn Gln Leu Tyr Asn Glu Leu Asn Leu Gly Arg Arg Glu
                405                 410                 415

Glu Tyr Asp Val Leu Asp Lys Arg Arg Gly Arg Asp Pro Glu Met Gly
            420                 425                 430

Gly Lys Pro Arg Arg Lys Asn Pro Gln Glu Gly Leu Tyr Asn Glu Leu
        435                 440                 445

Gln Lys Asp Lys Met Ala Glu Ala Tyr Ser Glu Ile Gly Met Lys Gly
    450                 455                 460

Glu Arg Arg Arg Gly Lys Gly His Asp Gly Leu Tyr Gln Gly Leu Ser
465                 470                 475                 480

Thr Ala Thr Lys Asp Thr Tyr Asp Ala Leu His Met Gln Ala Leu Pro
                485                 490                 495

Pro Arg
```

<210> SEQ ID NO 167
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 167

```
Gly Gly Gly Gly Ser Gly Gly Gly Gly Ser Gly Gly Gly Gly Ser
1               5                   10                  15
```

<210> SEQ ID NO 168
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

```
Gly Ser Gly Gly Gly Gly Ser Cys Pro Tyr Ser Asn Pro Ser Leu Cys
1               5                   10                  15

Ser Gly Gly Gly Gly Ser Cys Pro Tyr Ser Asn Pro Ser Leu Cys Ser
            20                  25                  30

Gly Gly Gly Gly Ser
        35
```

<210> SEQ ID NO 169
<211> LENGTH: 45
<212> TYPE: PRT
<213> ORGANISM: Homo sapiens

<400> SEQUENCE: 169

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45
```

<210> SEQ ID NO 170
<211> LENGTH: 21
<212> TYPE: PRT
<213> ORGANISM: Homo sapiens

<400> SEQUENCE: 170

```
Ile Tyr Ile Trp Ala Pro Leu Ala Gly Thr Cys Gly Val Leu Leu Leu
1               5                   10                  15

Ser Leu Val Ile Thr
            20
```

<210> SEQ ID NO 171
<211> LENGTH: 1560
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 171

```
atggcactgc ccgtgaccgc cctgctgctg cctctggccc tgctgctgca cgccgcccgg     60

cctgaggtgc agctgctgga gagcggagga ggcctggtgc agccaggagg cagcctgaga    120

ctgtcctgcg cagcctctgg cttcaccttc agcagctacg ccatgaactg ggtgaggcag    180

gcacctggca agggcctgga gtgggtgagc gccatctccg actctggcgg cagcacctac    240

tatgccgatt ccgtgaaggg ccgcttcaca atcagccggg ataactccaa gaataccctg    300

tacctgcaga tgaacagcct gagagccgag gatacagccg tgtactattg cgccaggtat    360

tggccaatgg acatctgggg ccagggcaca ctggtgaccg tgtctagcgg cggaggaggc    420

tccggaggag gaggctctgg cggcggcggc agcgagatcg tgctgacaca gtctccaggc    480

accctgagcc tgtccccagg agagagagcc accctgagct gtagggcctc tcagagcgtg    540
```

```
tcctctagct acctggcctg gtatcagcag aagccaggcc aggcccccag actgctgatg    600

tacgacgcca gcatcagggc aacaggcatc cccgatcggt tctccggctc tggcagcggc    660

accgacttta cactgaccat cagcaggctg gagcccgagg acttcgccgt gtactattgc    720

cagcagtatg gctcctggcc tctgacattt ggccagggca ccaaggtgga gatcaagggc    780

tccggcggcg gaggctcttg cccttacagc aacccatccc tgtgctctgg aggaggaggc    840

tcctgtccct atagcaatcc cagcctgtgc tccggcggag gaggctctac cacaacccct    900

gcaccacgcc cccctacacc agcacctacc atcgcctctc agcctctgag cctgcggccc    960

gaggcctgta ggcccgccgc cggcggcgcc gtgcacacac ggggcctgga ctttgcctgc   1020

gacatctaca tctgggcacc cctggccggc acatgtggcg tgctgctgct gagcctggtc   1080

atcaccctgt actgcaagag aggcaggaag aagctgctgt atatcttcaa gcagcccttc   1140

atgcggcccg tgcagacaac ccaggaggag gatggctgct cctgtcggtt cccagaggag   1200

gaggagggag gatgtgagct gcgcgtgaag ttttcccggt ctgccgacgc accagcatac   1260

cagcagggcc agaaccagct gtataacgag ctgaatctgg gccggagaga ggagtacgac   1320

gtgctggata agcggcgggg ccgggacccc gagatgggag gcaagcctcg gagaaagaac   1380

ccacaggagg gcctgtacaa tgagctgcag aaggataaga tggccgaggc ctattctgag   1440

atcggcatga agggagagag gcgccggggc aagggacacg acggcctgta ccagggcctg   1500

tccacagcca ccaaggacac ctatgatgcc ctgcacatgc aggccctgcc acccagatga   1560
```

<210> SEQ ID NO 172
<211> LENGTH: 2235
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 172

```
atggccctgc cagtgaccgc cctgctgctg ccactggccc tgctgctgca cgcagcaagg     60

ccatcagacc ctactagagt cgagaccgct accgagaccg cttggatctc tctggtgacc    120

gccctgcacc tggtgctggg cctgaacgcc gtgctgggcc tgctgctgct gaggaagcag    180

ttcccagcac actaccggag actgaggcac gcactgtggc caagcctgcc cgacctgcac    240

agggtgctgg gacagtatct gagggataca gccgccctga gcccacctaa ggcaaccgtg    300

tccgacacat gcgaggaggt ggaaccaagt ctgctggaaa tcctgccaaa atcctctgag    360

cggacacccc tgcccctgct cgaggacgag ggagtggcag gagcaccaac cggcagctcc    420

ccccagcctc tgcagccact gtccggagag gacgatgcat actgcacatt cccttctcgg    480

gacgatctgc tgctgttctc tccaagcgga cagggagagt ttcgggccct gaacgccaga    540

ctgcccctga ataccgacgc ctatctgagc ctgcaggagc tgcagggaca ggaccccaca    600

cacctggtgg gatccggagc caccaacttc tccctgctga agcaggccgg cgatgtggag    660

gagaatccag gccccatggc tctgcccgtc accgcactgc tgctgcccct ggctctgctg    720

ctgcacgccg caagacccga ggtccagctg ctggaatctg ggggaggact ggtgcagcct    780

ggaggcagcc tgagactgtc ctgcgcagca tctggcttca ccttcagctc ctacgccatg    840

aactgggtga ggcaggcacc aggcaaggga ctggagtggg tgtctgccat ctccgactct    900

ggcggcagca cctactatgc cgattccgtg aagggccgct tcacaatcag ccgggataac    960

tccaagaata ccctgtacct gcagatgaat tccctgagag ccgaggatac agccgtgtac   1020
```

-continued

```
tattgcgcca ggtattggcc catggacatc tggggccagg gcacactggt gaccgtgtct   1080

tccggaggag gaggctccgg aggaggaggc tctggcggcg gcggcagcga gatcgtgctg   1140

acacagtctc ctggcaccct gagcctgtcc ccaggagaga gagccaccct gagctgtagg   1200

gcctctcaga gcgtgtcctc tagctacctg gcctggtatc agcagaagcc cggccaggcc   1260

cctagactgc tgatgtacga cgccagcatc agggcaacag gcatccctga tcggttctcc   1320

ggctctggca gcggaaccga ctttacactg accatcagca ggctggagcc cgaggacttc   1380

gccgtgtact attgccagca gtatggctcc tggcctctga catttggcca gggcaccaag   1440

gtggagatca agggctccgg cggcggaggc tcttgcccat acagcaaccc atccctgtgc   1500

tctggaggag gaggctcctg tccttatagc aatcctagcc tgtgctccgg cggaggaggc   1560

tctaccacaa ccccagcacc aaggccacct acacctgcac caaccatcgc ctctcagcca   1620

ctgagcctga gacccgaggc ctgtaggcct gcagcaggag gagcagtgca cacccgggga   1680

ctggactttg cctgcgatat ctacatctgg gcaccactgg caggaacatg tggcgtgctg   1740

ctgctgagcc tggtcatcac cctgtactgc aagagaggca ggaagaagct gctgtatatc   1800

ttcaagcagc cctttatgcg ccctgtgcag acaacccagg aggaggatgg ctgctcctgt   1860

cggttcccag aggaggagga gggaggatgt gagctgcgcg tgaagttttc ccggtctgcc   1920

gacgcaccag cataccagca gggccagaac cagctgtata acgagctgaa tctgggccgg   1980

agagaggagt acgacgtgct ggataagagg aggggaagag atcccgagat gggaggcaag   2040

ccacggagaa agaacccccca ggagggcctg tacaatgagc tgcagaagga taagatggcc   2100

gaggcctata gcgagatcgg catgaaggga gagaggcgcc ggggcaaggg acacgacggc   2160

ctgtatcagg gcctgtccac cgctaccaaa gacacctatg atgctctgca catgcaggct   2220

ctgccaccaa gatga                                                    2235
```

<210> SEQ ID NO 173
<211> LENGTH: 744
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

```
Met Ala Leu Pro Val Thr Ala Leu Leu Leu Pro Leu Ala Leu Leu Leu
1               5                   10                  15

His Ala Ala Arg Pro Ser Asp Pro Thr Arg Val Glu Thr Ala Thr Glu
            20                  25                  30

Thr Ala Trp Ile Ser Leu Val Thr Ala Leu His Leu Val Leu Gly Leu
        35                  40                  45

Asn Ala Val Leu Gly Leu Leu Leu Leu Arg Lys Gln Phe Pro Ala His
    50                  55                  60

Tyr Arg Arg Leu Arg His Ala Leu Trp Pro Ser Leu Pro Asp Leu His
65                  70                  75                  80

Arg Val Leu Gly Gln Tyr Leu Arg Asp Thr Ala Ala Leu Ser Pro Pro
                85                  90                  95

Lys Ala Thr Val Ser Asp Thr Cys Glu Glu Val Glu Pro Ser Leu Leu
            100                 105                 110

Glu Ile Leu Pro Lys Ser Ser Glu Arg Thr Pro Leu Pro Leu Leu Glu
        115                 120                 125

Asp Glu Gly Val Ala Gly Ala Pro Thr Gly Ser Ser Pro Gln Pro Leu
    130                 135                 140
```

-continued

```
Gln Pro Leu Ser Gly Glu Asp Asp Ala Tyr Cys Thr Phe Pro Ser Arg
145                 150                 155                 160

Asp Asp Leu Leu Leu Phe Ser Pro Ser Gly Gln Gly Glu Phe Arg Ala
                165                 170                 175

Leu Asn Ala Arg Leu Pro Leu Asn Thr Asp Ala Tyr Leu Ser Leu Gln
            180                 185                 190

Glu Leu Gln Gly Gln Asp Pro Thr His Leu Val Gly Ser Gly Ala Thr
        195                 200                 205

Asn Phe Ser Leu Leu Lys Gln Ala Gly Asp Val Glu Glu Asn Pro Gly
    210                 215                 220

Pro Met Ala Leu Pro Val Thr Ala Leu Leu Leu Pro Leu Ala Leu Leu
225                 230                 235                 240

Leu His Ala Ala Arg Pro Glu Val Gln Leu Leu Glu Ser Gly Gly Gly
                245                 250                 255

Leu Val Gln Pro Gly Gly Ser Leu Arg Leu Ser Cys Ala Ala Ser Gly
            260                 265                 270

Phe Thr Phe Ser Ser Tyr Ala Met Asn Trp Val Arg Gln Ala Pro Gly
        275                 280                 285

Lys Gly Leu Glu Trp Val Ser Ala Ile Ser Asp Ser Gly Gly Ser Thr
    290                 295                 300

Tyr Tyr Ala Asp Ser Val Lys Gly Arg Phe Thr Ile Ser Arg Asp Asn
305                 310                 315                 320

Ser Lys Asn Thr Leu Tyr Leu Gln Met Asn Ser Leu Arg Ala Glu Asp
                325                 330                 335

Thr Ala Val Tyr Tyr Cys Ala Arg Tyr Trp Pro Met Asp Ile Trp Gly
            340                 345                 350

Gln Gly Thr Leu Val Thr Val Ser Ser Gly Gly Gly Gly Ser Gly Gly
        355                 360                 365

Gly Gly Ser Gly Gly Gly Gly Ser Glu Ile Val Leu Thr Gln Ser Pro
    370                 375                 380

Gly Thr Leu Ser Leu Ser Pro Gly Glu Arg Ala Thr Leu Ser Cys Arg
385                 390                 395                 400

Ala Ser Gln Ser Val Ser Ser Ser Tyr Leu Ala Trp Tyr Gln Gln Lys
                405                 410                 415

Pro Gly Gln Ala Pro Arg Leu Leu Met Tyr Asp Ala Ser Ile Arg Ala
            420                 425                 430

Thr Gly Ile Pro Asp Arg Phe Ser Gly Ser Gly Ser Gly Thr Asp Phe
        435                 440                 445

Thr Leu Thr Ile Ser Arg Leu Glu Pro Glu Asp Phe Ala Val Tyr Tyr
    450                 455                 460

Cys Gln Gln Tyr Gly Ser Trp Pro Leu Thr Phe Gly Gln Gly Thr Lys
465                 470                 475                 480

Val Glu Ile Lys Gly Ser Gly Gly Gly Gly Ser Cys Pro Tyr Ser Asn
                485                 490                 495

Pro Ser Leu Cys Ser Gly Gly Gly Gly Ser Cys Pro Tyr Ser Asn Pro
            500                 505                 510

Ser Leu Cys Ser Gly Gly Gly Gly Ser Thr Thr Thr Pro Ala Pro Arg
        515                 520                 525

Pro Pro Thr Pro Ala Pro Thr Ile Ala Ser Gln Pro Leu Ser Leu Arg
    530                 535                 540

Pro Glu Ala Cys Arg Pro Ala Ala Gly Gly Ala Val His Thr Arg Gly
545                 550                 555                 560
```

```
Leu Asp Phe Ala Cys Asp Ile Tyr Ile Trp Ala Pro Leu Ala Gly Thr
                565                 570                 575

Cys Gly Val Leu Leu Leu Ser Leu Val Ile Thr Leu Tyr Cys Lys Arg
            580                 585                 590

Gly Arg Lys Lys Leu Leu Tyr Ile Phe Lys Gln Pro Phe Met Arg Pro
        595                 600                 605

Val Gln Thr Thr Gln Glu Glu Asp Gly Cys Ser Cys Arg Phe Pro Glu
    610                 615                 620

Glu Glu Glu Gly Gly Cys Glu Leu Arg Val Lys Phe Ser Arg Ser Ala
625                 630                 635                 640

Asp Ala Pro Ala Tyr Gln Gln Gly Gln Asn Gln Leu Tyr Asn Glu Leu
                645                 650                 655

Asn Leu Gly Arg Arg Glu Glu Tyr Asp Val Leu Asp Lys Arg Arg Gly
            660                 665                 670

Arg Asp Pro Glu Met Gly Gly Lys Pro Arg Arg Lys Asn Pro Gln Glu
        675                 680                 685

Gly Leu Tyr Asn Glu Leu Gln Lys Asp Lys Met Ala Glu Ala Tyr Ser
    690                 695                 700

Glu Ile Gly Met Lys Gly Glu Arg Arg Arg Gly Lys Gly His Asp Gly
705                 710                 715                 720

Leu Tyr Gln Gly Leu Ser Thr Ala Thr Lys Asp Thr Tyr Asp Ala Leu
                725                 730                 735

His Met Gln Ala Leu Pro Pro Arg
            740
```

```
<210> SEQ ID NO 174
<211> LENGTH: 592
<212> TYPE: DNA
<213> ORGANISM: Woodchuck hepatitis virus

<400> SEQUENCE: 174

aatcaacctc tggattacaa aatttgtgaa agattgactg gtattcttaa ctatgttgct     60

ccttttacgc tatgtggata cgctgcttta atgcctttgt atcatgctat tgcttcccgt    120

atggctttca ttttctcctc cttgtataaa tcctggttgc tgtctcttta tgaggagttg    180

tggcccgttg tcaggcaacg tggcgtggtg tgcactgtgt ttgctgacgc aacccccact    240

ggttggggca ttgccaccac ctgtcagctc ctttccggga ctttcgcttt ccccctccct    300

attgccacgg cggaactcat cgccgcctgc cttgcccgct gctggacagg ggctcggctg    360

ttgggcactg acaattccgt ggtgttgtcg gggaagctga cgtcctttcc atggctgctc    420

gcctgtgttg ccacctggat tctgcgcggg acgtccttct gctacgtccc ttcggccctc    480

aatccagcgg accttccttc ccgcggcctg ctgccggctc tgcggcctct tccgcgtctt    540

cgccttcgcc ctcagacgag tcggatctcc ctttgggccg cctccccgcc tg            592


<210> SEQ ID NO 175
<211> LENGTH: 592
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 175

aatcaacctc tggattacaa aatttgtgaa agattgactg gtattcttaa ctatgttgct     60

ccttttacgc tatgtggata cgctgcttta atgcctttgt atcatgctat tgcttcccgt    120
```

atggctttca ttttctcctc cttgtataaa tcctggttgc tgtctcttta tgaggagttg 180
tggcccgttg tcaggcaacg tggcgtggtg tgcactgtgt ttgctgacgc aacccccact 240
ggttggggca ttgccaccac ctgtcagctc ctttccggga ctttcgcttt ccccctccct 300
attgccacgg cggaactcat cgccgcctgc cttgcccgct gctggacagg ggctcggctg 360
ttgggcactg acaattccgt ggtgttgtcg gggaaatcat cgtcctttcc ttggctgctc 420
gcctgtgttg ccacctggat tctgcgcggg acgtccttct gctacgtccc ttcggccctc 480
aatccagcgg accttccttc ccgcggcctg ctgccggctc tgcggcctct tccgcgtctt 540
cgccttcgcc ctcagacgag tcggatctcc ctttgggccg cctccccgcc tg 592

<210> SEQ ID NO 176
<211> LENGTH: 2358
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 176
atggccctgc cagtgaccgc cctgctgctg ccactggccc tgctgctgca cgcagcaagg 60
ccatcagacc ctactagagt cgagaccgct accgagaccg cttggatctc tctggtgacc 120
gccctgctgc tggtgctggg cctgaacgcc gtgctgggcc tgctgctgct gaggaagcag 180
ttcccagcac actaccggag actgaggcac gcactgtggc caagcctgcc cgacctgcac 240
agggtgctgg gacagtatct gagggataca gccgccctga gcccacctaa ggcaaccgtg 300
tccgacacat gcgaggaggt ggaaccaagt ctgctggaaa tcctgccaaa atcctctgag 360
cggacacccc tgcccctgct cgagcagcag gacaaggtgc ccgagcctgc ctccctgagc 420
tccaaccaca gcctgacctc ctgctttaca aatcagggct acttcttttt ccacctgcct 480
gacgccctgg agatcgaggc ctgtcaggat gagggagtgg caggagcacc taccggctct 540
agcccacagc cactgcagcc actgtctgga gaggacgatg cctactgcac attccccagc 600
cgggacgatc tgctgctgtt ttccccttct ggacagggag agttccgggc cctgaacgca 660
agactgccac tgaataccga cgcctatctg tctctgcagg agctgcaggg ccaggacccc 720
acacacctgg tgggatccgg agccaccaac ttctccctgc tgaagcaggc cggcgatgtg 780
gaggagaatc caggccccat ggctctgccc gtcaccgcac tgctgctgcc cctggctctg 840
ctgctgcacg ccgcaagacc cgaggtccag ctgctggaat ctgggggagg actggtgcag 900
cctggaggca gcctgagact gtcctgcgca gcatctggct tcaccttcag ctcctacgcc 960
atgaactggg tgaggcaggc accaggcaag ggactggagt gggtgtctgc catctccgac 1020
tctggcggca gcacctacta tgccgattcc gtgaagggcc gcttcacaat cagccgggat 1080
aactccaaga ataccctgta cctgcagatg aattccctga gagccgagga tacagccgtg 1140
tactattgcg ccaggtattg gcccatggac atctggggcc agggcacact ggtgaccgtg 1200
tcttccggag gaggaggctc cggaggagga ggctctggcg gcggcggcag cgagatcgtg 1260
ctgacacagt ctcctggcac cctgagcctg tccccaggag agagagccac cctgagctgt 1320
agggcctctc agagcgtgtc ctctagctac ctggcctggt atcagcagaa gcccggccag 1380
gcccctagac tgctgatgta cgacgccagc atcagggcaa caggcatccc tgatcggttc 1440
tccggctctg gcagcggaac cgactttaca ctgaccatca gcaggctgga gcccgaggac 1500
ttcgccgtgt actattgcca gcagtatggc tcctggcctc tgacatttgg ccagggcacc 1560
aaggtggaga tcaagggctc cggcggcgga ggctcttgcc catacagcaa cccatccctg 1620
tgctctggag gaggaggctc ctgtccttat agcaatccta gcctgtgctc cggcggagga 1680
ggctctacca caaccccagc accaaggcca cctacacctg caccaaccat cgcctctcag 1740
ccactgagcc tgagacccga ggcctgtagg cctgcagcag gaggagcagt gcacacccgg 1800
ggactggact ttgcctgcga tatctacatc tgggcaccac tggcaggaac atgtggcgtg 1860
ctgctgctga gcctggtcat caccctgtac tgcaagagag gcaggaagaa gctgctgtat 1920
atcttcaagc agccctttat gcgccctgtg cagacaaccc aggaggagga tggctgctcc 1980
tgtcggttcc cagaggagga ggagggagga tgtgagctgc gcgtgaagtt ttcccggtct 2040
gccgacgcac cagcatacca gcagggccag aaccagctgt ataacgagct gaatctgggc 2100
cggagagagg agtacgacgt gctggataag aggaggggaa gagatcccga gatgggaggc 2160
aagccacgga gaaagaaccc ccaggagggc ctgtacaatg agctgcagaa ggataagatg 2220
gccgaggcct atagcgagat cggcatgaag ggagagaggc gccggggcaa gggacacgac 2280
ggcctgtatc agggcctgtc caccgctacc aaagacacct atgatgctct gcacatgcag 2340
gctctgccac caagatga 2358

<210> SEQ ID NO 177
<211> LENGTH: 785
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 177

Met Ala Leu Pro Val Thr Ala Leu Leu Leu Pro Leu Ala Leu Leu Leu
1 5 10 15

His Ala Ala Arg Pro Ser Asp Pro Thr Arg Val Glu Thr Ala Thr Glu
20 25 30

Thr Ala Trp Ile Ser Leu Val Thr Ala Leu Leu Leu Val Leu Gly Leu
35 40 45

Asn Ala Val Leu Gly Leu Leu Leu Leu Arg Lys Gln Phe Pro Ala His
50 55 60

Tyr Arg Arg Leu Arg His Ala Leu Trp Pro Ser Leu Pro Asp Leu His
65 70 75 80

Arg Val Leu Gly Gln Tyr Leu Arg Asp Thr Ala Ala Leu Ser Pro Pro
85 90 95

Lys Ala Thr Val Ser Asp Thr Cys Glu Glu Val Glu Pro Ser Leu Leu
100 105 110

Glu Ile Leu Pro Lys Ser Ser Glu Arg Thr Pro Leu Pro Leu Leu Glu
115 120 125

Gln Gln Asp Lys Val Pro Glu Pro Ala Ser Leu Ser Ser Asn His Ser
130 135 140

Leu Thr Ser Cys Phe Thr Asn Gln Gly Tyr Phe Phe Phe His Leu Pro
145 150 155 160

Asp Ala Leu Glu Ile Glu Ala Cys Gln Asp Glu Gly Val Ala Gly Ala
165 170 175

Pro Thr Gly Ser Ser Pro Gln Pro Leu Gln Pro Leu Ser Gly Glu Asp
180 185 190

Asp Ala Tyr Cys Thr Phe Pro Ser Arg Asp Asp Leu Leu Leu Phe Ser
195 200 205

Pro Ser Gly Gln Gly Glu Phe Arg Ala Leu Asn Ala Arg Leu Pro Leu

-continued

```
    210                 215                 220

Asn Thr Asp Ala Tyr Leu Ser Leu Gln Glu Leu Gln Gly Gln Asp Pro
225                 230                 235                 240

Thr His Leu Val Gly Ser Gly Ala Thr Asn Phe Ser Leu Leu Lys Gln
                245                 250                 255

Ala Gly Asp Val Glu Glu Asn Pro Gly Pro Met Ala Leu Pro Val Thr
            260                 265                 270

Ala Leu Leu Leu Pro Leu Ala Leu Leu Leu His Ala Ala Arg Pro Glu
        275                 280                 285

Val Gln Leu Leu Glu Ser Gly Gly Gly Leu Val Gln Pro Gly Gly Ser
    290                 295                 300

Leu Arg Leu Ser Cys Ala Ala Ser Gly Phe Thr Phe Ser Ser Tyr Ala
305                 310                 315                 320

Met Asn Trp Val Arg Gln Ala Pro Gly Lys Gly Leu Glu Trp Val Ser
                325                 330                 335

Ala Ile Ser Asp Ser Gly Gly Ser Thr Tyr Tyr Ala Asp Ser Val Lys
            340                 345                 350

Gly Arg Phe Thr Ile Ser Arg Asp Asn Ser Lys Asn Thr Leu Tyr Leu
        355                 360                 365

Gln Met Asn Ser Leu Arg Ala Glu Asp Thr Ala Val Tyr Tyr Cys Ala
    370                 375                 380

Arg Tyr Trp Pro Met Asp Ile Trp Gly Gln Gly Thr Leu Val Thr Val
385                 390                 395                 400

Ser Ser Gly Gly Gly Gly Ser Gly Gly Gly Gly Ser Gly Gly Gly Gly
                405                 410                 415

Ser Glu Ile Val Leu Thr Gln Ser Pro Gly Thr Leu Ser Leu Ser Pro
            420                 425                 430

Gly Glu Arg Ala Thr Leu Ser Cys Arg Ala Ser Gln Ser Val Ser Ser
        435                 440                 445

Ser Tyr Leu Ala Trp Tyr Gln Gln Lys Pro Gly Gln Ala Pro Arg Leu
    450                 455                 460

Leu Met Tyr Asp Ala Ser Ile Arg Ala Thr Gly Ile Pro Asp Arg Phe
465                 470                 475                 480

Ser Gly Ser Gly Ser Gly Thr Asp Phe Thr Leu Thr Ile Ser Arg Leu
                485                 490                 495

Glu Pro Glu Asp Phe Ala Val Tyr Tyr Cys Gln Gln Tyr Gly Ser Trp
            500                 505                 510

Pro Leu Thr Phe Gly Gln Gly Thr Lys Val Glu Ile Lys Gly Ser Gly
        515                 520                 525

Gly Gly Gly Ser Cys Pro Tyr Ser Asn Pro Ser Leu Cys Ser Gly Gly
    530                 535                 540

Gly Gly Ser Cys Pro Tyr Ser Asn Pro Ser Leu Cys Ser Gly Gly Gly
545                 550                 555                 560

Gly Ser Thr Thr Thr Pro Ala Pro Arg Pro Pro Thr Pro Ala Pro Thr
                565                 570                 575

Ile Ala Ser Gln Pro Leu Ser Leu Arg Pro Glu Ala Cys Arg Pro Ala
            580                 585                 590

Ala Gly Gly Ala Val His Thr Arg Gly Leu Asp Phe Ala Cys Asp Ile
        595                 600                 605

Tyr Ile Trp Ala Pro Leu Ala Gly Thr Cys Gly Val Leu Leu Leu Ser
    610                 615                 620

Leu Val Ile Thr Leu Tyr Cys Lys Arg Gly Arg Lys Lys Leu Leu Tyr
625                 630                 635                 640
```

```
Ile Phe Lys Gln Pro Phe Met Arg Pro Val Gln Thr Thr Gln Glu Glu
                645                 650                 655

Asp Gly Cys Ser Cys Arg Phe Pro Glu Glu Glu Glu Gly Gly Cys Glu
            660                 665                 670

Leu Arg Val Lys Phe Ser Arg Ser Ala Asp Ala Pro Ala Tyr Gln Gln
        675                 680                 685

Gly Gln Asn Gln Leu Tyr Asn Glu Leu Asn Leu Gly Arg Arg Glu Glu
    690                 695                 700

Tyr Asp Val Leu Asp Lys Arg Arg Gly Arg Asp Pro Glu Met Gly Gly
705                 710                 715                 720

Lys Pro Arg Arg Lys Asn Pro Gln Glu Gly Leu Tyr Asn Glu Leu Gln
                725                 730                 735

Lys Asp Lys Met Ala Glu Ala Tyr Ser Glu Ile Gly Met Lys Gly Glu
            740                 745                 750

Arg Arg Arg Gly Lys Gly His Asp Gly Leu Tyr Gln Gly Leu Ser Thr
        755                 760                 765

Ala Thr Lys Asp Thr Tyr Asp Ala Leu His Met Gln Ala Leu Pro Pro
    770                 775                 780

Arg
785
```

<210> SEQ ID NO 178
<211> LENGTH: 2235
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 178

```
atggccctgc cagtgaccgc cctgctgctg ccactggccc tgctgctgca cgcagcaagg     60

ccatcagacc ctactagagt cgagaccgct accgagaccg cttggatctc tctggtgacc    120

gccctgctgc tggtgctggg cctgaacgcc gtgctgggcc tgctgctgct gaggaagcag    180

ttcccagcac actaccggag actgaggcac gcactgtggc caagcctgcc cgacctgcac    240

agggtgctgg gacagtatct gagggataca gccgccctga gcccacctaa ggcaaccgtg    300

tccgacacat gcgaggaggt ggaaccaagt ctgctggaaa tcctgccaaa atcctctgag    360

cggacacccc tgcccctgct cgaggacgag ggagtggcag gagcaccaac cggcagctcc    420

ccccagcctc tgcagccact gtccggagag gacgatgcat actgcacatt cccttctcgg    480

gacgatctgc tgctgttctc tccaagcgga cagggagagt ttcgggccct gaacgccaga    540

ctgcccctga ataccgacgc ctatctgagc ctgcaggagc tgcagggaca ggaccccaca    600

cacctggtgg gatccggagc caccaacttc tccctgctga agcaggccgg cgatgtggag    660

gagaatccag gccccatggc tctgcccgtc accgcactgc tgctgcccct ggctctgctg    720

ctgcacgccg caagacccga ggtccagctg ctggaatctg gggagagact ggtgcagcct    780

ggaggcagcc tgagactgtc ctgcgcagca tctggcttca ccttcagctc ctacgccatg    840

aactgggtga ggcaggcacc aggcaaggga ctggagtggg tgtctgccat ctccgactct    900

ggcggcagca cctactatgc cgattccgtg aagggccgct tcacaatcag ccgggataac    960

tccaagaata ccctgtacct gcagatgaat tccctgagag ccgaggatac agccgtgtac   1020

tattgcgcca ggtattggcc catggacatc tggggccagg gcacactggt gaccgtgtct   1080

tccggaggag gaggctccgg aggaggaggc tctggcggcg gcggcagcga gatcgtgctg   1140
```

acacagtctc ctggcaccct gagcctgtcc ccaggagaga gagccaccct gagctgtagg 1200
gcctctcaga gcgtgtcctc tagctacctg gcctggtatc agcagaagcc cggccaggcc 1260
cctagactgc tgatgtacga cgccagcatc agggcaacag gcatccctga tcggttctcc 1320
ggctctggca gcggaaccga ctttacactg accatcagca ggctggagcc cgaggacttc 1380
gccgtgtact attgccagca gtatggctcc tggcctctga catttggcca gggcaccaag 1440
gtggagatca agggctccgg cggcggaggc tcttgcccat acagcaaccc atccctgtgc 1500
tctggaggag gaggctcctg tccttatagc aatcctagcc tgtgctccgg cggaggaggc 1560
tctaccacaa ccccagcacc aaggccacct acacctgcac caaccatcgc ctctcagcca 1620
ctgagcctga gacccgaggc ctgtaggcct gcagcaggag gagcagtgca cacccgggga 1680
ctggactttg cctgcgatat ctacatctgg gcaccactgg caggaacatg tggcgtgctg 1740
ctgctgagcc tggtcatcac cctgtactgc aagagaggca ggaagaagct gctgtatatc 1800
ttcaagcagc cctttatgcg ccctgtgcag acaacccagg aggaggatgg ctgctcctgt 1860
cggttcccag aggaggagga gggaggatgt gagctgcgcg tgaagttttc ccggtctgcc 1920
gacgcaccag cataccagca gggccagaac cagctgtata acgagctgaa tctgggccgg 1980
agagaggagt acgacgtgct ggataagagg aggggaagag atcccgagat gggaggcaag 2040
ccacggagaa agaaccccca ggagggcctg tacaatgagc tgcagaagga taagatggcc 2100
gaggcctata gcgagatcgg catgaaggga gagaggcgcc ggggcaaggg acacgacggc 2160
ctgtatcagg gcctgtccac cgctaccaaa gacacctatg atgctctgca catgcaggct 2220
ctgccaccaa gatga 2235

<210> SEQ ID NO 179
<211> LENGTH: 744
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 179

Met Ala Leu Pro Val Thr Ala Leu Leu Leu Pro Leu Ala Leu Leu Leu
1 5 10 15

His Ala Ala Arg Pro Ser Asp Pro Thr Arg Val Glu Thr Ala Thr Glu
20 25 30

Thr Ala Trp Ile Ser Leu Val Thr Ala Leu Leu Leu Val Leu Gly Leu
35 40 45

Asn Ala Val Leu Gly Leu Leu Leu Leu Arg Lys Gln Phe Pro Ala His
50 55 60

Tyr Arg Arg Leu Arg His Ala Leu Trp Pro Ser Leu Pro Asp Leu His
65 70 75 80

Arg Val Leu Gly Gln Tyr Leu Arg Asp Thr Ala Ala Leu Ser Pro Pro
85 90 95

Lys Ala Thr Val Ser Asp Thr Cys Glu Glu Val Glu Pro Ser Leu Leu
100 105 110

Glu Ile Leu Pro Lys Ser Ser Glu Arg Thr Pro Leu Pro Leu Leu Glu
115 120 125

Asp Glu Gly Val Ala Gly Ala Pro Thr Gly Ser Ser Pro Gln Pro Leu
130 135 140

Gln Pro Leu Ser Gly Glu Asp Asp Ala Tyr Cys Thr Phe Pro Ser Arg
145 150 155 160

```
Asp Asp Leu Leu Leu Phe Ser Pro Ser Gly Gln Gly Glu Phe Arg Ala
                165                 170                 175

Leu Asn Ala Arg Leu Pro Leu Asn Thr Asp Ala Tyr Leu Ser Leu Gln
            180                 185                 190

Glu Leu Gln Gly Gln Asp Pro Thr His Leu Val Gly Ser Gly Ala Thr
        195                 200                 205

Asn Phe Ser Leu Leu Lys Gln Ala Gly Asp Val Glu Glu Asn Pro Gly
    210                 215                 220

Pro Met Ala Leu Pro Val Thr Ala Leu Leu Leu Pro Leu Ala Leu Leu
225                 230                 235                 240

Leu His Ala Ala Arg Pro Glu Val Gln Leu Leu Glu Ser Gly Gly Gly
                245                 250                 255

Leu Val Gln Pro Gly Gly Ser Leu Arg Leu Ser Cys Ala Ala Ser Gly
            260                 265                 270

Phe Thr Phe Ser Ser Tyr Ala Met Asn Trp Val Arg Gln Ala Pro Gly
        275                 280                 285

Lys Gly Leu Glu Trp Val Ser Ala Ile Ser Asp Ser Gly Gly Ser Thr
    290                 295                 300

Tyr Tyr Ala Asp Ser Val Lys Gly Arg Phe Thr Ile Ser Arg Asp Asn
305                 310                 315                 320

Ser Lys Asn Thr Leu Tyr Leu Gln Met Asn Ser Leu Arg Ala Glu Asp
                325                 330                 335

Thr Ala Val Tyr Tyr Cys Ala Arg Tyr Trp Pro Met Asp Ile Trp Gly
            340                 345                 350

Gln Gly Thr Leu Val Thr Val Ser Ser Gly Gly Gly Gly Ser Gly Gly
        355                 360                 365

Gly Gly Ser Gly Gly Gly Gly Ser Glu Ile Val Leu Thr Gln Ser Pro
    370                 375                 380

Gly Thr Leu Ser Leu Ser Pro Gly Glu Arg Ala Thr Leu Ser Cys Arg
385                 390                 395                 400

Ala Ser Gln Ser Val Ser Ser Ser Tyr Leu Ala Trp Tyr Gln Gln Lys
                405                 410                 415

Pro Gly Gln Ala Pro Arg Leu Leu Met Tyr Asp Ala Ser Ile Arg Ala
            420                 425                 430

Thr Gly Ile Pro Asp Arg Phe Ser Gly Ser Gly Ser Gly Thr Asp Phe
        435                 440                 445

Thr Leu Thr Ile Ser Arg Leu Glu Pro Glu Asp Phe Ala Val Tyr Tyr
    450                 455                 460

Cys Gln Gln Tyr Gly Ser Trp Pro Leu Thr Phe Gly Gln Gly Thr Lys
465                 470                 475                 480

Val Glu Ile Lys Gly Ser Gly Gly Gly Gly Ser Cys Pro Tyr Ser Asn
                485                 490                 495

Pro Ser Leu Cys Ser Gly Gly Gly Gly Ser Cys Pro Tyr Ser Asn Pro
            500                 505                 510

Ser Leu Cys Ser Gly Gly Gly Gly Ser Thr Thr Thr Pro Ala Pro Arg
        515                 520                 525

Pro Pro Thr Pro Ala Pro Thr Ile Ala Ser Gln Pro Leu Ser Leu Arg
    530                 535                 540

Pro Glu Ala Cys Arg Pro Ala Ala Gly Gly Ala Val His Thr Arg Gly
545                 550                 555                 560

Leu Asp Phe Ala Cys Asp Ile Tyr Ile Trp Ala Pro Leu Ala Gly Thr
                565                 570                 575
```

Cys Gly Val Leu Leu Leu Ser Leu Val Ile Thr Leu Tyr Cys Lys Arg
580 585 590

Gly Arg Lys Lys Leu Leu Tyr Ile Phe Lys Gln Pro Phe Met Arg Pro
595 600 605

Val Gln Thr Thr Gln Glu Glu Asp Gly Cys Ser Cys Arg Phe Pro Glu
610 615 620

Glu Glu Glu Gly Gly Cys Glu Leu Arg Val Lys Phe Ser Arg Ser Ala
625 630 635 640

Asp Ala Pro Ala Tyr Gln Gln Gly Gln Asn Gln Leu Tyr Asn Glu Leu
645 650 655

Asn Leu Gly Arg Arg Glu Glu Tyr Asp Val Leu Asp Lys Arg Arg Gly
660 665 670

Arg Asp Pro Glu Met Gly Gly Lys Pro Arg Arg Lys Asn Pro Gln Glu
675 680 685

Gly Leu Tyr Asn Glu Leu Gln Lys Asp Lys Met Ala Glu Ala Tyr Ser
690 695 700

Glu Ile Gly Met Lys Gly Glu Arg Arg Arg Gly Lys Gly His Asp Gly
705 710 715 720

Leu Tyr Gln Gly Leu Ser Thr Ala Thr Lys Asp Thr Tyr Asp Ala Leu
725 730 735

His Met Gln Ala Leu Pro Pro Arg
740

<210> SEQ ID NO 180
<211> LENGTH: 180
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 180

Ser Asp Pro Thr Arg Val Glu Thr Ala Thr Glu Thr Ala Trp Ile Ser
1 5 10 15

Leu Val Thr Ala Leu His Leu Val Leu Gly Leu Asn Ala Val Leu Gly
20 25 30

Leu Leu Leu Leu Arg Lys Gln Phe Pro Ala His Tyr Arg Arg Leu Arg
35 40 45

His Ala Leu Trp Pro Ser Leu Pro Asp Leu His Arg Val Leu Gly Gln
50 55 60

Tyr Leu Arg Asp Thr Ala Ala Leu Ser Pro Pro Lys Ala Thr Val Ser
65 70 75 80

Asp Thr Cys Glu Glu Val Glu Pro Ser Leu Leu Glu Ile Leu Pro Lys
85 90 95

Ser Ser Glu Arg Thr Pro Leu Pro Leu Asp Glu Gly Val Ala Gly Ala
100 105 110

Pro Thr Gly Ser Ser Pro Gln Pro Leu Gln Pro Leu Ser Gly Glu Asp
115 120 125

Asp Ala Tyr Cys Thr Phe Pro Ser Arg Asp Asp Leu Leu Leu Phe Ser
130 135 140

Pro Ser Gly Gln Gly Glu Phe Arg Ala Leu Asn Ala Arg Leu Pro Leu
145 150 155 160

Asn Thr Asp Ala Tyr Leu Ser Leu Gln Glu Leu Gln Gly Gln Asp Pro
165 170 175

Thr His Leu Val
180

<210> SEQ ID NO 181
<211> LENGTH: 221
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 181

```
Ser Asp Pro Thr Arg Val Glu Thr Ala Thr Glu Thr Ala Trp Ile Ser
1               5                   10                  15

Leu Val Thr Ala Leu Leu Leu Val Leu Gly Leu Asn Ala Val Leu Gly
            20                  25                  30

Leu Leu Leu Leu Arg Lys Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Gln Gln Asp Lys Val Pro Glu
            100                 105                 110

Pro Ala Ser Leu Ser Ser Asn His Ser Leu Thr Ser Cys Phe Thr Asn
        115                 120                 125

Gln Gly Tyr Phe Phe Phe His Leu Pro Asp Ala Leu Glu Ile Glu Ala
    130                 135                 140

Cys Gln Asp Glu Gly Val Ala Gly Ala Pro Thr Gly Ser Ser Pro Gln
145                 150                 155                 160

Pro Leu Gln Pro Leu Ser Gly Glu Asp Asp Ala Tyr Cys Thr Phe Pro
                165                 170                 175

Ser Arg Asp Asp Leu Leu Leu Phe Ser Pro Ser Gly Gln Gly Glu Phe
            180                 185                 190

Arg Ala Leu Asn Ala Arg Leu Pro Leu Asn Thr Asp Ala Tyr Leu Ser
        195                 200                 205

Leu Gln Glu Leu Gln Gly Gln Asp Pro Thr His Leu Val
    210                 215                 220
```

<210> SEQ ID NO 182
<211> LENGTH: 180
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 182

```
Ser Asp Pro Thr Arg Val Glu Thr Ala Thr Glu Thr Ala Trp Ile Ser
1               5                   10                  15

Leu Val Thr Ala Leu Leu Leu Val Leu Gly Leu Asn Ala Val Leu Gly
            20                  25                  30

Leu Leu Leu Leu Arg Lys Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80
```

```
Asp Thr Cys Glu Glu Val Glu Pro Ser Leu Leu Glu Ile Leu Pro Lys
                85                  90                  95

Ser Ser Glu Arg Thr Pro Leu Pro Leu Asp Glu Gly Val Ala Gly Ala
            100                 105                 110

Pro Thr Gly Ser Ser Pro Gln Pro Leu Gln Pro Leu Ser Gly Glu Asp
        115                 120                 125

Asp Ala Tyr Cys Thr Phe Pro Ser Arg Asp Asp Leu Leu Leu Phe Ser
    130                 135                 140

Pro Ser Gly Gln Gly Glu Phe Arg Ala Leu Asn Ala Arg Leu Pro Leu
145                 150                 155                 160

Asn Thr Asp Ala Tyr Leu Ser Leu Gln Glu Leu Gln Gly Gln Asp Pro
                165                 170                 175

Thr His Leu Val
            180


<210> SEQ ID NO 183
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Cys Pro Tyr Ser Asn Pro Ser Leu Cys
1               5


<210> SEQ ID NO 184
<211> LENGTH: 203
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

Ser Asp Pro Thr Arg Val Glu Thr Ala Thr Glu Thr Ala Trp Ile Ser
1               5                   10                  15

Leu Val Thr Ala Leu His Leu Val Leu Gly Leu Asn Ala Val Leu Gly
            20                  25                  30

Leu Leu Leu Leu Arg Lys Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Leu Glu Asp Glu Gly Val Ala
            100                 105                 110

Gly Ala Pro Thr Gly Ser Ser Pro Gln Pro Leu Gln Pro Leu Ser Gly
        115                 120                 125

Glu Asp Asp Ala Tyr Cys Thr Phe Pro Ser Arg Asp Asp Leu Leu Leu
    130                 135                 140

Phe Ser Pro Ser Gly Gln Gly Glu Phe Arg Ala Leu Asn Ala Arg Leu
145                 150                 155                 160

Pro Leu Asn Thr Asp Ala Tyr Leu Ser Leu Gln Glu Leu Gln Gly Gln
                165                 170                 175
```

```
Asp Pro Thr His Leu Val Gly Ser Gly Ala Thr Asn Phe Ser Leu Leu
            180                 185                 190

Lys Gln Ala Gly Asp Val Glu Glu Asn Pro Gly
        195                 200


<210> SEQ ID NO 185
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Ser Asp Pro Thr Arg Val Glu Thr Ala Thr Glu Thr Ala Trp Ile Ser
1               5                   10                  15

Leu Val Thr Ala Leu Leu Leu Val Leu Gly Leu Asn Ala Val Leu Gly
            20                  25                  30

Leu Leu Leu Leu Arg Lys Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Leu Glu Gln Gln Asp Lys Val
            100                 105                 110

Pro Glu Pro Ala Ser Leu Ser Ser Asn His Ser Leu Thr Ser Cys Phe
        115                 120                 125

Thr Asn Gln Gly Tyr Phe Phe Phe His Leu Pro Asp Ala Leu Glu Ile
    130                 135                 140

Glu Ala Cys Gln Asp Glu Gly Val Ala Gly Ala Pro Thr Gly Ser Ser
145                 150                 155                 160

Pro Gln Pro Leu Gln Pro Leu Ser Gly Glu Asp Asp Ala Tyr Cys Thr
                165                 170                 175

Phe Pro Ser Arg Asp Asp Leu Leu Leu Phe Ser Pro Ser Gly Gln Gly
            180                 185                 190

Glu Phe Arg Ala Leu Asn Ala Arg Leu Pro Leu Asn Thr Asp Ala Tyr
        195                 200                 205

Leu Ser Leu Gln Glu Leu Gln Gly Gln Asp Pro Thr His Leu Val Gly
    210                 215                 220

Ser Gly Ala Thr Asn Phe Ser Leu Leu Lys Gln Ala Gly Asp Val Glu
225                 230                 235                 240

Glu Asn Pro Gly


<210> SEQ ID NO 186
<211> LENGTH: 203
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Ser Asp Pro Thr Arg Val Glu Thr Ala Thr Glu Thr Ala Trp Ile Ser
1               5                   10                  15
```

-continued

```
Leu Val Thr Ala Leu Leu Leu Val Leu Gly Leu Asn Ala Val Leu Gly
            20                  25                  30

Leu Leu Leu Leu Arg Lys Gln Phe Pro Ala His Tyr Arg Arg Leu Arg
        35                  40                  45

His Ala Leu Trp Pro Ser Leu Pro Asp Leu His Arg Val Leu Gly Gln
    50                  55                  60

Tyr Leu Arg Asp Thr Ala Ala Leu Ser Pro Pro Lys Ala Thr Val Ser
65                  70                  75                  80

Asp Thr Cys Glu Glu Val Glu Pro Ser Leu Leu Glu Ile Leu Pro Lys
                85                  90                  95

Ser Ser Glu Arg Thr Pro Leu Pro Leu Leu Glu Asp Glu Gly Val Ala
            100                 105                 110

Gly Ala Pro Thr Gly Ser Ser Pro Gln Pro Leu Gln Pro Leu Ser Gly
        115                 120                 125

Glu Asp Asp Ala Tyr Cys Thr Phe Pro Ser Arg Asp Asp Leu Leu Leu
    130                 135                 140

Phe Ser Pro Ser Gly Gln Gly Glu Phe Arg Ala Leu Asn Ala Arg Leu
145                 150                 155                 160

Pro Leu Asn Thr Asp Ala Tyr Leu Ser Leu Gln Glu Leu Gln Gly Gln
                165                 170                 175

Asp Pro Thr His Leu Val Gly Ser Gly Ala Thr Asn Phe Ser Leu Leu
            180                 185                 190

Lys Gln Ala Gly Asp Val Glu Glu Asn Pro Gly
        195                 200
```

<210> SEQ ID NO 187
<211> LENGTH: 1189
<212> TYPE: DNA
<213> ORGANISM: Homo sapiens

<400> SEQUENCE: 187

```
gcgtgaggct ccggtgcccg tcagtgggca gagcgcacat cgcccacagt ccccgagaag     60

ttgggggggag gggtcggcaa ttgaaccggt gcctagagaa ggtggcgcgg ggtaaactgg    120

gaaagtgatg tcgtgtactg gctccgcctt tttcccgagg gtgggggaga accgtatata    180

agtgcagtag tcgccgtgaa cgttcttttt cgcaacgggt ttgccgccag aacacaggta    240

agtgccgtgt gtggttcccg cgggcctggc ctctttacgg gttatggccc ttgcgtgcct    300

tgaattactt ccacgcccct ggctgcagta cgtgattctt gatcccgagc ttcgggttgg    360

aagtgggtgg gagagttcga ggccttgcgc ttaaggagcc ccttcgcctc gtgcttgagt    420

tgaggcctgg cctgggcgct ggggccgccg cgtgcgaatc tggtggcacc ttcgcgcctg    480

tctcgctgct ttcgataagt ctctagccat ttaaaatttt tgatgacctg ctgcgacgct    540

tttttctgg caagatagtc ttgtaaatgc gggccaagat ctgcacactg gtatttcggt    600

ttttggggcc gcgggcggcg acggggcccg tgcgtcccag cgcacatgtt cggcgaggcg    660

gggcctgcga gcgcggccac cgagaatcgg acgggggtag tctcaagctg gccggcctgc    720

tctggtgcct ggcctcgcgc cgccgtgtat cgccccgccc tgggcggcaa ggctggcccg    780

gtcggcacca gttgcgtgag cggaaagatg gccgcttccc ggccctgctg cagggagctc    840

aaaatggagg acgcggcgct cgggagagcg ggcgggtgag tcacccacac aaaggaaaag    900

ggcctttccg tcctcagccg tcgcttcatg tgactccacg gagtaccggg cgccgtccag    960

gcacctcgat tagttctcga gcttttggag tacgtcgtct ttaggttggg gggaggggtt   1020

ttatgcgatg gagtttcccc acactgagtg ggtggagact gaagttaggc cagcttggca   1080
```

-continued

```
cttgatgtaa ttctccttgg aatttgccct ttttgagttt ggatcttggt tcattctcaa   1140

gcctcagaca gtggttcaaa gttttttct tccatttcag gtgtcgtga                1189


<210> SEQ ID NO 188
<211> LENGTH: 237
<212> TYPE: DNA
<213> ORGANISM: Homo sapiens

<400> SEQUENCE: 188

gcgtgaggct ccggtgcccg tcagtgggca gagcgcacat cgcccacagt ccccgagaag     60

ttggggggag gggtcggcaa ttgaaccggt gcctagagaa ggtggcgcgg ggtaaactgg    120

gaaagtgatg tcgtgtactg gctccgcctt tttcccgagg gtgggggaga accgtatata    180

agtgcagtag tcgccgtgaa cgttcttttt cgcaacgggt ttgccgccag aacacag       237
```

BCMA CAR-T CELLS WITH ENHANCED ACTIVITIES

CROSS REFERENCE TO RELATED APPLICATIONS

The present application claims the benefit of priority to U.S. Provisional Application No. 62/980,914, filed on Feb. 24, 2020; U.S. Provisional Application No. 63/020,713, filed on May 6, 2020; U.S. Provisional Application No. 63/053,409, filed on Jul. 17, 2020; and U.S. Provisional Application No. 63/092,681, filed on Oct. 16, 2020, the contents of all of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Feb. 22, 2021, is named AT-034-05_SL.txt and is 308,283 bytes in size.

FIELD

The instant disclosure relates to CAR-T cells, especially BCMA specific CAR-T cells with enhanced activities, and methods of making and uses thereof.

BACKGROUND

Adoptive transfer of immune cells (e.g. T cells) genetically modified to recognize malignancy-associated antigens is showing promise as a new approach to treating cancer. For example, T cells can be genetically modified to express chimeric antigen receptors (CARs), which are fusion proteins comprised of an antigen recognition moiety and T cell activation domains.

One CAR-T cell that would be useful is one that recognizes B cell maturation antigen (BCMA, CD269, or TNFRSF17). BCMA is a member of the tumor necrosis factor receptor (TNFR) superfamily and is involved in pro-survival signaling. BCMA was identified in a malignant human T cell lymphoma containing a t(4; 16) translocation. BCMA is expressed at high levels on normal and malignant plasma cells at all stages of multiple myeloma (MM) and some other plasma cell malignancies (e.g., diffused large B-cell lymphoma, DLBCL). BCMA is also expressed on most or all myeloma cells, and expression is absent from non-B cell lineages. Exemplary BCMA CARs are disclosed and described in U.S. Pat. No. 10,294,304, the entirety of which is hereby incorporated by reference herein. BCMA CAR-T cells may be useful in treating a variety of diseases, including multiple myeloma (MM), a malignancy characterized by an accumulation of clonal plasma cells. MM largely remains incurable, and most subjects develop resistance over time.

T cell proliferation, cytotoxic potency and persistence is driven by signal transduction pathways. Conventional CAR designs provide two signals—CD3zeta activation (Signal 1) and co-stimulation (Signal 2, e.g. via 4-1BB, OX40, and/or CD28 expression). In some contexts, a third signal (Signal 3), cytokine-induced cytokine receptor signaling (e.g. cytokine support for immune potentiation), may be desirable. Approaches to provide Signal 3 have however been met with significant limitations.

In general, one approach to provide cytokine support includes combining CAR-T cell therapy with systemic infusions of recombinant cytokines/cytokine mimetics, and engineering CAR-T cells to secrete/express cytokines extracellularly. As cytokines have pleiotropic effects and can also impact the function of other cell types, the systemic administration or production of immune-potentiating cytokines by CAR-T cells have at least two major drawbacks: (i) these approaches can cause systemic toxicity in humans, and (ii) in the context of allogeneic CAR-T cell therapy, these approaches may cause bystander host immune-activation that could accelerate the rejection of allogeneic CAR-T cells, thereby compromising therapeutic efficacy. Another approach to provide cytokine support was based on introducing a constitutively activated dimerized cytokine receptor, an IL-7Ra—this limits the nature (IL-7 signaling only) and magnitude of signaling output. Yet another approach to provide cytokine support involved incorporating Signal 3 directly into the CAR molecule (Nat Med. 2018 March; 24(3):352-359). A limitation of this approach is that the strength of Signal 3 depends on the strength of CAR activation. In the absence of target (and CAR activation), Signal 3 would not be transduced.

Needed are solutions to circumvent these drawbacks by targeting cytokine signals specifically to BCMA CAR-T cells in a tunable way, thus allowing for an improved safety profile and therapeutic efficacy.

SUMMARY

The present disclosure provides BCMA CAR immune cells, such as BCMA CAR-T cells, that contain constitutively active chimeric cytokine receptors (CACCRs). When present on BCMA chimeric antigen receptor (CAR)-bearing immune cells (CAR-I cells, e.g. BCMA CAR-T cells), such CACCRs allow for increased immune cell activation, proliferation, persistence, and/or potency. The enhanced activities of BCMA CAR-T cells are dependent on the presence of the target BCMA. Also provided are methods of making and using the CACCRs described herein in BCMA CAR immune cells, such as BCMA CAR-T cells.

Accordingly, in one aspect, provided herein is a BCMA CAR-I cell, e.g. a BCMA CAR-T cell that contains a CACCR composed of two monomers, each monomer comprising: (a) a transmembrane domain; (b) a Janus Kinase (JAK)-binding domain; and (c) a recruiting domain, wherein the monomers are constitutively dimerized.

In some embodiments, the CACCR's transmembrane domain and/or JAK-binding domain is derived from the TPOR/MPLR receptor. In some embodiments, the transmembrane domain and/or the JAK binding domain is derived from amino acids 478-582 of the naturally occurring TPOR/MPLR receptor of SEQ ID NO: 6. In some embodiments, the TPOR/MPLR receptor comprises one or more of the amino acid substitutions selected from H499L, S505N, W515K, and G509N. In some embodiments, the TPOR/MPLR receptor comprises the H499L, S505N and W515K substitutions, or the S505N and W515K substitutions.

In some embodiments, the recruiting domain is a STAT-recruiting domain. In some embodiments, the recruiting domain comprises the STAT-recruiting domain from IL7Ra, for example, IL7Ra(316-459). In some embodiments, the recruiting domain comprises the STAT-recruiting domain from IL2Rb, for example, IL2Rb (333-551), IL2Rb(393-433, 518-551), IL2Rb(339-379, 393-433, 518-551), IL2Rb (333-551, Y381S, Y384S, Y387S), or IL2Rb(333-551, Y364S, Y381S, Y384S, Y387S). In some embodiments, the recruiting domain comprises the STAT-recruiting domain from IL12Rb1, for example, IL12Rb1(622-662). In some embodiments, the recruiting domain comprises the STAT-recruiting domain from IL12Rb2, for example, IL12Rb2 (714-862) or IL12Rb2(775-825). In some embodiments, the recruiting domain comprises the STAT-recruiting domain from IL21R, for example, IL21R(322-538).

In a related aspect provided herein is a polynucleotide encoding any one of the CACCRs of the disclosure, and an expression vector comprising such polynucleotide. In some embodiments, the polynucleotide further encodes for a chimeric antigen receptor (CAR), wherein the CAR binds to BCMA (a "BCMA CAR" or a "BCMA specific CAR") (e.g., human BCMA, Uniprot accession number: Q02223-2).

In another aspect, provided herein is an engineered immune cell comprising at least one BCMA chimeric antigen receptor and at least one CACCR of the disclosure. In some embodiments the immune cell is a T cell. In some embodiments the immune cell is an allogeneic immune cell. In other embodiments, the immune cell is an autologous immune cell. The immune cell may be selected from the group consisting of: T cell, dendritic cell, killer dendritic cell, mast cell, NK-cell, macrophage, monocyte, B-cell and an immune cell derived from a stem cell. In a related aspect, provided herein is a pharmaceutical composition comprising any of the engineered immune cells of the disclosure, and a kit comprising such a pharmaceutical composition. In a related aspect, the engineered immune cell comprises one or more polynucleotides that encode a BCMA CAR and a CACCR of the disclosure. In a related aspect, the engineered immune cell comprises a bicistronic or multicistronic polynucleotide that encodes a BCMA CAR and one or more than one CACCR of the disclosure.

In another aspect, provided herein is a method of treating a cancer in a subject, comprising administering to the subject a therapeutically effective amount of any of the engineered immune cells described herein.

In another aspect, a method of making an engineered immune cell is provided comprising providing a cell, for example, an immune cell, a T cell, dendritic cell, killer dendritic cell, mast cell, NK-cell, macrophage, monocyte, B-cell and an immune cell derived from a stem cell, and introducing into the cell at least one polynucleotide that encodes a BCMA CAR and at least one polynucleotide that encodes a CACCR of the disclosure. In some embodiments, the cell is introduced with one or more polynucleotide molecules that encode a BCMA CAR and a CACCR. In some embodiments, a first vector comprises a BCMA CAR polynucleotide and a second vector comprises a CACCR polynucleotide. In some embodiments, one vector comprises both a BCMA CAR polynucleotide and a CACCR polynucleotide. In some embodiments, the vector is a viral vector such as a lentiviral vector. In some embodiments, the cell is an autologous cell, which can mean that it is derived from the same person who will be treated with the engineered immune cell prepared from that cell. In other embodiments, the cell is an allogeneic cell, which can mean that it is derived from a person other than the person who will be treated with the engineered immune cell, e.g., from a healthy donor. In some embodiments, the allogeneic engineered immune cell further comprises one or more genetic modifications at the TCR alpha constant (TRAC) locus to reduce or negate the expression of the endogenous TCR alpha receptor. In some embodiments, the engineered immune cell further comprises one or more genetic modifications at the CD52 gene to reduce or negate the expression of CD52. In various embodiments, the BCMA CAR polynucleotide and/or the CACCR polynucleotide, and any vector that may comprise either or both polynucleotides is driven by the EF1 alpha promoter. In some embodiments, at least one of the BCMA CAR polynucleotide, the CACCR polynucleotide, and the vector or vectors that comprise either or both polynucleotides, further encodes at least one selectable marker that facilitates and/or enables the identification of cells that contain the BCMA CAR polynucleotide and/or the CACCR polynucleotide. In various embodiments, the BCMA CAR polynucleotide and/or the CACCR polynucleotide, and any vector that may comprise either or both polynucleotides further comprises a wild type or mutant WPRE. In some embodiments, the vector further comprises a mutant WPRE. In various embodiments, the BCMA CAR polynucleotide and/or the CACCR polynucleotide, and any vector that may comprise either or both polynucleotides, may be introduced into the cell by methods known in the art, including but not limited to various methods of electroporation, transfection and viral transduction. In some embodiments, a patient in need of treatment with the engineered cell is a person who has a disease or condition that can be treated with the engineered cell or who might benefit from treatment with the engineered cell. In some embodiments, the condition is multiple myeloma. In some embodiments, the disease or condition is relapsed/refractory multiple myeloma. In some embodiments, the disease is relapsed multiple myeloma. In some embodiments, the disease is a plasma cell malignancy, for example, diffused large B-cell lymphoma (DLBCL). In certain embodiments, the patient who has received the engineered immune cells is administered an effective amount of rituximab or dasatinib to reduce or eliminate the engineered immune cells.

BRIEF DESCRIPTION OF THE DRAWINGS

FIG. 2B and FIG. 2C each shows a vector that expresses from a promoter a CD8 signal sequence, a CACCR, a P2A peptide, a CD8 signal sequence, and a BCMA-CAR, with or without a mutant WPRE (Woodchuck hepatitis virus Posttranscriptional Regulatory Element), the CACCR depicted comprising TpoR(478-582; H499L; S505N; W515K) and IL2Rb (339-379,393-433, 518-551). The schematic displays a BCMA CAR containing the scFv of clone P5A2, with two copies of rituximab mimotopes (R2), 41BB and CD3 zeta. FIG. 2D shows a vector that expresses from a promoter a CD8 signal sequence, a CACCR, a P2A peptide, a CD8 signal sequence, a BCMA CAR, and a mutant WPRE, the CACCR comprising TpoR (478-582; H499L; S505N; W515K) and IL2Rb (393-433, 518-551).

FIGS. 22A-22B show lack of expansion of CACCR-BCMA CART cells in the absence of target or exogenous cytokine IL-15 (FIG. 22A) or IL-2 (FIG. 22B). FIG. 22C shows results of Ki-67 staining of CAR T cell culture in the absence of target, while FIG. 22D shows that the CAR T cells were able to expand in the presence of irradiated target cells (iTarget) and IL2. The data presented are mean±SD from three donors.

DETAILED DESCRIPTION

Figure 1:
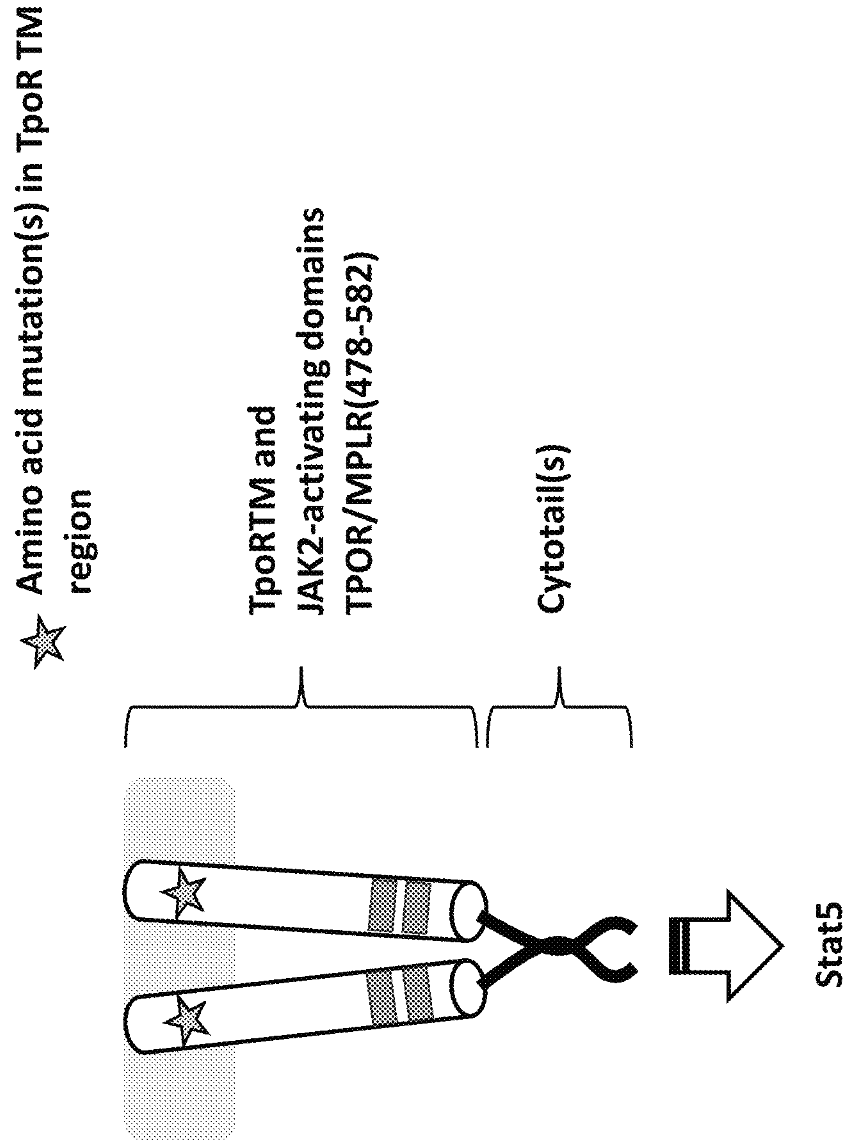
FIG. 1 shows a schematic of an exemplary engineered CACCR of the disclosure.

The present disclosure provides the combination of a BCMA CAR and constitutively active chimeric cytokine receptors (CACCRs). The BCMA CARs and CACCRs disclosed herein are polypeptides that each comprises domains of different proteins and amino acid sequences, as further detailed herein. The presence of a constitutively active, tunable chimeric cytokine receptor allows for the immune potentiation of Signal 3 to meet the need for immune potentiation. Accordingly, when present on BCMA chimeric antigen receptor (CAR)-bearing immune cells (CAR-I cells, e.g. CAR-T cells) as disclosed herein, such CACCRs allow for increased immune cell activation, proliferation, persistence, and/or potency. Also provided herein are methods of making and using the CACCRs described herein in combination with BCMA specific CARs.

The CACCRs for use as disclosed herein are tunable, and have flexible cytokine signaling outputs for the enhancement of BCMA CAR-T cell activity, persistence, and the like. The components, methods of making and use are described in turn below.

I. Constitutively Active Chimeric Cytokine Receptors (CACCRs)

The CACCRs of the disclosure are composed of two monomers, each monomer comprising: (a) a transmembrane domain; (b) a JAK-binding domain; and (c) a recruiting domain, wherein the monomers are constitutively dimerized. In some embodiments, the CACCR of the disclosure does not comprise an extracellular ligand-binding domain.

In some embodiments, the monomers are identical, giving rise to a constitutively active homodimer. In such embodiments, the number of proteins that need to be expressed in a vector are reduced. In some embodiments, the monomers are not identical, giving rise to a constitutively active heterodimer, which may be desirable under certain circumstances.

The monomers of the CACCRs of the disclosure are capable of spontaneously dimerizing, and can activate signaling in the absence of any exogenous stimulation or ligand (ligand-independent dimerization). The level of activity can be controlled by mutations introduced into the transmembrane domain of the CACCRs. A skilled artisan will appreciate that the monomers of the CACCRs are not dimerized 100% of the time, and may exist as a monomer.

A. Transmembrane Domains

The CACCRs of the disclosure comprise transmembrane domains. The transmembrane domains of the disclosure contain sequences such that they allow for constitutive dimerization of two monomers, thus allowing constitutive JAK activation on the intracellular portion, and constitutive recruitment and phosphorylation of, for example, STAT on the cytoplasmic region of the receptor.

The transmembrane domains are on the N-terminus and are coupled to intracellular/cytoplasmic domains on the C-terminus. In some embodiments, the coupling is achieved optionally through a linker.

As used herein, the transmembrane domains are capable of insertion into the membrane of a cell in which it is expressed. In some embodiments, the CACCR transmembrane domains of the disclosure span a cellular membrane, and comprise an extracellular portion, and/or an intracellular portion. In some embodiments, the CACCR transmembrane domains of the disclosure span a cellular membrane, comprise an intracellular portion, and do not comprise an extracellular ligand binding portion.

In some embodiments, the transmembrane domains of the disclosure are engineered (synthetic) and do not resemble any naturally occurring transmembrane domain, e.g. they are non-naturally occurring.

In other embodiments, the transmembrane domains of the disclosure are derived from naturally occurring receptors.

In some embodiments, the transmembrane domains and/or JAK-activating domains of the disclosure are derived from, for example, one or more of the following receptors: erythropoietin receptor (EpoR), Interleukin 6 signal transducer (GP130 or IL6ST), prolactin receptor (PrlR), growth hormone receptor (GHR), granulocyte colony-stimulating factor receptor (GCSFR), and thrombopoietin receptor/myeloproliferative leukemia protein receptor (TPOR/MPLR). When derived from naturally occurring receptors, the entire receptor, or the entire transmembrane sequence of the receptor may not be necessary to effectuate constitutive activation and constitutive JAK binding/activation on the intracellular portion. Accordingly fragments of naturally occurring receptors may be utilized. Furthermore, certain mutations may be introduced into the transmembrane domains derived from naturally occurring receptors, to further tune the downstream signaling.

In some embodiments, the transmembrane domain and/or JAK-activating domain of the disclosure is derived from the naturally occurring EpoR receptor.

In some embodiments, the transmembrane domain and/or JAK-activating domain of the disclosure is derived from the naturally occurring GP130 receptor.

In some embodiments, the transmembrane domain and/or JAK-activating domain of the disclosure is derived from the naturally occurring PrlR receptor.

In some embodiments, the transmembrane domain and/or JAK-activating domain of the disclosure is derived from the naturally occurring GHR receptor.

In some embodiments, the transmembrane domain and/or JAK-activating domain of the disclosure is derived from the naturally occurring GCSF receptor.

In some embodiments, the transmembrane domain and/or JAK-activating domain of the disclosure is derived from the naturally occurring TPOR receptor.

Table 1a provides exemplary full-length sequences of naturally occurring receptors provided in the disclosure, from which the transmembrane proteins are derived. The sequences provided in Table 1a are reference sequences, in relation to which later mutations are expressed, for example in Tables 1b and 1c.

TABLE 1a

Exemplary Naturally Occurring Receptors

| Naturally Occurring Receptor Name | SEQ ID NO: |
|---|---|
| >AAI12154.1 Erythropoietin receptor [*Homo sapiens*]<br>MDHLGASLWPQVGSLCLLLAGAAWAPPPNLPDPKFESKAALLAARGPEELLCFT<br>ERLEDLVCFWEEAASAGVGPGNYSFSYQLEDEPWKLCRLHQAPTARGAVRFWC<br>SLPTADTSSFVPLELRVTAASGAPRYHRVIHINEVVLLDAPVGLVARLADESGHV<br>VLRWLPPPETPMTSHIRYEVDVSAGNGAGSVQRVEILEGRTECVLSNLRGRTRYT<br>FAVRARMAEPSFGGFWSAWSEPVSLLTPSDLDPLILTLSLILVVILVLLTVLALLSH<br>RRALKQKIWPGIPSPESEFEGLFTTHKGNFQLWLYQNDGCLWWSPCTPFTEDPPA<br>SLEVLSERCWGTMQAVEPGTDDEGPLLEPVGSEHAQDTYLVLDKWLLPRNPPSE<br>DLPGPGGSVDIVAMDEGSEASSCSSALASKPSPEGASAASFEYTILDPSSQLLRPW<br>TLCPELPPTPPHLKYLYLVVSDSGISTDYSSGDSQGAQGGLSDGPYSNPYENSLIP<br>AAEPLPPSYVACS | 1 |
| >AAI17403.1 Interleukin 6 signal transducer (GP130, oncostatin M receptor) [*Homo sapiens*]<br>MLTLQTWLVQALFIFLTTESTGELLDPCGYISPESPVVQLHSNFTAVCVLKEKCM<br>DYFHVNANYIVWKTNHFTIPKEQYTIINRTASSVTFTDIASLNIQLTCNILTFGQLE<br>QNVYGITIISGLPPEKPKNLSCIVNEGKKMRCEWDRGRETHLETNFTLKSEWATH<br>KFADCKAKRDTPTSCTVDYSTVYFVNIEVWVEAENALGKVTSDHINFDPVYKVK<br>PNPPHNLSVINSEELSSILKLTWTNPSIKSVIILKYNIQYRTKDASTWSQIPPEDTAS<br>TRSSFTVQDLKPFTEYVFRIRCMKEDGKGYWSDWSEEASGITYEDRPSKAPSFWY<br>KIDPSHTQGYRTVQLVWKTLPPFEANGKILDYEVTLTRWKSHLQNYTVNATKLT<br>VNLTNDRYVATLTVRNLVGKSDAAVLTIPACDFQATHPVMDLKAFPKDNMLWV<br>EWTTPRESVKKYILEWCVLSDKAPCITDWQQEDGTVHRTYLRGNLAESKCYLIT<br>VTPVYADGPGSPESIKAYLKQAPPSKGPTVRTKKVGKNEAVLEWDQLPVDVQNG<br>FIRNYTIFYRTIIGNETAVNVDSSHTEYTLSSLTSDTLYMVRMAAYTDEGGKDGPE<br>FTFTTPKFAQGEIEAIVVPVCLAFLLTTLLGVLFCFNKRDLIKKHIWPNVPDPSKSH<br>IAQWSPHTPPRHNFNSKDQMYSDGNFTDVSVVEIEANDKKPFPEDLKSLDLFKKE<br>KINTEGHSSGIGGSSCMSSSRPSISSSDENESSQNTSSTVQYSTVVHSGYRHQVPSV<br>QVFSRSESTQPLLDSEERPEDLQLVDHVDGGDGILPRQQYFKQNCSQHESSPDISH<br>FERSKQVSSVNEEDFVRLKQQISDHISQSCGSGQMKMFQEVSAADAFGPGTEGQ<br>VERFETVGMEAATDEGMPKSYLPQTVRQGGYMPQ | 2 |

TABLE 1a-continued

| Exemplary Naturally Occurring Receptors | |
|---|---|
| Naturally Occurring Receptor Name | SEQ ID NO: |
| >XP_011512371.1 prolactin receptor isoform X2 [*Homo sapiens*]<br>MKENVASATVFTLLLFLNTCLLNGQLPPGKPEIFKCRSPNKETFTCWWRPGTDGG<br>LPTNYSLTYHREGETLMHECPDYITGGPNSCHFGKQYTSMWRTYIMMVNATNQ<br>MGSSFSDELYVDVTYIVQPDPPLELAVEVKQPEDRKPYLWIKWSPPTLIDLKTGW<br>FTLLYEIRLKPEKAAEWEIHFAGQQTEFKILSLHPGQKYLVQVRCKPDHGYWSA<br>WSPATFIQIPSDFTMNDTTVWISVAVLSAVICLIIVWAVALKGYSMVTCIFPPVPGP<br>KIKGFDAHLLEKGKSEELLSALGCQDFPPTSDYEDLLVEYLEVDDSEDQHLMSVH<br>SKEHPSQGMKPTYLDPDTDSGRGSCDSPSLLSEKCEEPQANPSTFYDPEVIEKPEN<br>PETTHTWDPQCISMEGKIPYFHAGGSKCSTWPLPQPSQHNPRSSYHNITDVCELA<br>VGPAGAPATLLNEAGKDALKSSQTIKSREEGKATQQREVESFHSETDQDTPWLLP<br>QEKTPFGSAKPLDYVEIHKVNKDGALSLLPKQRENSGKPKKPGTPENNKEYAKV<br>SGVMDNNILVLVPDPHAKNVACFEESAKEAPPSLEQNQAEKALANFTATSSKCR<br>LQLGGLDYLDPACFTHSFH | 3 |
| >NP_000154.1 growth hormone receptor isoform 1 precursor<br>[*Homo sapiens*]<br>MDLWQLLLTLALAGSSDAFSGSEATAAILSRAPWSLQSVNPGLKTNSSKEPKFTK<br>CRSPERETFSCHWTDEVHHGTKNLGPIQLFYTRRNTQEWTQEWKECPDYVSAGE<br>NSCYFNSSFTSIWIPYCIKLTSNGGTVDEKCFSVDEIVQPDPPIALNWTLLNVSLTG<br>IHADIQVRWEAPRNADIQKGWMVLEYELQYKEVNETKWKMMDPILTTSVPVYS<br>LKVDKEYEVRVRSKQRNSGNYGEFSEVLYVTLPQMSQFTCEEDFYFPWLLIIIFGI<br>FGLTVMLFVFLFSKQQRIKMLILPPVPVPKIKGIDPDLLKEGKLEEVNTILAIHDSY<br>KPEFHSDDSWVEFIELDIDEPDEKTEESDTDRLLSSDHEKSHSNLGVKDGDSGRTS<br>CCEPDILETDFNANDIHEGTSEVAQPQRLKGEADLLCLDQKNQNNSPYHDACPAT<br>QQPSVIQAEKNKPQPLPTEGAESTHQAAHIQLSNPSSLSNIDFYAQV<br>SDITPAGSVVLSPGQKNKAGMSQCDMHPEMVSLCQENFLMDNAYFCEADAKKC<br>IPVAPHIKVESHIQPSLNQEDIYITTESLTTAAGRPGTGEHVPGSEMPVPDYTSIHIV<br>QSPQGLILNATALPLPDKEFLSSCGYVSTDQLNKIMP | 4 |
| >XP_016855859.1 granulocyte colony-stimulating factor<br>receptor isoform X1 [*Homo sapiens*]<br>MARLGNCSLTWAALIILLLPGSLEECGHISVSAPIVHLGDPITASCIIKQNCSHLDPE<br>PQILWRLGAELQPGGRQQRLSDGTQESIITLPHLNHTQAFLSCCLNWGNSLQILDQ<br>VELRAGYPPAIPHNLSCLMNLTTSSLICQWEPGPETHLPTSFTLKSFKSRGNCQTQ<br>GDSILDCVPKDGQSHCCIPRKHLLLYQNMGIWVQAENALGTSMSPQLCLDPMDV<br>VKLEPPMLRTMDPSPEAAPPQAGCLQLCWEPWQPGLHINQKCELRHKPQRGEAS<br>WALVGPLPLEALQYELCGLLPATAYTLQIRCIRWPLPGHWSDWSPSLELRTTERA<br>PTVRLDTWWRQRQLDPRTVQLFWKPVPLEEDSGRIQGYVVSWRPSGQAGAILPL<br>CNTTELSCTFHLPSEAQEVALVAYNSAGTSRPTPVVFSESRGPALTRLHAMARDP<br>HSLWVGWEPPNPWPQGYVIEWGLGPPSASNSNKTWRMEQNGRATGFLLKENIR<br>PFQLYEIIVTPLYQDTMGPSQHVYAYSQEMAPSHAPELHLKHIGKTWAQLEWVP<br>EPPELGKSPLTHYTIFWTNAQNQSFSAILNASSRGFVLHGLEPASLYHIHLMAASQ<br>AGAINSTVLTLMTLTPEGSELHIILGLFGLLLLLTCLCGTAWLCCSPNRKNPLWPS<br>VPDPAHSSLGSWVPTIMEELPGPRQGQWLGQTSEMSRALTPHPCVQDAFQLPGL<br>GTPPITKLTVLEEDEKKPVPWESHNSSETCGLPTLVQTYVLQGDPRAVSTQPQSQS<br>GTSDQVLYGQLLGSPTSPGPGHYLRCDSTQPLLAGLTPSPKSYENLWFQASPLGT<br>LVTPAPSQEDDCVFGPLLNFPLLQGIRVHGMEALGSF | 5 |
| >NP_005364.1 thrombopoietin receptor precursor [*Homo sapiens*]<br>MPSWALFMVTSCLLLAPQNLAQVSSQDVSLLASDSEPLKCFSRTFEDLTCFWDEE<br>EAAPSGTYQLLYAYPREKPRACPLSSQSMPHFGTRYVCQFPDQEEVRLFFPLHLW<br>VKNVFLNQTRTQRVLFVDSVGLPAPPSIIKAMGGSQPGELQISWEEPAPEISDFLR<br>YELRYGPRDPKNSTGPTVIQLIATETCCPALQRPHSASALDQSPCAQPTMPWQDG<br>PKQTSPSREASALTAEGGSCLISGLQPGNSYWLQLRSEPDGISLGGSWGSWSLPVT<br>VDLPGDAVALGLQCFTLDLKNVTCQWQQQDHASSQGFFYHSRARCCPRDRYPI<br>WENCEEEEKTNPGLQTPQFSRCHFKSRNDSIIHILVEVTTAPGTVHSYLGSPFWIH<br>QAVRLPTPNLHWREISSGHLELEWQHPSSWAAQETCYQLRYTGEGHQDWKVLE<br>PPLGARGGTLELRPRSRYRLQLRARLNGPTYQGPWSSWSDPTRVETATETAWISL<br>VTALHLVLGLSAVLGLLLLRWQFPAHYRRLRHALWPSLPDLHRVLGQYLRDTA<br>ALSPPKATVSDTCEEVEPSLLEILPKSSERTPLPLCSSQAQMDYRRLQPSCLGTMPL<br>SVCPPMAESGSCCTTHIANHSYLPLSYWQQP | 6 |

In some embodiments, the transmembrane domain of the disclosure is derived from a truncated version of the naturally occurring TPOR/MPLR (myeloproliferative leukemia protein) receptor show in Table 1a.

In some embodiments, the transmembrane domain of the CACCR comprises amino acids 478-582 of the TPOR receptor of Table 1a.

Table 1b provides exemplary transmembrane domain amino acid sequences of the disclosure, wherein the transmembrane domain is derived from the naturally occurring TPOR receptor. In the sequences listed in Table 1b, the TPOR receptor transmembrane amino acid sequence either comprises the SEQ ID NO: 7 ("naturally occurring transmembrane sequence") or differs from SEQ ID NO: 7 in comprising one or more amino acid substitutions of SEQ ID NO: 7 ("modified transmembrane sequence").

TABLE 1b

Exemplary transmembrane domain amino acid sequences

| Transmembrane Domain | Amino acid sequence | SEQ ID NO: |
|---|---|---|
| TPOR/MPLR(478-582) | SDPTRVETATETAWISLVTALHLVLGLSAVLGLL LLRWQFPAHYRRLRHALWPSLPDLHRVLGQYLR DTAALSPPKATVSDTCEEVEPSLLEILPKSSERTPL PL | 7 |
| TPOR/MPLR(478-582; H499L, S505N) | SDPTRVETATETAWISLVTAL**L**LVLGL**N**AVLGLL LLRWQFPAHYRRLRHALWPSLPDLHRVLGQYLR DTAALSPPKATVSDTCEEVEPSLLEILPKSSERTPL PL | 8 |
| TPOR/MPLR(478-582; S505N) | SDPTRVETATETAWISLVTALHLVLGL**N**AVLGLL LLRWQFPAHYRRLRHALWPSLPDLHRVLGQYLR DTAALSPPKATVSDTCEEVEPSLLEILPKSSERTPL PL | 9 |
| TPOR/MPLR(478-582; H499L,W515K) | SDPTRVETATETAWISLVTAL**L**LVLGLSAVLGLL LLR**K**QFPAHYRRLRHALWPSLPDLHRVLGQYLR DTAALSPPKATVSDTCEEVEPSLLEILPKSSERTPL PL | 10 |
| TPOR/MPLR(478-582; W515K) | SDPTRVETATETAWISLVTALHLVLGLSAVLGLL LLR**K**QFPAHYRRLRHALWPSLPDLHRVLGQYLR DTAALSPPKATVSDTCEEVEPSLLEILPKSSERTPL PL | 11 |
| TPOR/MPLR(478-582; H499L, S505N, W515K) | SDPTRVETATETAWISLVTAL**L**LVLGL**N**AVLGLL LLR**K**QFPAHYRRLRHALWPSLPDLHRVLGQYLR DTAALSPPKATVSDTCEEVEPSLLEILPKSSERTPL PL | 12 |
| TPOR/MPLR(478-582; S505N, W515K) | SDPTRVETATETAWISLVTALHLVLGL**N**AVLGLL LLR**K**QFPAHYRRLRHALWPSLPDLHRVLGQYLR DTAALSPPKATVSDTCEEVEPSLLEILPKSSERTPL PL | 13 |
| TPOR/MPLR(478-582; H499L, G509N) | SDPTRVETATETAWISLVTAL**L**LVLGLSAVL**N**LL LLRWQFPAHYRRLRHALWPSLPDLHRVLGQYLR DTAALSPPKATVSDTCEEVEPSLLEILPKSSERTPL PL | 14 |

In some embodiments, the transmembrane domain of the CACCR comprises amino acids 478-582 of the TPOR receptor, and an amino acid substitution at least at H499. In some embodiments, the transmembrane domain of the CACCR comprises amino acids 478-582 of the TPOR receptor, and the amino acid substitution H499L.

In some embodiments, the transmembrane domain of the CACCR comprises amino acids 478-582 of the TPOR receptor, and an amino acid substitution at least at S505. In some embodiments, the transmembrane domain of the CACCR comprises amino acids 478-582 of the TPOR receptor, and the amino acid substitution S505N.

In some embodiments, the transmembrane domain of the CACCR comprises amino acids 478-582 of the TPOR receptor, and an amino acid substitution at least at G509. In some embodiments, the transmembrane domain of the CACCR comprises amino acids 478-582 of the TPOR receptor, and the amino acid substitution G509N.

In some embodiments, the transmembrane domain of the CACCR comprises amino acids 478-582 of the TPOR receptor, and an amino acid substitution at least at W515. In some embodiments, the transmembrane domain of the CACCR comprises amino acids 478-582 of the TPOR receptor, and the amino acid substitution W515K.

In some embodiments, the transmembrane domain of the CACCR comprises amino acids 478-582 of the TPOR receptor, and an amino acid substitution at H499 and S505 (sequence provided in Table 1b).

In some embodiments, the transmembrane domain of the CACCR comprises amino acids 478-582 of the TPOR receptor, and an amino acid substitution at H499 and W515 (sequence provided in Table 1b).

In some embodiments, the transmembrane domain of the CACCR comprises amino acids 478-582 of the TPOR receptor, and an amino acid substitution at H499, S505, and W515 (sequence provided in Table 1b).

In some embodiments, the transmembrane domain of the CACCR comprises amino acids 478-582 of the TPOR receptor, and an amino acid substitution at S505 and W515 (sequence provided in Table 1b).

In some embodiments, the transmembrane domain of the CACCR comprises amino acids 478-582 of the TPOR receptor, and an amino acid substitution at H499 and G509 (sequence provided in Table 1b).

In some embodiments, the transmembrane domain of the CACCR comprises amino acids 478-582 of the TPOR receptor, and the amino acid substitutions H499L and S505N (sequence provided in Table 1b).

In some embodiments, the transmembrane domain of the CACCR comprises amino acids 478-582 of the TPOR receptor, and the amino acid substitutions H499L and W515K (sequence provided in Table 1b).

In some embodiments, the transmembrane domain of the CACCR comprises amino acids 478-582 of the TPOR receptor, and the amino acid substitutions H499L and G509N (sequence provided in Table 1b).

In some embodiments, the transmembrane domain of the CACCR comprises amino acids 478-582 of the TPOR receptor, and the amino acid substitutions S505N and W515K (sequence provided in Table 1b).

In some embodiments, the transmembrane domain of the CACCR comprises amino acids 478-582 of the TPOR receptor, and the amino acid substitutions H499L, S505N, and W515K (sequence provided in Table 1b).

In some embodiments, the transmembrane domain of the CACCR comprises amino acids 478-582 of the TPOR receptor, and an amino acid substitution at H499 and S505 (sequence provided in Table 1b).

The CACCRs of the disclosure are tunable, to achieve the level of Signal 3/immune potentiation required in a BCMA CAR-bearing immune cell (e.g. BCMA CAR-T cell) and desired in a particular context or condition.

In some embodiments, a low level of STAT5 activation is desired in a BCMA CAR-bearing immune cell (e.g. BCMA CAR-T cell). By way of example, in such embodiments, the transmembrane domain of the CACCR comprising amino acids 478-582 of the TPOR receptor, and the amino acid substitution S505N, W515K, or H499L/G509N may be introduced.

In some embodiments, an increased level of STAT5 activation is desired in a BCMA CAR-bearing immune cell (e.g. BCMA CAR-T cell). By way of example, in such embodiments, the transmembrane domain of the CACCR comprising amino acids 478-582 of the TPOR receptor, and the amino acid substitutions H499L, S505N, and W515K may be introduced. By way of another example, in such embodiments, the transmembrane domain of the CACCR comprising amino acids 478-582 of the TPOR receptor, and the amino acid substitutions S505N and W515K may be introduced.

In some embodiments, increased differentiation into memory T cells is desired in a BCMA CAR-bearing immune cell (e.g. BCMA CAR-T cell). By way of example, in such embodiments, the transmembrane domain of the CACCR comprising amino acids 478-582 of the TPOR receptor, and the amino acid substitutions W515K, or H499L/G509N may be introduced.

In some embodiments, increased differentiation into memory T cells is desired in a BCMA CAR-bearing immune cell (e.g. BCMA CAR-T cell). By way of example, in such embodiments, the transmembrane domain of the CACCR comprising amino acids 478-582 of the TPOR receptor, and the amino acid substitutions S505N/W515K and H499L/S505N/W515K may be introduced.

Also substitutions to increase cytotoxic potency, durability of response, and increased persistence are provided herein, for example S505N/W515K and H499L/S505N/W515K substitutions.

TABLE 1c

Exemplary Transmembrane + JAK2 Binding Domain Sequences

| Transmembrane and JAK2 binding domain | Amino acid sequence | SEQ ID NO: |
|---|---|---|
| GCSFR(614-710) | LTLMTLTPEGSELHIILGLFGLLLLLTCLCGTAWL CCSPNRKNPLWPSVPDPAHSSLGSWVPTIMEEDA FQLPGLGTPPITKLTVLEEDEKKPVPWE | 15 |
| GP130(609-700) | TTPKFAQGEIEAIVVPVCLAFLLTTLLGVLFCFNK RDLIKKHIWPNVPDPSKSHIAQWSPHTPPRHNFN SKDQMYSDGNFTDVSVVEIEAND | 16 |
| TPOR/MPLR(478-582) | SDPTRVETATETAWISLVTALHLVLGLSAVLGLL LLRWQFPAHYRRLRHALWPSLPDLHRVLGQYLR DTAALSPPKATVSDTCEEVEPSLLEILPKSSERTPL PL | 17 |
| TPOR/MPLR(N − 1) | SDPTRVETATETWISLVTALHLVLGLSAVLGLLL LRWQFPAHYRRLRHALWPSLPDLHRVLGQYLRD TAALSPPKATVSDTCEEVEPSLLEILPKSSERTPLP L | 18 |
| TPOR/MPLR(N − 2) | SDPTRVETATETISLVTALHLVLGLSAVLGLLLLR WQFPAHYRRLRHALWPSLPDLHRVLGQYLRDT AALSPPKATVSDTCEEVEPSLLEILPKSSERTPLPL | 19 |
| TPOR/MPLR(N − 2 + 1) | SDPTRVETATETLISLVTALHLVLGLSAVLGLLLL RWQFPAHYRRLRHALWPSLPDLHRVLGQYLRDT AALSPPKATVSDTCEEVEPSLLEILPKSSERTPLPL | 20 |
| TPOR/MPLR(N − 3) | SDPTRVETATETSLVTALHLVLGLSAVLGLLLLR WQFPAHYRRLRHALWPSLPDLHRVLGQYLRDT AALSPPKATVSDTCEEVEPSLLEILPKSSERTPLPL | 21 |
| TPOR/MPLR(N − 4) | SDPTRVETATETLVTALHLVLGLSAVLGLLLLRW QFPAHYRRLRHALWPSLPDLHRVLGQYLRDTAA LSPPKATVSDTCEEVEPSLLEILPKSSERTPLPL | 22 |
| TPOR/MPLR(N − 4 + 1) | SDPTRVETATETILVTALHLVLGLSAVLGLLLLR WQFPAHYRRLRHALWPSLPDLHRVLGQYLRDT AALSPPKATVSDTCEEVEPSLLEILPKSSERTPLPL | 23 |
| TPOR/MPLR(N − 5) | SDPTRVETATETVTALHLVLGLSAVLGLLLLRW QFPAHYRRLRHALWPSLPDLHRVLGQYLRDTAA LSPPKATVSDTCEEVEPSLLEILPKSSERTPLPL | 24 |

TABLE 1c-continued

| Exemplary Transmembrane + JAK2 Binding Domain Sequences | | |
|---|---|---|
| Transmembrane and JAK2 binding domain | Amino acid sequence | SEQ ID NO: |
| TPOR/MPLR(N − 6) | SDPTRVETATETTALHLVLGLSAVLGLLLLRWQFPAHYRRLRHALWPSLPDLHRVLGQYLRDTAALSPPKATVSDTCEEVEPSLLEILPKSSERTPLPL | 25 |
| TPOR/MPLR(N − 7) | SDPTRVETATETALHLVLGLSAVLGLLLLRWQFPAHYRRLRHALWPSLPDLHRVLGQYLRDTAALSPPKATVSDTCEEVEPSLLEILPKSSERTPLPL | 26 |
| TPOR/MPLR(N − 8) | SDPTRVETATETLHLVLGLSAVLGLLLLRWQFPAHYRRLRHALWPSLPDLHRVLGQYLRDTAALSPPKATVSDTCEEVEPSLLEILPKSSERTPLPL | 27 |
| TPOR/MPLR(N − 9) | SDPTRVETATETHLVLGLSAVLGLLLLRWQFPAHYRRLRHALWPSLPDLHRVLGQYLRDTAALSPPKATVSDTCEEVEPSLLEILPKSSERTPLPL | 28 |
| TPOR/MPLR(N − 10) | SDPTRVETATETLVLGLSAVLGLLLLRWQFPAHYRRLRHALWPSLPDLHRVLGQYLRDTAALSPPKATVSDTCEEVEPSLLEILPKSSERTPLPL | 29 |
| TPOR/MPLR(N − 11) | SDPTRVETATETVLGLSAVLGLLLLRWQFPAHYRRLRHALWPSLPDLHRVLGQYLRDTAALSPPKATVSDTCEEVEPSLLEILPKSSERTPLPL | 30 |
| TPOR/MPLR(N − 12) | SDPTRVETATETLGLSAVLGLLLLRWQFPAHYRRLRHALWPSLPDLHRVLGQYLRDTAALSPPKATVSDTCEEVEPSLLEILPKSSERTPLPL | 31 |
| TPOR/MPLR(N − 13) | SDPTRVETATETGLSAVLGLLLLRWQFPAHYRRLRHALWPSLPDLHRVLGQYLRDTAALSPPKATVSDTCEEVEPSLLEILPKSSERTPLPL | 32 |
| TPOR/MPLR(N − 14) | SDPTRVETATETLSAVLGLLLLRWQFPAHYRRLRHALWPSLPDLHRVLGQYLRDTAALSPPKATVSDTCEEVEPSLLEILPKSSERTPLPL | 33 |
| TPOR/MPLR(N − 15) | SDPTRVETATETSAVLGLLLLRWQFPAHYRRLRHALWPSLPDLHRVLGQYLRDTAALSPPKATVSDTCEEVEPSLLEILPKSSERTPLPL | 34 |
| TPOR/MPLR(N − 16) | SDPTRVETATETAVLGLLLLRWQFPAHYRRLRHALWPSLPDLHRVLGQYLRDTAALSPPKATVSDTCEEVEPSLLEILPKSSERTPLPL | 35 |
| TPOR/MPLR(N − 17) | SDPTRVETATETVLGLLLLRWQFPAHYRRLRHALWPSLPDLHRVLGQYLRDTAALSPPKATVSDTCEEVEPSLLEILPKSSERTPLPL | 36 |
| TPOR/MPLR(N − 18) | SDPTRVETATETLGLLLLRWQFPAHYRRLRHALWPSLPDLHRVLGQYLRDTAALSPPKATVSDTCEEVEPSLLEILPKSSERTPLPL | 37 |
| TPOR/MPLR(N + 1) | SDPTRVETATETAWLISLVTALHLVLGLSAVLGLLLLRWQFPAHYRRLRHALWPSLPDLHRVLGQYLRDTAALSPPKATVSDTCEEVEPSLLEILPKSSERTPLPL | 38 |
| TPOR/MPLR(N + 2) | SDPTRVETATETAWVLISLVTALHLVLGLSAVLGLLLLRWQFPAHYRRLRHALWPSLPDLHRVLGQYLRDTAALSPPKATVSDTCEEVEPSLLEILPKSSERTPLPL | 39 |
| TPOR/MPLR(N + 3) | SDPTRVETATETAWLVLISLVTALHLVLGLSAVLGLLLLRWQFPAHYRRLRHALWPSLPDLHRVLGQYLRDTAALSPPKATVSDTCEEVEPSLLEILPKSSERTPLPL | 40 |
| TPOR/MPLR(N + 4) | SDPTRVETATETAWILVLISLVTALHLVLGLSAVLGLLLLRWQFPAHYRRLRHALWPSLPDLHRVLGQYLRDTAALSPPKATVSDTCEEVEPSLLEILPKSSERTPLPL | 41 |

TABLE 1c-continued

| Exemplary Transmembrane + JAK2 Binding Domain Sequences | | |
|---|---|---|
| Transmembrane and JAK2 binding domain | Amino acid sequence | SEQ ID NO: |
| TPOR/MPLR(N + 5) | SDPTRVETATETAWLILVLISLVTALHLVLGLSAV LGLLLLRWQFPAHYRRLRHALWPSLPDLHRVLG QYLRDTAALSPPKATVSDTCEEVEPSLLEILPKSS ERTPLPL | 42 |
| TPOR/MPLR(N + 6) | SDPTRVETATETAWLLILVLISLVTALHLVLGLSA VLGLLLLRWQFPAHYRRLRHALWPSLPDLHRVL GQYLRDTAALSPPKATVSDTCEEVEPSLLEILPKS SERTPLPL | 43 |
| TPOR/MPLR(N + 7) | SDPTRVETATETAWVLLILVLISLVTALHLVLGLS AVLGLLLLRWQFPAHYRRLRHALWPSLPDLHRV LGQYLRDTAALSPPKATVSDTCEEVEPSLLEILPK SSERTPLPL | 44 |
| TPOR/MPLR(N + 8) | SDPTRVETATETAWLVLLILVLISLVTALHLVLGL SAVLGLLLLRWQFPAHYRRLRHALWPSLPDLHR VLGQYLRDTAALSPPKATVSDTCEEVEPSLLEILP KSSERTPLPL | 45 |

B. Janus Kinase (JAK)-Binding Domains

The CACCRs of the disclosure comprise intracellular JAK-binding domains. The JAK-binding domain is coupled to the C-terminus of the transmembrane domain, either directly, or via a linker. The JAK-binding domain is coupled to the transmembrane domain on the intracellular side of the chimeric cytokine receptor.

In some embodiments, the JAK-binding domain is a JAK-1-binding domain, a JAK-2 binding domain, a JAK-3 binding domain, or a TYK2 binding domain.

In some embodiments, the JAK-binding domains of the CACCRs of the disclosure are naturally occurring, and derived from a naturally occurring receptor.

In some embodiments, the JAK-binding domains of the CACCRs of the disclosure are synthetic.

Table 1b and Table 1c provide exemplary amino acid sequences for transmembrane and JAK2 binding domains of the disclosure. In some embodiments, the CACCR of the disclosure comprises a transmembrane and JAK2 binding domain comprising an amino acid sequence selected from the sequences in Tables 1b and 1c. An amino acid sequence that comprises both a transmembrane and a JAK2 binding domain is a polypeptide that may be referred to herein as a “TM/JAK polypeptide.” Thus, for example, Table 1c lists exemplary TM/JAK polypeptides such as TPOR/MPLR (478-582), and similarly Table 1b lists variants of TPOR/MPLR(478-582) that are also TM/JAK polypeptides, such as TPOR/MPLR(478-582; H499L, S505N, W515K) and TPOR/MPLR(478-582; S505N, W515K). In some embodiments, the CACCR of the disclosure comprises a transmembrane and JAK2 binding domain comprising an amino acid sequence that is at least 80%, 85%, 90%, 95%, 98%, 99%, or 100% identical to any one of the sequences in Tables 1b and 1c.

C. Recruiting Domains

The CACCRs of the disclosure comprise cytoplasmic recruiting domains. The recruiting domain can be a STAT-recruiting domain, an AP1-recruiting domain, a Myc/Max-recruiting domain, or an NFkB-recruiting domain. In some embodiments, the recruiting domain is a Signal Transducer and Activator of Transcription (STAT)-recruiting (STAT-activating) domains, for example, from receptor tails (cytotails) or from cytokine receptor tails. These intracellular recruiting domains of the CACCRs of the disclosure allow for the propagation of Signal 3 in an immune cell comprising a BCMA CAR and a chimeric cytokine receptor (e.g. a BCMA CAR-T cell with a chimeric cytokine receptor of the disclosure). Cytokine signaling propagated through the STAT-recruiting domain allows for the cytokine-based immune potentiation of the cell. In some embodiments, the immune-potentiation is homeostatic, e.g. signaling gives rise to increase in immune cells bearing the CAR. In some embodiments, the immune-potentiation is inflammatory, e.g. signaling gives rise to an increase in the potency of the immune cells bearing the CAR. In some embodiments, the immune-potentiation prevents exhaustion, e.g. signaling maintains the long-term functionality of immune cells bearing the CAR.

In some embodiments, the recruiting domains of the disclosure are synthetic, and do not resemble any naturally occurring receptor fragment. In some embodiments, the immune-potentiation prevents exhaustion, e.g. signaling maintains the long-term functionality of immune cells bearing the BCMA CAR.

In some embodiments, the Stat-recruiting domains of the disclosure are synthetic, and do not resemble any naturally occurring receptor fragment.

In other embodiments, the Stat-recruiting domains of the disclosure are derived from cytoplasmic tails of naturally occurring receptors, e.g. derived from naturally occurring cytokine receptors. These cytoplasmic tails of naturally occurring receptors may be the regions downstream of the JAK-activating domains of the transmembrane domain of the receptor. The Stat-recruiting domains of the chimeric cytokine receptors comprise at least one STAT-recruiting domain from at least one receptor. In some embodiments, the Stat-recruiting domain comprises at least one STAT1-recruiting domain. In some embodiments, the Stat-recruiting domain comprises at least one STAT2-recruiting domain. In some embodiments, the Stat-recruiting domain comprises at least one STAT3-recruiting domain. In some embodiments, the Stat-recruiting domain comprises at least one STAT4-recruiting domain. In some embodiments, the Stat-recruiting domain comprises at least one STAT5-recruiting domain. In some embodiments, the Stat-recruiting domain comprises at least one STAT6-recruiting domain. In some embodiments, the Stat-recruiting domain comprises at least one STAT7-recruiting domain.

In some embodiments, the naturally occurring receptor from which the Stat-recruiting domain is derived, is not a cytokine receptor.

In some embodiments, the naturally occurring receptor from which the Stat-recruiting domain is derived, is a cytokine receptor. Exemplary cytokine receptors through which T cell-immune potentiating cytokines signal include, but are not limited to IL-2 receptor, IL-7 receptor, IL-12 receptor, IL-15 receptor and IL-21 receptor. In alternative embodiments, the receptor from which the Stat-recruiting domain is derived, is not a cytokine receptor. By choosing the Stat-recruiting domain of the CACCR, the receptor can be redirected to signaling of choice.

In some embodiments, the CACCR of the disclosure comprises a recruiting domain connected to the C-terminus of the transmembrane/JAK2 binding domain, with or without a linker. In some embodiments, the linker comprises one or more amino acid residues.

Table 2a provides exemplary receptors from which recruiting domains of the CACCRs of the disclosure are derived. Table 2b provides exemplary amino acid sequences of recruiting domains of the disclosure. In some embodiments, the CACCR of the disclosure comprises a recruiting domain comprising the amino acid sequence selected from one or more of the receptor sequences in Table 2b. In some embodiments, the CACCR of the disclosure comprises a recruiting domain comprising an amino acid sequence that is at least 80%, 85%, 90%, 95%, 98%, 99%, or 100% identical to any one of the sequences in Table 2b.

TABLE 2a

| Exemplary Receptors Source of Recruiting Domains |
|---|
| BLNK |
| IL2RG |
| EGFR |
| EpoR |
| GHR |
| IFNAR1 |
| IFNAR2 |
| IFNAR1/2 |
| IFNLR1 |
| IL10R1 |
| IL12Rb1 |
| IL12Rb2 |
| IL21R |
| IL2Rb |
| IL2small |
| IL7R |
| IL7Ra |
| IL9R |
| IL15R |
| IL21R |

TABLE 2b

| Recruiting Domain (Cytotail) Sequences | | |
|---|---|---|
| Cytotail sequences | Amino acid sequence | SEQ ID NO: |
| IL7R(316-459) | ARDEVEGFLQDTFPQQLEESEKQRLGGDVQSPN CPSEDVVITPESFGRDSSLTCLAGNVSACDAPILS SSRSLDCRESGKNGPHVYQDLLLSLGTTNSTLPPP FSLQSGILTLNPVAQGQPILTSLGSNQEEAYVTMS SFYQNQ | 46 |
| IL2Rb(333-551) | VTQLLLQQDKVPEPASLSSNHSLTSCFTNQGYFF FHLPDALEIEACQVYFTYDPYSEEDPDEGVAGAP TGSSPQPLQPLSGEDDAYCTFPSRDDLLLFSPSLL GGPSPPSTAPGGSGAGEERMPPSLQERVPRDWDP QPLGPPTPGVPDLVDFQPPPELVLREAGEEVPDA GPREGVSFPWSRPPGQGEFRALNARLPLNTDAYL SLQELQGQDPTHLV | 47 |
| IFNAR1(508-557) | ISTIATVEETNQTDEDHKKYSSQTSQDSGNYSNE DESESKTSEELQQDFV | 48 |
| IFNAR2(310-515) | KKKVWDYNYDDESDSDTEAAPRTSGGGYTMHG LTVRPLGQASATSTESQLIDPESEEEPDLPEVDVE LPTMPKDSPQQLELLSGPCERRKSPLQDPFPEEDY SSTEGSGGRITFNVDLNSVFLRVLDDEDSDDLEA PLMLSSHLEEMVDPEDPDNVQSNHLLASGEGTQ PTFPSPSSEGLWSEDAPSDQSDTSESDVDLGDGYI MR | 49 |
| IFNAR1/2(IFNAR1 residues 508-557-IFNAR2 residues 310-515) | ISTIATVEETNQTDEDHKKYSSQTSQDSGNYSNE DESESKTSEELQQDFVKKKVWDYNYDDESDSDT EAAPRTSGGGYTMHGLTVRPLGQASATSTESQLI DPESEEEPDLPEVDVELPTMPKDSPQQLELLSGPC ERRKSPLQDPFPEEDYSSTEGSGGRITFNVDLNSV FLRVLDDEDSDDLEAPLMLSSHLEEMVDPEDPD NVQSNHLLASGEGTQPTFPSPSSEGLWSEDAPSD QSDTSESDVDLGDGYIMR | 50 |
| IFNLR1(300-520) | RGVRPTPRVRAPATQQTRWKKDLAEDEEEEDEE DTEDGVSFQPYIEPPSFLGQEHQAPGHSEAGGVD SGRPRAPLVPSEGSSAWDSSDRSWASTVDSSWD | 51 |

TABLE 2b-continued

Recruiting Domain (Cytotail) Sequences

| Cytotail sequences | Amino acid sequence | SEQ ID NO: |
|---|---|---|
| | RAGSSGYLAEKGPGQGPGGDGHQESLPPPEFSKD SGFLEELPEDNLSSWATWGTLPPEPNLVPGGPPV SLQTLTFCWESSPEEEEEARESEIEDSDAGSWGAE STQRTEDRGRTLGHYMAR | |
| IL2RG (335-369) | IPPKGGALGEGPGASPCNQHSPYWAPPCYTLKPE T | 52 |
| IL9R(356-521) | TALLTCGPARPWKSVALEEEQEGPGTRLPGNLSS EDVLPAGCTEWRVQTLAYLPQEDWAPTSLTRPA PPDSEGSRSSSSSSSSNNNNYCALGCYGGWHLSA LPGNTQSSGPIPALACGLSCDHQGLETQQGVAW VLAGHCQRPGLHEDLQGMLLPSVLSKARSWTF | 53 |
| IL21R(322-538) | PRSPAKRLQLTELQEPAELVESDGVPKPSFWPTA QNSGGSAYSEERDRPYGLVSIDTVTVLDAEGPCT WPCSCEDDGYPALDLDAGLEPSPGLEDPLLDAG TTVLSCGCVSAGSPGLGGPLGSLLDRLKPPLADG EDWAGGLPWGGRSPGGVSESEAGSPLAGLDMD TFDSGFVGSDCSSPVECDFTSPGDEGPPRSYLRQ WVVIPPPLSSPGPQAS | 54 |
| GHR(353-638) | PDEKTEESDTDRLLSSDHEKSHSNLGVKDGDSGR TSCCEPDILETDFNANDIHEGTSEVAQPQRLKGE ADLLCLDQKNQNNSPYHDACPATQQPSVIQAEK NKPQPLPTEGAESTHQAAHIQLSNPSSLSNIDFYA QVSDITPAGSVVLSPGQKNKAGMSQCDMHPEM VSLCQENFLMDNAYFCEADAKKCIPVAPHIKVES HIQPSLNQEDIYITTESLTTAAGRPGTGEHVPGSE MPVPDYTSIHIVQSPQGLILNATALPLPDKEFLSS CGYVSTDQLNKIMP | 55 |
| EpoR(339-508) | WGTMQAVEPGTDDEGPLLEPVGSEHAQDTYLVL DKWLLPRNPPSEDLPGPGGSVDIVAMDEGSEASS CSSALASKPSPEGASAASFEYTILDPSSQLLRPWT LCPELPPTPPHLKYLYLVVSDSGISTDYSSGDSQG AQGGLSDGPYSNPYENSLIPAAEPLPPSYVACS | 56 |
| murine IL2Rb(337-539) | AVQLLLLQKDSAPLPSPSGHSQASCFTNQGYFFF HLPNALEIESCQVYFTYDPCVEEEVEEDGSRLPE GSPHPPLLPLAGEQDDYCAFPPRDDLLLFSPSLST PNTAYGGSRAPEERSPLSLHEGLPSLASRDLMGL QRPLERMPEGDGEGLSANSSGEQASVPEGNLHG QDQDRGQGPILTLNTDAYLSLQELQAQDSVHLI | 57 |
| murine IL7Ra(316-459) | ARDEVESFLPNDLPAQPEELETQGHRAAVHSAN RSPETSVSPPETVRRESPLRCLARNLSTCNAPPLL SSRSPDYRDGDRNRPPVYQDLLPNSGNTNVPVPV PQPLPFQSGILIPVSQRQPISTSSVLNQEEAYVTMS SFYQNK | 58 |
| EGFR(955-1186) | VIQGDERMHLPSPTDSNFYRALMDEEDMDDVVD ADEYLIPQQGFFSSPSTSRTPLLSSLSATSNNSTVA CIDRNGLQSCPIKEDSFLQRYSSDPTGALTEDSID DTFLPVPEYINQSVPKRPAGSVQNPVYHNQPLNP APSRDPHYQDPHSTAVGNPEYLNTVQPTCVNSTF DSPAHWAQKGSHQISLDNPDYQQDFFPKEAKPN GIFKGSTAENAEYLRVAPQSSEFIGA | 59 |
| EGFR(955-1186; Y974F, d1045-1057) | VIQGDERMHLPSPTDSNFFRALMDEEDMDDVVD ADEYLIPQQGFFSSPSTSRTPLLSSLSATSNNSTVA CIDRNGLQSCPIKEDSFLQRIDDTFLPVPEYINQSV PKRPAGSVQNPVYHNQPLNPAPSRDPHYQDPHS TAVGNPEYLNTVQPTCVNSTFDSPAHWAQKGSH QISLDNPDYQQDFFPKEAKPNGIFKGSTAENAEY LRVAPQSSEFIGA | 60 |
| EGFR(955-1009; Y974F) | VIQGDERMHLPSPTDSNFFRALMDEEDMDDVVD ADEYLIPQQGFFSSPSTSRTP | 61 |
| EGFR(1019-1085) | NNSTVACIDRNGLQSCPIKEDSFLQRIDDTFLPVP EYINQSVPKRPAGSVQNPV | 62 |

TABLE 2b-continued

Recruiting Domain (Cytotail) Sequences

| Cytotail sequences | Amino acid sequence | SEQ ID NO: |
|---|---|---|
| EGFR(1037-1103; Y1068/1101F, d1045-1057) | KEDSFLQRIDDTFLPVPEFINQSVPKRPAGSVQNP VYHNQPLNPAPSRDPHFQD | 63 |
| EGFR(1066-1118; Y1068/1086F) | VPEFINQSVPKRPAGSVQNPVFHNQPLNPAPSRD PHYQDPHSTAVGNPEYLNTV | 64 |
| EGFR(1122-1165) | PEYLNTVQPTCVNSTFDSPAHWAQKGSHQISLDN PDYQQDFFPKEAKPNGIFKG | 65 |
| EGFR(1133-1186; Y1148F) | WAQKGSHQISLDNPDFQQDFFPKEAKPNGIFKGS TAENAEYLRVAPQSSEFIGA | 66 |
| IL12Rb2(775-825) | SDPKPENPACPWTVLPAGDLPTHDGYLPSNIDDL PSHEAPLADSLEELEPQ | 67 |
| IL7Ra(376-416) | ACDAPILSSSRSLDCRESGKNGPHVYQDLLLSLG TTNSTLP | 68 |
| IL7Ra(424-459) | GILTLNPVAQGQPILTSLGSNQEEAYVTMSSFYQ NQ | 69 |
| IL7Ra(376-416, 424-459) | ACDAPILSSSRSLDCRESGKNGPHVYQDLLLSLG TTNSTLPQGQPILTSLGSNQEEAYVTMSSFYQNQ | 70 |
| IL7Ra(424-459; Y456F) | GILTLNPVAQGQPILTSLGSNQEEAYVTMSSFFQN Q | 71 |
| IL7R(376-416, 424-459, Y456F) | ACDAPILSSSRSLDCRESGKNGPHVYQDLLLSLG TTNSTLPQGQPILTSLGSNQEEAYVTMSSFFQNQ | 72 |
| IL2Rbsmall(393-433) | DEGVAGAPTGSSPQPLQPLSGEDDAYCTFPSRDD LLLFSPSGQGEFRALNARLPLNTDAYLSLQELQG QDPTHLV | 73 |
| IL2Rbsmall(518-551) | GQGEFRALNARLPLNTDAYLSLQELQGQDPTHL V | 74 |
| IL2Rbsmall(339-379, 393-433) | QQDKVPEPASLSSNHSLTSCFTNQGYFFFHLPDA LEIEACQDEGVAGAPTGSSPQPLQPLSGEDDAYC TFPSRDDLLLFSPS | 75 |
| IL2Rbsmall(339-379, 518-551) | QQDKVPEPASLSSNHSLTSCFTNQGYFFFHLPDA LEIEACQ GQGEFRALNARLPLNTDAYLSLQELQGQDPTHL V | 76 |
| IL2Rbsmall(393-433, 518-551) | DEGVAGAPTGSSPQPLQPLSGEDDAYCTFPSRDD LLLFSPSGQGEFRALNARLPLNTDAYLSLQELQG QDPTHLV | 77 |
| IL2Rbsmall(339-379, 393-433, 518-551) | QQDKVPEPASLSSNHSLTSCFTNQGYFFFHLPDA LEIEACQDEGVAGAPTGSSPQPLQPLSGEDDAYC TFPSRDDLLLFSPSGQGEFRALNARLPLNTDAYLS LQELQGQDPTHLV | 78 |
| IFNAR2small(310-352) | KKKVWDYNYDDESDSDTEAAPRTSGGGYTMHG LTVRPLGQASA | 79 |
| IFNAR2small(486-515) | EGLWSEDAPSDQSDTSESDVDLGDGYIMR | 80 |
| IFNAR2small(310-352, 486-515) | KKKVWDYNYDDESDSDTEAAPRTSGGGYTMHG LTVRPLGQASA EGLWSEDAPSDQSDTSESDVDLGDGYIMR | 81 |
| BLNK(53-208) | ASESPADEEEQWSDDFDSDYENPDEHSDSEMYV MPAEENADDSYEPPPVEQETRPVHPALPFARGEY IDNRSSQRHSPPFSKTLPSKPSWPSEKARLTSTLP ALTALQKPQVPPKPKGLLEDEADYVVPVEDNDE NYIHPTESSSPPPEKAPMVNR | 82 |
| BLNK(53-208; Y72F) | ASESPADEEEQWSDDFDSDFENPDEHSDSEMYV MPAEENADDSYEPPPVEQETRPVHPALPFARGEY IDNRSSQRHSPPFSKTLPSKPSWPSEKARLTSTLP | 83 |

TABLE 2b-continued

Recruiting Domain (Cytotail) Sequences

| Cytotail sequences | Amino acid sequence | SEQ ID NO: |
|---|---|---|
| | ALTALQKPQVPPKPKGLLEDEADYVVPVEDNDE NYIHPTESSSPPPEKAPMVNR | |
| BLNK(53-208; Y72F, Y96F) | ASESPADEEEQWSDDFDSDFENPDEHSDSEMYV MPAEENADDSFEPPPVEQETRPVHPALPFARGEY IDNRSSQRHSPPFSKTLPSKPSWPSEKARLTSTLP ALTALQKPQVPPKPKGLLEDEADYVVPVEDNDE NYIHPTESSSPPPEKAPMVNR | 84 |
| EpoR(339-508) | WGTMQAVEPGTDDEGPLLEPVGSEHAQDTYLVL DKWLLPRNPPSEDLPGPGGSVDIVAMDEGSEASS CSSALASKPSPEGASAASFEYTILDPSSQLLRPWT LCPELPPTPPHLKYLYLVVSDSGISTDYSSGDSQG AQGGLSDGPYSNPYENSLIPAAEPLPPSYVACS | 85 |
| IL12Rb2(714-862) | VTPVFRHPPCSNWPQREKGIQGHQASEKDMMHS ASSPPPPRALQAESRQLVDLYKVLESRGSDPKPE NPACPWTVLPAGDLPTHDGYLPSNIDDLPSHEAP LADSLEELEPQHISLSVFPSSSLHPLTFSCGDKLTL DQLKMRCDSLML | 86 |
| IL12Rb1(622-662) | WDKGERTEPLEKTELPEGAPELALDTELSLEDGD RCKAKM | 87 |
| IL10R1(304-578) | VSPELKNLDLHGSTDSGFGSTKPSLQTEEPQFLLP DPHPQADRTLGNREPPVLGDSCSSGSSNSTDSGIC LQEPSLSPSTGPTWEQQVGSNSRGQDDSGIDLVQ NSEGRAGDTQGGSALGHHSPPEPEVPGEEDPAA VAFQGYLRQTRCAEEKATKTGCLEEESPLTDGL GPKFGRCLVDEAGLHPPALAKGYLKQDPLEMTL ASSGAPTGQWNQPTEEWSLLALSSCSDLGISDWS FAHDLAPLGCVAAPGGLLGSFNSDLVTLPLISSLQ SSE | 88 |
| IL2Rb(333-551, Y381S, Y384S, Y387S) | VTQLLLQQDKVPEPASLSSNHSLTSCFTNQGYFF FHLPDALEIEACQV**S**FT**S**DP**S**SEEDPDEGVAGAPT GSSPQPLQPLSGEDDAYCTFPSRDDLLLFSPSLLG GPSPPSTAPGGSGAGEERMPPSLQERVPRDWDPQ PLGPPTPGVPDLVDFQPPPELVLREAGEEVPDAG PREGVSFPWSRPPGQGEFRALNARLPLNTDAYLS LQELQGQDPTHLV | 106 |
| IL2Rb(333-551, Y364S, Y381S, Y384S, Y387S) | VTQLLLQQDKVPEPASLSSNHSLTSCFTNQG**S**FFF HLPDALEIEACQV**S**FT**S**DP**S**SEEDPDEGVAGAPTG SSPQPLQPLSGEDDAYCTFPSRDDLLLFSPSLLGG PSPPSTAPGGSGAGEERMPPSLQERVPRDWDPQP LGPPTPGVPDLVDFQPPPELVLREAGEEVPDAGP REGVSFPWSRPPGQGEFRALNARLPLNTDAYLSL QELQGQDPTHLV | 142 |

In some embodiments, the Stat-recruiting domain of a CACCR of the disclosure comprises a STAT-recruiting domain from one receptor.

In order to generate multiple outputs, two or more STAT-recruiting domains may be joined in tandem to mimic signaling from one or more cytokines.

In some embodiments, the two or more STAT-recruiting domains may be joined in tandem with or without a linker. In some embodiments, the linker comprises one or more amino acid residues.

In some embodiments, the STAT-recruiting domain comprises portions of more than one receptor, e.g. comprising more than one STAT-recruiting domain. In such embodiments, a tandem cytokine signaling domain is provided, allowing for enhanced signaling. Accordingly, in some embodiments, the STAT-recruiting domain of a monomer of the CACCR of the disclosure comprises the STAT-recruiting domains from more than one receptor, e.g. comprises the STAT-recruiting domains from two, three, four, five, or even six receptors. For example, in some embodiments, STAT-recruiting domains can be linked in tandem to stimulate multiple pathways (e.g., the IL7R(316-459)-IL12Rb2(775-825) fragment fusion for pro-persistence STAT5 and pro-inflammatory STAT4; IL7R(316-459)-IL2Rbsmall(393-433, 518-551) for pro-persistence; IL7R(316-459)-EGFR (1122-1165) for pro-persistence and anti-exhaustion; IL2Rbsmall(393-433, 518-551)-EGFR(1122-1165) for pro-persistence and anti-exhaustion).

When generating multiple outputs, the proximity of individual STAT-recruiting domains to the cell membrane can influence the strength of their respective signaling outputs. Table 2c shows examples of CACCRs with the dual outputs, where each output can be placed either proximal or distal to the cell membrane. In some embodiments, the CACCRs of the disclosure comprise a recruiting domain with dual outputs selected from Table 2c.

TABLE 2c

| Examples of CACCRs with dual outputs | | |
|---|---|---|
| Dual output STAT-recruiting domain | Membrane proximal | Membrane distal |
| IL2Rbsmall(393-433, 518-551)/IL21R(322-538) | IL2Rbsmall (393-433, 518-551) | IL21R(322-538) |
| IL2Rb(333-551)/IL21R(322-538) | IL2Rb(333-551) | IL21R(322-538) |
| IL21R(322-538)/IL2Rbsmall(393-433, 518-551) | IL21R(322-538) | IL2Rbsmall (393-433, 518-551) |
| IL21R(322-538)/IL2Rb(333-551) | IL21R(322-538) | IL2Rb(333-551) |
| IL2Rbsmall(339-379, 393-433, 518-551)/IL21R(322-538) | IL2Rbsmall (339-379, 393-433, 518-551) | IL21R(322-538) |
| IL21R(322-538)/IL2Rbsmall(339-379, 393-433, 518-551) | IL21R(322-538) | IL2Rbsmall (339-379, 393-433, 518-551) |
| IL2Rb(333-551)/IL12Rb1(622-662) | IL2Rb(333-551) | IL12Rb1 (622-662) |
| IL2Rbsmall(393-433, 518-551)/IL12Rb1(622-662) | IL2Rbsmall (393-433, 518-551) | IL12Rb1 (622-662) |
| IL2Rbsmall(339-379, 393-433, 518-551)/IL12Rb1(622-662) | IL2Rbsmall (339-379, 393-433, 518-551) | IL12Rb1 (622-662) |
| IL12Rb1(622-662)/IL2Rb(333-551) | IL12Rb1 (622-662) | IL2Rb(333-551) |
| IL12Rb1(622-662)/IL2Rbsmall(393-433, 518-551) | IL12Rb1 (622-662) | IL2Rbsmall (393-433, 518-551) |
| IL12Rb1(622-662)/IL2Rbsmall(339-379, 393-433, 518-551) | IL12Rb1 (622-662) | IL2Rbsmall (339-379, 393-433, 518-551) |
| IL2Rb(333-551)/IL12Rb2(714-862) | IL2Rb(333-551) | IL12Rb2 (714-862) |
| IL2Rbsmall(393-433, 518-551)/IL12Rb2(714-862) | IL2Rbsmall (393-433, 518-551) | IL12Rb2 (714-862) |
| IL2Rbsmall(339-379, 393-433, 518-551)/IL12Rb2(714-862) | IL2Rbsmall (339-379, 393-433, 518-551) | IL12Rb2 (714-862) |
| IL2Rb(333-551)/IL12Rb2(775-825) | IL2Rb(333-551) | IL12Rb2 (775-825) |
| IL2Rbsmall(393-433, 518-551)/IL12Rb2(775-825) | IL2Rbsmall (393-433, 518-551) | IL12Rb2 (775-825) |
| IL2Rbsmall(339-379, 393-433, 518-551)/IL12Rb2(775-825) | IL2Rbsmall (339-379, 393-433, 518-551) | IL12Rb2 (775-825) |
| IL12Rb2(714-862)/IL2Rb(333-551) | IL12Rb2 (714-862) | IL2Rb(333-551) |
| IL12Rb2(714-862)/IL2Rbsmall(393-433, 518-551) | IL12Rb2 (714-862) | IL2Rbsmall (393-433, 518-551) |

TABLE 2c-continued

| Examples of CACCRs with dual outputs | | |
|---|---|---|
| Dual output STAT-recruiting domain | Membrane proximal | Membrane distal |
| IL12Rb2(714-862)/IL2Rbsmall(339-379, 393-433, 518-551) | IL12Rb2 (714-862) | IL2Rbsmall (339-379, 393-433, 518-551) |
| IL12Rb2(775-825)/IL2Rb(333-551) | IL12Rb2 (775-825) | IL2Rb(333-551) |
| IL12Rb2(775-825)/IL2Rbsmall(393-433, 518-551) | IL12Rb2 (775-825) | IL2Rbsmall (393-433, 518-551) |
| IL12Rb2(775-825)/IL2Rbsmall(339-379, 393-433, 518-551) | IL12Rb2 (775-825) | IL2Rbsmall (339-379, 393-433, 518-551) |
| IL7Ra (316-459)/IL21R(322-538) | IL7Ra (316-459) | IL21R(322-538) |
| IL7Ra (376-416, 424-459, Y456F)/IL21R(322-538) | IL7Ra (376-416, 424-459, Y456F) | IL21R(322-538) |
| IL21R(322-538)/IL7Ra (316-459) | IL21R(322-538) | IL7Ra (316-459) |
| IL21R(322-538)/IL7Ra(376-416, 424-459, Y456F) | IL21R(322-538) | IL7Ra (376-416, 424-459, Y456F) |
| IL7Ra (316-459)/IL12Rb1(622-662) | IL7Ra (316-459) | IL12Rb1 (622-662) |
| IL7Ra (376-416, 424-459, Y456F)/IL12Rb1(622-662) | IL7Ra (376-416, 424-459, Y456F) | IL12Rb1 (622-662) |
| IL7Ra (316-459)/IL12Rb2(714-862) | IL7Ra (316-459) | IL12Rb2 (714-862) |
| IL7Ra (376-416, 424-459, Y456F)/IL12Rb2(714-862) | IL7Ra (376-416, 424-459, Y456F) | IL12Rb2 (714-862) |
| IL7Ra (316-459)/IL12Rb2(775-825) | IL7Ra (316-459) | IL12Rb2 (775-825) |
| IL7Ra (376-416, 424-459, Y456F)/IL12Rb2(775-825) | IL7Ra (376-416, 424-459, Y456F) | IL12Rb2 (775-825) |
| IL12Rb1(622-662)/IL7Ra (316-459) | IL12Rb1 (622-662) | IL7Ra (316-459) |
| IL12Rb1(622-662)/IL7Ra (376-416, 424-459, Y456F) | IL12Rb1 (622-662) | IL7Ra (376-416, 424-459, Y456F) |
| IL12Rb2(714-862)/IL7Ra (316-459) | IL12Rb2 (714-862) | IL7Ra (316-459) |
| IL12Rb2(714-862)/IL7Ra (376-416, 424-459, Y456F) | IL12Rb2 (714-862) | IL7Ra (376-416, 424-459, Y456F) |
| IL12Rb2(775-825)/IL7Ra (316-459) | IL12Rb2 (775-825) | IL7Ra (316-459) |
| IL12Rb2(775-825)/IL7Ra (376-416, 424-459, Y456F) | IL12Rb2 (775-825) | IL7Ra (376-416, 424-459, Y456F) |
| IL7Ra (316-459)/IL2Rb(333-551) | IL7Ra (316-459) | IL2Rb(333-551) |
| IL7Ra (376-416, 424-459, Y456F)/IL2Rb(333-551) | IL7Ra (376-416, 424-459, Y456F) | IL2Rb(333-551) |
| IL7Ra (316-459)/IL2Rbsmall(393-433, 518-551) | IL7Ra (316-459) | IL2Rbsmall (393-433, 518-551) |
| IL7Ra (376-416, 424-459, Y456F)/IL2Rbsmall(393-433, 518-551) | IL7Ra (376-416, 424-459, Y456F) | IL2Rbsmall (393-433, 518-551) |
| IL7Ra (316-459)/IL2Rbsmall(339-379, 393-433, 518-551) | IL7Ra (316-459) | IL2Rbsmall (339-379, 393-433, 518-551) |
| IL7Ra (376-416, 424-459, Y456F)/IL2Rbsmall(339-379, 393-433, 518-551) | IL7Ra (376-416, 424-459, Y456F) | IL2Rbsmall (339-379, 393-433, 518-551) |

TABLE 2c-continued

Examples of CACCRs with dual outputs

| Dual output STAT-recruiting domain | Membrane proximal | Membrane distal |
| --- | --- | --- |
| IL2Rb(333-551)/IL7Ra (316-459) | IL2Rb(333-551) | IL7Ra (316-459) |
| IL2Rb(333-551)/ IL7Ra (376-416, 424-459, Y456F) | IL2Rb(333-551) | IL7Ra (376-416, 424-459, Y456F) |
| IL2Rbsmall(393-433, 518-551)/ IL7Ra (316-459) | IL2Rbsmall (393-433, 518-551) | IL7Ra (316-459) |
| IL2Rbsmall(393-433, 518-551)/ IL7Ra (376-416, 424-459, Y456F) | IL2Rbsmall (393-433, 518-551) | IL7Ra (376-416, 424-459, Y456F) |
| IL2Rbsmall(339-379, 393-433, 518-551)/IL7Ra (316-459) | IL2Rbsmall (339-379, 393-433, 518-551) | IL7Ra (316-459) |
| IL2Rbsmall(339-379, 393-433, 518-551)/ IL7Ra (376-416, 424-459, Y456F) | IL2Rbsmall (339-379, 393-433, 518-551) | IL7Ra (376-416, 424-459, Y456F) |
| IL12Rb1(622-662)/IL21R (322-538) | IL12Rb1 (622-662) | IL21R(322-538) |
| IL12Rb2(714-862)/IL21R (322-538) | IL12Rb2 (714-862) | IL21R(322-538) |
| IL12Rb2(775-825)/IL21R (322-538) | IL12Rb2 (775-825) | IL21R(322-538) |
| IL21R (322-538)/IL12Rb1(622-662) | IL21R(322-538) | IL12Rb1 (622-662) |
| IL21R (322-538)/IL12Rb2(714-862) | IL21R(322-538) | IL12Rb2 (714-862) |
| IL21R (322-538)/IL12Rb2(775-825) | IL21R(322-538) | IL12Rb2 (775-825) |

Without being bound to theory or mechanism, in some embodiments, a JAK-protein (JAK1, JAK2, JAK3, or TYK2) is bound to a dimerized CACCR of the disclosure. The two bound JAK-proteins are activated, which are capable of phosphorylating tyrosine residues on the recruiting domain of the CACCR. The phosphorylated recruiting domains are then capable of binding the recruited proteins (e.g. a phosphorylated STAT-recruiting domain binds a STAT-protein), which in turn effectuate transcription events in the nucleus.

D. Exemplary CACCRs

Table 3 shows exemplary CACCR sequences of the disclosure. The receptors may be expressed with a signal sequence, e.g. a CD8SS of sequence MALPVTALLL-PLALLLHAARP (SEQ ID NO: 89).

In some embodiments, the CACCR of the disclosure comprises any one of the sequences in Table 3. In some embodiments, the CACCR comprises an amino acid sequence that is at least about 800%, 85%, 90%, 95%, 96%, 98%, 99% or 100% identical to any one of the amino acid sequences of SEQ ID NO: 90-98, and 107-139. In some embodiments, the CACCR of the disclosure comprises any one of the amino acid sequences of SEQ ID NO: 90-100, 107-139, 143, and 180-186.

In some embodiments, the CACCR comprises the transmembrane domain and/or JAK-binding domain derived from the TPOR/MPLR receptor. In some embodiments, the CACCR of the disclosure comprises amino acids 478-582 of the naturally occurring TPOR/MPLR receptor of SEQ ID NO: 6. In some embodiments, the CACCR of the disclosure comprises the amino acid sequence that is at least about 80%, 85%, 90%, 95%, 96%, 98%, 99% or 100% identical to the amino acid sequence of SEQ ID NO: 17. In some embodiments, the CACCR of the disclosure comprises the amino acid sequence of SEQ ID NO: 17. In some embodiments, the CACCR further comprises a recruiting domain comprising the amino acid sequence of one or more of the receptor sequences presented in Table 2b. In some embodiments, the CACCR further comprises one or more recruiting domains selected from the group consisting of the STAT-recruiting domains from IL7Ra, IL2Rb, IL12Rb1, IL12Rb2, and IL21R. In some embodiments, the recruiting domain comprises the STAT-recruiting domain from IL7Ra. In some embodiments, the STAT-recruiting domain from IL7Ra comprises the amino acid sequence that is at least about 80%, 85%, 90%, 95%, 96%, 98%, 99% or 100% identical to the amino acid sequence of SEQ ID NO: 46, 68, 69, 70, 71 or 72. In some embodiments, the STAT-recruiting domain from IL7Ra comprises the amino acid sequence of SEQ ID NO: 46, 68, 69, 70, 71 or 72. In some embodiments, the recruiting domain comprises the STAT-recruiting domain from IL2Rb. In some embodiments, the STAT-recruiting domain from IL2Rb comprises the amino acid sequence that is at least about 80%, 85%, 90%, 95%, 96%, 98%, 99% or 100% identical to the amino acid sequence of SEQ ID NO: 47, 73, 74, 75, 76, 77, 78, 106, or 142. In some embodiments, the STAT-recruiting domain from IL2Rb comprises the amino acid sequence of SEQ ID NO: 47, 73, 74, 75, 76, 77, 78, 106 or 142. In some embodiments, the recruiting domain comprises the STAT-recruiting domain from IL12Rb1 or IL12Rb2. In some embodiments, the STAT-recruiting domain from IL12Rb1 or IL12Rb2 comprises the amino acid sequence that is at least about 80%, 85%, 90%, 95%, 96%, 98%, 99% or 100% identical to the amino acid sequence of SEQ ID NO: 67, 86, or 87. In some embodiments, the STAT-recruiting domain from IL12Rb1 or IL12Rb2 comprises the amino acid sequence of SEQ ID NO: 67, 86, or 87. In some embodiments, the recruiting domain comprises the STAT-recruiting domain from IL21R. In some embodiments, the STAT-recruiting domain from IL21R comprises the amino acid sequence that is at least about 80%, 85%, 90%, 95%, 96%, 98%, 99% or 100% identical to the amino acid sequence of SEQ ID NO: 54. In some embodiments, the STAT-recruiting domain from IL21R comprises the amino acid sequence of SEQ ID NO: 54. In some embodiments, the CACCR comprises one or more recruiting domains presented in Table 2c. In some embodiments, the recruiting domains comprises the STAT-recruiting domains from IL7Ra and IL2Rb. In some embodiments, the recruiting domain comprises the STAT-recruiting domains from IL7Ra and IL12Rb1. In some embodiments, the recruiting domain comprises the STAT-recruiting domains form IL7Ra and IL12Rb2. In some embodiments, the CACCR comprises the amino acid sequence that is at least about 80%, 85%, 90%, 95%, 96%, 98%, 99% or 100% identical to the amino acid sequence of SEQ ID NO: 90 or 119, with or without a signal sequence. In some embodiments, the CACCR comprises the amino acid sequence of SEQ ID NO: 90 or 119, with or without a signal sequence.

In some embodiments, the CACCR of the disclosure comprises the transmembrane domain and/or JAK-binding domain from a TPOR/MPLR receptor that comprises one or more amino acid substitutions at H499, S505, G509 or W515. In some embodiments, the TPOR/MPLR receptor comprises a H499L substitution. In some embodiments, the TPOR/MPLR receptor comprises a S505N substitution. In some embodiments, the TPOR/MPLR receptor comprises a G509N substitution. In some embodiments, the TPOR/MPLR receptor comprises a W515K substitution. In some embodiments, the CACCR further comprises a recruiting domain comprising the amino acid sequence of one or more of the receptor sequences presented in Table 2b. In some embodiments, the CACCR further comprises one or more recruiting domains selected from the group consisting of the STAT-recruiting domains from IL7Ra, IL2Rb, IL12Rb1, IL12Rb2, and IL21R. In some embodiments, the recruiting domain comprises the STAT-recruiting domain from IL7Ra. In some embodiments, the STAT-recruiting domain from IL7Ra comprises the amino acid sequence that is at least about 80%, 85%, 90%, 95%, 96%, 98%, 99% or 100% identical to the amino acid sequence of SEQ ID NO: 46, 68, 69, 70, 71 or 72. In some embodiments, the STAT-recruiting domain from IL7Ra comprises the amino acid sequence of SEQ ID NO: 46, 68, 69, 70, 71 or 72. In some embodiments, the recruiting domain comprises the STAT-recruiting domain from IL2Rb. In some embodiments, the STAT-recruiting domain from IL2Rb comprises the amino acid sequence that is at least about 80%, 85%, 90%, 95%, 96%, 98%, 99% or 100% identical to the amino acid sequence of SEQ ID NO: 47, 73, 74, 75, 76, 77, 78, 106, or 142. In some embodiments, the STAT-recruiting domain from IL2Rb comprises the amino acid sequence of SEQ ID NO: 47, 73, 74, 75, 76, 77, 78, 106 or 142. In some embodiments, the recruiting domain comprises the STAT-recruiting domain from IL12Rb1 or IL12Rb2. In some embodiments, the STAT-recruiting domain from IL12Rb1 or IL12Rb2 comprises the amino acid sequence that is at least about 80%, 85%, 90%, 95%, 96%, 98%, 99% or 100% identical to the amino acid sequence of SEQ ID NO: 67, 86, or 87. In some embodiments, the STAT-recruiting domain from IL12Rb1 or IL12Rb2 comprises the amino acid sequence of SEQ ID NO: 67, 86, or 87. In some embodiments, the recruiting domain comprises the STAT-recruiting domain from IL21R. In some embodiments, the STAT-recruiting domain from IL21R comprises the amino acid sequence that is at least about 80%, 85%, 90%, 95%, 96%, 98%, 99% or 100% identical to the amino acid sequence of SEQ ID NO: 54. In some embodiments, the STAT-recruiting domain from IL21R comprises the amino acid sequence of SEQ ID NO: 54. In some embodiments, the CACCR comprises one or more recruiting domains presented in Table 2c. In some embodiments, the recruiting domains comprises the STAT-recruiting domains from IL7Ra and IL2Rb. In some embodiments, the recruiting domain comprises the STAT-recruiting domains from IL7Ra and IL12Rb1. In some embodiments, the recruiting domain comprises the STAT-recruiting domains form IL7Ra and IL12Rb2. In some embodiments, the CACCR comprises the amino acid sequence that is at least about 80%, 85%, 90%, 95%, 96%, 98%, 99% or 100% identical to the amino acid sequence of SEQ ID NO: 92, 94, 121, or 123, with or without a signal sequence. In some embodiments, the CACCR comprises the amino acid sequence of SEQ ID NO: 92, 94, 121, or 123, with or without a signal sequence.

In some embodiments, the CACCR of the disclosure comprises the transmembrane domain and/or JAK-binding domain from a TPOR/MPLR receptor that comprises the H499L and S505N substitutions. In some embodiments, the CACCR further comprises a recruiting domain comprising the amino acid sequence of one or more of the receptor sequences presented in Table 2b. In some embodiments, the CACCR further comprises one or more recruiting domains selected from the group consisting of the STAT-recruiting domains from IL7Ra, IL2Rb, IL12Rb1, IL12Rb2, and IL21R. In some embodiments, the recruiting domain comprises the STAT-recruiting domain from IL7Ra. In some embodiments, the STAT-recruiting domain from IL7Ra comprises the amino acid sequence that is at least about 80%, 85%, 90%, 95%, 96%, 98%, 99% or 100% identical to the amino acid sequence of SEQ ID NO: 46, 68, 69, 70, 71 or 72. In some embodiments, the STAT-recruiting domain from IL7Ra comprises the amino acid sequence of SEQ ID NO: 46, 68, 69, 70, 71 or 72. In some embodiments, the recruiting domain comprises the STAT-recruiting domain from IL2Rb. In some embodiments, the STAT-recruiting domain from IL2Rb comprises the amino acid sequence that is at least about 80%, 85%, 90%, 95%, 96%, 98%, 99% or 100% identical to the amino acid sequence of SEQ ID NO: 47, 73, 74, 75, 76, 77, 78, 106, or 142. In some embodiments, the STAT-recruiting domain from IL2Rb comprises the amino acid sequence of SEQ ID NO: 47, 73, 74, 75, 76, 77, 78, 106 or 142. In some embodiments, the recruiting domain comprises the STAT-recruiting domain from IL12Rb1 or IL12Rb2. In some embodiments, the STAT-recruiting domain from IL12Rb1 or IL12Rb2 comprises the amino acid sequence that is at least about 80%, 85%, 90%, 95%, 96%, 98%, 99% or 100% identical to the amino acid sequence of SEQ ID NO: 67, 86, or 87. In some embodiments, the STAT-recruiting domain from IL12Rb1 or IL12Rb2 comprises the amino acid sequence of SEQ ID NO: 67, 86, or 87. In some embodiments, the recruiting domain comprises the STAT-recruiting domain from IL21R. In some embodiments, the STAT-recruiting domain from IL21R comprises the amino acid sequence that is at least about 80%, 85%, 90%, 95%, 96%, 98%, 99% or 100% identical to the amino acid sequence of SEQ ID NO: 54. In some embodiments, the STAT-recruiting domain from IL21R comprises the amino acid sequence of SEQ ID NO: 54. In some embodiments, the CACCR comprises one or more recruiting domains presented in Table 2c. In some embodiments, the recruiting domains comprises the STAT-recruiting domains from IL7Ra and IL2Rb. In some embodiments, the recruiting domain comprises the STAT-recruiting domains from IL7Ra and IL12Rb1. In some embodiments, the recruiting domain comprises the STAT-recruiting domains form IL7Ra and IL12Rb2. In some embodiments, the CACCR comprises the amino acid sequence that is at least about 80%, 85%, 90%, 95%, 96%, 98%, 99% or 100% identical to the amino acid sequence of SEQ ID NO: 91, 98, 120, or 127, with or without a signal sequence. In some embodiments, the CACCR comprises the amino acid sequence of SEQ ID NO: 91, 98, 120, or 127, with or without a signal sequence.

In some embodiments, the CACCR of the disclosure comprises the transmembrane domain and/or JAK-binding domain from a TPOR/MPLR receptor that comprises the H499L and W515K substitutions or the H499L and G509N substitutions. In some embodiments, the CACCR further comprises a recruiting domain comprising the amino acid sequence of one or more of the receptor sequences presented in Table 2b. In some embodiments, the CACCR further comprises one or more recruiting domains selected from the group consisting of the STAT-recruiting domains from IL7Ra, IL2Rb, IL12Rb1, IL12Rb2, and IL21R. In some embodiments, the recruiting domain comprises the STAT-recruiting domain from IL7Ra. In some embodiments, the STAT-recruiting domain from IL7Ra comprises the amino acid sequence that is at least about 80%, 85%, 90%, 95%, 96%, 98%, 99% or 100% identical to the amino acid sequence of SEQ ID NO: 46, 68, 69, 70, 71 or 72. In some embodiments, the STAT-recruiting domain from IL7Ra comprises the amino acid sequence of SEQ ID NO: 46, 68, 69, 70, 71 or 72. In some embodiments, the recruiting domain comprises the STAT-recruiting domain from IL2Rb.

In some embodiments, the STAT-recruiting domain from IL2Rb comprises the amino acid sequence that is at least about 80%, 85%, 90%, 95%, 96%, 98%, 99% or 100% identical to the amino acid sequence of SEQ ID NO: 47, 73, 74, 75, 76, 77, 78, 106, or 142. In some embodiments, the STAT-recruiting domain from IL2Rb comprises the amino acid sequence of SEQ ID NO: 47, 73, 74, 75, 76, 77, 78, 106 or 142. In some embodiments, the recruiting domain comprises the STAT-recruiting domain from IL12Rb1 or IL12Rb2. In some embodiments, the STAT-recruiting domain from IL12Rb1 or IL12Rb2 comprises the amino acid sequence that is at least about 80%, 85%, 90%, 95%, 96%, 98%, 99% or 100% identical to the amino acid sequence of SEQ ID NO: 67, 86, or 87. In some embodiments, the STAT-recruiting domain from IL12Rb1 or IL12Rb2 comprises the amino acid sequence of SEQ ID NO: 67, 86, or 87. In some embodiments, the recruiting domain comprises the STAT-recruiting domain from IL21R. In some embodiments, the STAT-recruiting domain from IL21R comprises the amino acid sequence that is at least about 80%, 85%, 90%, 95%, 96%, 98%, 99% or 100% identical to the amino acid sequence of SEQ ID NO: 54. In some embodiments, the STAT-recruiting domain from IL21R comprises the amino acid sequence of SEQ ID NO: 54. In some embodiments, the CACCR comprises one or more recruiting domains presented in Table 2c. In some embodiments, the recruiting domains comprises the STAT-recruiting domains from IL7Ra and IL2Rb. In some embodiments, the recruiting domain comprises the STAT-recruiting domains from IL7Ra and IL12Rb1. In some embodiments, the recruiting domain comprises the STAT-recruiting domains form IL7Ra and IL12Rb2. In some embodiments, the CACCR comprises the amino acid sequence that is at least about 80%, 85%, 90%, 95%, 96%, 98%, 99% or 100% identical to the amino acid sequence of SEQ ID NO: 97, or 126, with or without a signal sequence. In some embodiments, the CACCR comprises the amino acid sequence of SEQ ID NO: 97, or 126, with or without a signal sequence.

In some embodiments, the CACCR of the disclosure comprises the transmembrane domain and/or JAK-binding domain from a TPOR/MPLR receptor that comprises the S505N and W515K substitutions. In some embodiments, the CACCR further comprises a recruiting domain comprising the amino acid sequence of one or more of the receptor sequences presented in Table 2b. In some embodiments, the CACCR further comprises one or more recruiting domains selected from the group consisting of the STAT-recruiting domains from IL7Ra, IL2Rb, IL12Rb1, IL12Rb2, and IL21R. In some embodiments, the recruiting domain comprises the STAT-recruiting domain from IL7Ra. In some embodiments, the STAT-recruiting domain from IL7Ra comprises the amino acid sequence that is at least about 80%, 85%, 90%, 95%, 96%, 98%, 99% or 100% identical to the amino acid sequence of SEQ ID NO: 46, 68, 69, 70, 71 or 72. In some embodiments, the STAT-recruiting domain from IL7Ra comprises the amino acid sequence of SEQ ID NO: 46, 68, 69, 70, 71 or 72. In some embodiments, the recruiting domain comprises the STAT-recruiting domain from IL2Rb. In some embodiments, the STAT-recruiting domain from IL2Rb comprises the amino acid sequence that is at least about 80%, 85%, 90%, 95%, 96%, 98%, 99% or 100% identical to the amino acid sequence of SEQ ID NO: 47, 73, 74, 75, 76, 77, 78, 106, or 142. In some embodiments, the STAT-recruiting domain from IL2Rb comprises the amino acid sequence of SEQ ID NO: 47, 73, 74, 75, 76, 77, 78, 106 or 142. In some embodiments, the recruiting domain comprises the STAT-recruiting domain from IL12Rb1 or IL12Rb2. In some embodiments, the STAT-recruiting domain from IL12Rb1 or IL12Rb2 comprises the amino acid sequence that is at least about 80%, 85%, 90%, 95%, 96%, 98%, 99% or 100% identical to the amino acid sequence of SEQ ID NO: 67, 86, or 87. In some embodiments, the STAT-recruiting domain from IL12Rb1 or IL12Rb2 comprises the amino acid sequence of SEQ ID NO: 67, 86, or 87. In some embodiments, the recruiting domain comprises the STAT-recruiting domain from IL21R. In some embodiments, the STAT-recruiting domain from IL21R comprises the amino acid sequence that is at least about 80%, 85%, 90%, 95%, 96%, 98%, 99% or 100% identical to the amino acid sequence of SEQ ID NO: 54. In some embodiments, the STAT-recruiting domain from IL21R comprises the amino acid sequence of SEQ ID NO: 54. In some embodiments, the CACCR comprises one or more recruiting domains presented in Table 2c. In some embodiments, the recruiting domains comprises the STAT-recruiting domains from IL7Ra and IL2Rb. In some embodiments, the recruiting domain comprises the STAT-recruiting domains from IL7Ra and IL12Rb1. In some embodiments, the recruiting domain comprises the STAT-recruiting domains form IL7Ra and IL12Rb2. In some embodiments, the CACCR comprises the amino acid sequence that is at least about 80%, 85%, 90%, 95%, 96%, 98%, 99% or 100% identical to the amino acid sequence of SEQ ID NO: 96, 107, 109, 111, 113, 115, 117, 125, 128, 129, 132, 134, 136, or 138, with or without a signal sequence. In some embodiments, the CACCR comprises the amino acid sequence of SEQ ID NO: 96, 107, 109, 111, 113, 115, 117, 125, 128, 129, 132, 134, 136, or 138, with or without a signal sequence.

In some embodiments, the CACCR of the disclosure comprises the transmembrane domain and/or JAK-binding domain from a TPOR/MPLR receptor that comprises the H499L and W515K substitutions. In some embodiments, the CACCR further comprises a recruiting domain comprising the amino acid sequence of one or more of the receptor sequences presented in Table 2b. In some embodiments, the CACCR further comprises one or more recruiting domains selected from the group consisting of the STAT-recruiting domains from IL7Ra, IL2Rb, IL12Rb1, IL12Rb2, and IL21R. In some embodiments, the recruiting domain comprises the STAT-recruiting domain from IL7Ra. In some embodiments, the STAT-recruiting domain from IL7Ra comprises the amino acid sequence that is at least about 80%, 85%, 90%, 95%, 96%, 98%, 99% or 100% identical to the amino acid sequence of SEQ ID NO: 46, 68, 69, 70, 71 or 72. In some embodiments, the STAT-recruiting domain from IL7Ra comprises the amino acid sequence of SEQ ID NO: 46, 68, 69, 70, 71 or 72. In some embodiments, the recruiting domain comprises the STAT-recruiting domain from IL2Rb. In some embodiments, the STAT-recruiting domain from IL2Rb comprises the amino acid sequence that is at least about 80%, 85%, 90%, 95%, 96%, 98%, 99% or 100% identical to the amino acid sequence of SEQ ID NO: 47, 73, 74, 75, 76, 77, 78, 106, or 142. In some embodiments, the STAT-recruiting domain from IL2Rb comprises the amino acid sequence of SEQ ID NO: 47, 73, 74, 75, 76, 77, 78, 106 or 142. In some embodiments, the recruiting domain comprises the STAT-recruiting domain from IL12Rb1 or IL12Rb2. In some embodiments, the STAT-recruiting domain from IL12Rb1 or IL12Rb2 comprises the amino acid sequence that is at least about 80%, 85%, 90%, 95%, 96%, 98%, 99% or 100% identical to the amino acid sequence of SEQ ID NO: 67, 86, or 87. In some embodiments, the STAT-recruiting domain from IL12Rb1 or IL12Rb2 comprises the amino acid sequence of SEQ ID NO: 67, 86, or 87. In some embodiments, the recruiting domain comprises the STAT-recruiting domain from IL21R. In some embodiments, the STAT-recruiting domain from IL21R comprises the amino acid sequence that is at least about 80%, 85%, 90%, 95%, 96%, 98%, 99% or 100% identical to the amino acid sequence of SEQ ID NO: 54. In some embodiments, the STAT-recruiting domain from IL21R comprises the amino acid sequence of SEQ ID NO: 54. In some embodiments, the CACCR comprises one or more recruiting domains presented in Table 2c. In some embodiments, the recruiting domains comprises the STAT-recruiting domains from IL7Ra and IL2Rb. In some embodiments, the recruiting domain comprises the STAT-recruiting domains from IL7Ra and IL12Rb1. In some embodiments, the recruiting domain comprises the STAT-recruiting domains form IL7Ra and IL12Rb2. In some embodiments, the CACCR comprises the amino acid sequence that is at least about 80%, 85%, 90%, 95%, 96%, 98%, 99% or 100% identical to the amino acid sequence of SEQ ID NO: 93, with or without a signal sequence. In some embodiments, the CACCR comprises the amino acid sequence of SEQ ID NO: 93, with or without a signal sequence.

In some embodiments, the CACCR of the disclosure comprises the transmembrane domain and/or JAK-binding domain from a TPOR/MPLR receptor that comprises the H499L, S505N and W515K substitutions. In some embodiments, the CACCR further comprises a recruiting domain comprising the amino acid sequence of one or more of the receptor sequences presented in Table 2b. In some embodiments, the CACCR further comprises one or more recruiting domains selected from the group consisting of the STAT-recruiting domains from IL7Ra, IL2Rb, IL12Rb1, IL12Rb2, and IL21R. In some embodiments, the recruiting domain comprises the STAT-recruiting domain from IL7Ra. In some embodiments, the STAT-recruiting domain from IL7Ra comprises the amino acid sequence that is at least about 80%, 85%, 90%, 95%, 96%, 98%, 99% or 100% identical to the amino acid sequence of SEQ ID NO: 46, 68, 69, 70, 71 or 72. In some embodiments, the STAT-recruiting domain from IL7Ra comprises the amino acid sequence of SEQ ID NO: 46, 68, 69, 70, 71 or 72. In some embodiments, the recruiting domain comprises the STAT-recruiting domain from IL2Rb. In some embodiments, the STAT-recruiting domain from IL2Rb comprises the amino acid sequence that is at least about 80%, 85%, 90%, 95%, 96%, 98%, 99% or 100% identical to the amino acid sequence of SEQ ID NO: 47, 73, 74, 75, 76, 77, 78, 106, or 142. In some embodiments, the STAT-recruiting domain from IL2Rb comprises the amino acid sequence of SEQ ID NO: 47, 73, 74, 75, 76, 77, 78, 106 or 142. In some embodiments, the recruiting domain comprises the STAT-recruiting domain from IL12Rb1 or IL12Rb2. In some embodiments, the STAT-recruiting domain from IL12Rb1 or IL12Rb2 comprises the amino acid sequence that is at least about 80%, 85%, 90%, 95%, 96%, 98%, 99% or 100% identical to the amino acid sequence of SEQ ID NO: 67, 86, or 87. In some embodiments, the STAT-recruiting domain from IL12Rb1 or IL12Rb2 comprises the amino acid sequence of SEQ ID NO: 67, 86, or 87. In some embodiments, the recruiting domain comprises the STAT-recruiting domain from IL21R. In some embodiments, the STAT-recruiting domain from IL21R comprises the amino acid sequence that is at least about 80%, 85%, 90%, 95%, 96%, 98%, 99% or 100% identical to the amino acid sequence of SEQ ID NO: 54. In some embodiments, the STAT-recruiting domain from IL21R comprises the amino acid sequence of SEQ ID NO: 54. In some embodiments, the CACCR comprises one or more recruiting domains presented in Table 2c. In some embodiments, the recruiting domains comprises the STAT-recruiting domains from IL7Ra and IL2Rb. In some embodiments, the recruiting domain comprises the STAT-recruiting domains from IL7Ra and IL12Rb1. In some embodiments, the recruiting domain comprises the STAT-recruiting domains form IL7Ra and IL12Rb2. In some embodiments, the CACCR comprises the amino acid sequence that is at least about 80%, 85%, 90%, 95%, 96%, 98%, 99% or 100% identical to the amino acid sequence of SEQ ID NO: 95, 108, 110, 112, 114, 116, 118, 124, 130, 131, 133, 135, 137, 139, 180, 181, 182, 184, 185, or 186, with or without a signal sequence. In some embodiments, the signal sequence comprises the amino acid sequence of SEQ ID NO: 89. In some embodiments, the CACCR comprises the amino acid sequence of SEQ ID NO: 95, 108, 110, 112, 114, 116, 118, 124, 130, 131, 133, 135, 137, 139, 180, 181, 182, 184, 185, or 186, with or without a signal sequence. In some embodiments, the signal sequence comprises the amino acid sequence of SEQ ID NO: 89. In some embodiments, the CACCR comprises an extra-cellular ligand binding domain. In some embodiments, the CACCR does not comprise an extra-cellular ligand binding domain. CACCRs are described in co-pending application US2020/0291090, which is hereby incorporated by reference in its entirety.

TABLE 3

Exemplary CACCR sequences

| Receptor | Amino acid sequence | SEQ ID NO: |
| --- | --- | --- |
| TPOR/MPLR(478-582).IL7Ra(316-459) | SDPTRVETATETAWISLVTALHLVLGLSAVLGLL LLRWQFPAHYRRLRHALWPSLPDLHRVLGQYLR DTAALSPPKATVSDTCEEVEPSLLEILPKSSERTPL PLARDEVEGFLQDTFPQQLEESEKQRLGGDVQSP NCPSEDVVITPESFGRDSSLTCLAGNVSACDAPIL SSSRSLDCRESGKNGPHVYQDLLLSLGTTNSTLPP PFSLQSGILTLNPVAQGQPILTSLGSNQEEAYVTM SSFYQNQ | 90 |
| TPOR/MPLR(478-582; H499L,S505N).IL7Ra (316-459) | SDPTRVETATETAWISLVTALLLVLGLNAVLGLL LLRWQFPAHYRRLRHALWPSLPDLHRVLGQYLR DTAALSPPKATVSDTCEEVEPSLLEILPKSSERTPL PLARDEVEGFLQDTFPQQLEESEKQRLGGDVQSP NCPSEDVVITPESFGRDSSLTCLAGNVSACDAPIL SSSRSLDCRESGKNGPHVYQDLLLSLGTTNSTLPP PFSLQSGILTLNPVAQGQPILTSLGSNQEEAYVTM SSFYQNQ | 91 |

TABLE 3-continued

Exemplary CACCR sequences

| Receptor | Amino acid sequence | SEQ ID NO: |
|---|---|---|
| TPOR/MPLR(478-582;S505N).IL7Ra (316-459) | SDPTRVETATETAWISLVTALHLVLGLNAVLGLL LLRWQFPAHYRRLRHALWPSLPDLHRVLGQYLR DTAALSPPKATVSDTCEEVEPSLLEILPKSSERTPL PLARDEVEGFLQDTFPQQLEESEKQRLGGDVQSP NCPSEDVVITPESFGRDSSLTCLAGNVSACDAPIL SSSRSLDCRESGKNGPHVYQDLLLSLGTTNSTLPP PFSLQSGILTLNPVAQGQPILTSLGSNQEEAYVTM SSFYQNQ | 92 |
| TPOR/MPLR(478-582; H499L,W515K).IL7Ra (316-459) | SDPTRVETATETAWISLVTALLLVLGLSAVLGLL LLRKQFPAHYRRLRHALWPSLPDLHRVLGQYLR DTAALSPPKATVSDTCEEVEPSLLEILPKSSERTPL PLARDEVEGFLQDTFPQQLEESEKQRLGGDVQSP NCPSEDVVITPESFGRDSSLTCLAGNVSACDAPIL SSSRSLDCRESGKNGPHVYQDLLLSLGTTNSTLPP PFSLQSGILTLNPVAQGQPILTSLGSNQEEAYVTM SSFYQNQ | 93 |
| TPOR/MPLR(478-582;W515K).IL7Ra (316-459) | SDPTRVETATETAWISLVTALHLVLGLSAVLGLL LLRKQFPAHYRRLRHALWPSLPDLHRVLGQYLR DTAALSPPKATVSDTCEEVEPSLLEILPKSSERTPL PLARDEVEGFLQDTFPQQLEESEKQRLGGDVQSP NCPSEDVVITPESFGRDSSLTCLAGNVSACDAPIL SSSRSLDCRESGKNGPHVYQDLLLSLGTTNSTLPP PFSLQSGILTLNPVAQGQPILTSLGSNQEEAYVTM SSFYQNQ | 94 |
| TPOR/MPLR(478-582;H499L,S505N, W515K).IL7Ra (316-459) | SDPTRVETATETAWISLVTALLLVLGLNAVLGLL LLRKQFPAHYRRLRHALWPSLPDLHRVLGQYLR DTAALSPPKATVSDTCEEVEPSLLEILPKSSERTPL PLARDEVEGFLQDTFPQQLEESEKQRLGGDVQSP NCPSEDVVITPESFGRDSSLTCLAGNVSACDAPIL SSSRSLDCRESGKNGPHVYQDLLLSLGTTNSTLPP PFSLQSGILTLNPVAQGQPILTSLGSNQEEAYVTM SSFYQNQ | 95 |
| TPOR/MPLR(478-582;S505N, W515K).IL7Ra (316-459) | SDPTRVETATETAWISLVTALHLVLGLNAVLGLL LLRKQFPAHYRRLRHALWPSLPDLHRVLGQYLR DTAALSPPKATVSDTCEEVEPSLLEILPKSSERTPL PLARDEVEGFLQDTFPQQLEESEKQRLGGDVQSP NCPSEDVVITPESFGRDSSLTCLAGNVSACDAPIL SSSRSLDCRESGKNGPHVYQDLLLSLGTTNSTLPP PFSLQSGILTLNPVAQGQPILTSLGSNQEEAYVTM SSFYQNQ | 96 |
| TPOR/MPLR(478-582;H499L, G509N).IL7Ra (316-459) | SDPTRVETATETAWISLVTALLLVLGLSAVLNLL LLRWQFPAHYRRLRHALWPSLPDLHRVLGQYLR DTAALSPPKATVSDTCEEVEPSLLEILPKSSERTPL PLARDEVEGFLQDTFPQQLEESEKQRLGGDVQSP NCPSEDVVITPESFGRDSSLTCLAGNVSACDAPIL SSSRSLDCRESGKNGPHVYQDLLLSLGTTNSTLPP PFSLQSGILTLNPVAQGQPILTSLGSNQEEAYVTM SSFYQNQ | 97 |
| TPOR/MPLR(478-582; H499L,S505N).IL7Ra (316-459) | SDPTRVETATETAWISLVTALLLVLGLNAVLGLL LLRWQFPAHYRRLRHALWPSLPDLHRVLGQYLR DTAALSPPKATVSDTCEEVEPSLLEILPKSSERTPL PLARDEVEGFLQDTFPQQLEESEKQRLGGDVQSP NCPSEDVVITPESFGRDSSLTCLAGNVSACDAPIL SSSRSLDCRESGKNGPHVYQDLLLSLGTTNSTLPP PFSLQSGILTLNPVAQGQPILTSLGSNQEEAYVTM SSFYQNQ | 98 |
| TpoR(478-582; S505N,W515K).IL2Rb (393-433,518-551) | SDPTRVETATETAWISLVTALHLVLGLNAVLGLL LLRKQFPAHYRRLRHALWPSLPDLHRVLGQYLR DTAALSPPKATVSDTCEEVEPSLLEILPKSSERTPL PLLEDEGVAGAPTGSSPQPLQPLSGEDDAYCTFP SRDDLLLFSPSGQGEFRALNARLPLNTDAYLSLQ ELQGQDPTHLV | 99 |

TABLE 3-continued

Exemplary CACCR sequences

| Receptor | Amino acid sequence | SEQ ID NO: |
|---|---|---|
| TpoR(478-582;<br>H499L,S505N,<br>W515K).IL2Rb<br>(339-379,393-433,<br>518-551) | SDPTRVETATETAWISLVTALLLVLGLNAVLGLL<br>LLRKQFPAHYRRLRHALWPSLPDLHRVLGQYLR<br>DTAALSPPKATVSDTCEEVEPSLLEILPKSSERTPL<br>PLLEQQDKVPEPASLSSNHSLTSCFTNQGYFFFHL<br>PDALEIEACQDEGVAGAPTGSSPQPLQPLSGEDD<br>AYCTFPSRDDLLLFSPSGQGEFRALNARLPLNTD<br>AYLSLQELQGQDPTHLV | 100 |
| CD8SS-<br>TPOR/MPLR(478-<br>582;S505N,<br>W515K).IL12Rb2<br>(714-862) | MALPVTALLLPLALLLHAARPSDPTRVETATETA<br>WISLVTALHLVLGLNAVLGLLLLRKQFPAHYRR<br>LRHALWPSLPDLHRVLGQYLRDTAALSPPKATV<br>SDTCEEVEPSLLEILPKSSERTPLPLVTPVFRHPPC<br>SNWPQREKGIQGHQASEKDMMHSASSPPPPRAL<br>QAESRQLVDLYKVLESRGSDPKPENPACPWTVL<br>PAGDLPTHDGYLPSNIDDLPSHEAPLADSLEELEP<br>QHISLSVFPSSSLHPLTFSCGDKLTLDQLKMRCDS<br>LML | 107 |
| CD8SS-<br>TPOR/MPLR(478-<br>582;H499L,S505N,<br>W515K).IL12Rb2<br>(714-862) | MALPVTALLLPLALLLHAARPSDPTRVETATETA<br>WISLVTALLLVLGLNAVLGLLLLRKQFPAHYRR<br>LRHALWPSLPDLHRVLGQYLRDTAALSPPKATV<br>SDTCEEVEPSLLEILPKSSERTPLPLVTPVFRHPPC<br>SNWPQREKGIQGHQASEKDMMHSASSPPPPRAL<br>QAESRQLVDLYKVLESRGSDPKPENPACPWTVL<br>PAGDLPTHDGYLPSNIDDLPSHEAPLADSLEELEP<br>QHISLSVFPSSSLHPLTFSCGDKLTLDQLKMRCDS<br>LML | 108 |
| CD8SS-<br>TPOR/MPLR(478-<br>582;S505N,<br>W515K).IL12Rb2<br>(775-825) | MALPVTALLLPLALLLHAARPSDPTRVETATETA<br>WISLVTALHLVLGLNAVLGLLLLRKQFPAHYRR<br>LRHALWPSLPDLHRVLGQYLRDTAALSPPKATV<br>SDTCEEVEPSLLEILPKSSERTPLPLSDPKPENPAC<br>PWTVLPAGDLPTHDGYLPSNIDDLPSHEAPLADS<br>LEELEPQ | 109 |
| CD8SS-<br>TPOR/MPLR(478-<br>582;H499L,S505N,<br>W515K).IL12Rb2<br>(775-825) | MALPVTALLLPLALLLHAARPSDPTRVETATETA<br>WISLVTALLLVLGLNAVLGLLLLRKQFPAHYRR<br>LRHALWPSLPDLHRVLGQYLRDTAALSPPKATV<br>SDTCEEVEPSLLEILPKSSERTPLPLSDPKPENPAC<br>PWTVLPAGDLPTHDGYLPSNIDDLPSHEAPLADS<br>LEELEPQ | 110 |
| CD8SS-<br>TPOR/MPLR<br>(478-582;S505N,<br>W515K).IL2Rb<br>(333-551) | MALPVTALLLPLALLLHAARPSDPTRVETATETA<br>WISLVTALHLVLGLNAVLGLLLLRKQFPAHYRR<br>LRHALWPSLPDLHRVLGQYLRDTAALSPPKATV<br>SDTCEEVEPSLLEILPKSSERTPLPLVTQLLLQQD<br>KVPEPASLSSNHSLTSCFTNQGYFFFHLPDALEIE<br>ACQVYFTYDPYSEEDPDEGVAGAPTGSSPQPLQP<br>LSGEDDAYCTFPSRDDLLLFSPSLLGGPSPPSTAP<br>GGSGAGEERMPPSLQERVPRDWDPQPLGPPTPG<br>VPDLVDFQPPPELVLREAGEEVPDAGPREGVSFP<br>WSRPPGQGEFRALNARLPLNTDAYLSLQELQGQ<br>DPTHLV | 111 |
| CD8SS-<br>TPOR/MPLR(478-<br>582;H499L,S505N,<br>W515K).IL2Rb<br>(333-551) | MALPVTALLLPLALLLHAARPSDPTRVETATETA<br>WISLVTALLLVLGLNAVLGLLLLRKQFPAHYRR<br>LRHALWPSLPDLHRVLGQYLRDTAALSPPKATV<br>SDTCEEVEPSLLEILPKSSERTPLPLVTQLLLQQD<br>KVPEPASLSSNHSLTSCFTNQGYFFFHLPDALEIE<br>ACQVYFTYDPYSEEDPDEGVAGAPTGSSPQPLQP<br>LSGEDDAYCTFPSRDDLLLFSPSLLGGPSPPSTAP<br>GGSGAGEERMPPSLQERVPRDWDPQPLGPPTPG<br>VPDLVDFQPPPELVLREAGEEVPDAGPREGVSFP<br>WSRPPGQGEFRALNARLPLNTDAYLSLQELQGQ<br>DPTHLV | 112 |
| CD8SS-<br>TPOR/MPLR(478-<br>582;S505N,<br>W515K).IL2Rb<br>(393-433,518-551) | MALPVTALLLPLALLLHAARPSDPTRVETATETA<br>WISLVTALLLVLGLNAVLGLLLLRKQFPAHYRR<br>LRHALWPSLPDLHRVLGQYLRDTAALSPPKATV<br>SDTCEEVEPSLLEILPKSSERTPLPLDEGVAGAPT<br>GSSPQPLQPLSGEDDAYCTFPSRDDLLLFSPSGQG<br>EFRALNARLPLNTDAYLSLQELQGQDPTHLV | 113 |

TABLE 3-continued

Exemplary CACCR sequences

| Receptor | Amino acid sequence | SEQ ID NO: |
|---|---|---|
| CD8SS-TPOR/MPLR(478-582;H499L,S505N,W515K).IL2Rb(393-433,518-551) | MALPVTALLLPLALLLHAARPSDPTRVETATETA WISLVTALLLVLGLNAVLGLLLLRKQFPAHYRR LRHALWPSLPDLHRVLGQYLRDTAALSPPKATV SDTCEEVEPSLLEILPKSSERTPLPLDEGVAGAPT GSSPQPLQPLSGEDDAYCTFPSRDDLLLFSPSGQG EFRALNARLPLNTDAYLSLQELQGQDPTHLV | 114 |
| CD8SS-TPOR/MPLR(478-582;S505N,W515K).IL2Rb (339-379,393-433,518-551) | MALPVTALLLPLALLLHAARPSDPTRVETATETA WISLVTALHLVLGLNAVLGLLLLRKQFPAHYRR LRHALWPSLPDLHRVLGQYLRDTAALSPPKATV SDTCEEVEPSLLEILPKSSERTPLPLQQDKVPEPAS LSSNHSLTSCFTNQGYFFFHLPDALEIEACQDEGV AGAPTGSSPQPLQPLSGEDDAYCTFPSRDDLLLFS PSGQGEFRALNARLPLNTDAYLSLQELQGQDPTH LV | 115 |
| CD8SS-TPOR/MPLR(478-582;H499L,S505N,W515K).IL2Rb(339-379,393-433,518-551) | MALPVTALLLPLALLLHAARPSDPTRVETATETA WISLVTALLLVLGLNAVLGLLLLRKQFPAHYRR LRHALWPSLPDLHRVLGQYLRDTAALSPPKATV SDTCEEVEPSLLEILPKSSERTPLPLQQDKVPEPAS LSSNHSLTSCFTNQGYFFFHLPDALEIEACQDEGV AGAPTGSSPQPLQPLSGEDDAYCTFPSRDDLLLFS PSGQGEFRALNARLPLNTDAYLSLQELQGQDPTH LV | 116 |
| CD8SS-TPOR/MPLR(478-582;S505N,W515K).IL7Ra (316-459).IL12Rb2 (775-825) | MALPVTALLLPLALLLHAARPSDPTRVETATETA WISLVTALHLVLGLNAVLGLLLLRKQFPAHYRR LRHALWPSLPDLHRVLGQYLRDTAALSPPKATV SDTCEEVEPSLLEILPKSSERTPLPLARDEVEGFLQ DTFPQQLEESEKQRLGGDVQSPNCPSEDVVITPES FGRDSSLTCLAGNVSACDAPILSSSRSLDCRESGK NGPHVYQDLLLSLGTTNSTLPPPFSLQSGILTLNP VAQGQPILTSLGSNQEEAYVTMSSFYQNQSDPKP ENPACPWTVLPAGDLPTHDGYLPSNIDDLPSHEA PLADSLEELEPQ | 117 |
| CD8SS-TPOR/MPLR(478-582;H499L,S505N,W515K).IL7Ra (316-459).IL12Rb2 (775-825) | MALPVTALLLPLALLLHAARPSDPTRVETATETA WISLVTALLLVLGLNAVLGLLLLRKQFPAHYRR LRHALWPSLPDLHRVLGQYLRDTAALSPPKATV SDTCEEVEPSLLEILPKSSERTPLPLARDEVEGFLQ DTFPQQLEESEKQRLGGDVQSPNCPSEDVVITPES FGRDSSLTCLAGNVSACDAPILSSSRSLDCRESGK NGPHVYQDLLLSLGTTNSTLPPPFSLQSGILTLNP VAQGQPILTSLGSNQEEAYVTMSSFYQNQSDPKP ENPACPWTVLPAGDLPTHDGYLPSNIDDLPSHEA PLADSLEELEPQ | 118 |
| TPOR/MPLR(478-582).IL7Ra(316-459) | SDPTRVETATETAWISLVTALHLVLGLSAVLGLL LLRWQFPAHYRRLRHALWPSLPDLHRVLGQYLR DTAALSPPKATVSDTCEEVEPSLLEILPKSSERTPL PLLEARDEVEGFLQDTFPQQLEESEKQRLGGDVQ SPNCPSEDVVITPESFGRDSSLTCLAGNVSACDAP ILSSSRSLDCRESGKNGPHVYQDLLLSLGTTNSTL PPPFSLQSGILTLNPVAQGQPILTSLGSNQEEAYV TMSSFYQNQ | 119 |
| TPOR/MPLR(478-582;H499L,S505N).IL7Ra (316-459) | SDPTRVETATETAWISLVTALLLVLGLNAVLGLL LLRWQFPAHYRRLRHALWPSLPDLHRVLGQYLR DTAALSPPKATVSDTCEEVEPSLLEILPKSSERTPL PLLEARDEVEGFLQDTFPQQLEESEKQRLGGDVQ SPNCPSEDVVITPESFGRDSSLTCLAGNVSACDAP ILSSSRSLDCRESGKNGPHVYQDLLLSLGTTNSTL PPPFSLQSGILTLNPVAQGQPILTSLGSNQEEAYV TMSSFYQNQ | 120 |
| TPOR/MPLR(478-582;S505N).IL7Ra (316-459) | SDPTRVETATETAWISLVTALHLVLGLNAVLGLL LLRWQFPAHYRRLRHALWPSLPDLHRVLGQYLR DTAALSPPKATVSDTCEEVEPSLLEILPKSSERTPL PLLEARDEVEGFLQDTFPQQLEESEKQRLGGDVQ SPNCPSEDVVITPESFGRDSSLTCLAGNVSACDAP ILSSSRSLDCRESGKNGPHVYQDLLLSLGTTNSTL PPPFSLQSGILTLNPVAQGQPILTSLGSNQEEAYV TMSSFYQNQ | 121 |

TABLE 3-continued

Exemplary CACCR sequences

| Receptor | Amino acid sequence | SEQ ID NO: |
|---|---|---|
| TPOR/MPLR(478-582;H499L, W515K).IL7Ra (316-459) | SDPTRVETATETAWISLVTALLLVLGLSAVLGLL LLRKQFPAHYRRLRHALWPSLPDLHRVLGQYLR DTAALSPPKATVSDTCEEVEPSLLEILPKSSERTPL PLLEARDEVEGFLQDTFPQQLEESEKQRLGGDVQ SPNCPSEDVVITPESFGRDSSLTCLAGNVSACDAP ILSSSRSLDCRESGKNGPHVYQDLLLSLGTTNSTL PPPFSLQSGILTLNPVAQGQPILTSLGSNQEEAYV TMSSFYQNQ | 122 |
| TPOR/MPLR(478-582;W515K).IL7Ra (316-459) | SDPTRVETATETAWISLVTALHLVLGLSAVLGLL LLRKQFPAHYRRLRHALWPSLPDLHRVLGQYLR DTAALSPPKATVSDTCEEVEPSLLEILPKSSERTPL PLLEARDEVEGFLQDTFPQQLEESEKQRLGGDVQ SPNCPSEDVVITPESFGRDSSLTCLAGNVSACDAP ILSSSRSLDCRESGKNGPHVYQDLLLSLGTTNSTL PPPFSLQSGILTLNPVAQGQPILTSLGSNQEEAYV TMSSFYQNQ | 123 |
| TPOR/MPLR(478-582;H499L,S505N, W515K).IL7Ra (316-459) | SDPTRVETATETAWISLVTALLLVLGLNAVLGLL LLRKQFPAHYRRLRHALWPSLPDLHRVLGQYLR DTAALSPPKATVSDTCEEVEPSLLEILPKSSERTPL PLLEARDEVEGFLQDTFPQQLEESEKQRLGGDVQ SPNCPSEDVVITPESFGRDSSLTCLAGNVSACDAP ILSSSRSLDCRESGKNGPHVYQDLLLSLGTTNSTL PPPFSLQSGILTLNPVAQGQPILTSLGSNQEEAYV TMSSFYQNQ | 124 |
| TPOR/MPLR(478-582;S505N, W515K).IL7Ra (316-459) | SDPTRVETATETAWISLVTALHLVLGLNAVLGLL LLRKQFPAHYRRLRHALWPSLPDLHRVLGQYLR DTAALSPPKATVSDTCEEVEPSLLEILPKSSERTPL PLLEARDEVEGFLQDTFPQQLEESEKQRLGGDVQ SPNCPSEDVVITPESFGRDSSLTCLAGNVSACDAP ILSSSRSLDCRESGKNGPHVYQDLLLSLGTTNSTL PPPFSLQSGILTLNPVAQGQPILTSLGSNQEEAYV TMSSFYQNQ | 125 |
| TPOR/MPLR(478-582;H499L, G509N).IL7Ra (316-459) | SDPTRVETATETAWISLVTALLLVLGLSAVLNLL LLRWQFPAHYRRLRHALWPSLPDLHRVLGQYLR DTAALSPPKATVSDTCEEVEPSLLEILPKSSERTPL PLLEARDEVEGFLQDTFPQQLEESEKQRLGGDVQ SPNCPSEDVVITPESFGRDSSLTCLAGNVSACDAP ILSSSRSLDCRESGKNGPHVYQDLLLSLGTTNSTL PPPFSLQSGILTLNPVAQGQPILTSLGSNQEEAYV TMSSFYQNQ | 126 |
| TPOR/MPLR(478-582;H499L, S505N).IL7Ra (316-459) | SDPTRVETATETAWISLVTALLLVLGLNAVLGLL LLRWQFPAHYRRLRHALWPSLPDLHRVLGQYLR DTAALSPPKATVSDTCEEVEPSLLEILPKSSERTPL PLLEARDEVEGFLQDTFPQQLEESEKQRLGGDVQ SPNCPSEDVVITPESFGRDSSLTCLAGNVSACDAP ILSSSRSLDCRESGKNGPHVYQDLLLSLGTTNSTL PPPFSLQSGILTLNPVAQGQPILTSLGSNQEEAYV TMSSFYQNQ | 127 |
| TPOR/MPLR(478-582;S505N, W515K).IL2Rb (333-551) | SDPTRVETATETAWISLVTALHLVLGLNAVLGLL LLRKQFPAHYRRLRHALWPSLPDLHRVLGQYLR DTAALSPPKATVSDTCEEVEPSLLEILPKSSERTPL PLLEVTQLLLQQDKVPEPASLSSNHSLTSCFTNQ GYFFFHLPDALEIEACQVYFTYDPYSEEDPDEGV AGAPTGSSPQPLQPLSGEDDAYCTFPSRDDLLLFS PSLLGGPSPPSTAPGGSGAGEERMPPSLQERVPRD WDPQPLGPPTPGVPDLVDFQPPPELVLREAGEEV PDAGPREGVSFPWSRPPGQGEFRALNARLPLNTD AYLSLQELQGQDPTHLV | 128 |
| TPOR/MPLR(478-582;S505N, W515K).IL12Rb2 (714-862) | SDPTRVETATETAWISLVTALHLVLGLNAVLGLL LLRKQFPAHYRRLRHALWPSLPDLHRVLGQYLR DTAALSPPKATVSDTCEEVEPSLLEILPKSSERTPL PLLEVTPVFRHPPCSNWPQREKGIQGHQASEKD MMHSASSPPPPRALQAESRQLVDLYKVLESRGS DPKPENPACPWTVLPAGDLPTHDGYLPSNIDDLP SHEAPLADSLEELEPQHISLSVFPSSSLHPLTFSCG DKLTLDQLKMRCDSLML | 129 |

TABLE 3-continued

Exemplary CACCR sequences

| Receptor | Amino acid sequence | SEQ ID NO: |
|---|---|---|
| TPOR/MPLR(478-582;H499L,S505N,W515K).IL2Rb(333-551) | SDPTRVETATETAWISLVTALLLVLGLNAVLGLL LLRKQFPAHYRRLRHALWPSLPDLHRVLGQYLR DTAALSPPKATVSDTCEEVEPSLLEILPKSSERTPL PLLEVTQLLLQQDKVPEPASLSSNHSLTSCFTNQ GYFFFHLPDALEIEACQVYFTYDPYSEEDPDEGV AGAPTGSSPQPLQPLSGEDDAYCTFPSRDDLLLFS PSLLGGPSPPSTAPGGSGAGEERMPPSLQERVPRD WDPQPLGPPTPGVPDLVDFQPPPELVLREAGEEV PDAGPREGVSFPWSRPPGQGEFRALNARLPLNTD AYLSLQELQGQDPTHLV | 130 |
| TPOR/MPLR(478-582;H499L,S505N,W515K).IL12Rb2(714-862) | SDPTRVETATETAWISLVTALLLVLGLNAVLGLL LLRKQFPAHYRRLRHALWPSLPDLHRVLGQYLR DTAALSPPKATVSDTCEEVEPSLLEILPKSSERTPL PLLEVTPVFRHPPCSNWPQREKGIQGHQASEKD MMHSASSPPPPRALQAESRQLVDLYKVLESRGS DPKPENPACPWTVLPAGDLPTHDGYLPSNIDDLP SHEAPLADSLEELEPQHISLSVFPSSSLHPLTFSCG DKLTLDQLKMRCDSLML | 131 |
| TPOR/MPLR(478-582;S505N,W515K).IL12Rb2(775-825) | SDPTRVETATETAWISLVTALHLVLGLNAVLGLL LLRKQFPAHYRRLRHALWPSLPDLHRVLGQYLR DTAALSPPKATVSDTCEEVEPSLLEILPKSSERTPL PLLESDPKPENPACPWTVLPAGDLPTHDGYLPSN IDDLPSHEAPLADSLEELEPQ | 132 |
| TPOR/MPLR(478-582;H499L;S505N,W515K).IL12Rb2(775-825) | SDPTRVETATETAWISLVTALLLVLGLNAVLGLL LLRKQFPAHYRRLRHALWPSLPDLHRVLGQYLR DTAALSPPKATVSDTCEEVEPSLLEILPKSSERTPL PLLESDPKPENPACPWTVLPAGDLPTHDGYLPSN IDDLPSHEAPLADSLEELEPQ | 133 |
| TPOR/MPLR(478-582;S505N,W515K).IL7Ra(316-459).IL12Rb2(775-825) | SDPTRVETATETAWISLVTALHLVLGLNAVLGLL LLRKQFPAHYRRLRHALWPSLPDLHRVLGQYLR DTAALSPPKATVSDTCEEVEPSLLEILPKSSERTPL PLLEARDEVEGFLQDTFPQQLEESEKQRLGGDVQ SPNCPSEDVVITPESFGRDSSLTCLAGNVSACDAP ILSSSRSLDCRESGKNGPHVYQDLLLSLGTTNSTL PPPFSLQSGILTLNPVAQGQPILTSLGSNQEEAYV TMSSFYQNQSRSDPKPENPACPWTVLPAGDLPTH DGYLPSNIDDLPSHEAPLADSLEELEPQ | 134 |
| TPOR/MPLR(478-582;H499L,S505N,W515K).IL7Ra(316-459).IL12Rb2(775-825) | SDPTRVETATETAWISLVTALLLVLGLNAVLGLL LLRKQFPAHYRRLRHALWPSLPDLHRVLGQYLR DTAALSPPKATVSDTCEEVEPSLLEILPKSSERTPL PLLEARDEVEGFLQDTFPQQLEESEKQRLGGDVQ SPNCPSEDVVITPESFGRDSSLTCLAGNVSACDAP ILSSSRSLDCRESGKNGPHVYQDLLLSLGTTNSTL PPPFSLQSGILTLNPVAQGQPILTSLGSNQEEAYV TMSSFYQNQSRSDPKPENPACPWTVLPAGDLPTH DGYLPSNIDDLPSHEAPLADSLEELEPQ | 135 |
| TPOR/MPLR(478-582;S505N,W515K).IL2Rb(333-551;Y381S,Y384S,Y387S) | SDPTRVETATETAWISLVTALHLVLGLNAVLGLL LLRKQFPAHYRRLRHALWPSLPDLHRVLGQYLR DTAALSPPKATVSDTCEEVEPSLLEILPKSSERTPL PLLEVTQLLLQQDKVPEPASLSSNHSLTSCFTNQ GYFFFHLPDALEIEACQVSFTSDPSSEEDPDEGVA GAPTGSSPQPLQPLSGEDDAYCTFPSRDDLLLFSP SLLGGPSPPSTAPGGSGAGEERMPPSLQERVPRD WDPQPLGPPTPGVPDLVDFQPPPELVLREAGEEV PDAGPREGVSFPWSRPPGQGEFRALNARLPLNTD AYLSLQELQGQDPTHLV | 136 |
| TPOR/MPLR(478-582;H499L,S505N,W515K).IL2Rb(333-551;Y381S,Y384S,Y387S) | SDPTRVETATETAWISLVTALLLVLGLNAVLGLL LLRKQFPAHYRRLRHALWPSLPDLHRVLGQYLR DTAALSPPKATVSDTCEEVEPSLLEILPKSSERTPL PLLEVTQLLLQQDKVPEPASLSSNHSLTSCFTNQ GYFFFHLPDALEIEACQVSFTSDPSSEEDPDEGVA GAPTGSSPQPLQPLSGEDDAYCTFPSRDDLLLFSP SLLGGPSPPSTAPGGSGAGEERMPPSLQERVPRD WDPQPLGPPTPGVPDLVDFQPPPELVLREAGEEV PDAGPREGVSFPWSRPPGQGEFRALNARLPLNTD AYLSLQELQGQDPTHLV | 137 |

TABLE 3-continued

Exemplary CACCR sequences

| Receptor | Amino acid sequence | SEQ ID NO: |
|---|---|---|
| TPOR/MPLR(478-582;S505N, W515K).IL2Rb(333-551;Y364S,Y381S, Y384S,Y387S) | SDPTRVETATETAWISLVTALHLVLGLNAVLGLL LLRKQFPAHYRRLRHALWPSLPDLHRVLGQYLR DTAALSPPKATVSDTCEEVEPSLLEILPKSSERTPL PLLEVTQLLLQQDKVPEPASLSSNHSLTSCFTNQ GSFFFHLPDALEIEACQVSFTSDPSSEEDPDEGVA GAPTGSSPQPLQPLSGEDDAYCTFPSRDDLLLFSP SLLGGPSPPSTAPGGSGAGEERMPPSLQERVPRD WDPQPLGPPTPGVPDLVDFQPPPELVLREAGEEV PDAGPREGVSFPWSRPPGQGEFRALNARLPLNTD AYLSLQELQGQDPTHLV | 138 |
| TPOR/MPLR(478-582;H499L,S505N, W515K).IL2Rb(333-551;Y364S,Y381S, Y384S,Y387S) | SDPTRVETATETAWISLVTALLLVLGLNAVLGLL LLRKQFPAHYRRLRHALWPSLPDLHRVLGQYLR DTAALSPPKATVSDTCEEVEPSLLEILPKSSERTPL PLLEVTQLLLQQDKVPEPASLSSNHSLTSCFTNQ GSFFFHLPDALEIEACQVSFTSDPSSEEDPDEGVA GAPTGSSPQPLQPLSGEDDAYCTFPSRDDLLLFSP SLLGGPSPPSTAPGGSGAGEERMPPSLQERVPRD WDPQPLGPPTPGVPDLVDFQPPPELVLREAGEEV PDAGPREGVSFPWSRPPGQGEFRALNARLPLNTD AYLSLQELQGQDPTHLV | 139 |
| TpoR(478-582; H499L,S505N, W515K).IL2Rb (393-433,518-551) | SDPTRVETATETAWISLVTALLLVLGLNAVLGLL LLRKQFPAHYRRLRHALWPSLPDLHRVLGQYLR DTAALSPPKATVSDTCEEVEPSLLEILPKSSERTPL PLLEDEGVAGAPTGSSPQPLQPLSGEDDAYCTFP SRDDLLLFSPSGQGEFRALNARLPLNTDAYLSLQ ELQGQDPTHLV | 143 |
| TpoR(478-582;S505N, W515K).IL2Rb (393-433,518-551) | SDPTRVETATETAWISLVTALHLVLGLNAVLGLL LLRKQFPAHYRRLRHALWPSLPDLHRVLGQYLR DTAALSPPKATVSDTCEEVEPSLLEILPKSSERTPL PLDEGVAGAPTGSSPQPLQPLSGEDDAYCTFPSR DDLLLFSPSGQGEFRALNARLPLNTDAYLSLQEL QGQDPTHLV | 180 |
| TpoR(478-582; H499L,S505N, W515K).IL2Rb (339-379,393-433,518-551) | SDPTRVETATETAWISLVTALLLVLGLNAVLGLL LLRKQFPAHYRRLRHALWPSLPDLHRVLGQYLR DTAALSPPKATVSDTCEEVEPSLLEILPKSSERTPL PLQQDKVPEPASLSSNHSLTSCFTNQGYFFFHLPD ALEIEACQDEGVAGAPTGSSPQPLQPLSGEDDAY CTFPSRDDLLLFSPSGQGEFRALNARLPLNTDAY LSLQELQGQDPTHLV | 181 |
| TpoR(478-582; H499L,S505N, W515K).IL2Rb (393-433,518-551) | SDPTRVETATETAWISLVTALLLVLGLNAVLGLL LLRKQFPAHYRRLRHALWPSLPDLHRVLGQYLR DTAALSPPKATVSDTCEEVEPSLLEILPKSSERTPL PLDEGVAGAPTGSSPQPLQPLSGEDDAYCTFPSR DDLLLFSPSGQGEFRALNARLPLNTDAYLSLQEL QGQDPTHLV | 182 |
| TpoR(478-582;S505N, W515K).IL2Rb (393-433,518-551).P2A | SDPTRVETATETAWISLVTALHLVLGLNAVLGLL LLRKQFPAHYRRLRHALWPSLPDLHRVLGQYLR DTAALSPPKATVSDTCEEVEPSLLEILPKSSERTPL PLLEDEGVAGAPTGSSPQPLQPLSGEDDAYCTFP SRDDLLLFSPSGQGEFRALNARLPLNTDAYLSLQ ELQGQDPTHLV**GSGATNFSLLKQAGDVEENPG** | 184 |
| TpoR(478-582;H499L,S505N, W515K).IL2Rb (339-379,393-433, 518-551).P2A | SDPTRVETATETAWISLVTALLLVLGLNAVLGLL LLRKQFPAHYRRLRHALWPSLPDLHRVLGQYLR DTAALSPPKATVSDTCEEVEPSLLEILPKSSERTPL PLLEQQDKVPEPASLSSNHSLTSCFTNQGYFFFHL PDALEIEACQDEGVAGAPTGSSPQPLQPLSGEDD AYCTFPSRDDLLLFSPSGQGEFRALNARLPLNTD AYLSLQELQGQDPTHLV**GSGATNFSLLKQAGD VEENPG** | 185 |

TABLE 3-continued

| Exemplary CACCR sequences | | |
|---|---|---|
| Receptor | Amino acid sequence | SEQ ID NO: |
| TpoR(478-582; H499L,S505N, W515K).IL2Rb (393-433,518-551).P2A | SDPTRVETATETAWISLVTAL**L**LVLGL**N**AVLGLL LLR**K**QFPAHYRRLRHALWPSLPDLHRVLGQYLR DTAALSPPKATVSDTCEEVEPSLLEILPKSSERTPL PLLEDEGVAGAPTGSSPQPLQPLSGEDDAYCTFP SRDDLLLFSPSGQGEFRALNARLPLNTDAYLSLQ ELQGQDPTHLV**GSGATNFSLLKQAGDVEENPG** | 186 |

*The underlined LE and SR are exemplary optional linker that may be inserted between two domains.

E. Expression of CACCRs

Provided herein are polynucleotides encoding any one of the CACCRs provided herein. Likewise, provided herein are expression vectors comprising such polynucleotides. In some embodiments, the vector is a viral vector. In some embodiments, the vector is not a viral vector. In some embodiments, the vector is a lentiviral vector. In some embodiments, the expression vector comprises a promoter, which may be selected from those known in the art. An exemplary promoter that can be used in the invention is the human elongation factor-1 alpha (EF-1 alpha or EF-1α) promoter, which may be used in its full-length form, or truncated forms, or other variant forms (as described in the literature and disclosed in, e.g., Wakabayashi-Ito, N. et al., J. Biol. Chem. 1994:269(47): 29831-29837; Montiel-Equihua, C. A. et al., Mol. Therapy, 2012, 20(7): 1400-1409). Any version of the EF1 alpha promoter is suitable and may be used as the sole promoter or together with other promoter elements. In some embodiments, the expression vector is a lentiviral vector and the promoter is a full-length EF-1 alpha promoter. Exemplary full-length EF1 alpha promoter is shown below:

(SEQ ID NO: 187)

```
GCGTGAGGCTCCGGTGCCCGTCAGTGGGCAGAGCGCACATCGCCCACAG
TCCCCGAGAAGTTGGGGGGAGGGGTCGGCAATTGAACCGGTGCCTAGAG
AAGGTGGCGCGGGGTAAACTGGGAAAGTGATGTCGTGTACTGGCTCCGC
CTTTTTCCCGAGGGTGGGGGAGAACCGTATATAAGTGCAGTAGTCGCCG
TGAACGTTCTTTTTCGCAACGGGTTTGCCGCCAGAACACAGGTAAGTGC
CGTGTGTGGTTCCCGCGGGCCTGGCCTCTTTACGGGTTATGGCCCTTGC
GTGCCTTGAATTACTTCCACGCCCCTGGCTGCAGTACGTGATTCTTGAT
CCCGAGCTTCGGGTTGGAAGTGGGTGGGAGAGTTCGAGGCCTTGCGCTT
AAGGAGCCCCTTCGCCTCGTGCTTGAGTTGAGGCCTGGCCTGGGCGCTG
GGGCCGCCGCGTGCGAATCTGGTGGCACCTTCGCGCCTGTCTCGCTGCT
TTCGATAAGTCTCTAGCCATTTAAAATTTTTGATGACCTGCTGCGACGC
TTTTTTTCTGGCAAGATAGTCTTGTAAATGCGGGCCAAGATCTGCACAC
TGGTATTTCGGTTTTTGGGGCCGCGGGCGGCGACGGGGCCCGTGCGTCC
CAGCGCACATGTTCGGCGAGGCGGGGCCTGCGAGCGCGGCCACCGAGAA
TCGGACGGGGGTAGTCTCAAGCTGGCCGGCCTGCTCTGGTGCCTGGCCT
CGCGCCGCCGTGTATCGCCCCGCCCTGGGCGGCAAGGCTGGCCCGGTCG
```

-continued

```
GCACCAGTTGCGTGAGCGGAAAGATGGCCGCTTCCCGGCCCTGCTGCAG
GGAGCTCAAAATGGAGGACGCGGCGCTCGGGAGAGCGGGCGGGTGAGTC
ACCCACACAAAGGAAAAGGGCCTTTCCGTCCTCAGCCGTCGCTTCATGT
GACTCCACGGAGTACCGGGCGCCGTCCAGGCACCTCGATTAGTTCTCGA
GCTTTTGGAGTACGTCGTCTTTAGGTTGGGGGGAGGGGTTTTATGCGAT
GGAGTTTCCCCACACTGAGTGGGTGGAGACTGAAGTTAGGCCAGCTTGG
CACTTGATGTAATTCTCCTTGGAATTTGCCCTTTTTGAGTTTGGATCTT
GGTTCATTCTCAAGCCTCAGACAGTGGTTCAAAGTTTTTTTCTTCCATT
TCAGGTGTCGTGA
```

Exemplary EF1 alpha short promoter is shown below:

(SEQ ID NO: 188)

```
GCGTGAGGCTCCGGTGCCCGTCAGTGGGCAGAGCGCACATCGCCCACAG
TCCCCGAGAAGTTGGGGGGAGGGGTCGGCAATTGAACCGGTGCCTAGAG
AAGGTGGCGCGGGGTAAACTGGGAAAGTGATGTCGTGTACTGGCTCCGC
CTTTTTCCCGAGGGTGGGGGAGAACCGTATATAAGTGCAGTAGTCGCCG
TGAACGTTCTTTTTCGCAACGGGTTTGCCGCCAGAACACAG
```

In some embodiments, the expression vector comprises a polynucleotide expressing a CACCR and a polynucleotide expressing a chimeric antigen receptor (CAR).

Figure 2A:
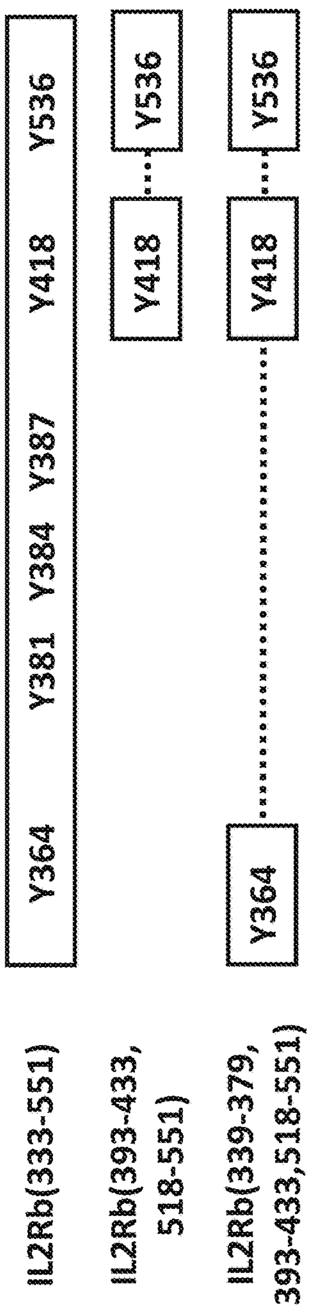
FIG. 2A shows schematic representations of exemplary recruiting domains of the CACCR of the disclosure that comprise one or more polypeptide subregions of the IL2Rb intracellular domain.
Figure 2B:
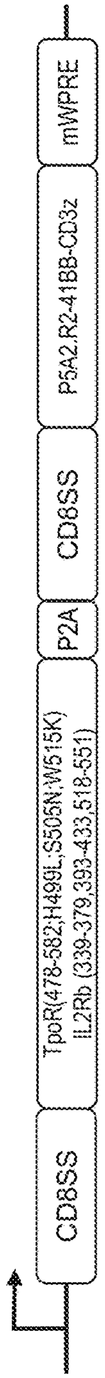
FIGS. 2B-2D show schematics of exemplary vectors that can be used to co-express certain combinations of a CACCR and BCMA CAR of the disclosure.
Figure 2C:
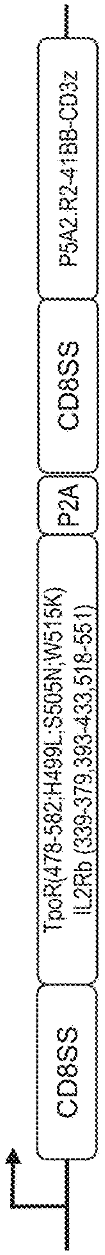
Figure 2D:
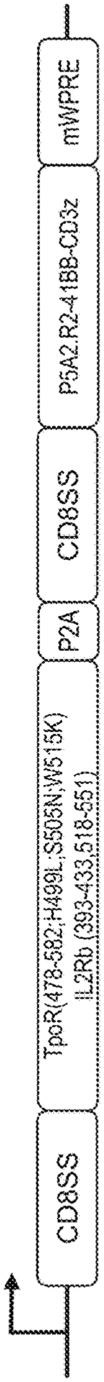

In some embodiments, the CACCR and the CAR are expressed as a single polypeptide chain, separated by a linker. FIGS. 2B-2D show schematics of vectors that can be used to co-express the CACCR and a BCMA CAR of the disclosure. One or more recruiting domains may be joined in tandem in the CACCR to mimic signaling from one or more cytokines.

II. CAR-Bearing Immune Cells

Provided herein are engineered immune cells comprising a polynucleotide encoding a B-cell maturation antigen (BCMA) chimeric antigen receptor (CAR) and a CACCR of the disclosure; and provided herein are engineered immune cells expressing a BCMA chimeric antigen receptor (BCMA CAR-T cell) and a CACCR of the disclosure. Examples of immune cells include T cells, e.g., alpha/beta T cells and gamma/delta T cells, B cells, natural killer (NK) cells, natural killer T (NKT) cells, invariant NKT cells, mast cells, myeloid-derived phagocytes, dendritic cells, killer dendritic cells, macrophages, and monocytes. In some embodiments, the engineered immune cells are CD4+ and/or CD8+ T cells. In some embodiments, the engineered immune cells are T cells exerting one or more T cell effector functions (or effector T cells). Immune cells also refer to cells derived from, for example without limitation, a stem cell. The stem cells can be adult stem cells, non-human embryonic stem cells, more particularly non-human stem cells, cord blood stem cells, progenitor cells, bone marrow stem cells, induced pluripotent stem cells, totipotent stem cells or hematopoietic stem cells. The immune cells can be obtained from a natural source such as from a human patient or can be prepared from, for example, donor cells, stem cells or non-stem cells, according to methods known in the art.

Accordingly, in some embodiments, provided herein are BCMA CAR-T cells comprising a CACCR of the disclosure.

In some embodiments, a BCMA CAR can comprise an extracellular ligand-binding domain (e.g., a single chain variable fragment (scFv)), a transmembrane domain, and an intracellular signaling domain. In some embodiments, the extracellular ligand-binding domain, transmembrane domain, and intracellular signaling domain are in one polypeptide, i.e., in a single chain. Multichain BCMA CARs and polypeptides are also provided herein. In some embodiments, the multichain BCMA CARs comprise: a first polypeptide comprising a transmembrane domain and at least one extracellular ligand-binding domain, and a second polypeptide comprising a transmembrane domain and at least one intracellular signaling domain, wherein the polypeptides assemble together to form a multichain CAR.

The extracellular ligand-binding domain of a BCMA CAR specifically binds to BCMA.

In some embodiments, the extracellular ligand-binding domain of a BCMA CAR comprises an scFv comprising the light chain variable (VL) region and the heavy chain variable (VH) region of a BCMA specific monoclonal antibody joined by a flexible linker. Single chain variable region fragments are made by linking light and/or heavy chain variable regions by using a short linking peptide (Bird et al., Science 242:423-426, 1988) (e.g. glycine-serine containing linkers). In general, linkers can be short, flexible polypeptides and are generally comprised of about 20 or fewer amino acid residues. Linkers can in turn be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art.

The intracellular signaling domain of a BCMA CAR according to the invention is responsible for intracellular signaling following the binding of extracellular ligand-binding domain to the target resulting in the activation of the immune cell and immune response (Signals 1 and/or 2). The intracellular signaling domain has the ability to activate at least one of the normal effector functions of the immune cell in which the CAR is expressed. For example, the effector function of a T cell can be a cytolytic activity or helper activity including the secretion of cytokines.

In some embodiments, an intracellular signaling domain for use in a BCMA CAR can be the cytoplasmic sequences of, for example without limitation, the T cell receptor and co-receptors that act in concert to initiate signal transduction following antigen receptor engagement, as well as any derivative or variant of these sequences and any synthetic sequence that has the same functional capability. Intracellular signaling domains comprise two distinct classes of cytoplasmic signaling sequences: those that initiate antigen-dependent primary activation, and those that act in an antigen-independent manner to provide a secondary or co-stimulatory signal. Primary cytoplasmic signaling sequences can comprise signaling motifs which are known as immunoreceptor tyrosine-based activation motifs or "ITAMs". ITAMs are well defined signaling motifs found in the intracytoplasmic tail of a variety of receptors that serve as binding sites for syk/zap70 class tyrosine kinases. Examples of ITAMs used in the invention can include as non-limiting examples those derived from TCRζ, FcRγ, FcRβ, FcRε, CD3γ, CD3δ, CD3ε, CD5, CD22, CD79a, CD79b and CD66d. In some embodiments, the intracellular signaling domain of the BCMA CAR can comprise the CD3ζ signaling domain. In some embodiments the intracellular signaling domain of the BCMA CAR of the invention comprises a domain of a co-stimulatory molecule.

In some embodiments, the intracellular signaling domain of a BCMA CAR of the invention comprises a part of co-stimulatory molecule selected from the group consisting of fragment of 4-1BB (GenBank: AAA53133) and CD28 (NP_006130.1).

CARs are expressed on the surface membrane of the cell. Thus, the BCMA CAR comprises a transmembrane domain. Suitable transmembrane domains for a BCMA CAR disclosed herein have the ability to (a) be expressed at the surface of a cell, preferably an immune cell such as, for example without limitation, lymphocyte cells or Natural killer (NK) cells, and (b) interact with the ligand-binding domain and intracellular signaling domain for directing cellular response of immune cell against a predefined target cell. The transmembrane domain can be derived either from a natural or from a synthetic source. The transmembrane domain can be derived from any membrane-bound or transmembrane protein. As non-limiting examples, the transmembrane polypeptide can be a subunit of the T cell receptor such as α, β, γ or δ, polypeptide constituting CD3 complex, IL-2 receptor p55 (a chain), p75 (β chain) or γ chain, subunit chain of Fc receptors, in particular Fcγ receptor III or CD proteins. Alternatively, the transmembrane domain can be synthetic and can comprise predominantly hydrophobic residues such as leucine and valine. In some embodiments said transmembrane domain is derived from the human CD8a chain (e.g., NP_001139345.1).

The transmembrane domain of the BCMA CAR can further comprise a stalk domain between the extracellular ligand-binding domain and said transmembrane domain. A stalk domain may comprise up to 300 amino acids, preferably 10 to 100 amino acids and most preferably 25 to 50 amino acids. Stalk region may be derived from all or part of naturally occurring molecules, such as from all or part of the extracellular region of CD8, CD4, or CD28, or from all or part of an antibody constant region. Alternatively, the stalk domain may be a synthetic sequence that corresponds to a naturally occurring stalk sequence, or may be an entirely synthetic stalk sequence. In some embodiments said stalk domain is a part of human CD8α chain (e.g., NP_001139345.1).

In another particular embodiment, said transmembrane and hinge domains of the BCMA CAR comprise a part of human CD8α chain.

Table 4 provides exemplary sequences of CAR components that can be used in the BCMA CARs disclosed herein and the antibody and/or CAR sequences exemplified herein.

TABLE 4

Amino Acid Sequences relating to BCMA CARs

| Domain | Amino acid sequence | SEQ ID NO: |
|---|---|---|
| CD8 hinge and transmembrane | TTTPAPRPPTPAPTIASQPLSLRPEACRPAAGGAV<br>HTRGLDFACDIYIWAPLAGTCGVLLLSLVITLYC | 101 |
| 4-1BB intracellular signaling | KRGRKKLLYIFKQPFMRPVQTTQEEDGCSCRFPE<br>EEEGGCEL | 102 |
| CD3z intracellular signaling | RVKFSRSADAPAYQQGQNQLYNELNLGRREEYD<br>VLDKRRGRDPEMGGKPRRKNPQEGLYNELQKD<br>KMAEAYSEIGMKGERRRGKGHDGLYQGLSTAT<br>KDTYDALHMQALPPR | 103 |
| BFP | MSELIKENMHMKLYMEGTVDNHHFKCTSEGEG<br>KPYEGTQTMRIKVVEGGPLPFAFDILATSFLYGS<br>KTFINHTQGIPDFFKQSFPEGFTWERVTTYEDGG<br>VLTATQDTSLQDGCLIYNVKIRGVNFTSNGPVM<br>QKKTLGWEAFTETLYPADGGLEGRNDMALKLV<br>GGSHLIANIKTTYRSKKPAKNLKMPGVYYVDYR<br>LERIKEANNETYVEQHEVAVARYCDLPSKLGHK<br>LN | 104 |
| P2A | GSGATNFSLLKQAGDVEENPGP | 105 |
| P5A2 anti-BCMA scFv | E V Q L L E S G G G L V Q P G G S L R L S C A A S<br>G F T F S S Y A M N W V R Q A P G K G L E W V S<br>A I S D S G G S T Y Y A D S V K G R F T I S R D N<br>S K N T L Y L Q M N S L R A E D T A V Y Y C A R<br>Y W P M D I W G Q G T L V T V S S G G G G S G G<br>G G S G G G G S E I V L T Q S P G T L S L S P G E<br>R A T L S C R A S Q S V S S S Y L A W Y Q Q K P<br>G Q A P R L L M Y D A S I R A T G I P D R F S G S<br>G S G T D F T L T I S R L E P E D F A V Y Y C Q Q<br>Y G S W P L T F G Q G T K V E I K | 140 |
| P5A2 anti-BCMA CAR [including safety switch, the parentheses indicate signal sequence] | (M A L P V T A L L L P L A L L L H A A R P) E V Q<br>L L E S G G G L V Q P G G S L R L S C A A S G F T<br>F S S Y A M N W V R Q A P G K G L E W V S A I S<br>D S G G S T Y Y A D S V K G R F T I S R D N S K N<br>T L Y L Q M N S L R A E D T A V Y Y C A R Y W P<br>M D I W G Q G T L V T V S S G G G G S G G G G S<br>G G G G S E I V L T Q S P G T L S L S P G E R A T<br>L S C R A S Q S V S S S Y L A W Y Q Q K P G Q A<br>P R L L M Y D A S I R A T G I P D R F S G S G S G<br>T D F T L T I S R L E P E D F A V Y Y C Q Q Y G S<br>W P L T F G Q G T K V E I K G S G G G G S C P Y<br>S N P S L C S G G G G S C P Y S N P S L C S G G G<br>G S T T T P A P R P P T P A P T I A S Q P L S L R P<br>E A C R P A A G G A V H T R G L D F A C D I Y I<br>W A P L A G T C G V L L L S L V I T L Y C K R G<br>R K K L L Y I F K Q P F M R P V Q T T Q E E D G C<br>S C R F P E E E E G G C E L R V K F S R S A D A P<br>A Y Q Q G Q N Q L Y N E L N L G R R E E Y D V L<br>D K R R G R D P E M G G K P R R K N P Q E G L Y<br>N E L Q K D K M A E A Y S E I G M K G E R R R G<br>K G H D G L Y Q G L S T A T K D T Y D A L H M<br>Q A L P P R | 141 |
| P5A2 VH | EVQLLESGGGLVQPGGSLRLSCAASGFTFSSYAM<br>NWVRQAPGKGLEWVSAISDSGGSTYYADSVKG<br>RFTISRDNSKNTLYLQMNSLRAEDTAVYYCARY<br>WPMDIWGQGTLVTVSS | 144 |
| P5A2 VL | EIVLTQSPGTLSLSPGERATLSCRASQSVSSSYLA<br>WYQQKPGQAPRLLMYDASIRATGIPDRFSGSGSG<br>TDFTLTISRLEPEDFAVYYCQQYGSWPLTFGQGT<br>KVEIK | 145 |
| VH CDR1 (Kabat) | SYAMN | 146 |
| VH CDR1 (Chothia); | GFTFSSY | 147 |
| VH CDR1 (extended) | GFTFSSYAMN | 148 |
| VH CDR2 (Chothia) | AISDSGGSTYYADSVKG | 149 |
| VH CDR2 (Kabat) | SDSGGS | 150 |

TABLE 4-continued

| Amino Acid Sequences relating to BCMA CARs | | |
|---|---|---|
| Domain | Amino acid sequence | SEQ ID NO: |
| VH CDR3 | YWPMDI | 151 |
| VL CDR1 | RASQSVSSSYLA | 152 |
| VL CDR2 | DASIRAT | 153 |
| VL CDR3 | QQYGSWPLT | 154 |
| C29 VH | EVQLLESGGGLVQPGGSLRLSCAASGFTFSSYPM SWVRQAPGKGLEWVSAIGGSGGSLPYADSVKGR FTISRDNSKNTLYLQMNSLRAEDTAVYYCARYW PMDIWGQGTLVTVSS | 155 |
| C29 VL | EIVLTQSPGTLSLSPGERATLSCRASQSVSSSYLA WYQQKPGQAPRLLMYDASIRATGIPDRFSGSGSG TDFTLTISRLEPEDFAVYYCQQYQSWPLTFGQGT KVEIK | 156 |
| VH CDR1 (Kabat) | SYPMS | 157 |
| VH CDR1 (Chothia); | GFTFSSY | 158 |
| VH CDR1 (extended) | GFTFSSYPMS | 159 |
| VH CDR2 (Chothia) | AIGGSGGSLPYADSVKG | 160 |
| VH CDR2 (Kabat) | GGSGGS | 161 |
| VH CDR3 | YWPMDI | 162 |
| VL CDR1 | RASQSVSSSYLA | 163 |
| VL CDR2 | DASIRAT | 164 |
| VL CDR3 | QQYQSWPLT | 165 |
| P5A2 BCMA CAR without a signal sequence | EVQLLESGGGLVQPGGSLRLSCAASGFTFSSYAM NWVRQAPGKGLEWVSAISDSGGSTYYADSVKG RFTISRDNSKNTLYLQMNSLRAEDTAVYYCARY WPMDIWGQGTLVTVSSGGGGSGGGGSGGGGSEI VLTQSPGTLSLSPGERATLSCRASQSVSSSYLAW YQQKPGQAPRLLMYDASIRATGIPDRFSGSGSGT DFTLTISRLEPEDFAVYYCQQYGSWPLTFGQGTK VEIKGSGGGGSCPYSNPSLCSGGGGSCPYSNPSLC SGGGGSTTTPAPRPPTPAPTIASQPLSLRPEACRPA AGGAVHTRGLDFACDIYIWAPLAGTCGVLLLSL VITLYCKRGRKKLLYIFKQPFMRPVQTTQEEDGC SCRFPEEEEGGCELRVKFSRSADAPAYQQGQNQL YNELNLGRREEYDVLDKRRGRDPEMGGKPRRK NPQEGLYNELQKDKMAEAYSEIGMKGERRRGK GHDGLYQGLSTATKDTYDALHMQALPPR | 166 |
| Linker | GGGGSGGGGSGGGGS | 167 |
| Off-switch ("R2") | GSGGGGSCPYSNPSLCSGGGGSCPYSNPSLCSGG GGS | 168 |
| CD8 Hinge | TTTPAPRPPTPAPTIASQPLSLRPEACRPAAGGAV HTRGLDFACD | 169 |
| CD8 TM | IYIWAPLAGTCGVLLLSLVIT | 170 |
| rituximab mimotope | CPYSNPSLC | 183 |

In some embodiments of the BCMA CAR, the intracellular signaling domain comprises a CD3ζ signaling domain. In some embodiments of the BCMA CAR, the intracellular signaling domain comprises a CD3ζ signaling domain and additionally a second signaling domain. In some embodiments of the BCMA CAR, the intracellular signaling domain comprises a CD3ζ signaling domain and a 4-1BB signaling domain. In some embodiments, the BCMA CARs disclosed herein comprise an extracellular ligand-binding domain that specifically binds BCMA, human CD8a hinge and transmembrane domains, the CD3ζ signaling domain, and 4-1BB signaling domain. In some embodiments, the BCMA specific CAR comprises the amino acid sequence of SEQ ID NO: 140 or 141. In some embodiments, the BCMA specific CAR comprises or consists of the amino acid sequence that is at least about 80%, 85%, 90%, 95%, 96%, 98%, 99% or 100% identical to the amino acid sequence of SEQ ID NO: 140. In some embodiments, the BCMA specific CAR comprises or consists of the amino acid sequence that is at least about 80%, 85%, 90%, 95%, 96%, 98%, 99% or 100% identical to the amino acid sequence of SEQ ID NO: 141. In some embodiments, the BCMA CAR comprises the amino acid sequence of SEQ ID NO: 141, without the CD8 alpha leader sequence or signal sequence (MALPVTALLLPLALLLHAARP, SEQ ID NO: 89). In some embodiments, the BCMA CAR comprises the amino acid sequence of SEQ ID NO: 166.

In some embodiments, a BCMA CAR of SEQ ID NO: 141 is encoded by the DNA sequence of SEQ ID NO: 171.

TABLE 5

BCMA CAR nucleotide sequences

| Name | Nucleotide sequence | SEQ ID NO: |
|---|---|---|
| BCMA CAR nt | ATGGCACTGCCCGTGACCGCCCTGCTGCTGCCTCTGGCCC TGCTGCTGCACGCCGCCCGGCCTGAGGTGCAGCTGCTGG AGAGCGGAGGAGGCCTGGTGCAGCCAGGAGGCAGCCTG AGACTGTCCTGCGCAGCCTCTGGCTTCACCTTCAGCAGCT ACGCCATGAACTGGGTGAGGCAGGCACCTGGCAAGGGCC TGGAGTGGGTGAGCGCCATCTCCGACTCTGGCGGCAGCA CCTACTATGCCGATTCCGTGAAGGGCCGCTTCACAATCAG CCGGGATAACTCCAAGAATACCCTGTACCTGCAGATGAA CAGCCTGAGAGCCGAGGATACAGCCGTGTACTATTGCGC CAGGTATTGGCCAATGGACATCTGGGGCCAGGGCACACT GGTGACCGTGTCTAGCGGCGGAGGAGGCTCCGGAGGAGG AGGCTCTGGCGGCGGCGGCAGCGAGATCGTGCTGACACA GTCTCCAGGCACCCTGAGCCTGTCCCCAGGAGAGAGAGC CACCCTGAGCTGTAGGGCCTCTCAGAGCGTGTCCTCTAGC TACCTGGCCTGGTATCAGCAGAAGCCAGGCCAGGCCCCC AGACTGCTGATGTACGACGCCAGCATCAGGGCAACAGGC ATCCCCGATCGGTTCTCCGGCTCTGGCAGCGGCACCGACT TTACACTGACCATCAGCAGGCTGGAGCCCGAGGACTTCG CCGTGTACTATTGCCAGCAGTATGGCTCCTGGCCTCTGAC ATTTGGCCAGGGCACCAAGGTGGAGATCAAGGGCTCCGG CGGCGGAGGCTCTTGCCCTTACAGCAACCCATCCCTGTGC TCTGGAGGAGGAGGCTCCTGTCCCTATAGCAATCCCAGC CTGTGCTCCGGCGGAGGAGGCTCTACCACAACCCCTGCA CCACGCCCCCCTACACCAGCACCTACCATCGCCTCTCAGC CTCTGAGCCTGCGGCCCGAGGCCTGTAGGCCCGCCGCCG GCGGCGCCGTGCACACACGGGGCCTGGACTTTGCCTGCG ACATCTACATCTGGGCACCCCTGGCCGGCACATGTGGCG TGCTGCTGCTGAGCCTGGTCATCACCCTGTACTGCAAGAG AGGCAGGAAGAAGCTGCTGTATATCTTCAAGCAGCCCTT CATGCGGCCCGTGCAGACAACCCAGGAGGAGGATGGCTG CTCCTGTCGGTTCCCAGAGGAGGAGGAGGGAGGATGTGA GCTGCGCGTGAAGTTTTCCCGGTCTGCCGACGCACCAGC ATACCAGCAGGGCCAGAACCAGCTGTATAACGAGCTGAA TCTGGGCCGGAGAGAGGAGTACGACGTGCTGGATAAGCG GCGGGGCCGGGACCCCGAGATGGGAGGCAAGCCTCGGA GAAAGAACCCACAGGAGGGCCTGTACAATGAGCTGCAG AAGGATAAGATGGCCGAGGCCTATTCTGAGATCGGCATG AAGGGAGAGAGGCGCCGGGGCAAGGGACACGACGGCCT GTACCAGGGCCTGTCCACAGCCACCAAGGACACCTATGA TGCCCTGCACATGCAGGCCCTGCCACCCAGATGA | 171 |

In an embodiment, a BCMA CAR polypeptide of the invention comprises the following domains: optionally a leader sequence, a heavy chain variable (VH) region, linker, light chain variable (VL) region, off-switch, CD8 hinge, CD8 transmembrane domain, 4-1BB signaling domain, and a CD3-zeta (CD3z or CD3ζ) domain. In some aspects of this embodiment, the BCMA CAR polypeptide comprises optionally a leader sequence that comprises the amino acid sequence shown in SEQ ID NO: 89, a VH region that comprises the amino acid sequence shown in SEQ ID NO: 144, a linker sequence that comprises the amino acid sequence shown in SEQ ID NO: 167, a VL region that comprises the amino acid sequence shown in SEQ ID NO: 145, an off-switch region that comprises the amino acid sequence shown in SEQ ID NO: 168, a CD8 hinge region that comprises the amino acid sequence shown in SEQ ID NO: 169, a CD8 TM region that comprises the amino acid sequence shown in SEQ ID NO: 170, a 4-1BB signaling domain that comprises the amino acid sequence shown in SEQ ID NO: 102, and a CD3z signaling domain that comprises the amino acid sequence shown in SEQ ID NO: 103. In some aspects of this embodiment, the BCMA CAR polypeptide comprises optionally a leader sequence that comprises the amino acid sequence shown in SEQ ID NO: 89, a VH region that comprises the amino acid sequence shown in SEQ ID NO: 144, a linker sequence that comprises the amino acid sequence shown in SEQ ID NO: 167, a VL region that comprises the amino acid sequence shown in SEQ ID NO: 145, an off-switch region that comprises the amino acid sequence shown in SEQ ID NO: 168, a CD8 hinge region and TM region that comprises the amino acid sequence shown in SEQ ID NO: 101, a 4-1BB signaling domain that comprises the amino acid sequence shown in SEQ ID NO: 102, and a CD3z signaling domain that comprises the amino acid sequence shown in SEQ ID NO: 103. In some embodiments, a different leader sequence is used.

In other aspects of this embodiment, the BCMA CAR polypeptide comprises optionally a leader sequence that comprises the amino acid sequence shown in SEQ ID NO: 89, a VH region that comprises the amino acid sequence shown in SEQ ID NO: 155, a linker sequence that comprises the amino acid sequence shown in SEQ ID NO: 167, a VL region that comprises the amino acid sequence shown in SEQ ID NO: 156, an off-switch region that comprises the amino acid sequence shown in SEQ ID NO: 168, a CD8 hinge region that comprises the amino acid sequence shown in SEQ ID NO: 169, a CD8 TM region that comprises the amino acid sequence shown in SEQ ID NO: 170, a 4-1BB signaling domain that comprises the amino acid sequence shown in SEQ ID NO: 102, and a CD3z signaling domain that comprises the amino acid sequence shown in SEQ ID NO: 103.

In another embodiment, a BCMA CAR polypeptide of the invention comprises the following domains: optionally a leader sequence, a heavy chain variable (VH) region, linker, light chain variable (VL) region, an off-switch, CD8 hinge, CD8 transmembrane domain, 4-1BB signaling domain, and a CD3-zeta (CD3z or CD3ζ) domain, wherein the off-switch optionally is omitted and/or only one or the other of the 4-1BB signaling domain and the CD3z signaling domain is present, but not both.

In aspects of either of these embodiments, the extracellular binding region of the BCMA CAR comprises a VH region that comprises a VH CDR1 comprising the amino acid sequence shown in SEQ ID NO: 146, 147, or 148; a VH CDR2 comprising the amino acid sequence shown in SEQ ID NO: 149 or 150; and a VH CDR3 comprising the amino acid sequence shown in SEQ ID NO: 151; and comprises a VL region comprising a VL CDR1 comprising the amino acid sequence shown in SEQ ID NO: 152; a VL CDR2 comprising the amino acid sequence shown in SEQ ID NO: 153; and a VL CDR3 comprising the amino acid sequence shown in SEQ ID NO: 154.

In alternative aspects of either of these embodiments, the extracellular binding region of the BCMA CAR comprises a VH region that comprises a VH CDR1 comprising the amino acid sequence shown in SEQ ID NO: 157, 158 or 159; a VH CDR2 comprising the amino acid sequence shown in SEQ ID NO: 160 or 161; and a VH CDR3 comprising the amino acid sequence shown in SEQ ID NO: 162; and comprises a VL region comprising a VL CDR1 comprising the amino acid sequence shown in SEQ ID NO: 163; a VL CDR2 comprising the amino acid sequence shown in SEQ ID NO: 164; and a VL CDR3 comprising the amino acid sequence shown in SEQ ID NO: 165.

In some embodiments, a BCMA CAR can be introduced into an immune cell as a transgene via a vector. In some embodiments, the vector can also contain, for example, a selection marker which provides for identification and/or selection of cells which received the vector.

In some embodiments of the invention, a bicistronic vector comprising the nucleotide sequence of SEQ ID NO: 172 encodes a predicted CACCR BCMA CAR polypeptide having the predicted amino acid sequence of SEQ ID NO: 173, which comprises the following domains: a CD8 alpha signal sequence (e.g. SEQ ID NO: 89), transmembrane/JAK2 binding domain—TpoR(478-582; S505N, W515K) (e.g. SEQ ID NO: 13), IL2Rb(393-433, 518-551) (e.g. SEQ ID NO: 77), P2A (e.g. SEQ ID NO: 105), CD8 alpha signal sequence (e.g., SEQ ID NO:89), and P5A2 anti-BCMA CAR with a safety switch (e.g. SEQ ID NO: 166). In aspects of this embodiment, the bicistronic vector further comprises, following the polypeptide coding sequence, a wild-type woodchuck hepatitis virus posttranscriptional regulatory element WPRE of e.g. nucleotide sequence SEQ ID NO: 174 or a mutant WPRE ("mWPRE") of e.g. nucleotide sequence of SEQ ID NO: 175. In other aspects of this embodiment, the bicistronic vector does not include a wild-type WPRE or a mutant WPRE. In some aspects, the disclosure provides an engineered immune cell that comprises the polynucleotide sequence of SEQ ID NO: 172 and expresses a CACCR comprising the amino acid sequence of SEQ ID NO: 184 or 99, and a BCMA CAR comprising the amino acid sequence of SEQ ID NO: 166. In some embodiments, the disclosure provides an engineered immune cell that expresses a CACCR comprising the amino acid sequence of SEQ ID NO: 180, 184 or 99, and a BCMA CAR comprising the amino acid sequence of SEQ ID NO: 166. In some embodiments, the engineered immune cell is an engineered T cell. In some embodiments, the engineered T cell is an allogeneic T cell. In some embodiments, the engineered T cell is an autologous T cell.

```
SEQ ID NO: 172:
atggccctgccagtgaccgccctgctgctgccactggccctgctgctgc

acgcagcaaggccatcagaccctactagagtcgagaccgctaccgagac

cgcttggatctctctggtgaccgccctgcacctggtgctgggcctgaac

gccgtgctgggcctgctgctgctgaggaagcagttcccagcacactacc

ggagactgaggcacgcactgtggccaagcctgcccgacctgcacagggt

gctgggacagtatctgagggatacagccgccctgagcccacctaaggca

accgtgtccgacacatgcgaggaggtggaaccaagtctgctggaaatcc

tgccaaaatcctctgagcggacacccctgcccctgctcgaggacgaggg

agtggcaggagcaccaaccggcagctccccccagcctctgcagccactg

tccggagaggacgatgcatactgcacattcccttctcgggacgatctgc

tgctgttctctccaagcggacagggagagtttcgggccctgaacgccag

actgcccctgaataccgacgcctatctgagcctgcaggagctgcaggga

caggaccccacacacctggtgggatccggagccaccaacttctccctgc
```

-continued

```
tgaagcaggccggcgatgtggaggagaatccaggccccatggctctgcc

cgtcaccgcactgctgctgcccctggctctgctgctgcacgccgcaaga

cccgaggtccagctgctggaatctgggggaggactggtgcagcctggag

gcagcctgagactgtcctgcgcagcatctggcttcaccttcagctccta

cgccatgaactgggtgaggcaggcaccaggcaagggactggagtgggtg

tctgccatctccgactctggcggcagcacctactatgccgattccgtga

agggccgcttcacaatcagccgggataactccaagaataccctgtacct

gcagatgaattccctgagagccgaggatacagccgtgtactattgcgcc

aggtattggcccatggacatctggggccagggcacactggtgaccgtgt

cttccggaggaggaggctccggaggaggaggctctggcggcggcggcag

cgagatcgtgctgacacagtctcctggcaccctgagcctgtccccagga

gagagagccaccctgagctgtagggcctctcagagcgtgtcctctagct

acctggcctggtatcagcagaagcccggccaggcccctagactgctgat

gtacgacgccagcatcagggcaacaggcatccctgatcggttctccggc

tctggcagcggaaccgactttacactgaccatcagcaggctggagcccg

aggacttcgccgtgtactattgccagcagtatggctcctggcctctgac

atttggccagggcaccaaggtggagatcaagggctccggcggcggaggc

tcttgcccatacagcaacccatccctgtgctctggaggaggaggctcct

gtccttatagcaatcctagcctgtgctccggggaggaggctctaccaca

accccagcaccaaggccacctacacctgcaccaaccatcgcctctcagc

cactgagcctgagacccgaggcctgtaggcctgcagcaggaggagcagt

gcacacccggggactggactttgcctgcgatatctacatctgggcacca

ctggcaggaacatgtggcgtgctgctgctgagcctggtcatcaccctgt

actgcaagagaggcaggaagaagctgctgtatatcttcaagcagccctt

tatgcgccctgtgcagacaacccaggaggaggatggctgctcctgtcgg

ttcccagaggaggaggagggaggatgtgagctgcgcgtgaagttttccc

ggtctgccgacgcaccagcataccagcagggccagaaccagctgtataa

cgagctgaatctgggccggagagaggagtacgacgtgctggataagagg

aggggaagagatcccgagatgggaggcaagccacggagaaagaaccccc

aggagggcctgtacaatgagctgcagaaggataagatggccgaggccta

tagcgagatcggcatgaagggagagaggcgccggggcaagggacacgac

ggcctgtatcagggcctgtccaccgctaccaaagacacctatgatgctc

tgcacatgcaggctctgccaccaagatga
```

```
SEQ ID NO: 173:
MALPVTALLLPLALLLHAARPSDPTRVETATETAWISLVTALHLVLGLN

AVLGLLLLRKQFPAHYRRLRHALWPSLPDLHRVLGQYLRDTAALSPPKA

TVSDTCEEVEPSLLEILPKSSERTPLPLLEDEGVAGAPTGSSPQPLQPL

SGEDDAYCTFPSRDDLLLFSPSGQGEFRALNARLPLNTDAYLSLQELQG

QDPTHLVGSGATNFSLLKQAGDVEENPGPMALPVTALLLPLALLLHAAR

PEVQLLESGGGLVQPGGSLRLSCAASGFTFSSYAMNWVRQAPGKGLEWV

SAISDSGGSTYYADSVKGRFTISRDNSKNTLYLQMNSLRAEDTAVYYCA
```

-continued

RYWPMDIWGQGTLVTVSSGGGGSGGGGSGGGGSEIVLTQSPGTLSLSPG

ERATLSCRASQSVSSSYLAWYQQKPGQAPRLLMYDASIRATGIPDRFSG

SGSGTDFTLTISRLEPEDFAVYYCQQYGSWPLTFGQGTKVEIKGSGGGG

SCPYSNPSLCSGGGGSCPYSNPSLCSGGGGSTTTPAPRPPTPAPTIASQ

PLSLRPEACRPAAGGAVHTRGLDFACDIYIWAPLAGTCGVLLLSLVITL

YCKRGRKKLLYIFKQPFMRPVQTTQEEDGCSCRFPEEEEGGCELRVKFS

RSADAPAYQQGQNQLYNELNLGRREEYDVLDKRRGRDPEMGGKPRRKNP

QEGLYNELQKDKMAEAYSEIGMKGERRRGKGHDGLYQGLSTATKDTYDA

LHMQALPPR

SEQ ID NO: 174: wt WPRE aatcaacctctggattacaaaatttgtgaaagattgactggtattctta actatgttgctccttttacgctatgtggatacgctgctttaatgccttt gtatcatgctattgcttcccgtatggctttcattttctcctccttgtat aaatcctggttgctgtctctttatgaggagttgtggcccgttgtcaggc aacgtggcgtggtgtgcactgtgtttgctgacgcaacccccactggttg gggcattgccaccacctgtcagctcctttccgggactttcgctttcccc ctccctattgccacggcggaactcatcgccgcctgccttgcccgctgct ggacaggggctcggctgttgggcactgacaattccgtggtgttgtcggg gaagctgacgtcctttccatggctgctcgcctgtgttgccacctggatt ctgcgcgggacgtccttctgctacgtcccttcggccctcaatccagcgg accttccttcccgcggcctgctgccggctctgcggcctcttccgcgtct tcgccttcgccctcagacgagtcggatctccctttgggccgcctccccg cctg SEQ ID NO: 175: mWPRE aatcaacctctggattacaaaatttgtgaaagattgactggtattctta actatgttgctccttttacgctatgtggatacgctgctttaatgccttt gtatcatgctattgcttcccgtatggctttcattttctcctccttgtat aaatcctggttgctgtctctttatgaggagttgtggcccgttgtcaggc aacgtggcgtggtgtgcactgtgtttgctgacgcaacccccactggttg gggcattgccaccacctgtcagctcctttccgggactttcgctttcccc ctccctattgccacggcggaactcatcgccgcctgccttgcccgctgct ggacaggggctcggctgttgggcactgacaattccgtggtgttgtcggg gaaatcatcgtcctttccttggctgctcgcctgtgttgccacctggatt ctgcgcgggacgtccttctgctacgtcccttcggccctcaatccagcgg accttccttcccgcggcctgctgccggctctgcggcctcttccgcgtct tcgccttcgccctcagacgagtcggatctccctttgggccgcctccccg cctg In embodiments of the invention, a bicistronic vector comprising the nucleotide sequence of SEQ ID NO: 176 encodes a predicted CACCR BCMA CAR polypeptide having the predicted amino acid sequence of SEQ ID NO: 177, which comprises the following domains: CD8 signal peptide (e.g. SEQ ID NO: 89), transmembrane/JAK2 binding domain—TpoR(478-582; H499L, S505N, W515K) (e.g. SEQ ID NO: 12), IL2Rb(339-379, 393-433, 518-551) (e.g. SEQ ID NO: 78), P2A (e.g. SEQ ID NO: 105), CD8 alpha signal sequence (e.g., SEQ ID NO:89), and P5A2 BCMA CAR with a safety switch (e.g. SEQ ID NO: 166). In aspects of this embodiment, the bicistronic vector further comprises, following the polypeptide coding sequence, a wild-type WPRE of e.g. SEQ ID NO: 174 or a mutant WPRE ("mWPRE") of e.g. nucleotide sequence of SEQ ID NO: 175. In other aspects of this embodiment, the bicistronic vector does not include a wild-type WPRE or a mutant WPRE. In some aspects, the disclosure provides an engineered immune cell that comprises the polynucleotide sequence of SEQ ID NO: 176 and expresses a CACCR comprising the amino acid sequence of SEQ ID NO: 185 or 100, and a BCMA CAR comprising the amino acid sequence of SEQ ID NO: 166. In some embodiments, the disclosure provides an engineered immune cell that expresses a CACCR comprising the amino acid sequence of SEQ ID NO: 181, 185 or 100, and a BCMA CAR comprising the amino acid sequence of SEQ ID NO: 166. In some embodiments, the engineered immune cell is an engineered T cell. In some embodiments, the engineered T cell is an allogeneic T cell. In some embodiments, the engineered T cell is an autologous T cell.

SEQ ID NO: 176:

atggccctgccagtgaccgccctgctgctgccactggccctgctgctgc acgcagcaaggccatcagaccctactagagtcgagaccgctaccgagac cgcttggatctctctggtgaccgccctgctgctggtgctgggcctgaac gccgtgctgggcctgctgctgctgaggaagcagttcccagcacactacc ggagactgaggcacgcactgtggccaagcctgcccgacctgcacagggt gctgggacagtatctgagggatacagccgccctgagcccacctaaggca accgtgtccgacacatgcgaggaggtggaaccaagtctgctggaaatcc tgccaaaatcctctgagcggacacccctgcccctgctcgagcagcagga caaggtgcccgagcctgcctccctgagctccaaccacagcctgacctcc tgctttacaaatcagggctacttctttttccacctgcctgacgccctgg agatcgaggcctgtcaggatgagggagtggcaggagcacctaccggctc tagcccacagccactgcagccactgtctggagaggacgatgcctactgc acattccccagccgggacgatctgctgctgttttccccttctggacagg gagagttccgggccctgaacgcaagactgccactgaataccgacgccta tctgtctctgcaggagctgcagggccaggaccccacacacctggtggga tccggagccaccaacttctccctgctgaagcaggccggcgatgtggagg agaatccaggccccatggctctgcccgtcaccgcactgctgctgcccct ggctctgctgctgcacgccgcaagacccgaggtccagctgctggaatct gggggaggactggtgcagcctggaggcagcctgagactgtcctgcgcag catctggcttcaccttcagctcctacgccatgaactgggtgaggcaggc accaggcaagggactggagtgggtgtctgccatctccgactctggcggc agcacctactatgccgattccgtgaagggccgcttcacaatcagccggg ataactccaagaataccctgtacctgcagatgaattccctgagagccga ggatacagccgtgtactattgcgccaggtattggcccatggacatctgg ggccagggcacactggtgaccgtgtcttccggaggaggaggctccggag -continued gaggaggctctggcggcggcggcagcgagatcgtgctgacacagtctcc tggcaccctgagcctgtccccaggagagagagccaccctgagctgtagg gcctctcagagcgtgtcctctagctacctggcctggtatcagcagaagc ccggccaggcccctagactgctgatgtacgacgccagcatcagggcaac aggcatccctgatcggttctccggctctggcagcggaaccgactttaca ctgaccatcagcaggctggagcccgaggacttcgccgtgtactattgcc agcagtatggctcctggcctctgacatttggccagggcaccaaggtgga gatcaagggctccggcggcggaggctcttgcccatacagcaacccatcc ctgtgctctggaggaggaggctcctgtccttatagcaatcctagcctgt gctccggcggaggaggctctaccacaaccccagcaccaaggccacctac acctgcaccaaccatcgcctctcagccactgagcctgagacccgaggcc tgtaggcctgcagcaggaggagcagtgcacacccggggactggactttg cctgcgatatctacatctgggcaccactggcaggaacatgtggcgtgct gctgctgagcctggtcatcaccctgtactgcaagagaggcaggaagaag ctgctgtatatcttcaagcagccctttatgcgccctgtgcagacaaccc aggaggaggatggctgctcctgtcggttcccagaggaggaggagggagg atgtgagctgcgcgtgaagttttcccggtctgccgacgcaccagcatac cagcagggccagaaccagctgtataacgagctgaatctgggccggagag aggagtacgacgtgctggataagaggagggggaagagatcccgagatggg aggcaagccacggagaaagaacccccaggagggcctgtacaatgagctg cagaaggataagatggccgaggcctatagcgagatcggcatgaagggag agaggcgccggggcaaggggcacgacggcctgtatcagggcctgtccac cgctaccaaagacacctatgatgctctgcacatgcaggctctgccacca agatga

SEQ ID NO: 177

MALPVTALLLPLALLLHAARPSDPTRVETATETAWISLVTALLLVLGLN

AVLGLLLLRKQFPAHYRRLRHALWPSLPDLHRVLGQYLRDTAALSPPKA

TVSDTCEEVEPSLLEILPKSSERTPLPLLEQQDKVPEPASLSSNHSLTS

CFTNQGYFFFHLPDALEIEACQDEGVAGAPTGSSPQPLQPLSGEDDAYC

TFPSRDDLLLFSPSGQGEFRALNARLPLNTDAYLSLQELQGQDPTHLVG

SGATNFSLLKQAGDVEENPGPMALPVTALLLPLALLLHAARPEVQLLES

GGGLVQPGGSLRLSCAASGFTFSSYAMNWVRQAPGKGLEWVSAISDSGG

STYYADSVKGRFTISRDNSKNTLYLQMNSLRAEDTAVYYCARYWPMDIW

GQGTLVTVSSGGGGSGGGGGGGGSEIVLTQSPGTLSLSPGERATLSCRA

SQSVSSSYLAWYQQKPGQAPRLLMYDASIRATGIPDRFSGSGSGTDFTL

TISRLEPEDFAVYYCQQYGSWPLTFGQGTKVEIKGSGGGGSCPYSNPSL

CSGGGGSCPYSNPSLCSGGGGSTTTPAPRPPTPAPTIASQPLSLRPEAC

RPAAGGAVHTRGLDFACDIYIWAPLAGTCGVLLLSLVITLYCKRGRKKL

LYIFKQPFMRPVQTTQEEDGCSCRFPEEEEGGCELRVKFSRSADAPAYQ

QGQNQLYNELNLGRREEYDVLDKRRGRDPEMGGKPRRKNPQEGLYNELQ

KDKMAEAYSEIGMKGERRRGKGHDGLYQGLSTATKDTYDALHMQALPPR

In embodiments of the invention, a bicistronic vector comprising the nucleotide sequence of SEQ ID NO: 178 encodes a predicted CACCR BCMA CAR polypeptide having the predicted amino acid sequence of SEQ ID NO: 179, which comprises the following domains: CD8 signal peptide (e.g. SEQ ID NO: 89), transmembrane/JAK2 binding domain—TpoR(478-582; H499L, S505N, W515K) (e.g. SEQ ID NO: 12), IL2Rb(393-433, 518-551) (e.g. SEQ ID NO: 77), P2A (e.g. SEQ ID NO: 105), CD8 alpha signal sequence (e.g., SEQ ID NO:89), and P5A2 BCMA CAR with a safety switch (e.g. SEQ ID NO: 141). In aspects of this embodiment, the bicistronic vector further comprises, following the polypeptide coding sequence, a wild-type WPRE of e.g. SEQ ID NO: 174 or a mutant WPRE ("mWPRE") of e.g. nucleotide sequence of SEQ ID NO: 175. In other aspects of this embodiment, the bicistronic vector does not include a wild-type WPRE or a mutant WPRE.

In some embodiments, the disclosure provides an engineered immune cell that comprises the polynucleotide sequence of SEQ ID NO: 178 and expresses a CACCR comprising the amino acid sequence of SEQ ID NO: 186 or 143 and a BCMA CAR comprising the amino acid sequence of SEQ ID NO: 166. In some embodiments, the disclosure provides an engineered immune cell that expresses a CACCR comprising the amino acid sequence of SEQ ID NO: 182, 186 or 143, and a BCMA CAR comprising the amino acid sequence of SEQ ID NO: 166. In some embodiments, the engineered immune cell is an engineered T cell. In some embodiments, the engineered T cell is an allogeneic T cell. In some embodiments, the engineered T cell is an autologous T cell.

SEQ ID NO: 178:

atggccctgccagtgaccgccctgctgctgccactggccctgctgctgc acgcagcaaggccatcagaccctactagagtcgagaccgctaccgagac cgcttggatctctctggtgaccgccctgctgctggtgctgggcctgaac gccgtgctgggcctgctgctgctgaggaagcagttcccagcacactacc ggagactgaggcacgcactgtggccaagcctgcccgacctgcacagggt gctgggacagtatctgagggatacagccgccctgagcccacctaaggca accgtgtccgacacatgcgaggaggtggaaccaagtctgctggaaatcc tgccaaaatcctctgagcggacacccctgcccctgctcgaggacgaggg agtggcaggagcaccaaccggcagctccccccagcctctgcagccactg tccggagaggacgatgcatactgcacattcccttctcgggacgatctgc tgctgttctctccaagcggacagggagagtttcgggccctgaacgccag actgcccctgaataccgacgcctatctgagcctgcaggagctgcaggga caggaccccacacacctggtgggatccggagccaccaacttctccctgc tgaagcaggccggcgatgtggaggagaatccaggccccatggctctgcc cgtcaccgcactgctgctgcccctggctctgctgctgcacgccgcaaga cccgaggtccagctgctggaatctgggggaggactggtgcagcctggag gcagcctgagactgtcctgcgcagcatctggcttcaccttcagctccta cgccatgaactgggtgaggcaggcaccaggcaagggactggagtgggtg tctgccatctccgactctggcggcagcacctactatgccgattccgtga agggccgcttcacaatcagccgggataactccaagaataccctgtacct -continued gcagatgaattccctgagagccgaggatacagccgtgtactattgcgcc aggtattggcccatggacatctggggccagggcacactggtgaccgtgt cttccggaggaggaggctccggaggaggaggctctggcggcggcggcag cgagatcgtgctgacacagtctcctggcaccctgagcctgtccccagga gagagagccaccctgagctgtagggcctctcagagcgtgtcctctagct acctggcctggtatcagcagaagcccggccaggcccctagactgctgat gtacgacgccagcatcagggcaacaggcatccctgatcggttctccggc tctggcagcggaaccgactttacactgaccatcagcaggctggagcccg aggacttcgccgtgtactattgccagcagtatggctcctggcctctgac atttggccagggcaccaaggtggagatcaagggctccggcggcggaggc tcttgcccatacagcaacccatccctgtgctctggaggaggaggctcct gtccttatagcaatcctagcctgtgctccggcggaggaggctctaccac aaccccagcaccaaggccacctacacctgcaccaaccatcgcctctcag ccactgagcctgagacccgaggcctgtaggcctgcagcaggaggagcag tgcacacccggggactggactttgcctgcgatatctacatctgggcacc actggcaggaacatgtggcgtgctgctgctgagcctggtcatcaccctg tactgcaagagaggcaggaagaagctgctgtatatcttcaagcagccct ttatgcgccctgtgcagacaacccaggaggaggatggctgctcctgtcg gttcccagaggaggaggagggaggatgtgagctgcgcgtgaagttttcc cggtctgccgacgcaccagcataccagcagggccagaaccagctgtata acgagctgaatctgggccggagagaggagtacgacgtgctggataagag gaggggaagagatcccgagatgggaggcaagccacggagaaagaacccc caggagggcctgtacaatgagctgcagaaggataagatggccgaggcct atagcgagatcggcatgaagggagagaggcgccggggcaagggacacga cggcctgtatcagggcctgtccaccgctaccaaagacacctatgatgct ctgcacatgcaggctctgccaccaagatga

SEQ ID NO: 179:
MALPVTALLLPLALLLHAARPSDPTRVETATETAWISLVTALLLVLGLN

AVLGLLLLRKQFPAHYRRLRHALWPSLPDLHRVLGQYLRDTAALSPPKA

TVSDTCEEVEPSLLEILPKSSERTPLPLLEDEGVAGAPTGSSPQPLQPL

SGEDDAYCTFPSRDDLLLFSPSGQGEFRALNARLPLNTDAYLSLQELQG

QDPTHLVGSGATNFSLLKQAGDVEENPGPMALPVTALLLPLALLLHAAR

PEVQLLESGGGLVQPGGSLRLSCAASGFTFSSYAMNWVRQAPGKGLEWV

SAISDSGGSTYYADSVKGRFTISRDNSKNTLYLQMNSLRAEDTAVYYCA

RYWPMDIWGQGTLVTVSSGGGGSGGGGSGGGGSEIVLTQSPGTLSLSPG

ERATLSCRASQSVSSSYLAWYQQKPGQAPRLLMYDASIRATGIPDRFSG

SGSGTDFTLTISRLEPEDFAVYYCQQYGSWPLTFGQGTKVEIKGSGGGG

SCPYSNPSLCSGGGGSCPYSNPSLCSGGGGSTTTPAPRPPTPAPTIASQ

PLSLRPEACRPAAGGAVHTRGLDFACDIYIWAPLAGTCGVLLLSLVITL

YCKRGRKKLLYIFKQPFMRPVQTTQEEDGCSCRFPEEEEGGCELRVKFS

-continued

RSADAPAYQQGQNQLYNELNLGRREEYDVLDKRRGRDPEMGGKPRRKNP

QEGLYNELQKDKMAEAYSEIGMKGERRRGKGHDGLYQGLSTATKDTYDA

LHMQALPPR

In some embodiments of the invention, a bicistronic vector encodes a polypeptide that is at least about 80%, 85%, 90%, 95%, 96%, 98%, 99% or 100% identical to the amino acid sequence of SEQ ID NO: 173, 177 or 179. In some embodiments, the invention further provides a cell, such as an immune cell, e.g. a T cell, that contains a bicistronic vector that encodes a polypeptide that is at least about 80%, 85%, 90%, 95%, 96%, 98%, 99% or 100% identical to the amino acid sequence of SEQ ID NO: 173, 177 or 179. In some embodiments, the invention further provides a method of treating a disease characterized by the expression of BCMA, such as multiple myeloma, comprising administering such a cell to a patient suffering from the disease.

In some embodiments, the CAR-immune cell (e.g., CAR-T cell) of the disclosure comprises a polynucleotide encoding a suicide polypeptide, such as for example RQR8 or R2. See, e.g., WO2013153391A, which is hereby incorporated by reference in its entirety. In some embodiments, a suicide polypeptide is expressed on the surface of the cell. In some embodiments, a suicide polypeptide is included in the CAR construct. In some embodiments, a suicide polypeptide is not part of the CAR construct.

In some embodiments, the extracellular domain of any one of the CARs disclosed herein may comprise one or more epitopes specific for (specifically recognized by) a monoclonal antibody. These epitopes are also referred to herein as mAb-specific epitopes. Exemplary mAb-specific epitopes are disclosed in International Patent Publication No. WO 2016/120216, which is incorporated herein in its entirety. In these embodiments, the extracellular domain of the CARs comprises antigen binding domains that specifically bind to a target of interest and one or more epitopes that bind to one or more monoclonal antibodies (mAbs). CARs comprising the mAb-specific epitopes can be single-chain or multi-chain.

The inclusion of epitopes specific for monoclonal antibodies in the extracellular domain of the CARs described herein allows sorting and depletion of engineered immune cells expressing the CARs. In some embodiments, allowing for depletion provides a safety switch in case of deleterious effects, e.g., upon administration to a subject.

Methods of preparing engineered immune cells for use in immunotherapy are also provided herein. In some embodiments, the methods comprise introducing a CACCR and a CAR into immune cells, and expanding the cells. In some embodiments, the invention relates to a method of engineering an immune cell comprising: providing a cell and expressing a CACCR, and expressing at the surface of the cell at least one CAR. In some embodiments, the method comprises: transfecting the cell with at least one polynucleotide encoding a CACCR, and at least one polynucleotide encoding a CAR, and expressing the polynucleotides in the cell. In some embodiments, the method comprises: transfecting the cell with at least one polynucleotide encoding a CACCR, at least one polynucleotide encoding a CAR, and expressing the polynucleotides in the cell.

In some embodiments, the polynucleotides encoding the CACCR and CAR are present in one or more expression vectors for stable expression in the cells. In some embodiments, the polynucleotides are present in viral vectors for stable expression in the cells. In some embodiments, the viral vectors may be for example, lentiviral vectors or adenoviral vectors.

In some embodiments, polynucleotides encoding polypeptides according to the present disclosure can be mRNA which is introduced directly into the cells, for example by electroporation. In some embodiments, CytoPulse electroporation technology, such as PulseAgile, can be used to transiently permeabilize living cells for delivery of material into the cells (e.g. U.S. Pat. No. 6,078,490; PCT/US2011/000827; and PCT/US2004/005237). Parameters can be modified in order to determine conditions for high transfection efficiency with minimal mortality.

Also provided herein are methods of transfecting an immune cell, e.g a T cell. In some embodiments, the method comprises: contacting a T cell with RNA and applying to the T cell an agile pulse sequence. In some embodiments, a method of transfecting an immune cell (e.g. T cell) comprising contacting the immune cell with RNA and applying to the cell an agile pulse sequence.

In some embodiments, the method can further comprise a step of genetically modifying a cell by inactivating at least one gene expressing, for example without limitation, a component of the TCR, a target for an immunosuppressive agent, an HLA gene, and/or an immune checkpoint protein such as, for example, PDCD1 or CTLA-4. By inactivating a gene it is intended that the gene of interest is not expressed in a functional protein form. In some embodiments, the gene to be inactivated is selected from the group consisting of, for example without limitation, TCRα, TCRβ, CD52, GR, deoxycytidine kinase (DCK), PD-1, and CTLA-4. In some embodiments the method comprises inactivating one or more genes by introducing into the cells a rare-cutting endonuclease able to selectively inactivate a gene by selective DNA cleavage. In some embodiments the rare-cutting endonuclease can be, for example, a transcription activator-like effector nuclease (TALE-nuclease) or CRISPR-based endonuclease (e.g Cas-9 or Cas12a).

In another aspect, a step of genetically modifying cells can comprise: modifying immune cells (e.g. T cells) by inactivating at least one gene expressing a target for an immunosuppressive agent, and; expanding the cells, optionally in the presence of the immunosuppressive agent.

In some embodiments, the engineered immune cells (e.g. T cells) provided herein exhibit improved cytotoxicity, increased expansion, and/or increased levels of memory phenotype markers relative to engineered immune cells that do not express the CACCR.

In some embodiments, the engineered immune cells (e.g. T cells) provided herein exhibit (i) increased in vivo persistence, (ii) increased STAT activation, (iii) increased cytotoxicity, (iv) increased levels of memory phenotype markers, (v) increased expansion (proliferation), or combinations of these functional features constitutively, relative to engineered immune cells that do not express the CACCR. In some embodiments, the improvement in the one or more functional features described herein is tunable, dependent upon the mutations/modifications introduced to the CACCR. In some embodiments, STATs activated by the engineered immune cell comprising one or more CACCRs disclosed are STAT1, STAT2, STAT3, STAT4, STAT5, STAT6, or combinations thereof. In one embodiment, memory phenotype markers that are increased or maintained by the immune cell comprising the CACCR include stem cell memory (Tscm) marker and central memory (Tcm) marker.

In some embodiments, the improvement in one or more functional features exhibited by an engineered immune cell comprising a CACCR provided herein is at least about 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 25 fold, 30 fold, 40 fold, 50 fold, 60 fold, 70 fold, 80 fold, 90 fold, 100 fold, 125 fold, 150 fold, 200 fold, 250 fold, 300 fold, 350 fold, 400 fold, 450 fold, or even about 500 fold, including values and ranges therebetween, compared to an immune cell that does not express the CACCR.

In some embodiments, the improvement in one or more functional features exhibited by an engineered immune cell comprising a CACCR provided herein is at least about 10%, 20%, 25%, 30%, 35%, 40%, 45%, 50%, 55%, 60%, 70%, 75%, 80%, 90%, 100%, 125%, 150%, 200%, 250%, 300%, 350%, 400%, or even about 500%, including values and ranges therebetween, compared to an engineered immune cell that does not express the CACCR.

III. Therapeutic Methods

Provided herein are pharmaceutical compositions comprising cells bearing the CACCRs and CARs of the disclosure.

Engineered CACCR-bearing and BCMA CAR-bearing immune cells (e.g. BCMA CAR-T cells) obtained by the methods described above, or cell lines derived from such engineered immune cells, can be used as a medicament. In some embodiments, such a medicament can be used for treating a disorder such as for example a viral disease, a bacterial disease, a cancer, an inflammatory disease, an immune disease, or an aging-associated disease. In some embodiments, the cancer is a solid cancer. In some embodiments the cancer is a liquid cancer. The cancer can be selected from the group consisting of gastric cancer, sarcoma, lymphoma, leukemia, head and neck cancer, thymic cancer, epithelial cancer, salivary cancer, liver cancer, stomach cancer, thyroid cancer, lung cancer, ovarian cancer, breast cancer, prostate cancer, esophageal cancer, pancreatic cancer, glioma, leukemia, multiple myeloma, B cell malignancy, diffused large B-cell lymphoma, renal cell carcinoma, bladder cancer, cervical cancer, choriocarcinoma, colon cancer, oral cancer, skin cancer, and melanoma. In some embodiments, the subject is a previously treated adult subject with locally advanced or metastatic melanoma, squamous cell head and neck cancer (SCHNC), ovarian carcinoma, sarcoma, or relapsed or refractory classic Hodgkin's Lymphoma (cHL).

In some embodiments, engineered immune cells, or a cell line derived from the engineered immune cells, can be used in the manufacture of a medicament for treatment of a disorder in a subject in need thereof. In some embodiments, the disorder can be, for example, a cancer, an autoimmune disorder, or an infection.

Also provided herein are methods for treating subjects in need of such treatment.

As used herein, the term "subject" refers to any vertebrate including, without limitation, humans and other primates (e.g., chimpanzees, cynomolgous monkeys, and other apes and monkey species), farm animals (e.g., cattle, sheep, pigs, goats and horses), domestic mammals (e.g., dogs and cats), laboratory animals (e.g., rabbits, rodents such as mice, rats, and guinea pigs), and birds (e.g., domestic, wild and game birds such as chickens, turkeys and other gallinaceous birds, ducks, geese, and the like). In some embodiments, the subject is a mammal. In exemplary embodiments, the subject is a human.

In some embodiments the method comprises providing immune cells of the disclosure, bearing the CACCRs and CARs (e.g., a BCMA CAR) described herein to a subject in need thereof.

In some embodiments, CACCR and CAR-bearing T cells of the invention can undergo robust in vivo T cell expansion and can persist for an extended amount of time.

Methods of treatment of the invention can be ameliorating, curative or prophylactic. The method of the invention may be either part of an autologous immunotherapy or part of an allogenic immunotherapy treatment.

In another aspect, the invention provides a method of inhibiting tumor growth or progression in a subject who has a tumor, comprising administering to the subject an effective amount of CACCR-expressing and CAR-expressing (e.g., BCMA CAR-expressing) immune cells as described herein. In another aspect, the invention provides a method of inhibiting or preventing metastasis of cancer cells in a subject, comprising administering to the subject in need thereof an effective amount of engineered immune cells as described herein. In another aspect, the invention provides a method of inducing tumor regression in a subject who has a tumor, comprising administering to the subject an effective amount of engineered immune cells as described herein.

In some embodiments, the engineered T cells herein can be administered parenterally in a subject. In some embodiments, the engineered T cells herein can be administered intravenously in a subject.

Also provided is the use of any of the engineered T cells provided herein in the manufacture of a medicament for the treatment of cancer or for inhibiting tumor growth or progression in a subject in need thereof.

In some embodiments, treatment can be administrated into subjects undergoing an immunosuppressive treatment. Indeed, the invention preferably relies on cells or population of cells, which have been made resistant to at least one immunosuppressive agent due to the inactivation of a gene encoding a receptor for such immunosuppressive agent. In this aspect, the immunosuppressive treatment should help the selection and expansion of the T cells according to the invention within the subject. The administration of the cells or population of cells according to the invention may be carried out in any convenient manner, including by aerosol inhalation, injection, ingestion, transfusion, implantation or transplantation. The compositions described herein may be administered to a subject subcutaneously, intradermally, intratumorally, intranodally, intramedullary, intramuscularly, by intravenous or intralymphatic injection, or intraperitoneally. Cells bearing the CACCRs and CARs (e.g. a BCMA CAR) of the disclosure or the pharmaceutical compositions thereof may be administered via one or more of the following routes of administration: intravenous, intraocular, intravitreal, intramuscular, subcutaneous, topical, oral, transdermal, intraperitoneal, intraorbital, by implantation, by inhalation, intrathecal, intraventricular, via the ear, or intranasal.

In some embodiments the administration of the cells or population of cells (bearing the CACCRs and CARs, e.g., a BCMA CAR, of the disclosure) can comprise administration of, for example, about $10^4$ to about $10^9$ cells per kg body weight including all integer values of cell numbers within those ranges. In some embodiments the administration of the cells or population of cells can comprise administration of about $10^4$ to $10^5$ cells per kg body weight, $10^5$ to $10^6$ cells per kg body weight, $10^6$ to $10^7$ cells per kg body weight, $10^7$ to $10^8$ cells per kg body weight, or $10^8$ to $10^9$ cells per kg body weight. The cells or population of cells can be administrated in one or more doses. In some embodiments, said effective amount of cells can be administrated as a single dose. In some embodiments, said effective amount of cells can be administrated as more than one dose over a period of time. Timing of administration is within the judgment of managing physician and depends on the clinical condition of the subject. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administrated will be dependent upon the age, health and weight of the recipient, kind of concurrent treatment, if any, frequency of treatment and the nature of the effect desired. In some embodiments, an effective amount of cells or composition comprising those cells are administrated parenterally. In some embodiments, administration can be an intravenous administration. In some embodiments, administration can be directly done by injection within a tumor.

In line with the above, an appropriate dosage of a cell of the invention (e.g., a CACCR-expressing and a BCMA CAR-expressing allogeneic or autologous T cells) may be between about 7x10^6 cells and about 480x10^6 cells. In certain embodiments, an appropriate dose may range from about 20x10^6 cells/dose to about 480x10^6 cells/dose, more particularly about 20x10^6 cells/dose, about 40x10^6 cells/dose, about 60x10^6 cells/dose, about 80x10^6 cells/dose, about 100x10^6 cells/dose, about 120x10^6 cells/dose, about 160x10^6 cells/dose, about 240x10^6 cells/dose, about 300x10^6 cells/dose, about 320x10^6 cells/dose, about 360x10^6 cells/dose, about 400x10^6 cells/dose, about 440x10^6 cells/dose, or about 480x10^6 cells/dose.

In certain embodiments, when the weight of the subject is 50 kg or more, and at least one dose of cells is to be administered to the patient, an appropriate dose may range from about 20x10^6 cells/dose to about 480x10^6 cells/dose, more particularly about 20x10^6 cells/dose, about 40x10^6 cells/dose, about 80x10^6 cells/dose, about 120x10^6 cells/dose, about 240x10^6 cells/dose, about 320x10^6 cells/dose, about 360x10^6 cells/dose, or about 480x10^6 cells/dose. In certain embodiments, when the weight of the subject is less than 50 kg, and at least one dose of cells is to be administered to the patient, an appropriate dose may range from about 7x10^6 cells/dose to about 360x10^6 cells/dose, more particularly about 7x10^6 cells/dose, about 14x10^6 cells/dose, about 20x10^6 cells/dose, about 80x10^6 cells/dose, about 240x10^6 cells/dose, or about 360x10^6 cells/dose.

The methods can further comprise administering one or more agents to a subject prior to administering the engineered immune cells bearing a CAR (e.g., a BCMA CAR) and a CACCR provided herein. In certain embodiments, the agent is a lymphodepleting (preconditioning) regimen. For example, methods of lymphodepleting a subject in need of such therapy comprise administering to the subject specified beneficial doses of cyclophosphamide (between 200 mg/m$^2$/day and 2000 mg/m$^2$/day, about 100 mg/m$^2$/day and about 2000 mg/m$^2$/day; e.g., about 100 mg/m$^2$/day, about 200 mg/m$^2$/day, about 300 mg/m$^2$/day, about 400 mg/m$^2$/day, about 500 mg/m$^2$/day, about 600 mg/m$^2$/day, about 700 mg/m$^2$/day, about 800 mg/m$^2$/day, about 900 mg/m$^2$/day, about 1000 mg/m$^2$/day, about 1500 mg/m$^2$/day or about 2000 mg/m$^2$/day) and specified doses of fludarabine (between 20 mg/m$^2$/day and 900 mg/m$^2$/day, between about 10 mg/m$^2$/day and about 900 mg/m$^2$/day; e.g., about 10 mg/m$^2$/day, about 20 mg/m$^2$/day, about 30 mg/m$^2$/day, about 40 mg/m$^2$/day, about 40 mg/m$^2$/day, about 50 mg/m$^2$/day, about 60 mg/m$^2$/day, about 70 mg/m$^2$/day, about 80 mg/m$^2$/day, about 90 mg/m$^2$/day, about 100 mg/m$^2$/day, about 500 mg/m$^2$/day or about 900 mg/m$^2$/day). An exemplary dosing regimen involves treating a subject comprising administering daily to the patient about 300 $mg/m^2$/day of cyclophosphamide in combination or before or after administering about 30 $mg/m^2$/day of fludarabine for three days prior to administration of a therapeutically effective amount of engineered immune cells to the patient.

In some embodiments, notably in the case when the engineered cells provided herein have been gene edited to eliminate or minimize surface expression of CD52, lymphodepletion further comprises administration of an anti-CD52 antibody, such as alemtuzumab (CAS (Chemical Abstract Service) Registry #216503-57-0). In some embodiments, the CD52 antibody is administered at a dose of about 1-20 mg/day IV, e.g., about 13 mg/day IV for 1, 2, 3 or more days, or about 20 mg/day IV for 1, 2, 3 or more days. In some embodiments, the CD52 antibody is administered at a dose of about 20-30 mg/day IV, e.g., about 30 mg/day IV for 1, 2, 3 or more days. The antibody can be administered in combination with, before, or after administration of other elements of a lymphodepletion regime (e.g., cyclophosphamide and/or fludarabine).

In some embodiments, an effective amount of engineered immune cells can be administrated to the patient after the initial or first dosing (i.e., redosing). The second or subsequent dosing can be the same as, or higher or lower than, the amount of engineered immune cells of previous dosing. In some embodiments, a lymphodepleting regimen is administered to the patient before a second or subsequent dosing of the engineered immune cells. In some embodiments, the second or subsequent dosing is not preceded with a lymphodepletion regimen.

In certain embodiments, compositions comprising CACCR and CAR-expressing (e.g., a BCMA CAR-expressing) immune effector cells disclosed herein may be administered in conjunction with any number of chemotherapeutic agents.

In certain embodiments, patients who have received CACCR BCMA CAR T cells of the disclosure are subsequently administered an effective amount of ribuximab and/or dasatinib to reduce or mitigate any potential safety concerns during the course of CAR T treatment. In certain embodiments, the patients receive BCMA CAR T therapy for the treatment of multiple myeloma or other BMCA positive cancers.

IV. Kits and Articles of Manufacture

The present disclosure provides kits comprising any one or more of the CACCR- and CAR-bearing cells described herein (e.g. a cell, for example an immune cell such as a T cell, bearing a CACCR and a BCMA CAR), and pharmaceutical compositions thereof. The present disclosure also provides articles of manufacture comprising any one or more of the CACCR- and CAR-bearing (e.g., BCMA CAR-bearing) CAR-I cells described herein (e.g. a cell, for example an immune cell such as a T cell, bearing a CACCR and a BCMA CAR), pharmaceutical compositions thereof, and kits described herein.

The following examples are included for illustrative purposes and are not intended to limit the scope of the disclosure.

All patent and non-patent documents referenced throughout this disclosure are incorporated by reference herein in their entirety for all purposes.

FIG. 1 shows a schematic representation of an engineered constitutively active chimeric cytokine receptor as disclosed herein and used in the following examples. FIG. 2 shows schematic representations of truncated cytotail polypeptides of the disclosure that are components of the CACCR in the following examples. FIGS. 2B-2D show exemplary bicistronic vectors for the expression of both a CACCR and a CAR, which can be used in experiments and procedures such as those described below for the generation of cells that co-express a CAR and a CACCR.

EXAMPLES

Example 1: Optimized IL2Rb-Derived Cytotails More Closely Mimic Signaling of IL-15, Rather than IL-2

IL-2 and IL-15 are two cytokines that naturally signal through a heterodimeric cytokine receptor comprised of the common-gamma chain and IL2Rb. In spite of sharing the same native receptors, IL-2 and IL-15 exert different effects on T cell differentiation and persistence. Whereas IL-2 induces short-lived effector differentiation, IL-15 promotes the generation of long-lived memory T cells. Furthermore, increased serum concentrations of IL-15 has been shown to correlate positively with patient response to CAR-T cell therapy. CACCRs that mimic the signaling and effects of IL-15, rather than IL-2, are therefore preferred. We sought to determine if the truncated IL2Rb cytotails more closely mimicked IL-2 or IL-15 signaling.

To this end, we utilized CAR-T cells comprising an exemplary BCMA CAR bearing the P5A2 scFv directed towards BCMA, coupled to rituximab mimotopes, 4-1BB and CD3z signaling domains (see U.S. Pat. No. 10,294,304, incorporated herein by reference). BCMA specific CAR-T cells co-expressing the truncated IL2Rb tails were generated, and their gene expression profiles compared to control CAR-T cells that had been exposed to exogenous recombinant human IL-2 or IL-15. To make lentivirus encoding a CACCR and BCMA CAR, HEK293T cells were plated at 0.45 million cells per mL in 2 mL of DMEM (Gibco) supplemented with 10% FBS (Hyclone) per well of a 6-well plate the day before transfection. On the day of transfection, the lentivirus was prepared by mixing together lentiviral packaging vectors 1.5 ug psPAX2, 0.5 ug pMD2G, and 0.5 ug of the appropriate transfer CAR vector in 250 uL Opti-MEM (Gibco) per well of the 6-well plate ("DNA mix"). 10 uL Lipofectamine 2000 (Invitrogen) in 250 uL Opti-MEM was incubated at room temperature for 5 minutes and then added to the DNA mix. The mixture was incubated at room temperature for 20 minutes and the total volume of 500 uL was slowly added to the sides of the wells containing HEK293T. One day post-transfection, the media from each well of HEK293T cells in the 6-well plate was replaced with 2 mL per well of T cell transduction media, i.e., X-Vivo-15 supplemented with 10% FBS. Two days post-transfection, the lentiviral supernatants from HEK293T cells were harvested and passed through a 0.45 micron filter (EMD Millipore) to remove cell debris, and crude lentiviral supernatants were used directly for T cell transduction. On Day 0, purified T cells were activated in X-Vivo-15 medium (Lonza) supplemented with 100 IU/mL human IL-2 (Miltenyi Biotec), 10% FBS (Hyclone), and human T TransAct (Miltenyi Biotec, Cat #130-111-160, 1:100 dilution) in a Grex-24 plate (Wilson Wolf, cat #80192M). On Day 2, T cells were resuspended at 0.5 million cells per mL in T cell transduction media, transduced with an equal volume of crude lentiviral supernatant along with 100 IU/mL human IL-2 in a Grex-24 plate. On Day 5, CACCR-expressing CAR-T cells were fed by replacing the spent media with T cell expansion media, i.e., X-Vivo-15 supplemented with 5% human AB serum (Gemini Bio), along with 100 IU/mL human IL-2. At this time, control CAR-T cells lacking CACCR were expanded in either 100 U/mL human IL-2 only, or 100 U/mL human IL-2 and 10 ng/mL human IL-15 (Miltenyi Biotec). Cells were expanded into larger G-Rex vessels (Wilson Wolf) as needed using T cell expansion media and the respective concentrations of recombinant cytokines. On Day 13, cells were stained with the Zombie NIR Fixable Viability Kit (Biolegend), labelled with a BUV395-conjugated CD3 antibody (Biolegend) and an anti-idiotype antibody specific for the P5A2 scFv, then FACS-sorted to enrich for CAR+ T cells. Sorted CAR+ T cells were then cultured in Grex-24 plates for a further 2 days in T cell expansion media, with CACCR BCMA CAR+ T cells left in the absence of exogenous cytokines, and with sorted control CAR+ T cells either left in the absence of exogenous cytokines, treated with 100 U/mL human IL-2, or treated with 10 ng/mL human IL-15. On Day 15, live CAR+ T cells were enriched using the Easy Sep Dead Cell Removal Kit (StemCell Technologies), and cell pellets were snap-frozen for subsequent RNA extraction and NanoString gene expression analysis (Human CAR-T Panel; NanoString Technologies). See FIG. 3A.

Figure 3A:
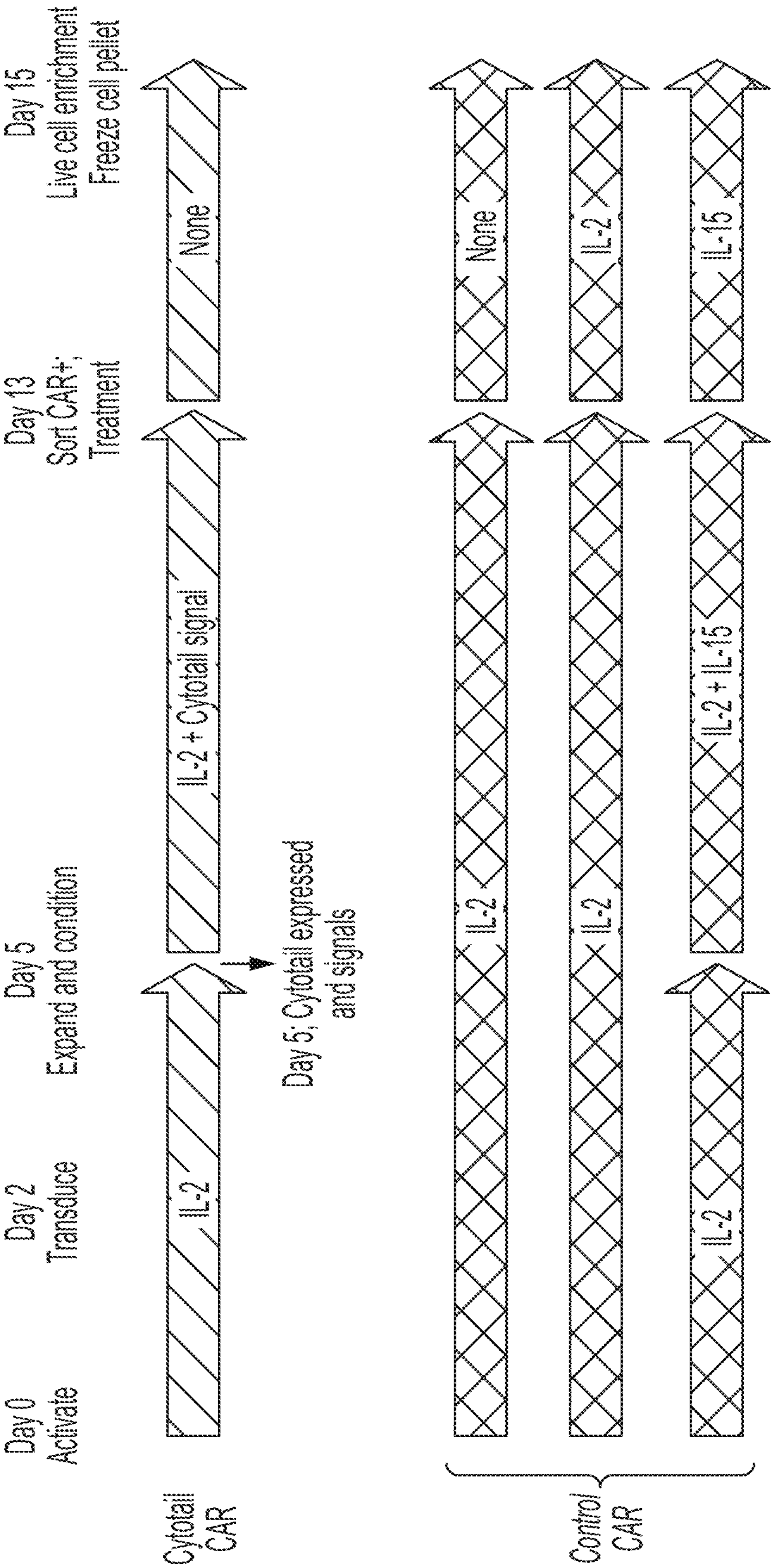
FIGS. 3A-3C show that CACCR CAR-T cells bearing truncated IL2Rb cytotails more closely mimic IL-15, rather than IL-2, signaling.
Figure 3B:
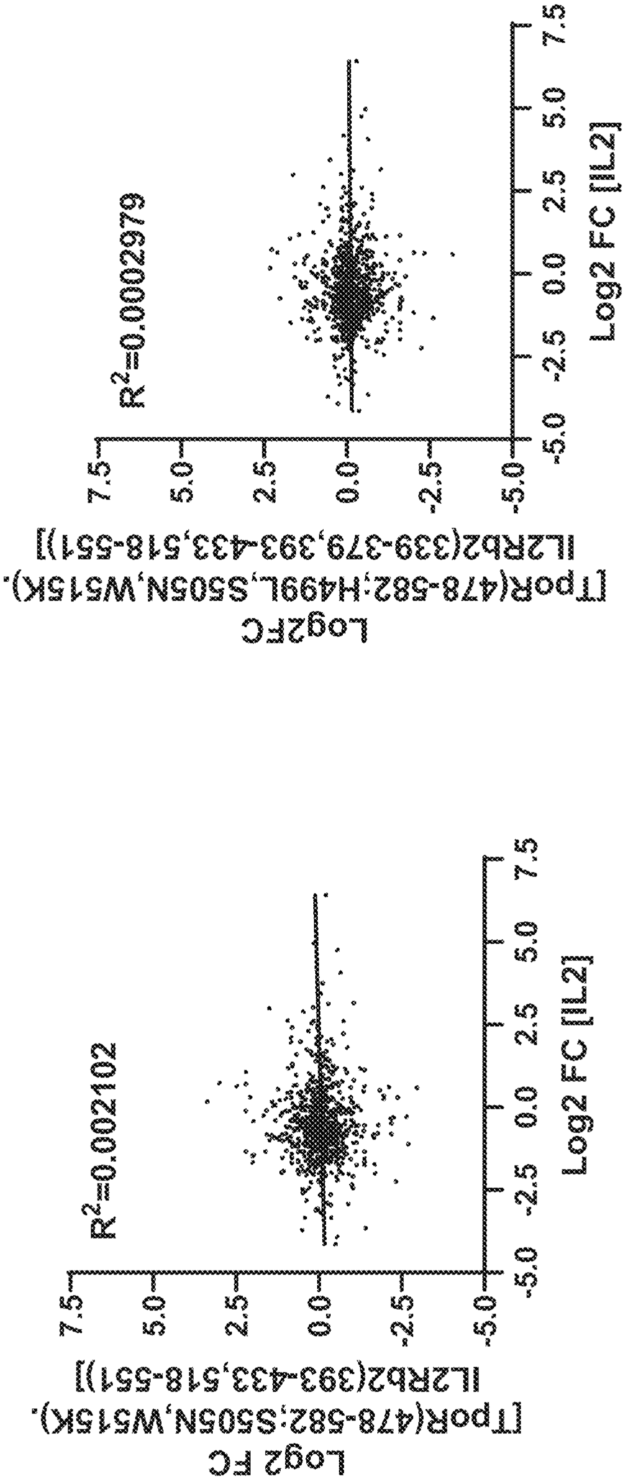
Figure 3C:
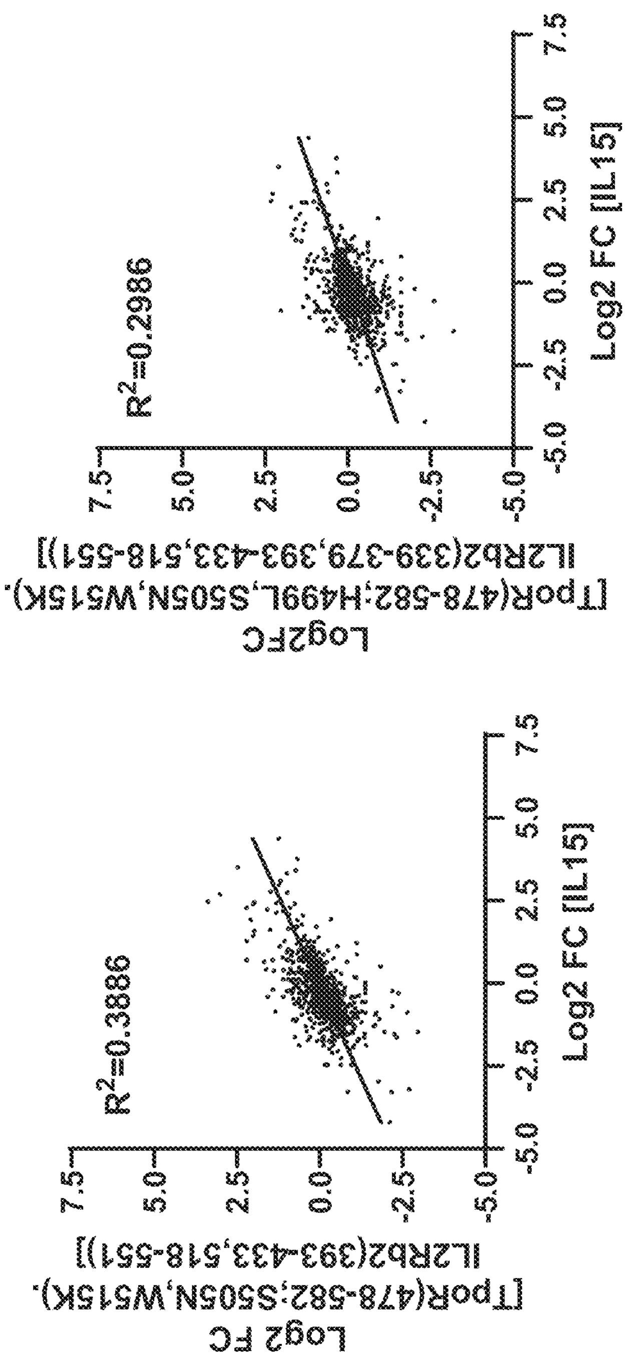

The data in FIGS. 3B-3C show that CACCR BCMA CAR-T cells bearing truncated IL2Rb tails more closely mimic IL-15, rather than IL-2, signaling. As an example, the CACCR TpoR(478-582; S505N, W515K). IL2Rb(393-433, 518-551) and TpoR(478-582; H499L, S505N, W515K). IL2Rb(339-379, 393-433, 518-551) were tested. FIG. 3A is a schematic diagram of the experimental design and workflow for sample preparation. FIG. 3B shows the gene expression profile of CACCR BCMA CAR-T cells compared to that of control CAR-T cells treated with IL-2 from Days 13-15. FIG. 3C shows the gene expression profile of CACCR CAR-T cells compared to that of control CAR-T cells treated with IL-15 from Days 13-15. Log 2 fold change (FC) of each sample was calculated by normalization to control CAR-T cells that were left untreated from Days 13-15. The R2 values and best-fit line (solid line) as determined by linear regression analysis are shown on each graph. Data shown is one representative of two donors. While the gene expression profiles of CACCR CAR-T cells showed no correlation with IL-2-treated samples (FIG. 3B), they correlated positively with IL-15-treated samples (FIG. 3C). These suggest that CACCR bearing the truncated IL2Rb tails more closely mimic the downstream signaling and transcriptional responses of IL-15, instead of IL-2.

Example 2: Constitutive Cytokine Receptors Enhance the In Vitro Cytotoxicity of CARs Directed Towards a Liquid Tumor Target The CACCRs were cloned into CAR construct directed towards a marker for a hematological malignancy (i.e. BCMA) and the long-term cytotoxicity against the BCMA positive target cell line was evaluated.

Target cells stably expressing the firefly luciferase and GFP reporters were generated by lentiviral transduction. 10,000 Luc-GFP-labelled target cells were plated in 100 uL per well in a white flat-bottomed 96-well tissue culture plate. Cryopreserved CAR-T cells (with TRAC/CD52 double knockouts) were thawed, counted, and the percentage of CAR-T cells across all samples were normalized to the sample with the lowest transduction efficiency by the addition of non-transduced (NTD) T cells. CAR-T cells in a volume of 100 uL were then added to each well of target cells at the indicated Effector:Target (E:T) ratios in triplicates. As a “Targets only” negative control, 100 uL of media, instead of T cells, was added to target cells. After two or three days, wells were mixed by gentle pipetting, and 100 uL of each T cell-containing well was transferred to a new white flat-bottomed 96-well tissue culture plate containing 10,000 freshly-plated Luc-GFP-labelled target cells in 100 uL. “Targets only” wells received fresh media in place of T cells. The new plate was incubated at 37° C., while the number of live target cells remaining in the old 96-well plate was determined using the ONE-Glo Luciferase Assay System (Promega) according to manufacturer’s instructions. The percentage of live target cells was calculated by normalizing the luciferase signal of to that of “Targets only” wells, and percentage cytotoxicity was calculated as 100%-% live target cells. Serial transfers to fresh target cells and luciferase readouts were performed every two or three days until all cytotoxic activity has ceased.

Figure 4:
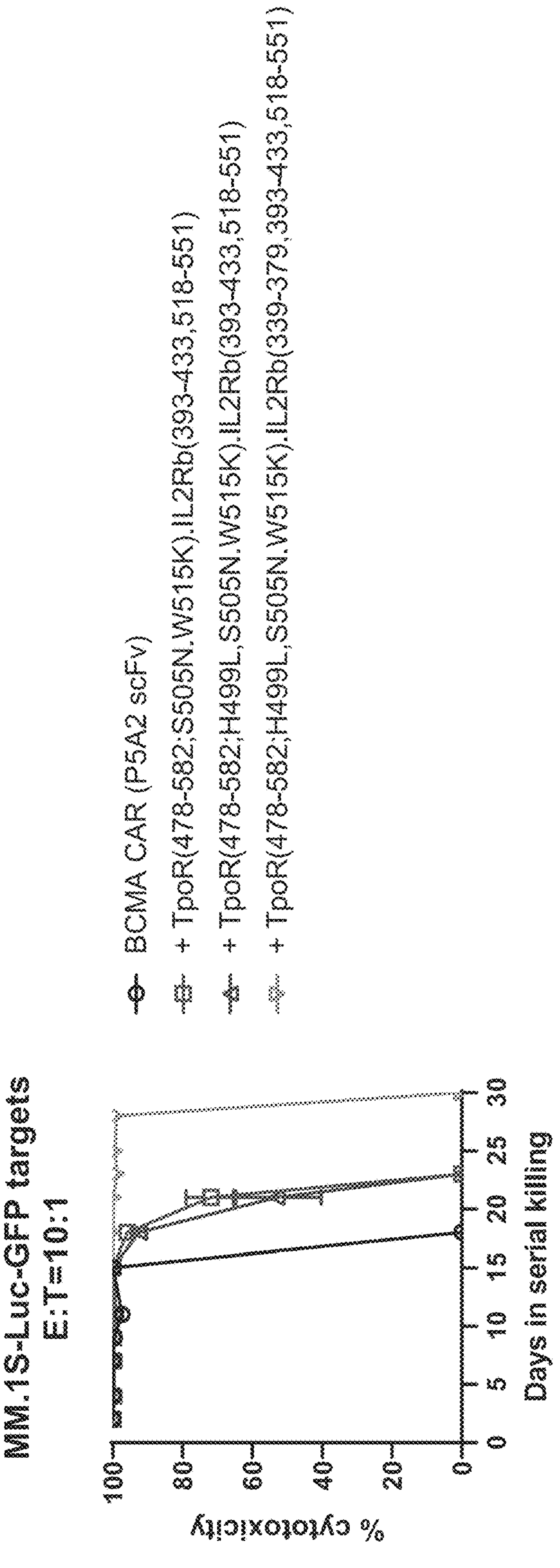
FIG. 4 shows that CACCRs improved the cytotoxic activity of TRAC/CD52 dKO CAR-T cells directed towards a liquid tumor target BCMA.

FIG. 4 shows that CACCRs improved the cytotoxic activity of CAR-T cells directed towards BCMA, a liquid tumor target. FIG. 4 shows the cytotoxicity of a BCMA CAR (P5A2 scFv) against the MM.1S multiple myeloma cell line at an E:T=10:1, indicating co-expression of a CACCR in the BCMA CAR T cells with TRAC/CD52 double knockouts (dKO) increased the long-term cytotoxicity of CAR-T cells. The CAR T cells used in the following examples all contained the TRAC/CD52 dKO.

Example 3: CACCRs Enhance the In Vivo Activity of CAR-T Cells

CAR-T cell therapies, such as those targeting CD19 and BCMA, have attained unprecedented clinical success in the treatment of hematological malignancies. While a high rate of complete responses has been achieved, this is transient as most patients eventually relapse. Furthermore, CAR-T cells have attained more limited success for the treatment of solid tumors. Among the reasons for relapse and the lack of response include insufficient CAR-T cell expansion and persistence, as well as CAR-T cell functional inhibition by immune-suppressive microenvironments. Since our in vitro characterization of CACCR CAR-T cells revealed improvements in target-driven proliferation, persistence, potency and exhaustion profiles, we next investigated whether these functional enhancements translated into improved anti-tumor activity in vivo.

To interrogate the in vivo activity of CACCR CAR-T cells in the context of hematological malignancies, we utilized CAR-T cells with TRAC/CD52 dKO bearing the BCMA specific P5A2 scFv coupled to 4-1BB and CD3C signaling domains in an orthotopic xenograft model of multiple myeloma. T cell receptor (TCR)-deficient BCMA CAR-T cells were generated by Transcription Activator-Like Effector Nucleases (TALEN)-mediated knockout to avoid potential confoundance from TCR-driven xenoreactivity. 8-10 weeks old female NSG mice were irradiated with 1 Gy one day prior to intravenous inoculation of $5\times10^6$ MM.1S-Luc-GFP. 14 days after tumor implantation, mice were randomized based on tumor burden, and dosed intravenously with either $1\times10^6$ or $3\times10^6$ of the indicated CAR-T cells (n=10 per group). Tumor progression was monitored by bioluminescent imaging. On Day 30 post T cell dose, mice that had received $3\times10^6$ CAR-T cells were bled for the enumeration of BCMA CAR-T cells in the periphery. Specifically, 50 uL of whole blood from each mouse was subjected to red blood cell lysis using ACK Lysing Buffer (Gibco), Fc-blocked and stained with the following antibody cocktail diluted in PBS+1% BSA: FITC-conjugated anti-mouse CD45 (Biolegend), BV421-conjugated anti-human CD45 (Biolegend)

and an anti-idiotype antibody specific for the P5A2 scFv. Finally, samples were washed in PBS and cell pellets were resuspended in 130 uL PBS+1% BSA containing 123 count eBeads counting beads (Thermo Fisher) (10 uL counting beads in 120 uL PBS+1% BSA) prior to FACS analysis.

Figure 5A:
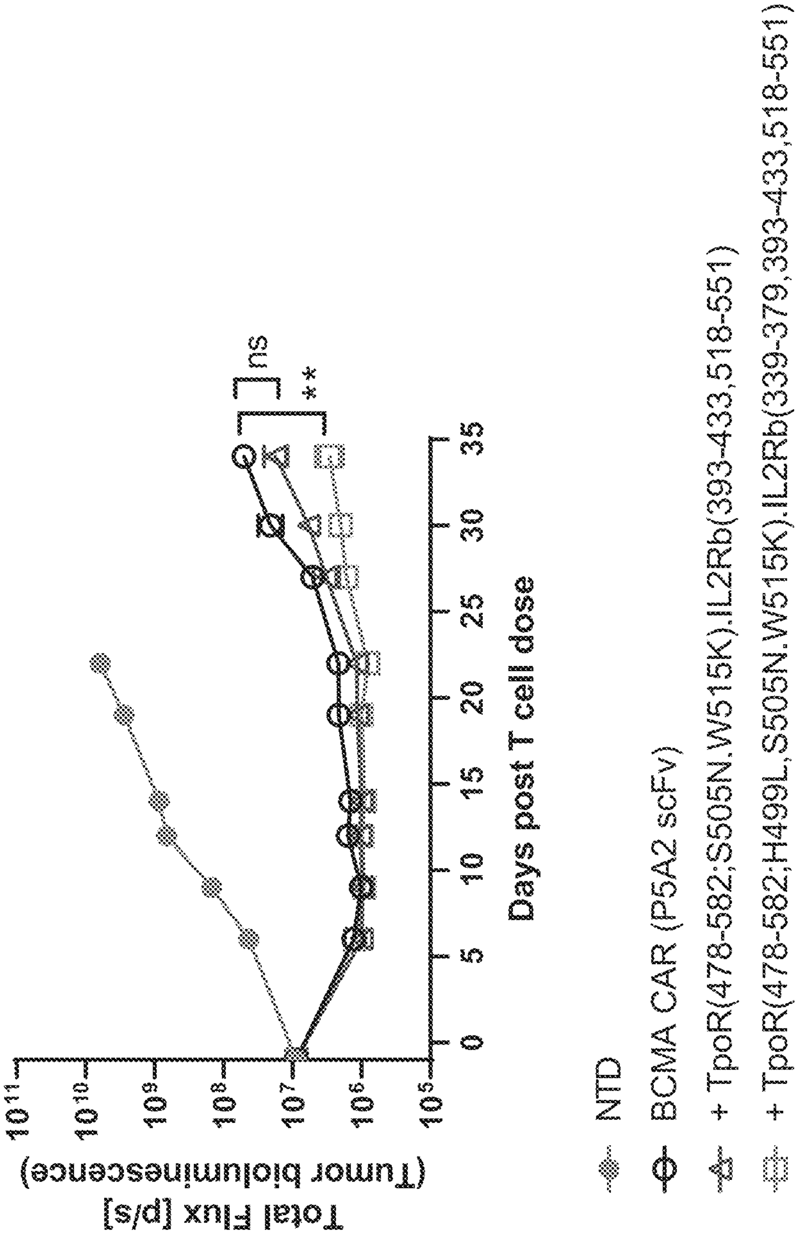
FIGS. 5A-5E show that CACCRs improved short term and long term in vivo anti-tumor activity and persistence of BCMA CAR-T cells against orthotopic multiple myeloma.
Figure 5B:
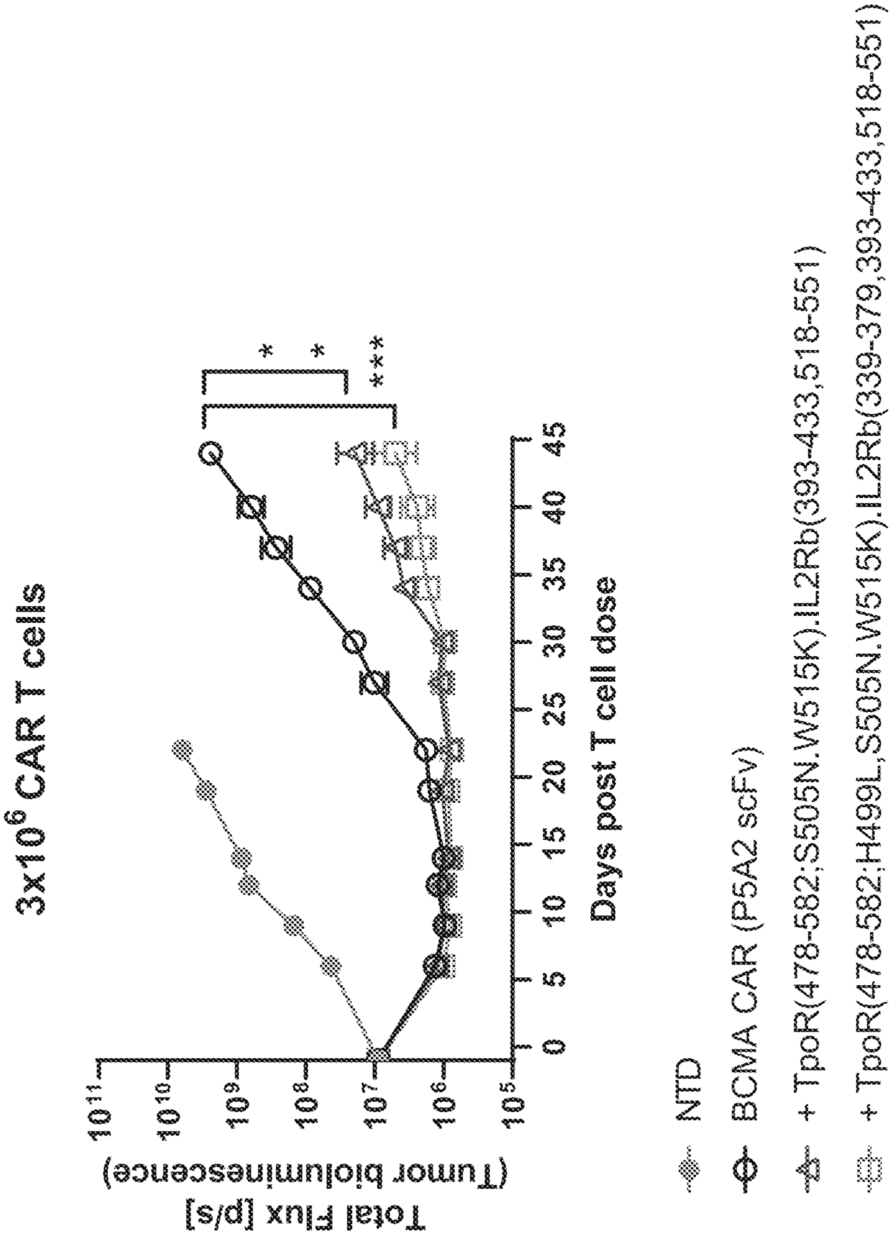
Figure 5C:
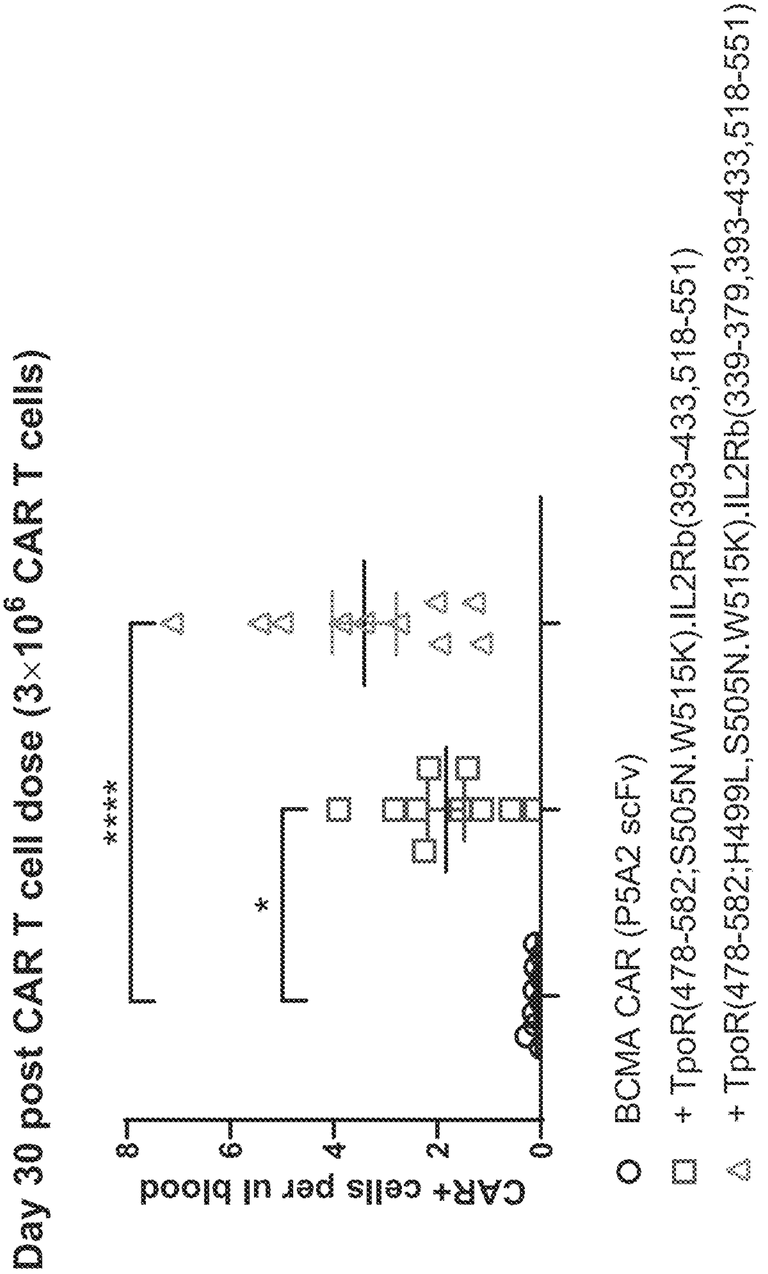

FIGS. 5A-5C show that CACCRs improved the in vivo anti-tumor activity and persistence of BCMA CAR-T cells against orthotopic multiple myeloma. FIGS. 5A-5B show tumor progression in response to treatment with either $1\times10^6$ or $3\times10^6$ of the indicated CAR-T cells, respectively. Although control BCMA CAR-T cells were able to mediate initial tumor regression, this response was short-lived as tumors relapsed 5 days after cell infusion. However, CACCR coexpressing CAR-T cells significantly delayed tumor relapse and improved the durability of response. Statistics in FIGS. 5A-5B represent $p<0.01$ and *$p<0.001$ based on repeated measures one-way ANOVA with Tukey's multiple comparisons from Days 6-34 for FIG. 5A and Days 6-44 for FIG. 5B. FIG. 5C shows the number of BCMA CAR-T cells present in the peripheral blood of mice treated with $3\times10^6$ CAR-T cells 30 days after T cell infusion. Coincident with tumor relapse observed in mice treated with control BCMA CAR-T cells, control BCMA CAR-T cells could no longer be detected in the periphery. In contrast, CACCR BCMA CAR-T cells that were superior at preventing tumor relapse were also more significantly abundant in vivo. Statistics in FIG. 5C represent *$p<0.05$ and ****$p<0.0001$ based on ordinary one-way ANOVA with Tukey's multiple comparisons. These suggest that improved CACCR CAR-T cell persistence in part mediated enhanced long-term tumor control and prolonged the durability of response.

Figure 5D:
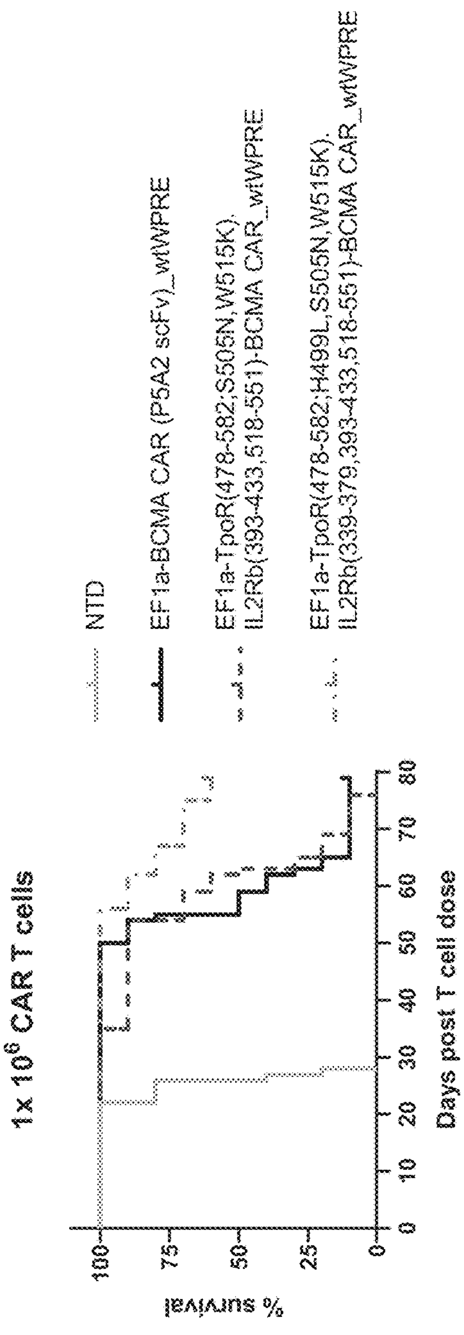
Figure 5E:
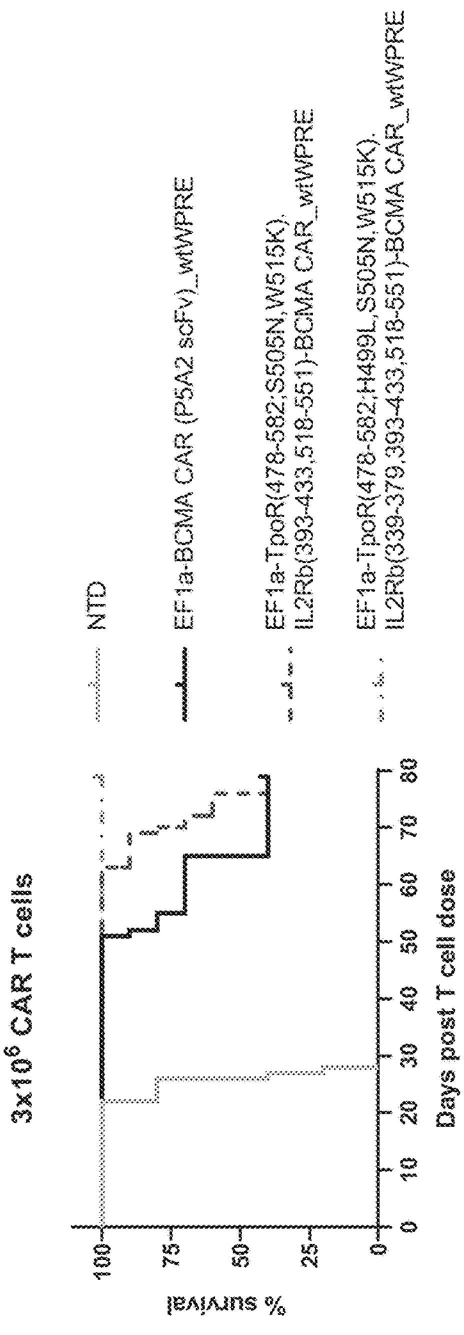
Figure 6A:
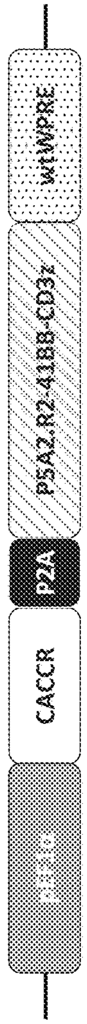
FIGS. 6A-6E show potency of CACCR-BCMA TRAC/CD52 dKO CAR T cells on BCMA-expressing target cell lines in vitro.
Figure 6B:
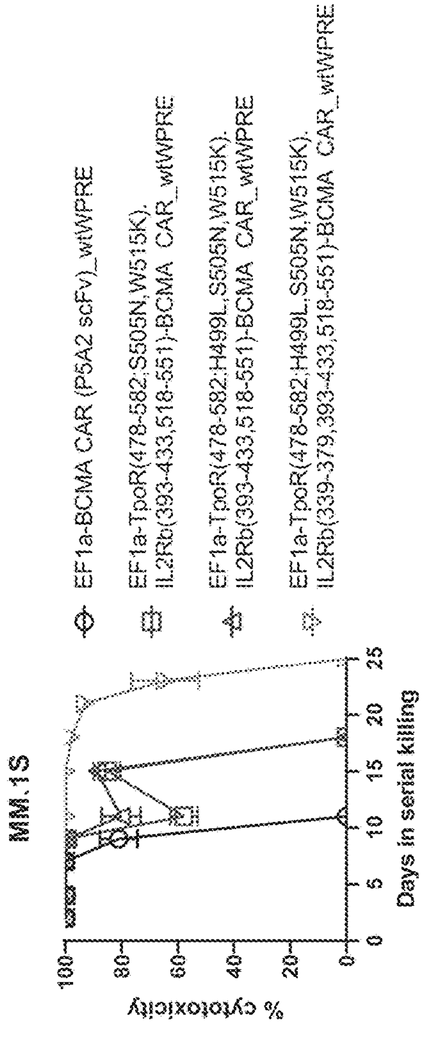
Figure 6C:
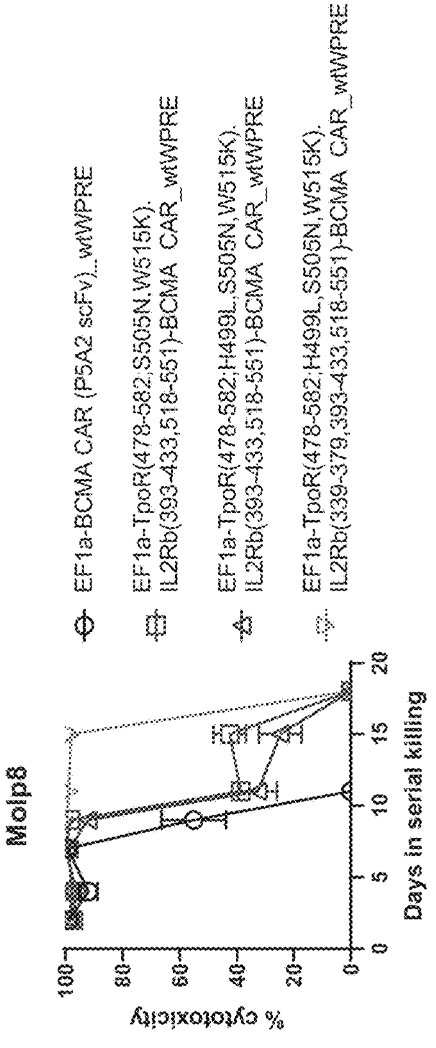
Figure 6D:
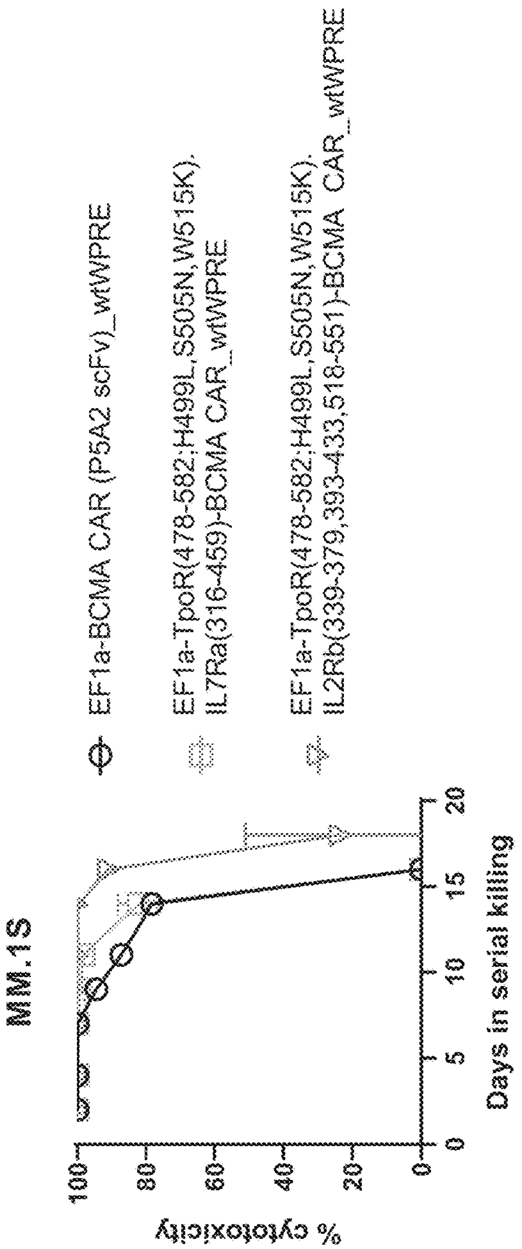
Figure 6E:
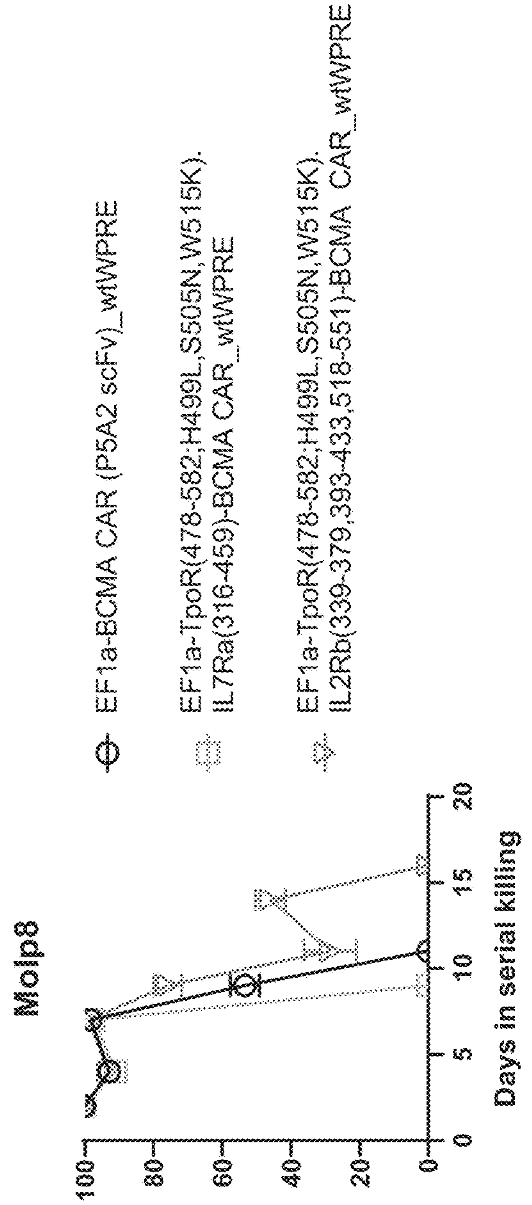

FIGS. 5D-5E show the long-term survival of mice that had received $1\times10^6$ or $3\times10^6$ CAR T cells, respectively. At both CAR T cell doses, BCMA CAR T cells bearing the TpoR(478-582; H499L, S505N, W515K). IL2Rb(339-379, 393-433, 528-551) CACCR dramatically prolonged overall survival.

Example 4: Evaluate CACCRs for BCMA CAR T Cells

The modular nature of CACCRs provide the flexibility of fusing signaling domains derived from different cytokine receptor of interest. Among these, IL-7, IL-2 and IL-15 have well-established roles in promoting T cell survival, expansion and effector function. We therefore hypothesized that BCMA CAR T cells may functionally benefit from CACCRs bearing the IL7Ra or IL2/15Rb signaling domains, and sought to identify which, if any, of these CACCRs could provide the most enhancement to BCMA CAR T cells.

BCMA-expressing MM.1S or Molp8 target cells stably expressing the firefly luciferase and GFP reporters were generated by lentiviral transduction. 10,000 Luc-GFP-labelled target cells were plated in 100 uL per well in a white flat-bottomed 96-well tissue culture plate. Cryopreserved TRAC/CD52 dKO CAR T cells were thawed, counted, and the percentage of CAR T cells across all samples were normalized to the sample with the lowest transduction efficiency by the addition of non-transduced (NTD) T cells. CAR T cells in a volume of 100 uL were then added to each well of target cells at an E:T=10:1 or 3:1 in triplicates. As a "Targets only" negative control, 100 uL of media, instead of T cells, was added to target cells. After two or three days, wells were mixed by gentle pipetting, and 100 uL of each T cell-containing well was transferred to a new white flat-bottomed 96-well tissue culture plate containing 10,000 freshly-plated Luc-GFP-labelled target cells in 100 uL. "Targets only" wells received fresh media in place of T cells. The new plate was incubated at 37° C., while the number of live target cells remaining in the old 96-well plate was determined using the ONE-Glo Luciferase Assay System (Promega) according to manufacturer's instructions. The percentage of live target cells was calculated by normalizing the luciferase signal of to that of "Targets only" wells, and percentage cytotoxicity was calculated as 100%-% live target cells. Serial transfers to fresh target cells and luciferase readouts were performed every two or three days until all cytotoxic activity has ceased.

FIG. 6 shows the functional screening of TRAC/CD52 dKO CACCR-BCMA CAR T cells bearing the indicated CACCRs using an in vitro serial killing assay. Two target cell lines expressing varying levels of endogenous BCMA were used—moderate-expressing MM.1S-Luc-GFP (high BCMA expressing cell line) and low-expressing Molp8-Luc-GFP (low BCMA expressing cell line). FIG. 6A shows a schematic of the bicistronic CACCR-BCMA CAR lentiviral construct. The BCMA CAR construct containing the clone P5A2 scFv and R2 was used throughout this example. The CACCR was cloned downstream of the EF1a promoter and upstream of a $2^{nd}$ generation BCMA CAR. A wildtype WPRE sequence was included to stabilize transcript expression. FIGS. 6B and 6C show the serial killing activity of CACCR-BCMA CARs bearing IL2Rb-derived CACCRs against MM.1S-Luc-GFP and Molp8-Luc-GFP, respectively. All IL2Rb-derived CACCRs tested improved the activity of BCMA CAR T cells, and the TpoR(478-582; H499L, S505N, W515K). IL2Rb(339-379, 393-433, 528-551) CACCR conferred the greatest enhancement. FIGS. 6D and 6E show the serial killing activity of CACCR-BCMA CAR bearing the most active IL2Rb-derived CACCR and an IL7Ra-bearing CACCR. Unlike the IL2Rb-derived CACCR, the IL7Ra-bearing CACCR did not enhance the activity of BCMA CAR T cells in either target cell line.

To evaluate the in vivo anti-tumor activity of CACCR-BCMA CARs, we utilized an orthotopic xenograft model of multiple myeloma in which disease initially establishes in the bone marrow and relapse subsequently occurs in extramedullary sites. Briefly, 8-10 weeks old female NSG mice were irradiated with 1 Gy one day prior to intravenous inoculation of $5\times10^6$ MM.1S-Luc-GFP. 15 days post tumor implantation, mice were randomized based on tumor burden and the indicated numbers of TRAC/CD52 dKO CACCR-BCMA CAR T cells were intravenously infused per mouse (n=10 mice per group). Thereafter, tumor burden was monitored twice weekly by bioluminescent imaging.

Figure 7A:
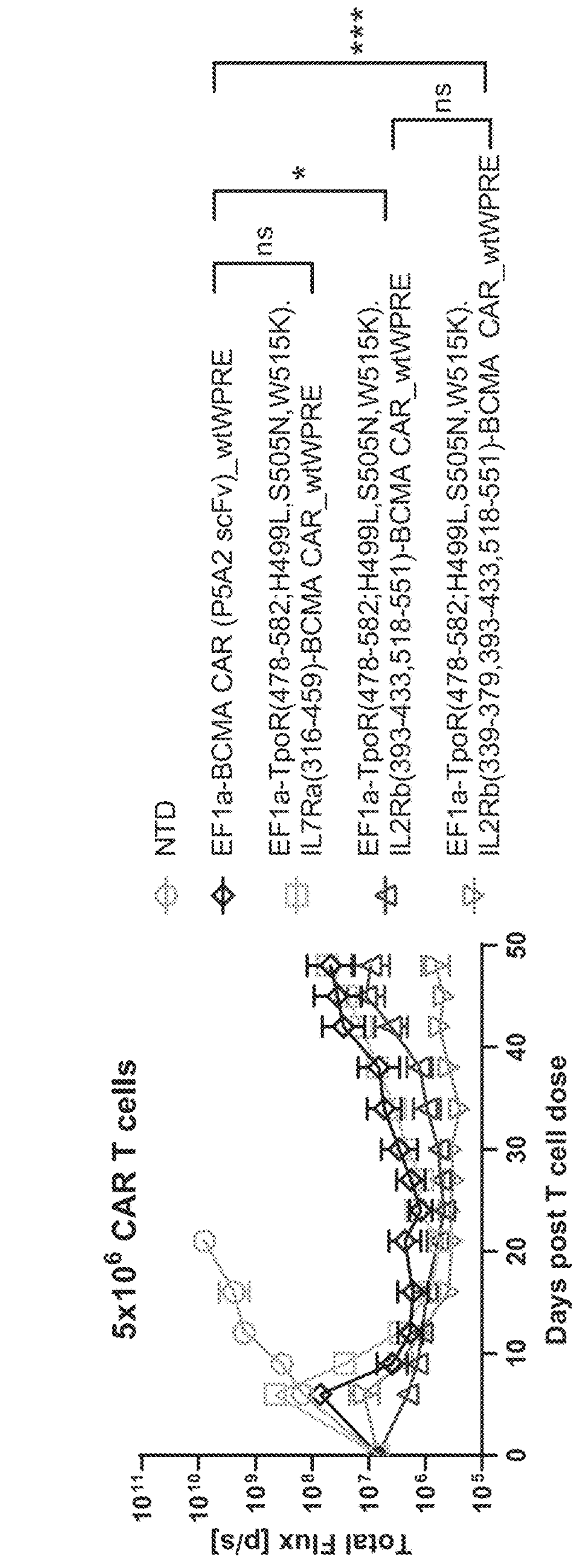
FIGS. 7A-7B show potency of CACCR-BCMA TRAC/CD52 dKO CAR T cells in vivo.
Figure 7B:
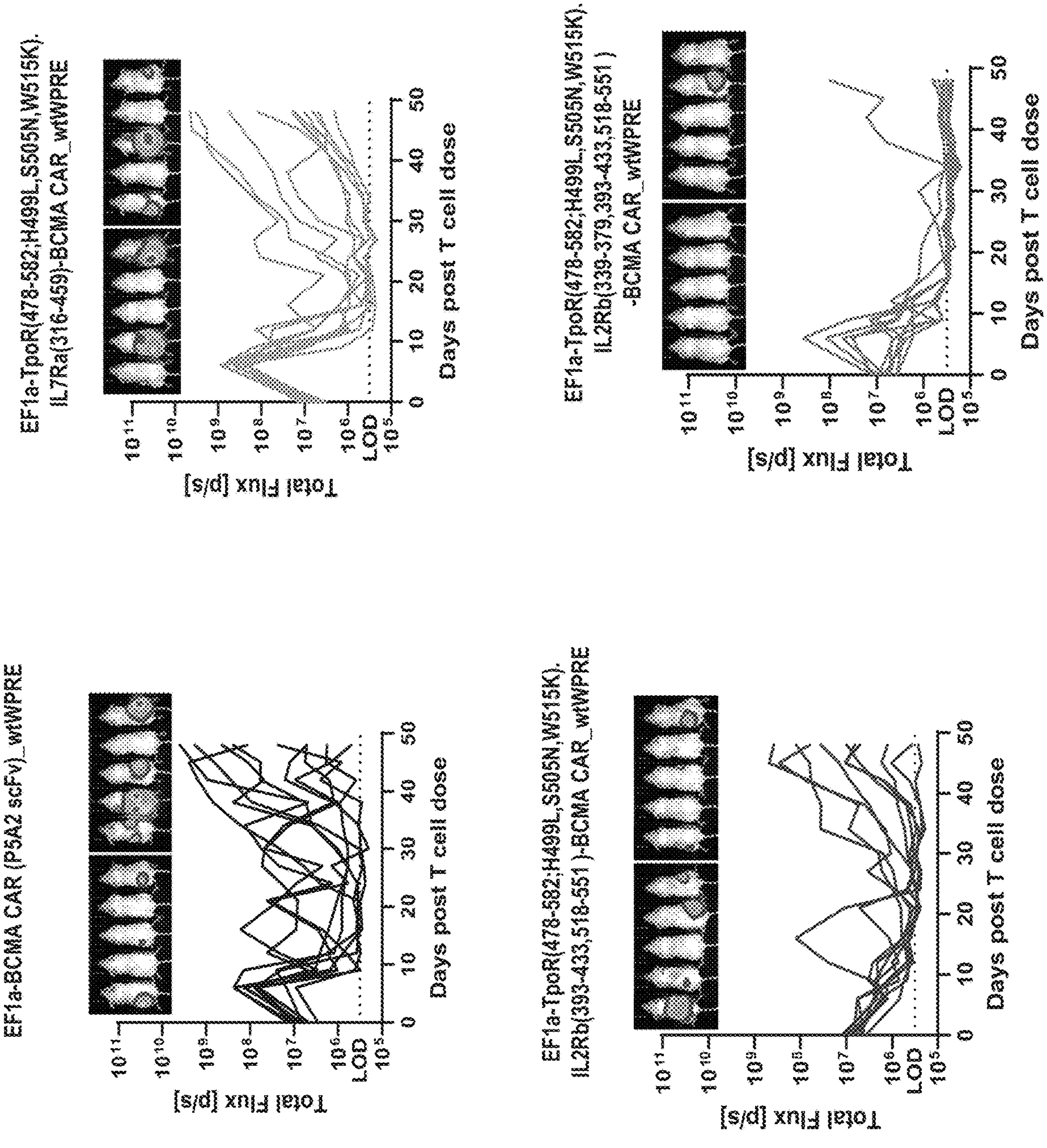

FIG. 7 shows the anti-tumor activity of $5\times10^6$ CACCR-BCMA CAR T cells bearing either an IL7Ra- or IL2Rb-derived CACCR relative to the unmodified BCMA CAR. FIG. 7A shows the tumor progression of each group. Under the experimental condition, although unmodified BCMA CAR T cells were able to mediate initial tumor regression, disease eventually relapsed. The IL7Ra-derived CACCR did not enhance the activity of BCMA CAR T cells. While the TpoR(478-582; H499L, S505N, W515K). IL2Rb(393-433, 528-551) CACCR showed some delay in tumor relapse, the TpoR(478-582; H499L, S505N, W515K). IL2Rb(339-379, 393-433, 528-551) CACCR provided the most durable response. The in vivo performance of these CACCRs corroborated the rank-ordering of in vitro activity in FIG. 6. Graph shows mean±sem; *$p<0.05$ and *$p<0.001$ based on RM one-way ANOVA with Tukey's multiple comparisons from Days 6-48. FIG. 7B shows the response of individual mice in each group. Mice that had received unmodified BCMA CAR T cells responded non-uniformly initially, and eventually all relapsed with extramedullary tumors. In contrast, mice that had received CACCR-BCMA CARs bearing the TpoR(478-582; H499L, S505N, W515K). IL2Rb(339-379, 393-433, 528-551) CACCR responded uniformly initially, and showed durable long-term responses with 9/10 mice remaining tumor-free at the end of the study.

Figure 8A:
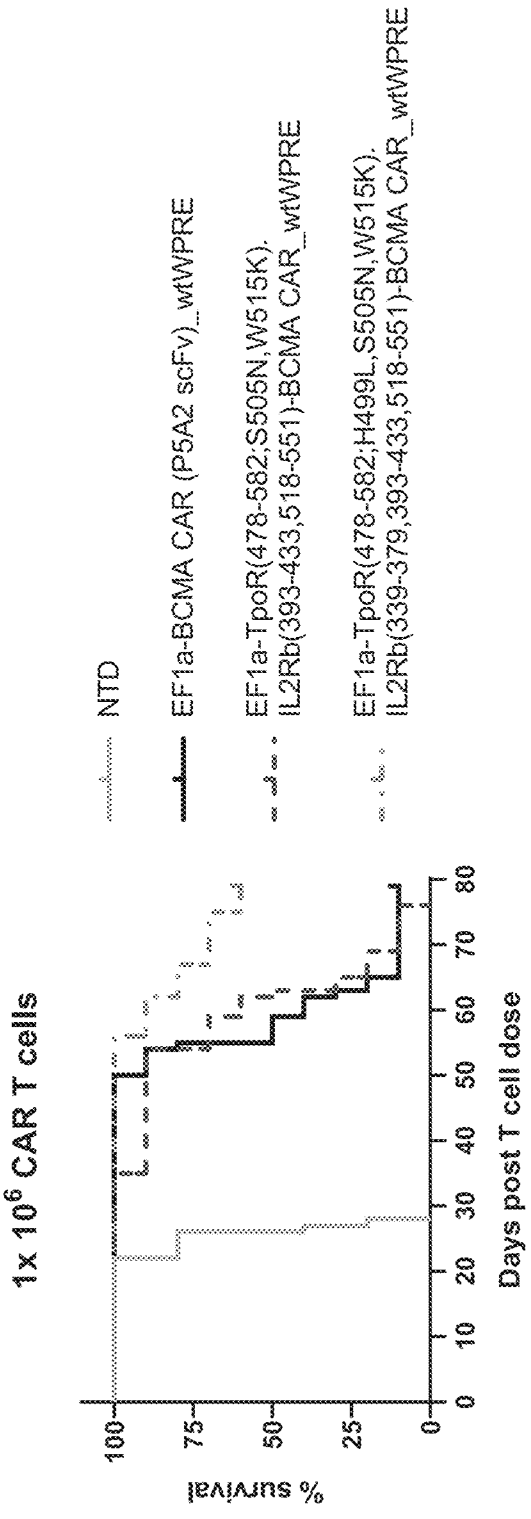
FIGS. 8A-8C show anti-tumor activities of two IL2Rb-derived CACCR-BCMA CAR T cells relative to the unmodified BCMA CAR T cells at a dose of either $1\times10^6$ or $3\times10^6$.
Figure 8B:
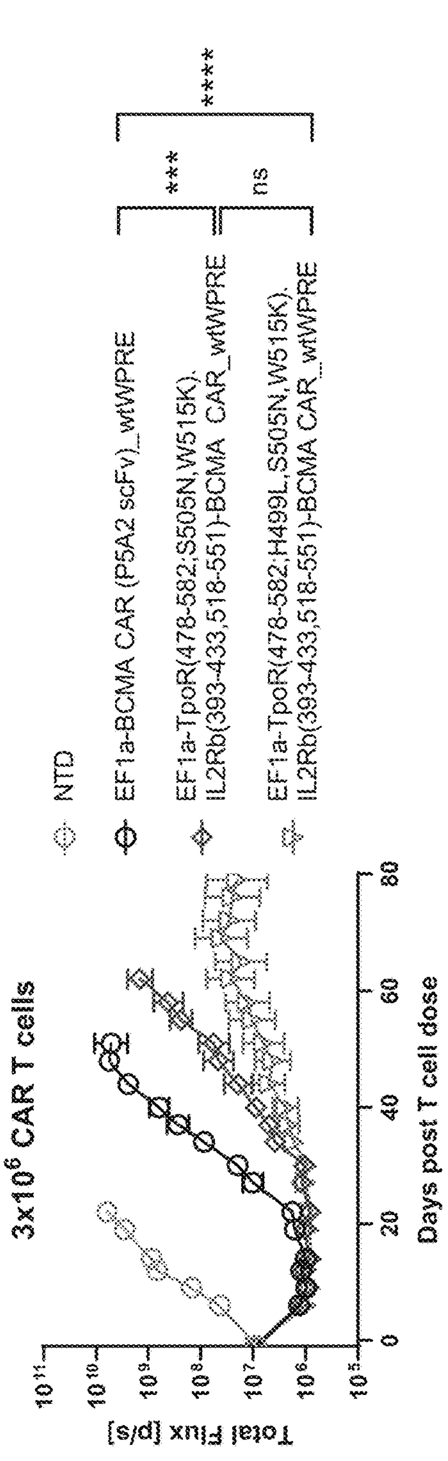
Figure 8C:
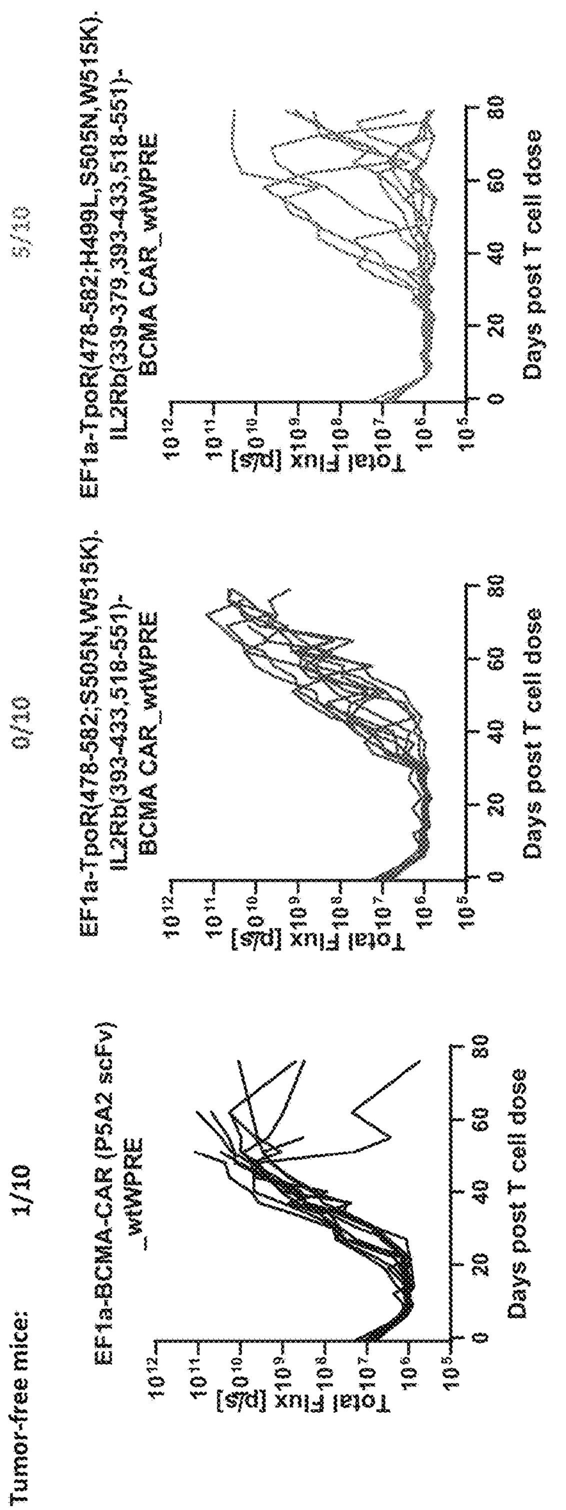

FIG. 8 shows anti-tumor activities of two IL2Rb-derived CACCRs relative to the unmodified BCMA CAR at a dose of either $1\times10^6$ or $3\times10^6$, all TRAC/CD52 dKO. Ten female NSG mice were tested per group. Each mice received $5\times10^6$ MM.1S luc2 GFP cells. FIG. 8A shows the overall survival of mice receiving a low dose of $1\times10^6$ CAR T cells. While the TpoR(478-582; S505N, W515K). IL2Rb(393-433, 528-551) CACCR had no effect on overall survival relative to unmodified BCMA CAR T cells, the TpoR(478-582; H499L, S505N, W515K). IL2Rb(339-379, 393-433, 528-551) CACCR dramatically prolonged overall survival. FIG. 8B shows tumor progression of mice that had received $3\times10^6$ CAR T cells. Although all groups underwent initial tumor regression, mice that had received the unmodified BCMA CAR T cells quickly relapsed. Both CACCRs were able to delay relapse, with the TpoR(478-582; H499L, S505N, W515K). IL2Rb(339-379, 393-433, 528-551) CACCR resulted in the most durable response. FIG. 8C shows the response of individual mice that had received $3\times10^6$ CAR T cells. Compared to 1/10 tumor-free mice in the unmodified BCMA CAR T-treated group, BCMA CAR T cells coexpressing the TpoR(478-582; H499L, S505N, W515K). IL2Rb(339-379, 393-433, 528-551) CACCR mediated tumor clearance in 5/10 mice by the end of the study. Taken together, these data demonstrate that among the IL7Ra- and IL2Rb-derived CACCRs tested, the TpoR(478-582; H499L, S505N, W515K). IL2Rb(339-379, 393-433, 528-551) CACCR conferred the greatest enhancement to BCMA CAR T cells.

Example 5: Manufacturability and Functional Activity of CACCR-BCMA CAR

CAR T cells are commonly generated by viral-based gene delivery, which imposes an upper limit on vector cargo size. While coexpressing additional modifications with a CAR in the same vector may enhance CAR T cell activity, increasing the cargo size may compromise transduction efficiency and product manufacturability. We next examined functional activity and $CAR^+$ T cell yield of a number of CACCR-BCMA CARs and compare to those of their unmodified counterpart.

BCMA CAR T cells were generated as follows. To make lentivirus encoding the respective BCMA CARs, HEK293T cells were plated at 0.45 million cells per mL in 2 mL of DMEM (Gibco) supplemented with 10% FBS (Hyclone) per well of a 6-well plate the day before transfection. On the day of transfection, the lentivirus was prepared by mixing together lentiviral packaging vectors 1.5 ug psPAX2, 0.5 ug pMD2G, and 0.5 ug of the appropriate transfer CAR vector in 250 uL Opti-MEM (Gibco) per well of the 6-well plate ("DNA mix"). 10 uL Lipofectamine 2000 (Invitrogen) in 250 uL Opti-MEM was incubated at room temperature for 5 minutes and then added to the DNA mix. The mixture was incubated at room temperature for 20 minutes and the total volume of 500 uL was slowly added to the sides of the wells containing HEK293T. 1 day post-transfection, the media from each well of HEK293T cells in the 6-well plate was replaced with 2 mL per well of T cell transduction media, i.e., X-Vivo-15 supplemented with 10% FBS. 2 days post-transfection, the lentiviral supernatants from HEK293T cells were harvested and passed through a 0.45 micron filter (EMD Millipore) to remove cell debris, and crude lentiviral supernatants were used directly for T cell transduction. On Day 0, purified T cells were activated in X-Vivo-15 medium (Lonza) supplemented with 100 IU/mL human IL-2 (Miltenyi Biotec), 10% FBS (Hyclone), and human T TransAct (Miltenyi Biotec, Cat #130-111-160, 1:100 dilution) in a Grex-24 plate (Wilson Wolf, cat #80192M). On Day 2, T cells were resuspended at 0.5 million cells per mL in T cell transduction media, transduced with an equal volume of crude lentiviral supernatant along with 100 IU/mL human IL-2 in a Grex-24 plate. On Day 5, cells were fed by replacing the spent media with T cell expansion media, i.e., X-Vivo-15 supplemented with 5% human AB serum (Gemini Bio), along with 100 IU/mL human IL-2. On Day 6, the TCRa constant (TRAC) and CD52 genes were knocked out by Transcription Activator-Like Effector Nucleases (TALEN)-mediated gene editing. See e.g., US2016/0145337. Cells were expanded into larger G-Rex vessels (Wilson Wolf) as needed using T cell expansion media and 100 IU/mL human IL-2. On Day 14, TCRa/b-cells were purified using the EasySep Human TCRa/b depletion kit (Stem Cell Technologies) and rested overnight in T cell expansion media and 100 IU/mL human IL-2 before cryopreservation on Day 15. On Days 5 and 15, CAR positivity was determined by flow cytometry using a PE-conjugated anti-idiotype antibody for the detection of the P5A2 scFv.

Figure 9A:
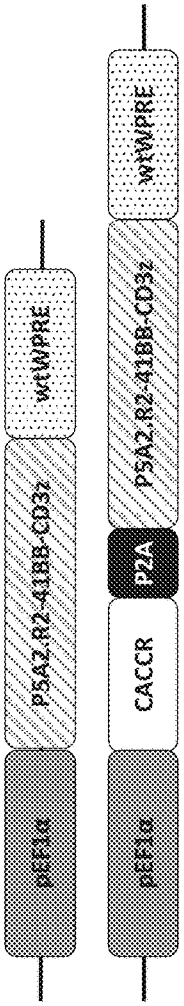
FIGS. 9A-9C show CAR+ percentage and yield of T cells bearing CACCR-BCMA CAR as compared to unmodified BCMA CAR, both transduced to T cells in a lentiviral construct.
Figure 9B:
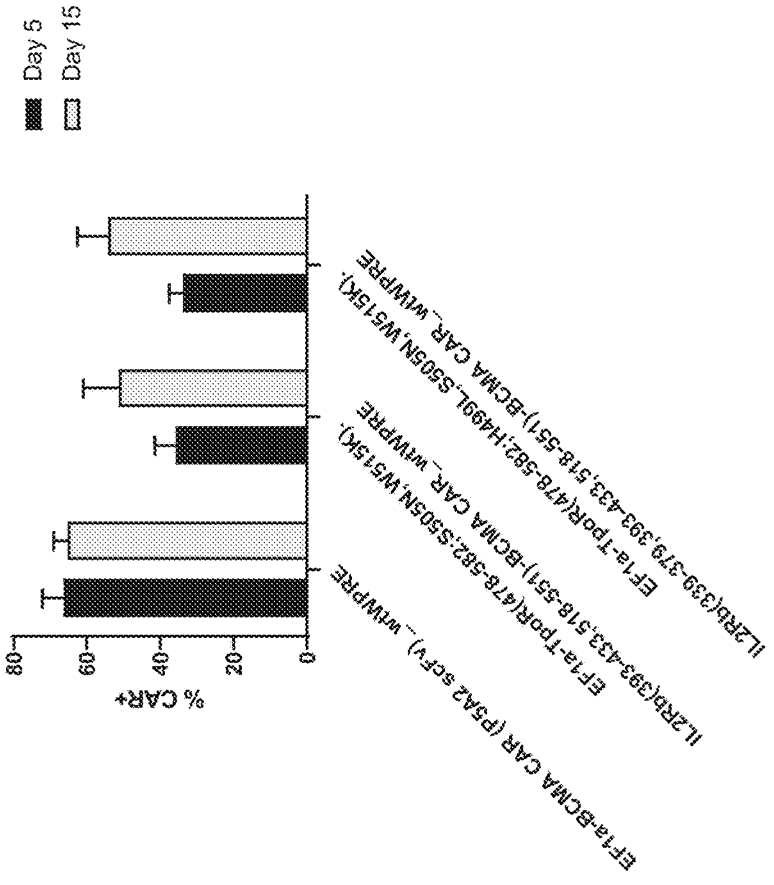
Figure 9C:
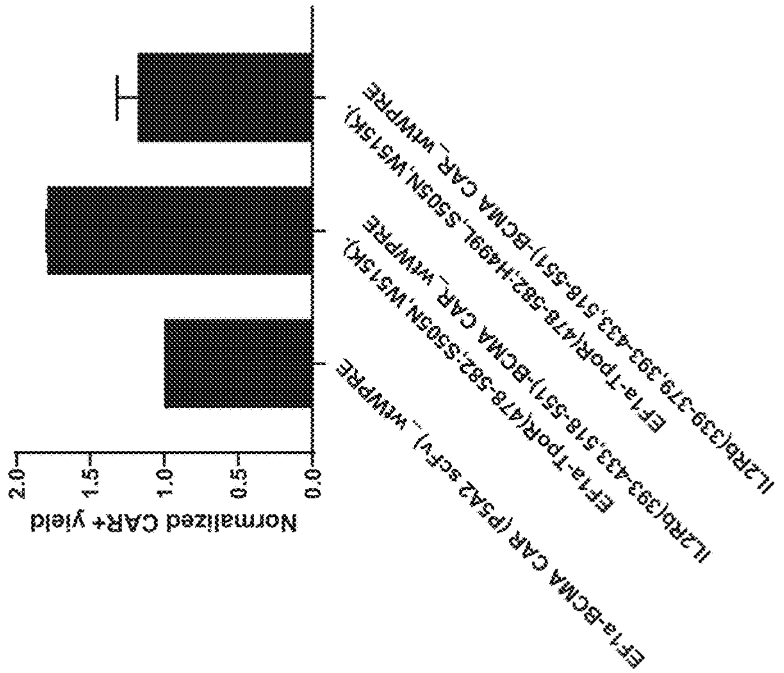
Figure 10A:
FIGS. 10A-10E show results of manufacturability and function analyses of CACCR-BCMA CAR T cells bearing the wildtype or mutant WPRE.
Figure 10B:
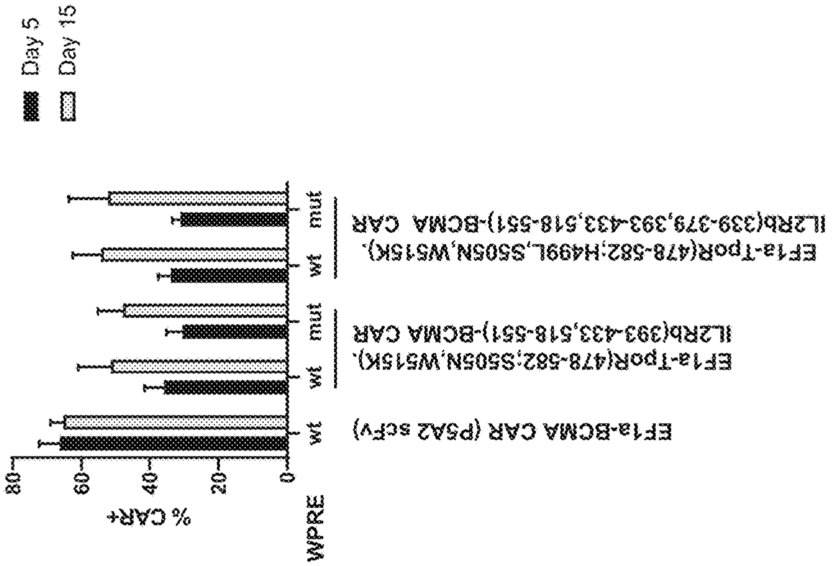
Figure 10C:
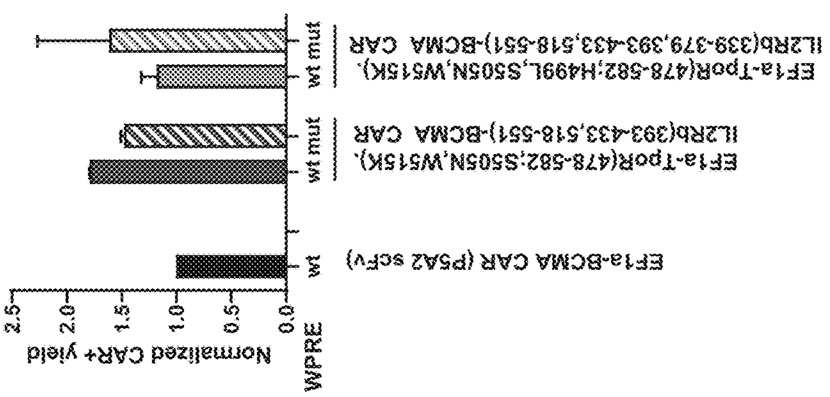
Figure 10D:
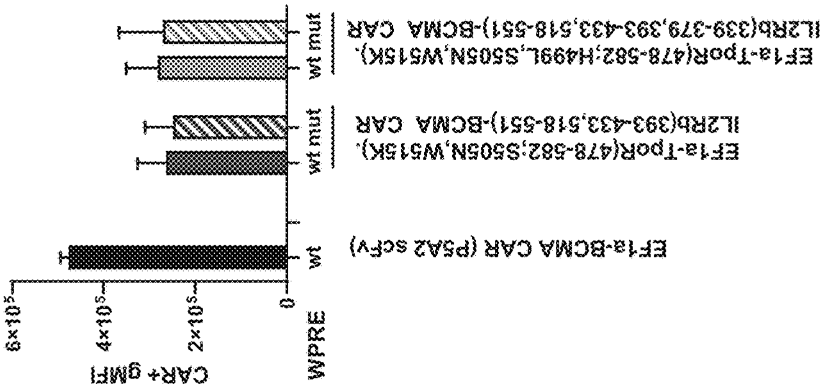
Figure 10E:
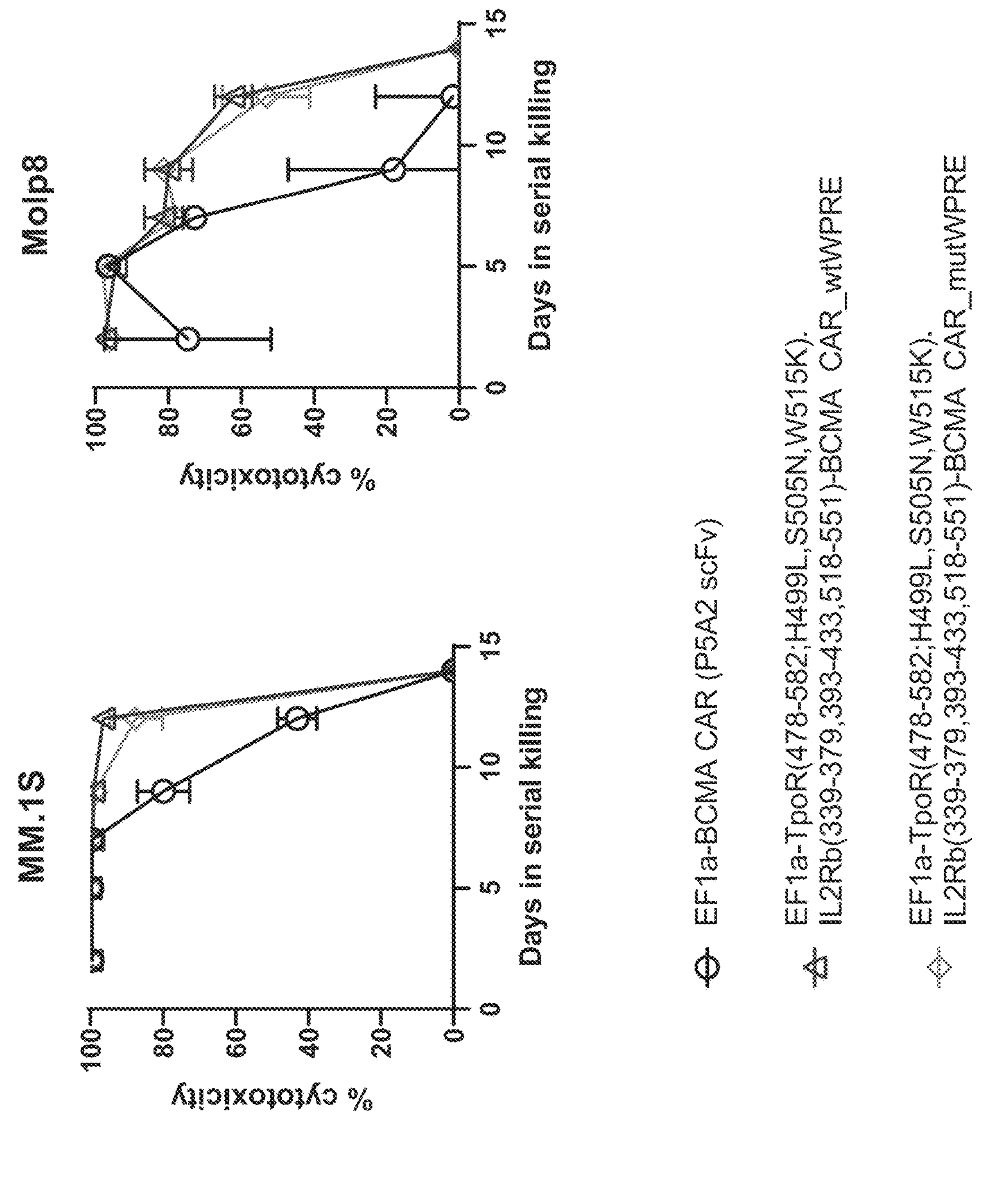
Figure 10F:
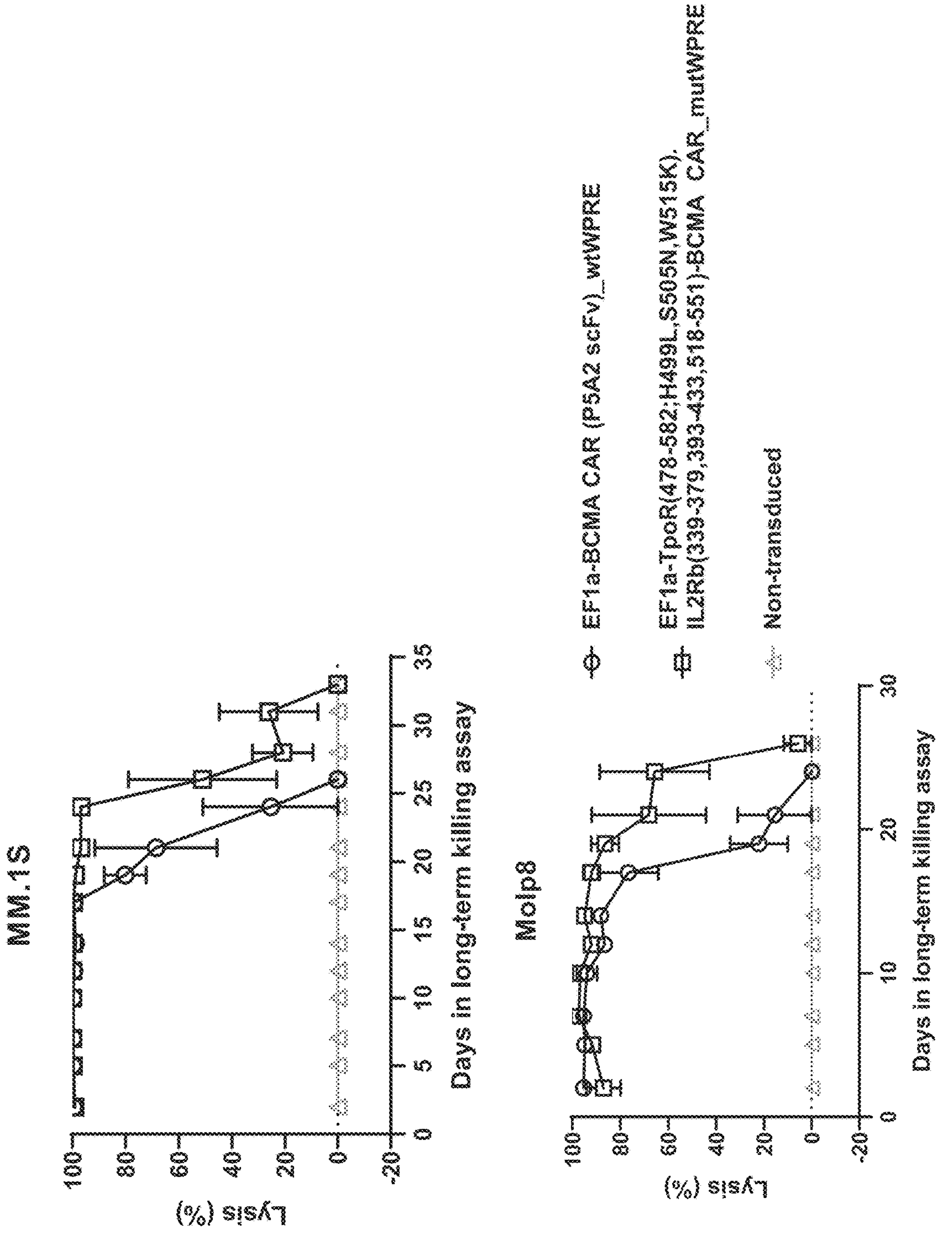
FIG. 10F shows similar results in CAR T cells derived from PBMC.
Figure 11A:
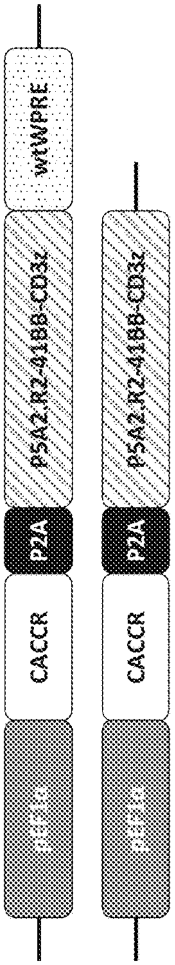
FIGS. 11A-11H show results of analysis of any effects of WPRE removal from the lentiviral constructs.
Figure 11B:
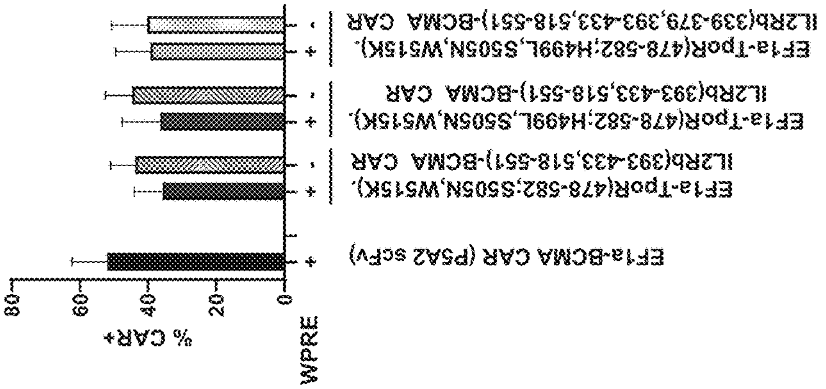
Figure 11C:
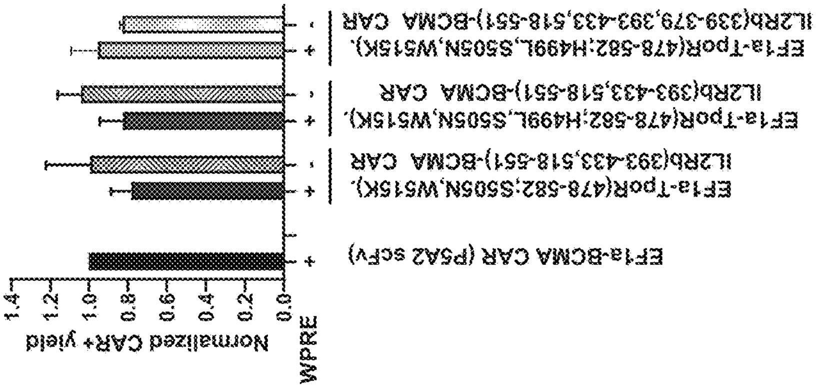
Figure 11E:
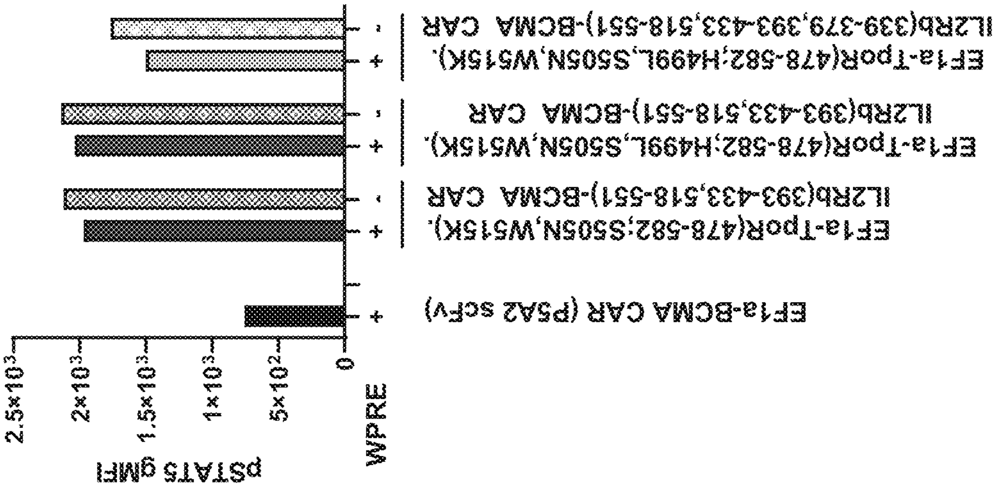
Figure 11D:
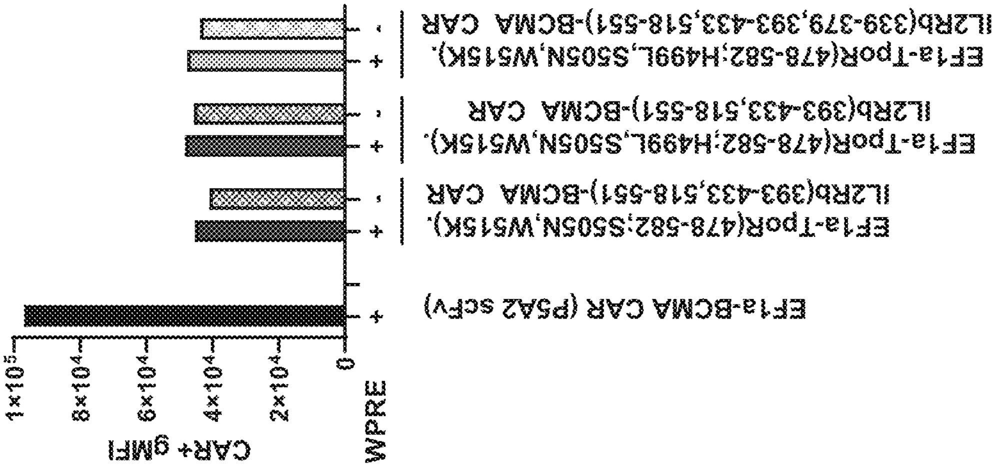
Figure 11F:
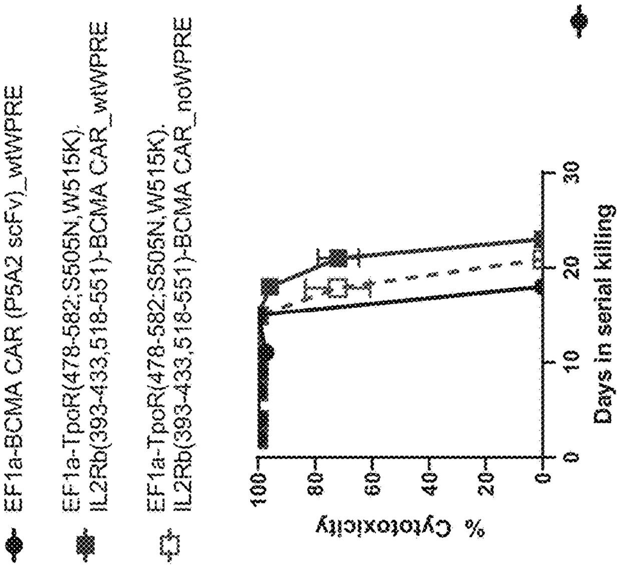
Figure 11G:
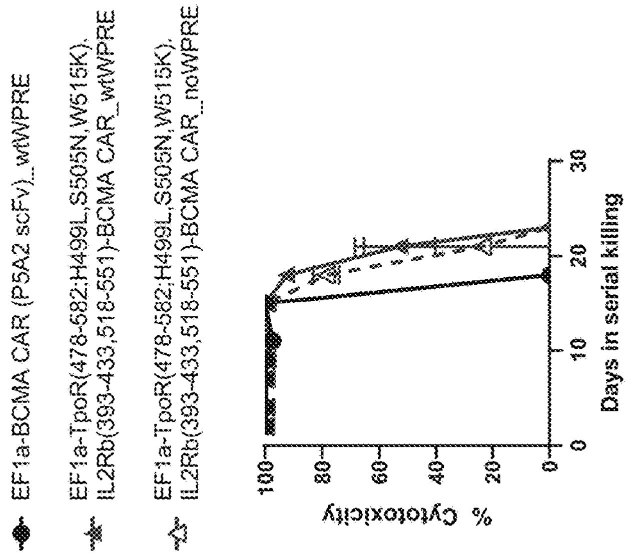
Figure 11H:
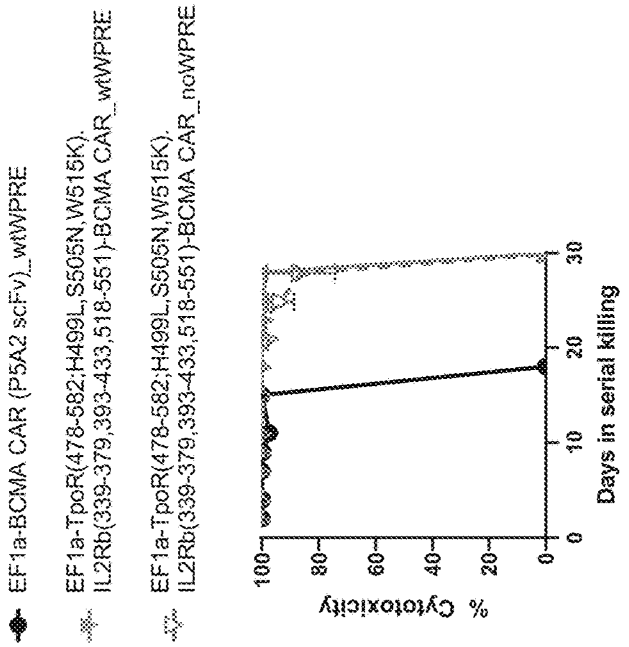
Figure 12B:
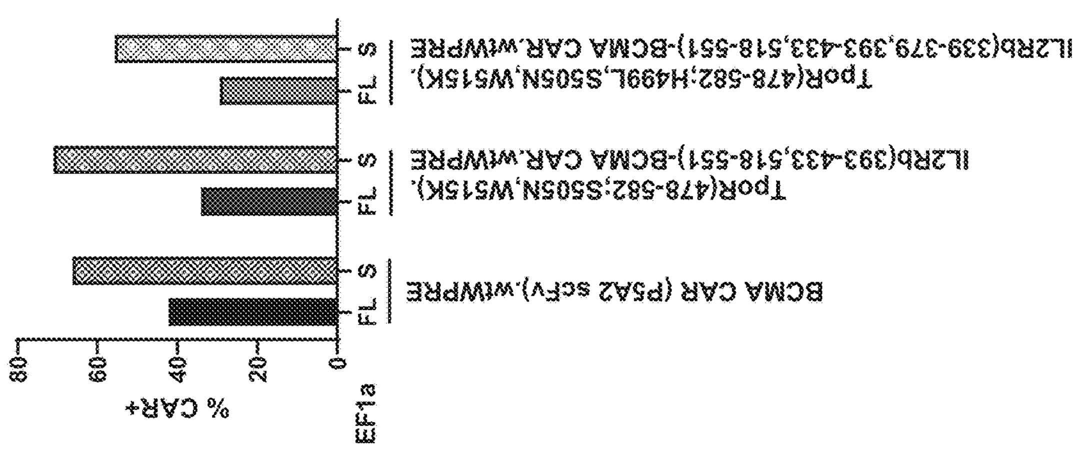
FIGS. 12A-12D show results of analysis of the effects of the full-length EF1a and the EF1a short promoters.
Figure 12A:
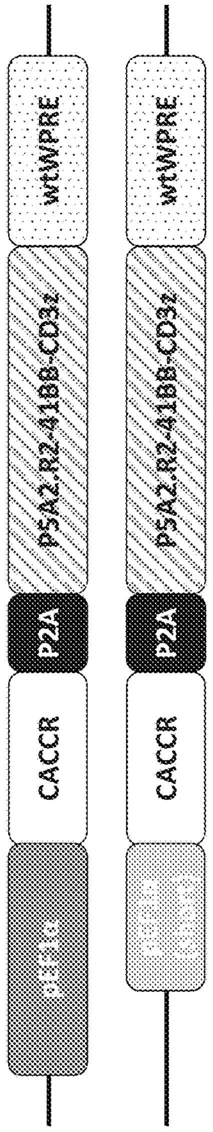
Figure 12C:
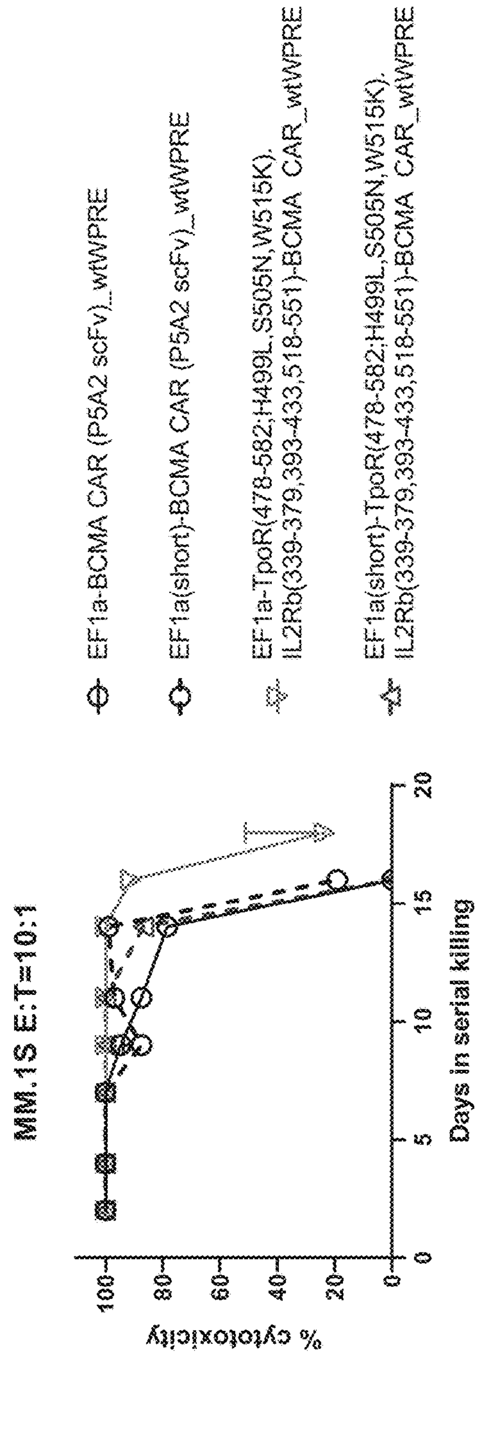
Figure 12D:
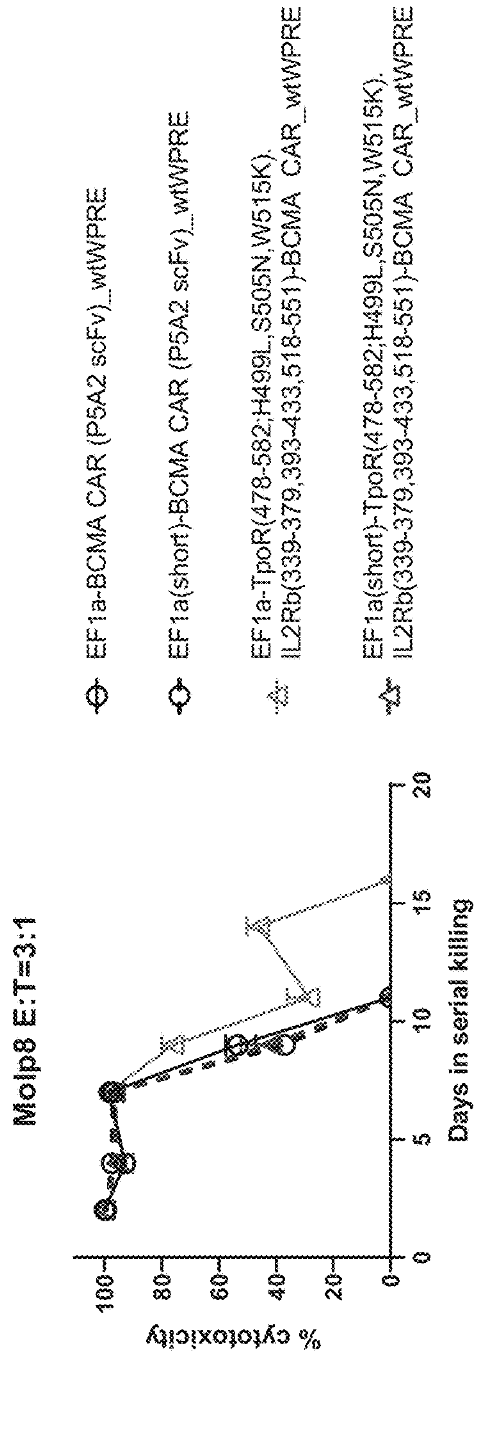
Figure 13B:
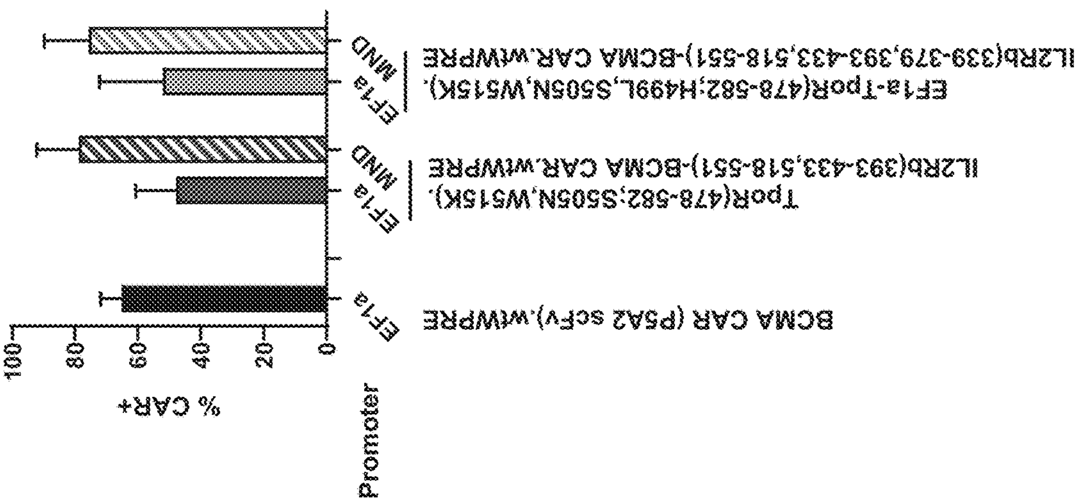
FIGS. 13A-13G show results of analysis of the effects of the full-length EF1a and the MND promoters. The data of EF1a promoter-driven BCMA CAR T without a CACCR (open circle) overlapped with the data of MND promoter-driven BCMA CAR T and CACCR (filled square) (FIG. 13F).
Figure 13A:
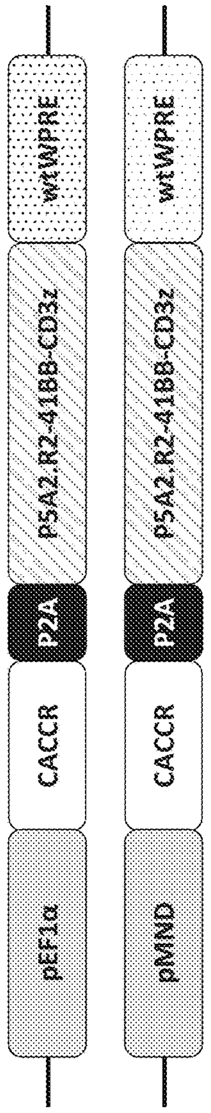
Figure 13D:
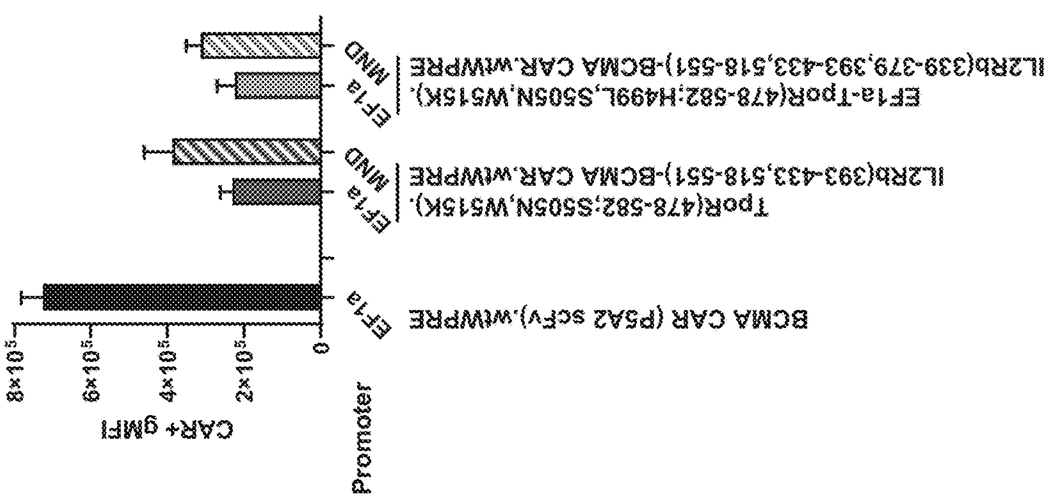
Figure 13C:
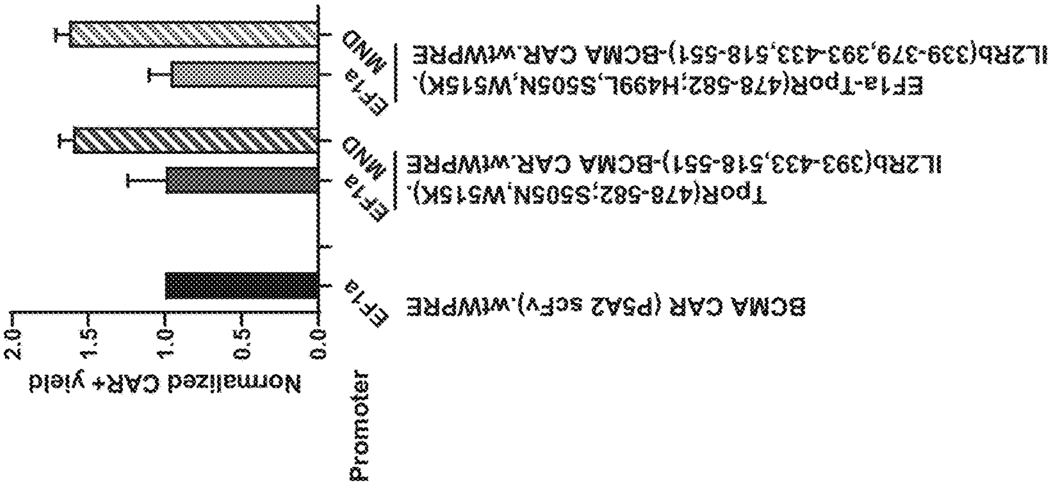
Figure 13E:
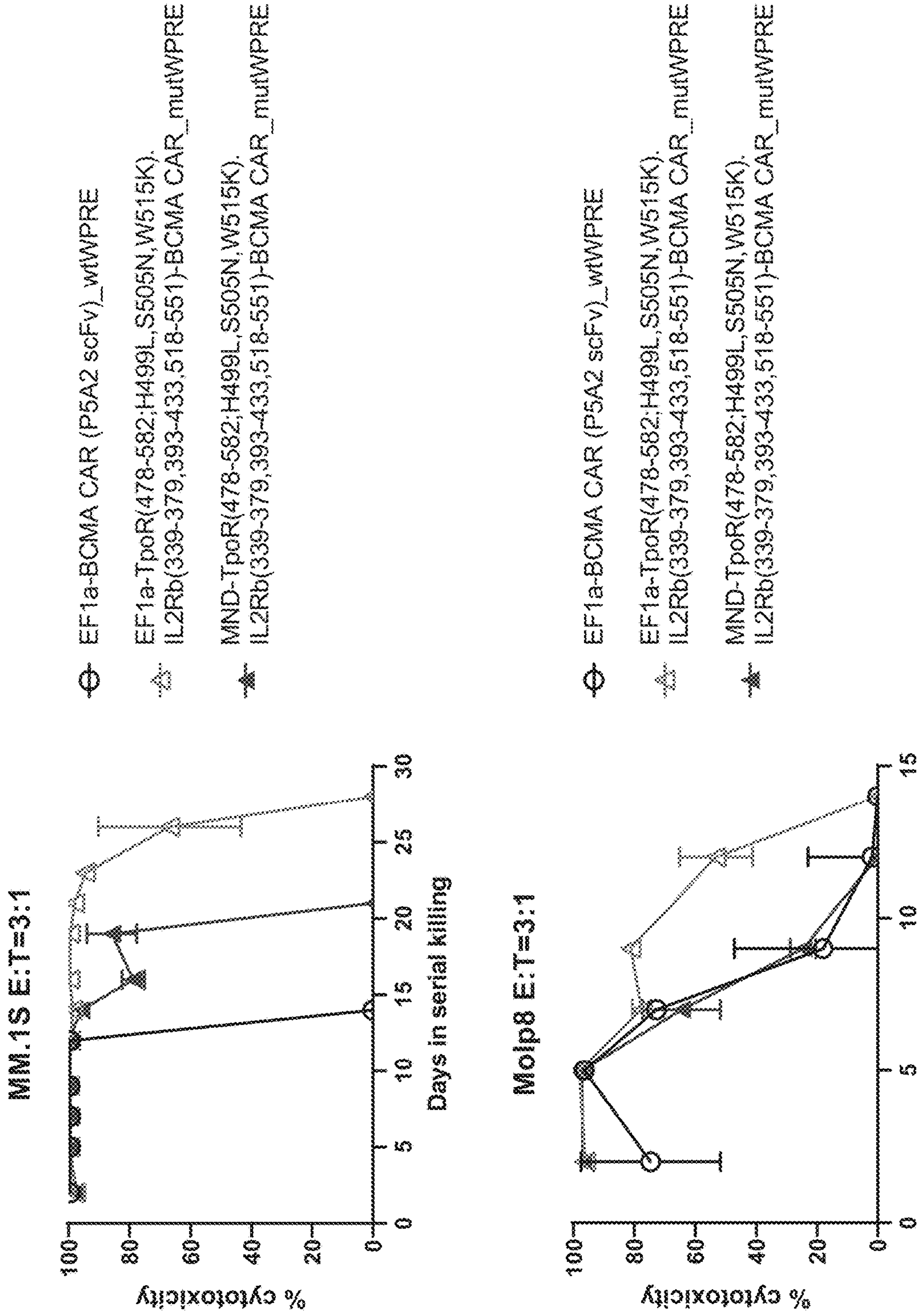
Figure 13F:
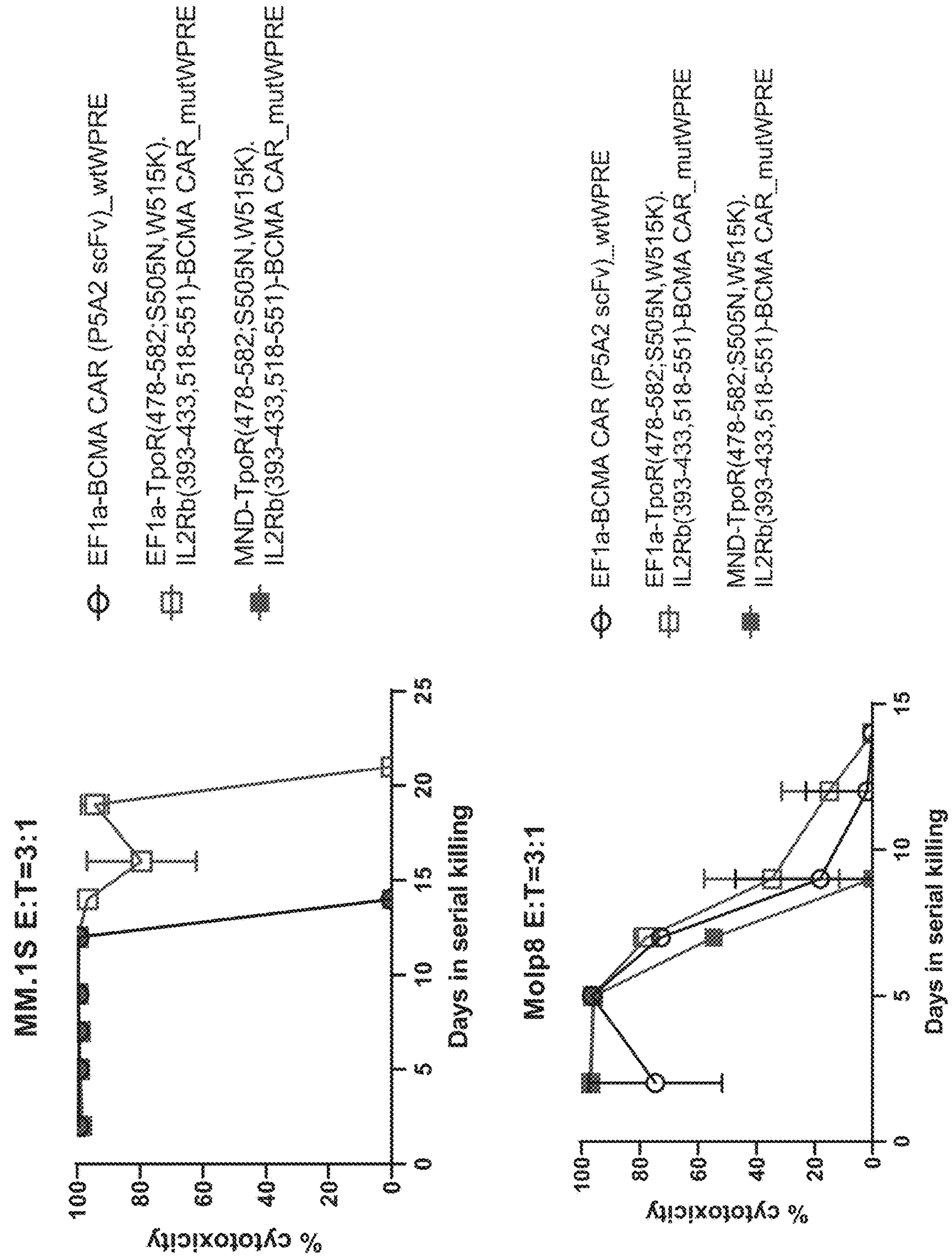
Figure 13G:
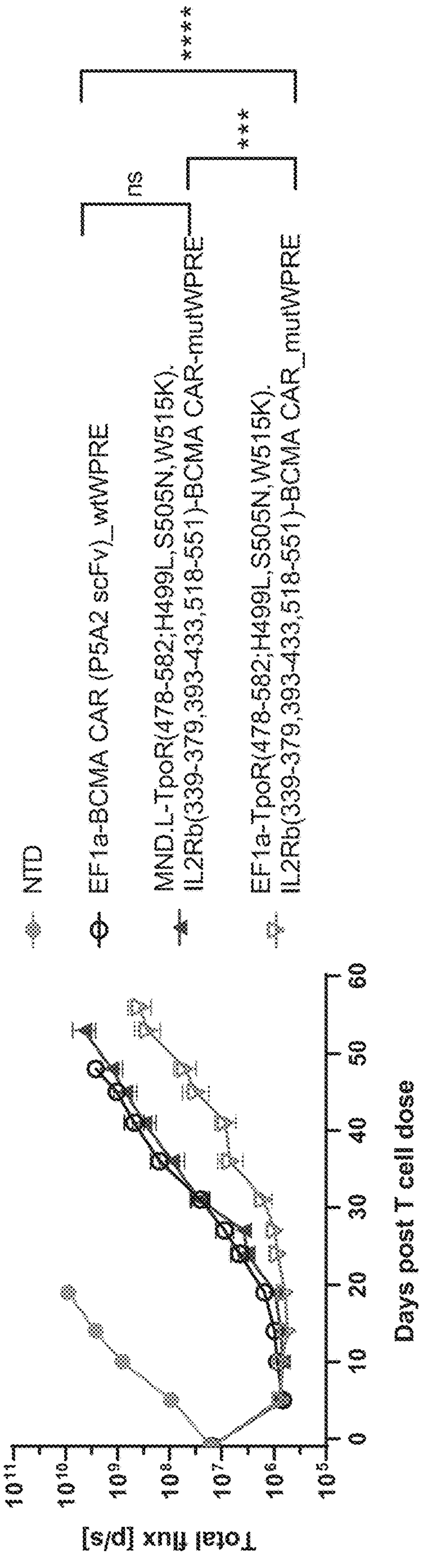

FIG. 9 shows the manufacturability and yield of T cells bearing CACCR-BCMA CAR transduced in a lentiviral construct. FIG. 9A shows a schematic of a CACCR-BCMA CAR lentiviral construct, in which the strong EF1a promoter drives expression of both the CACCR and the BCMA CAR from a bicistronic open reading frame and transcript expression is stabilized by the wildtype (wt) WPRE sequence. FIG. 9B shows the initial transduction efficiency on Day 5 (3 days post-transduction) and Day 15 (final day) of the CAR T cell production process. As expected, CACCR-BCMA CAR transduce less efficiently on Day 5 due to their larger cargo size. However, CACCRs confer CACCR-BCMA CARs with a proliferative advantage, allowing CACCR-BCMA $CAR^+$ T cells to enrich faster and reach comparable levels of CAR positivity at the end of production on Day 15. FIG. 9C shows that the yield of CACCR-BCMA $CAR^+$ T cells is equal to or greater than that of unmodified BCMA $CAR^+$ T cells. Yield is defined by the final number of CAR+ T cells obtained at the end of production per million pan-T cells starting material on Day 0 of production. Data in FIGS. 9B and 9C show mean±sem from 3 donors. Although CACCR-BCMA CARs have a larger cargo size, their lower initial transduction efficiency of CACCR-BCMA CARs was offset by their faster enrichment over the course of production, allowing them to retain comparable manufacturability to their unmodified counterparts.

It has been reported that the wildtype WPRE may encode a truncated X-protein that may pose an oncogenic risk. To mitigate this safety risk, wildtype WPRE may be mutated (e.g. by inactivating the start codon) to abrogate X-protein expression. As the CACCR-BCMA CAR lentiviral vector initially tested contained the wildtype WPRE sequence, we sought to determine if substitution to the mutant sequence would impact the expression and functionality of CACCR-BCMA CAR.

BCMA CAR T cells were generated as follows. To make lentivirus encoding the respective BCMA CARs, HEK293T cells were plated at 0.45 million cells per mL in 2 mL of DMEM (Gibco) supplemented with 10% FBS (Hyclone) per well of a 6-well plate the day before transfection. On the day of transfection, the lentivirus was prepared by mixing together lentiviral packaging vectors 1.5 ug psPAX2, 0.5 ug pMD2G, and 0.5 ug of the appropriate transfer CAR vector in 250 uL Opti-MEM (Gibco) per well of the 6-well plate ("DNA mix"). 10 uL Lipofectamine 2000 (Invitrogen) in 250 uL Opti-MEM was incubated at room temperature for 5 minutes and then added to the DNA mix. The mixture was incubated at room temperature for 20 minutes and the total volume of 500 uL was slowly added to the sides of the wells containing HEK293T. One day post-transfection, the media from each well of HEK293T cells in the 6-well plate was replaced with 2 mL per well of T cell transduction media, i.e., X-Vivo-15 supplemented with 10% FBS. 2 days post-transfection, the lentiviral supernatants from HEK293T cells were harvested and passed through a 0.45 micron filter (EMD Millipore) to remove cell debris, and crude lentiviral supernatants were used directly for T cell transduction. On Day 0, purified T cells were activated in X-Vivo-15 medium (Lonza) supplemented with 100 IU/mL human IL-2 (Miltenyi Biotec), 10% FBS (Hyclone), and human T TransAct (Miltenyi Biotec, Cat #130-111-160, 1:100 dilution) in a Grex-24 plate (Wilson Wolf, cat #80192M). On Day 2, T cells were resuspended at 0.5 million cells per mL in T cell transduction media, transduced with an equal volume of crude lentiviral supernatant along with 100 IU/mL human IL-2 in a Grex-24 plate. On Day 5, cells were fed by replacing the spent media with T cell expansion media, i.e., X-Vivo-15 supplemented with 5% human AB serum (Gemini Bio), along with 100 IU/mL human IL-2. On Day 6, the TCRa constant (TRAC) and CD52 genes were knocked out by Transcription Activator-Like Effector Nucleases (TALEN)-mediated gene editing. Cells were expanded into larger G-Rex vessels (Wilson Wolf) as needed using T cell expansion media and 100 IU/mL human IL-2. On Day 14, TCRa/b$^-$ cells were purified using the EasySep Human TCRa/b depletion kit (Stem Cell Technologies) and rested overnight in T cell expansion media and 100 IU/mL human IL-2 before cryopreservation on Day 15. On Days 5 and 15, CAR positivity was determined by flow cytometry using a PE-conjugated anti-idiotype antibody for the detection of the P5A2 scFv.

The in vitro cytotoxicity of BCMA CAR T cells were evaluated in a serial killing assay as follows. BCMA-expressing MM.1S or Molp8 target cells stably expressing the firefly luciferase and GFP reporters were generated by lentiviral transduction. 10,000 Luc-GFP-labelled target cells were plated in 100 uL per well in a white flat-bottomed 96-well tissue culture plate. Cryopreserved TRAC/CD52 dKO CAR T cells were thawed, counted, and the percentage of CAR T cells across all samples were normalized to the sample with the lowest transduction efficiency by the addition of non-transduced (NTD) T cells. CAR T cells in a volume of 100 uL were then added to each well of target cells at an E:T=3:1 in triplicates. As a "Targets only" negative control, 100 uL of media, instead of T cells, was added to target cells. After two or three days, wells were mixed by gentle pipetting, and 100 uL of each T cell-containing well was transferred to a new white flat-bottomed 96-well tissue culture plate containing 10,000 freshly plated Luc-GFP-labelled target cells in 100 uL. "Targets only" wells received fresh media in place of T cells. The new plate was incubated at 37° C., while the number of live target cells remaining in the old 96-well plate was determined using the ONE-Glo Luciferase Assay System (Promega) according to manufacturer's instructions. The percentage of live target cells was calculated by normalizing the luciferase signal of to that of "Targets only" wells, and percentage cytotoxicity was calculated as 100%—% live target cells. Serial transfers to fresh target cells and luciferase readouts were performed every two or three days until all cytotoxic activity has ceased.

FIG. 10 shows the effects of substitution to the mutant (mut) WPRE sequence on CACCR-BCMA CART cell manufacturability and function. FIG. 10A shows a schematic for vectors used with either the wildtype or mutant WPRE sequences. FIG. 10B shows the initial and final CAR positivity of CACCR-BCMA CARs. CACCR-BCMA CAR transduction efficiency (Day 5) and enrichment (Day 15) were not impacted by the switch to mutWPRE. FIG. 10C shows that the final CAR$^+$ yield of CACCR-BCMA CARs were not impacted by the switch to mutWPRE. FIG. 10D shows that although CACCR-BCMA CAR T cells had a lower CAR expression than their unmodified counterpart, CAR expression levels on CACCR-BCMA CAR T cells were not impacted by the switch to mutWPRE. Data in FIG. 10B-10D show mean±sem from 3 donors. FIG. 10E shows the in vitro serial killing activity of CACCR-BCMA CARs against the MM.1S-Luc-GFP and Molp8-Luc-GFP cell lines. Compared to unmodified BCMA CAR T cells, CACCR-BCMA CAR T cells bearing either the wildtype or mutant WPRE both showed enhanced serial killing activity, demonstrating that the switch to mutWPRE does not impair CACCR-BCMA CAR function. Data shown is mean±sem from one out of two donors that yielded similar results.

Serial killing was performed using PBMC-based TRAC/CD52 dKO CAR T cells at an E:T=10:1. Enhanced serial killing activity was maintained in PBMC-derived CACCR BCMA CAR T cells. See FIG. 10F. Data shown represents mean±sem of 3 donors.

As shown in FIG. 9, the lower initial transduction efficiencies of CACCR-BCMA CARs were offset by the faster enrichment and growth advantage of the transduced CAR T cells, resulting in comparable yields of CAR T cells to that of unmodified CAR T cells. Nevertheless, we sought to further improve CACCR-BCMA CAR T cell transduction efficiencies and yields by exploring alternative vector designs that reduced the size of the cargo, at the same time, maintaining CACCR-BCMA CAR functional enhancements. By benchmarking yields and functional activity to the original vectors shown in FIG. 10A, three vector designs were interrogated: (i) an EF1a-driven vector without the 3' WPRE sequence, (ii) a vector driven by the minimal EF1a (short) promoter, and (iii) a vector driven by the MND promoter (_myeloproliferative sarcoma virus enhancer negative control region deleted, dl587rev primer-binding site substituted).

TRAC/CD52 dKO CACCR-BCMA CAR T cells were generated and characterized as previously described.

To evaluate CACCR signaling, CACCR-BCMA CAR T cells at the end of the production process were serum starved in 100 uL serum-free RPMI (Corning) for 4 hours in humidified incubator at 37° C. with 5% $CO_2$. As a positive control, exogenous recombinant human IL-2 (10 ng/mL; Miltenyi) was added to unmodified CAR T cells during the last 30 minutes of the 4-hour serum starvation. After 4 hours, an antibody cocktail comprising BUV395-conjugated anti-human CD3 (Biolegend) and FITC-conjugated v5 tag monoclonal antibody (Thermo Fisher) were added to the cells and allowed to incubate for the final 20 minutes. Cells were then fixed by adding 35 uL of 16% paraformaldehyde to each 100 uL sample and allowed to incubate for 15 minutes at 37° C. Cells were then washed three times with PBS, and permeabilized in 100% cold methanol for 1 or 2 nights at −20° C.

On the day of FACS analysis, cells were washed three times with PBS, Fc-blocked, and stained with AlexaFluor647-conjugated anti-mouse/human Stat5 (pY694) (BD Biosciences) diluted in PBS+1% BSA. After a one hour incubation at room temperature in the dark, cells were washed three times before FACS analysis.

Serial killing assays were performed at the indicated E:T ratios as previously described.

In some cases, in vivo anti-tumor activity was assessed using an orthotopic model of multiple myeloma. 8-10 weeks old female NSG mice were irradiated with 1 Gy one day prior to intravenous inoculation of $5\times10^6$ MM.1S-Luc-GFP. 14 days after tumor implantation, mice were randomized based on tumor burden, and dosed intravenously with $3\times10^6$ of the indicated CAR T cells (n=10 per group). Tumor progression was monitored by bioluminescent imaging.

FIG. 11 shows the effects of WPRE removal from the original vector. FIG. 11A is a schematic of CACCR-BCMA CAR vectors used. FIGS. 11B and 11C show the final CAR positivity and $CAR^+$ yields, respectively, of the indicated constructs. Despite a vector cargo reduction, removing WPRE did not significantly improve the final CACCR-BCMA CAR percentage or yield. FIGS. 11C & 11D show CAR expression level and CACCR signaling strength as determined by pSTAT5 staining intensity, respectively. WPRE removal did not reduce CAR expression or CACCR signaling strength in the quiescent CACCR-BCMA CAR T cell product. Data in FIGS. 11B-11D show mean±sem of 3 donors. FIGS. 11F-11H show serial killing activity of three different IL2Rb-derived CACCR-BCMA CARs with or without WPRE. While cytotoxicity of the TpoR(478-582; S505N, W515K). IL2Rb(393-433, 528-551) (FIG. 11F) and TpoR(478-582; H499L, S505N, W515K). IL2Rb(393-433, 528-551) CACCRs were slightly reduced upon WPRE removal, the most active TpoR(478-582; H499L, S505N, W515K). IL2Rb(339-379, 393-433, 528-551) CACCR was not impacted by WPRE removal. Data in FIGS. 11F-11H show mean±sem from one out of two donors that yielded similar results.

FIG. 12 shows the effects of substituting the full-length (FL) EF1a promoter for the weaker minimal EF1a(short) (S) promoter. FIG. 12A is a schematic of CACCR-BCMA CAR vectors used. FIG. 12B shows the final CAR positivity of the indicated constructs driven by the full-length (FL) or short (S) EF1a promoters. Utilizing the smaller EF1a(short) promoter improved overall transduction efficiency and final CAR percentage for both the unmodified and CACCR-BCMA CAR T cells. FIGS. 12C and 12D show serial killing activity of CAR T cells driven by the EF1a or EF1a(short) promoter against MM.1S-Luc-GFP and Molp8-Luc-GFP target cells, respectively. While substitution to the EF1a (short) promoter did not affect the activity of unmodified BCMA CAR T cells, EF1a(short)-driven CACCR-BCMA CAR T cells were less efficacious than their EF1a (full-length)-driven counterparts. Although constructs with the EF1a(short) promoter improved CACCR-BCMA CAR manufacturability, the accompanying loss in CACCR-BCMA CAR activity undermined further use of EF1a(short) CACCR CAR constructs. Data shown is from one representative donor.

FIG. 13 shows the effects of substituting the full-length (FL) EF1a promoter for the MND promoter. FIG. 13A is a schematic of CACCR-BCMA CAR vectors used. FIGS. 13B & 13C show the final CAR positivity and yield of the indicated constructs driven by the EF1a or MND promoters. Utilizing the smaller MND promoter improved overall transduction efficiency, final CAR percentage and yield of CACCR-BCMA CART cells. FIG. 13D shows CAR expression level. CACCR-BCMA CAR T cells driven by the MND promoter have higher CAR expression, suggesting that the MND promoter is stronger than the EF1a promoter. Data in FIGS. 13B-13D show mean±sd of 2 donors. FIGS. 13E & 13F show serial killing activity of CAR T cells driven by the EF1a or MND promoter against MM.1S-Luc-GFP and Molp8-Luc-GFP. FIG. 13E shows that activity of the TpoR (478-582; H499L, S505N, W515K). IL2Rb(339-379, 393-433, 528-551) CACCR was reduced when driven by the MND promoter. This was corroborated with an alternate CACCR in FIG. 13F, where substitution to the MND promoter abrogated enhancement by the TpoR(478-582; S505N, W515K). IL2Rb(393-433, 528-551) CACCR. Data in FIGS. 13E & 13F show mean±sem from one out of two donors that yielded similar results. FIG. 13G shows in vivo anti-tumor activity of CACCR-BCMA CARs driven by either the EF1a or MND promoter. Compared to the EF1a-driven CACCR-BCMA CAR T cells that enhanced anti-tumor efficacy, substitution to the MND promoter abrogated all functional enhancements. Data in FIG. 13G shows mean±sem; *$p<0.01$ and **$p<0.0001$ based on RM one-way ANOVA with Tukey's multiple comparisons from Days 5-48.

Taken together, the original vector format of EF1a-TpoR (478-582; H499L, S505N, W515K). IL2Rb(339-379, 393-433, 528-551)-BCMA CAR.WPRE remained the most functionally active while retaining comparable manufacturability to its unmodified BCMA CAR counterpart. Since the use of wildtype or mutant WPRE did not impact CACCR-BCMA CARactivity (FIG. 10) and mutWPRE mitigates potential safety risks associated with the X-protein expression, EF1a-TpoR(478-582; H499L, S505N, W515K). IL2Rb(339-379, 393-433, 528-551)-BCMA CAR.mutWPRE was selected for further studies.

Example 6: Functional Characterization of Potency and Persistence of CACCR-BCMA CARs To elucidate the mechanisms by which CACCR-BCMA CARs improve CAR T cell activity, we characterized the function and phenotype of CACCR-BCMA CART cells following repeated target exposure in vitro.

TRAC/CD52 dKO CAR T cells were generated as previously described. On Day 0 of the assay, cryopreserved TRAC/CD52 dKO CAR T cells were thawed, and the percentage of CAR T cells across all samples were normalized to the sample with the lowest transduction efficiency by the addition of non-transduced (NTD) T cells. $3\times10^5$ CAR+ T cells and $1\times10^5$ MM.1S-Luc-GFP-target cells were plated at an E:T of 3:1 in a total volume of 750 uL per well in a 48-well tissue culture plate. Duplicate wells were set up for each condition. As a comparator, 10 ng/mL recombinant human IL-15 (Miltenyi) was added to cocultures of unmodified CAR T cells and target cells. Every 2 or 3 days thereafter, wells were mixed thoroughly by gentle pipetting, and 200 uL from each well was removed be to either discarded or used for flow cytometric analysis as outlined below. Wells were then replenished with $2\times10^5$ fresh MM.1S-Luc-GFP-target cells in a volume of 200 uL. In IL-15-treated wells, 10 ng/mL recombinant human IL-15 was replenished twice weekly.

To assess CAR T cell expansion and memory T cell differentiation, 200 uL was removed from each well of the 48-well plate and re-plated into a well of a 96-well U-bottom plate. Cells were washed with PBS and stained with the Zombie-NIR Fixable Viability kit (Biolegend). Cells were then washed with PBS, Fc-blocked, and stained with a PE-conjugated anti-idiotype antibody for the detection of the P5A2 scFv, BV605-conjugated anti-human CD4 (Biolegend), BV510-conjugated anti-human CD8 (Biolegend), PE/Cy7-conjugated anti-human CD62L (Biolegend) and BV785-conjugated anti-human CD45RO diluted in PBS+1% BSA. After washing, cells were resuspended 100 uL PBS+1% BSA containing 123 count eBeads counting beads (Thermo Fisher) (10 uL counting beads in 90 uL PBS+1% BSA) prior to flow cytometric analysis.

To evaluate activation-induced cell death (AICD), 200 uL was removed from each well of the 48-well plate and re-plated into two wells of a 96-well U-bottom plate at 100 uL per well. $1\times10^5$ MM.1S-Luc-GFP-target cells in a volume of 100 uL was added to one of these wells in the 96-well U-bottom plate, while the other well was left unstimulated as a baseline comparison. After 4 hours, the percentages of dead CAR T cells were determined by flow cytometry. Briefly, cells were washed with PBS and stained with the Zombie-NIR Fixable Viability kit (Biolegend). Cells were then washed with PBS, Fc-blocked, and stained with a PE-conjugated anti-idiotype antibody for the detection of the P5A2 scFv, BV605-conjugated anti-human CD4 (Biolegend) and BV510-conjugated anti-human CD8 (Biolegend) diluted in PBS+1% BSA.

For intracellular cytokine staining, 200 uL was removed from each well of the 48-well plate and 100 uL was re-plated into a well of a 96-well U-bottom plate. $1\times10^5$ MM.1S-Luc-GFP-target cells in a volume of 100 uL was added to one of these wells in the 96-well U-bottom plate, along with a Protein Transport Inhibitor Cocktail (Invitrogen). After 4 hours, cells were stained for surface markers and intracellular cytokines. Briefly, cells were washed with PBS and stained with the Zombie-NIR Fixable Viability kit (Biolegend). Cells were then washed with PBS, Fc-blocked, and stained with a PE-conjugated anti-idiotype antibody for the detection of the P5A2 scFv, BV605-conjugated anti-human CD4 (Biolegend) and BV510-conjugated anti-human CD8 (Biolegend) diluted in PBS+1% BSA. After washing, cells were fixed and permeabilized using the BD Cytofix/Cytoperm kit (BD Biosciences) according to manufacturer's instructions and stained with a PE/Cy7-conjugated anti-human IFNg (Biolegend), BV785-conjugated anti-human TNFa (Biolegend) and PE/Dazzle594-conjugated anti-human IL-2 (Biolegend) prior to flow cytometric analysis.

Figure 14:
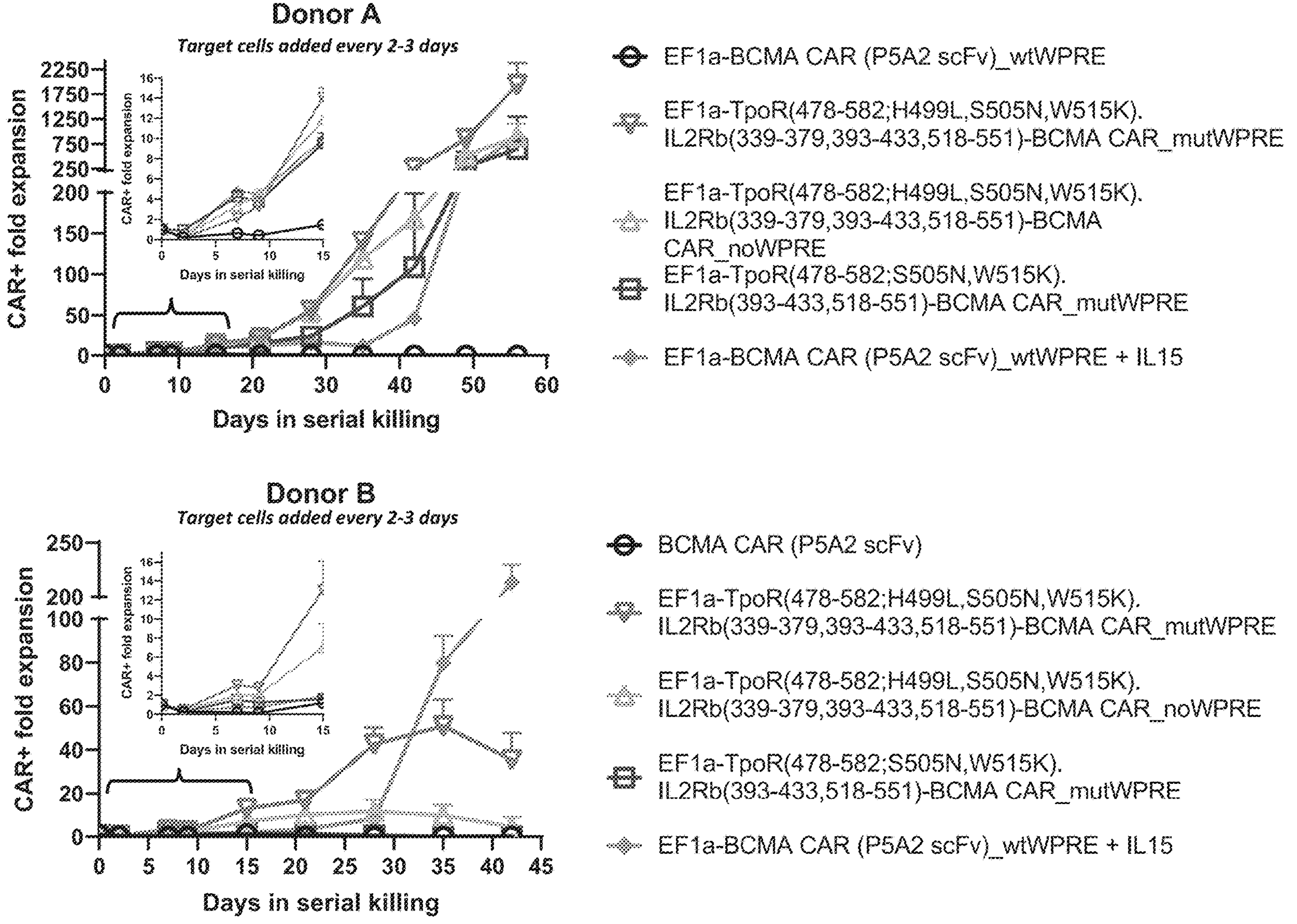
FIG. 14 shows proliferation profile of CACCR-BCMA CAR T cells upon repeated target exposure as compared to unmodified BCMA CAR T cells.

FIG. 14 shows CAR T cell expansion following repeated target exposures in two donors. Shown insets are CAR T cell expansion profiles during the first 15 days of the assay. In both donors, the CACCR-BCMA CAR (EF1a-TpoR(478-582; H499L, S505N, W515K). IL2Rb(339-379, 393-433, 528-551)-BCMA CAR_mutWPRE) demonstrated the greatest target-driven expansion capacity. Data are presented as mean±sem.

Figure 15A:
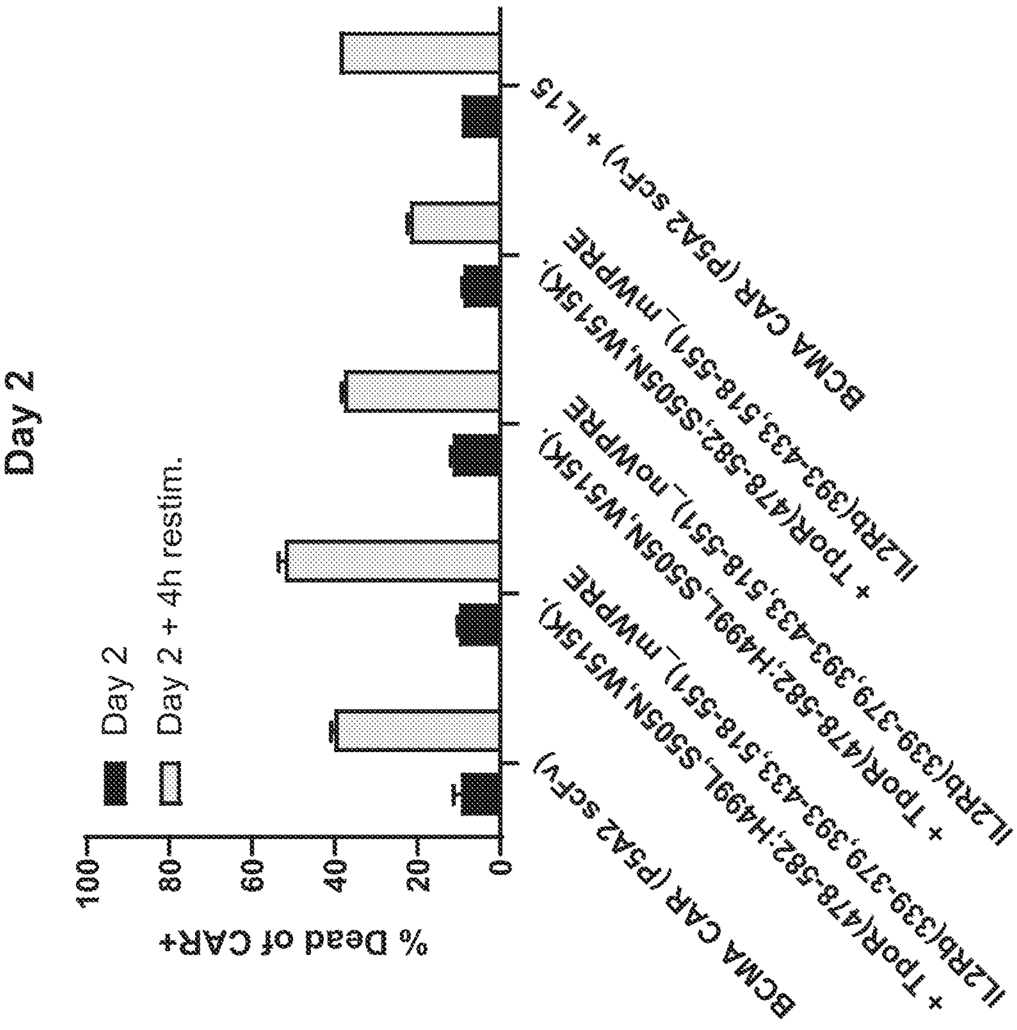
FIGS. 15A-15B show the sensitivity of CAR T cells to activation-induced cell death (AICD) with increasing exposure to target cells: mWPRE, mutant WPRE; restim, restimulation.
Figure 15B:
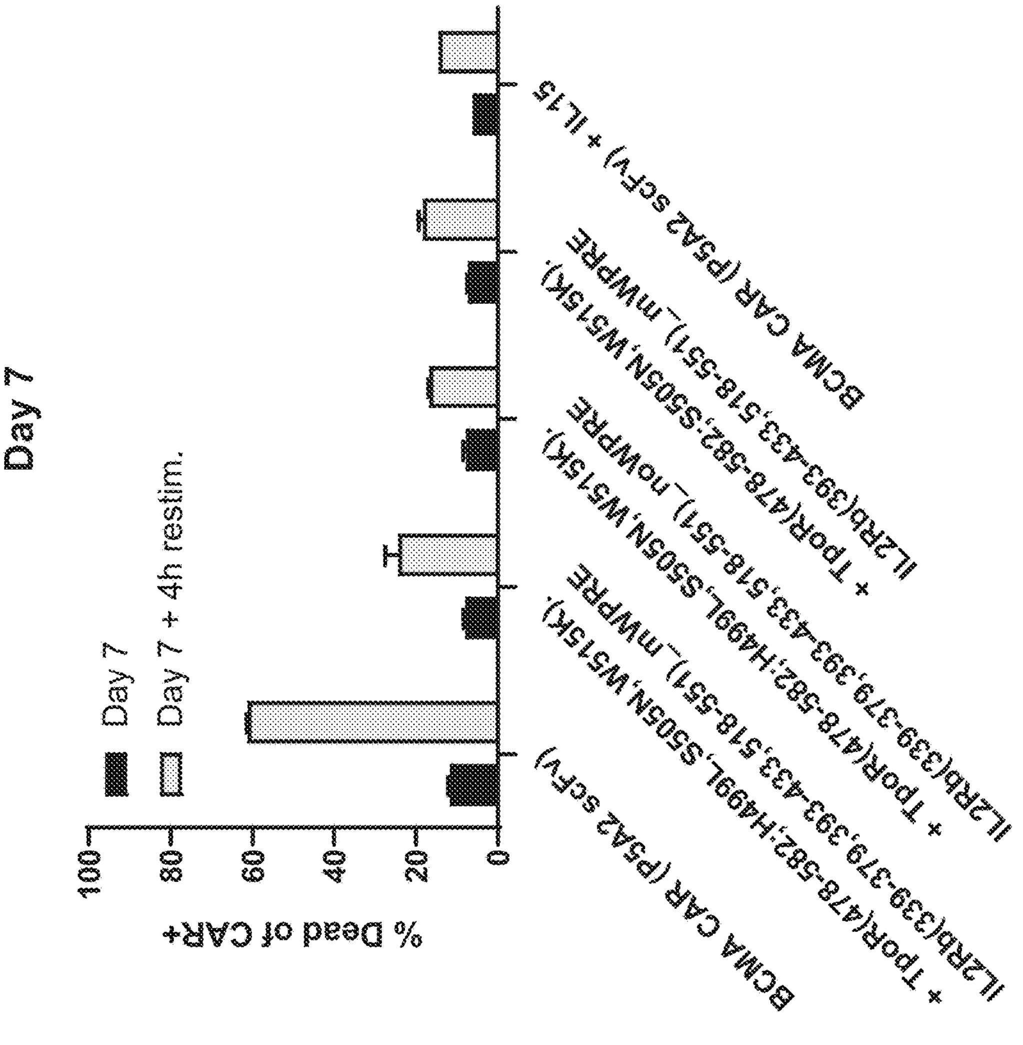

FIG. 15 shows the sensitivity of CAR T cells to AICD with increasing exposure to target cells. FIG. 15A shows that CAR T cells that had undergone one prior round of target exposure (on Day 0) were comparably sensitive to AICD following a second target exposure, regardless of CACCR expression or IL-15 treatment. FIG. 15B shows that after multiple rounds of target exposure on Day 7, unmodified BCMA CAR T cells were highly sensitive to AICD, whereas CACCR-BCMA CART cells and IL-15-treated BCMA CAR T cells were protected from AICD. Without intending to be limited to a specific mechanism, the data suggest that cytokine signaling—through CACCRs or supplemented IL-15—can help CAR T cells resist AICD and improve survival, particularly following chronic target exposure. Data are presented as mean±sd from one out of two donors that yielded similar results.

Figure 16A:
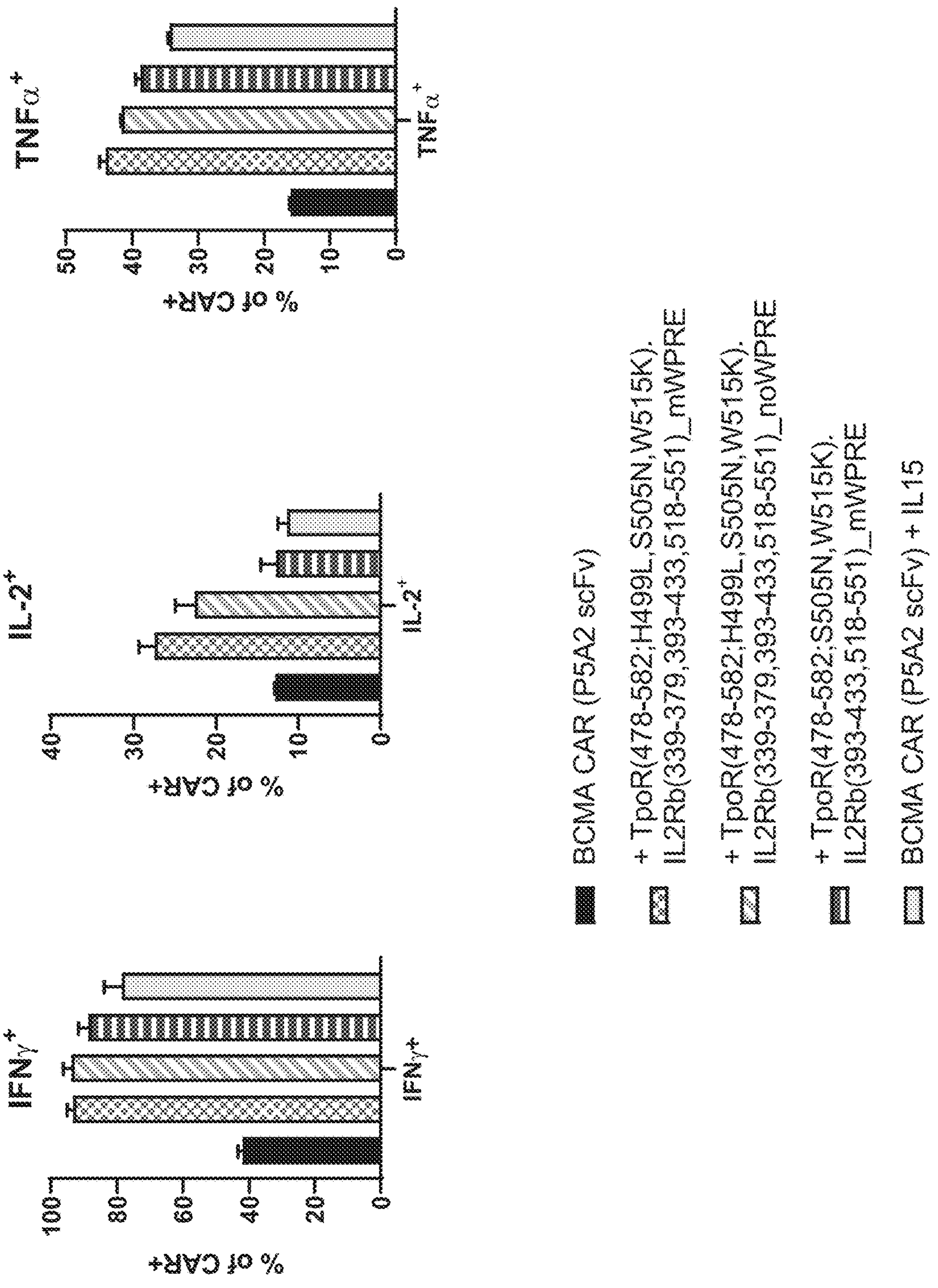
FIGS. 16A-16B show cytokine expression profiles of CAR T cells based on intracellular cytokine staining of Day 7 of the assay.
Figure 16B:

FIG. 16 shows cytokine expression profiles of CAR T cells based on intracellular cytokine staining on Day 7 of the assay. FIG. 16A shows the percentage of CAR+ T cells that expressed the indicated cytokines. Compared to the unmodified BCMA CAR, CACCR-BCMA CART cells and IL-15-treated CAR T cells expressed higher levels of effector cytokines. FIG. 16B shows CAR T cell polyfunctionality, as determined by their ability to coexpress 2 or 3 effector cytokines. Compared to unmodified BCMA CAR T cells, CART cells with the EF1a-TpoR(478-582; H499L, S505N, W515K). IL2Rb(339-379, 393-433, 528-551)-BCMA CAR mutWPRE construct demonstrated the greatest extent of polyfunctionality. Data shows mean±sd from one out of two donors that yielded similar results.

Figure 17:
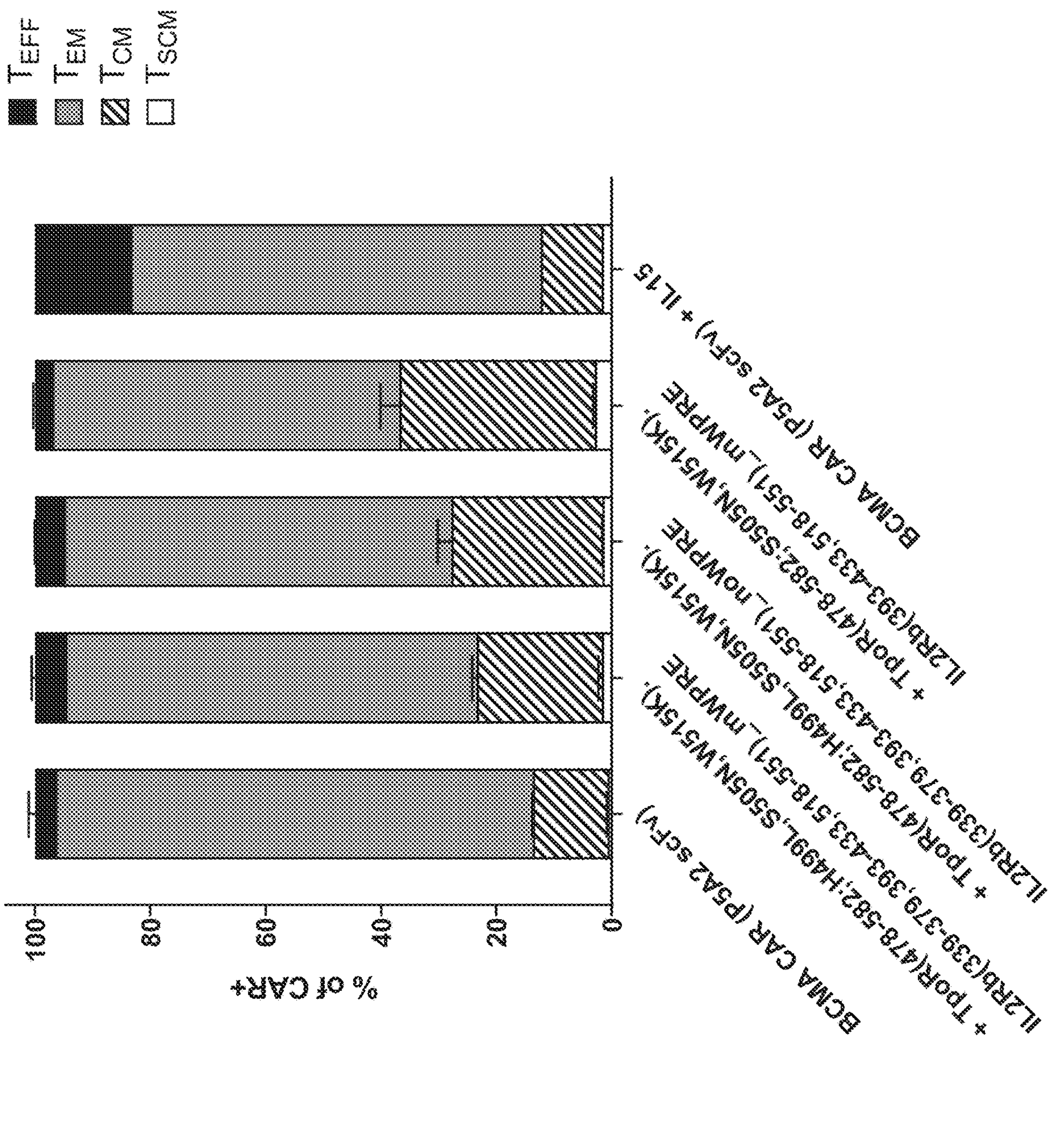
FIG. 17 shows memory phenotype of CAR T cells on Day 15 of the assay.

FIG. 17 shows the memory phenotype of CAR T cells on Day 15 of the assay. Compared to unmodified BCMA CAR T cells, CACCR-BCMA CART cells showed a slight enrichment of the stem cell memory ($T_{SCM}$) and central memory ($T_{CM}$) populations, which are known to mediate long-term CAR T cell persistence.

To monitor the in vivo pharmacokinetics of CACCR-BCMA CART cells, we tracked CAR T cell expansion and persistence in an orthotopic model of multiple myeloma using the Molp8-Luc-GFP cell line. The Molp8-Luc-GFP cell line expresses lower levels of BCMA than MM.1S-Luc-GFP and represents a model of multiple myeloma that is highly treatment-resistant. Briefly, 8-10 weeks old female NSG mice were irradiated with 1 Gy one day prior to intravenous inoculation of $2\times10^6$ Molp8-Luc-GFP. 8 days post tumor implantation, mice were randomized based on tumor burden and either $1\times10^6$ or $5\times10^6$ TRAC/CD52 dKO BCMA CAR T cells were intravenously infused per mouse (n=10 mice per group). Thereafter, tumor burden was monitored twice weekly by bioluminescent imaging, and mice that had received $5\times10^6$ CAR T cells were bled at the indicated timepoints for the enumeration of BCMA CAR T cells in the periphery. Specifically, 50 uL of whole blood from each mouse was subjected to red blood cell lysis using ACK Lysing Buffer (Gibco), Fc-blocked and stained with the following antibody cocktail diluted in PBS+1% BSA: FITC-conjugated anti-mouse CD45 (Biolegend), BV421-conjugated anti-human CD45 (Biolegend) and PE-conjugated anti-idiotype antibody for the detection of the P5A2 scFv. Finally, samples were washed in PBS and cell pellets were resuspended in 250 uL PBS+1% BSA containing 123 count eBeads counting beads (Thermo Fisher) (10 uL counting beads in 240 uL PBS+1% BSA) prior to flow cytometric analysis.

Figure 18A:
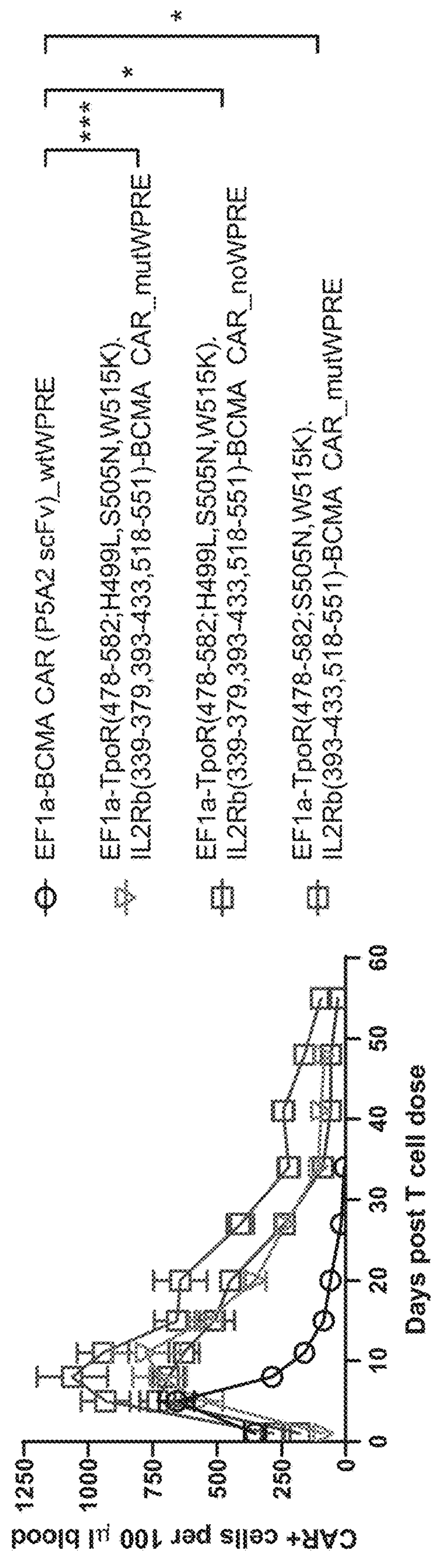
FIGS. 18A-18B show expansion and persistence of BCMA CAR T cells in Molp8-Luc-GFP-bearing mice that had received $5\times10^6$ CAR T cells.
Figure 18B:
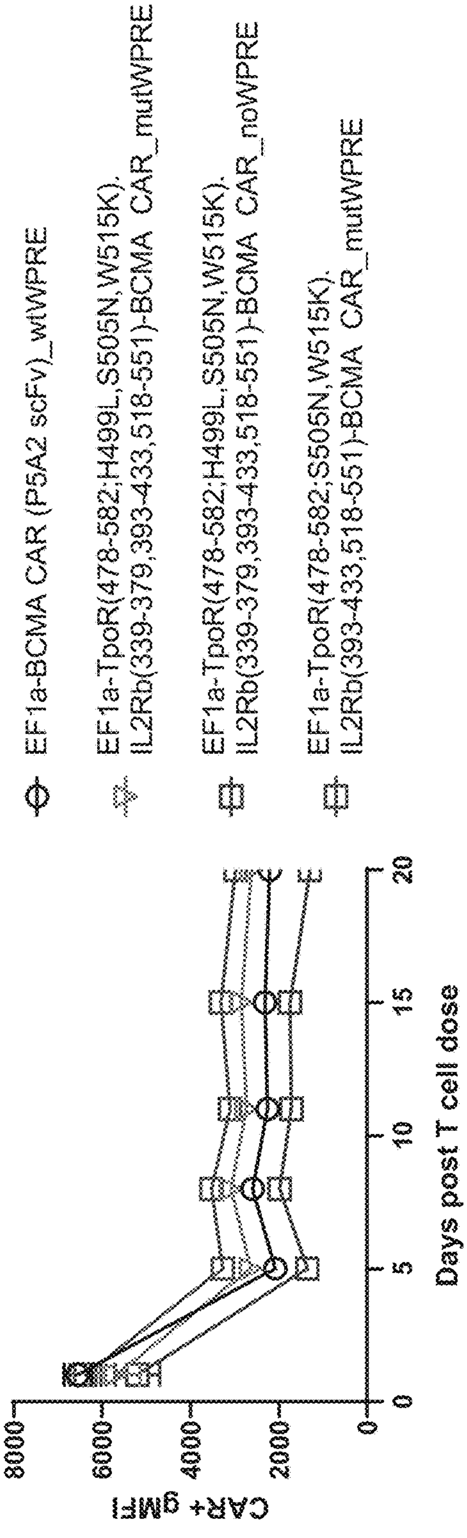

FIG. 18 shows the expansion and persistence of BCMA CAR T cells in Molp8-Luc-GFP-bearing mice that had received $5\times10^6$ CAR T cells. FIG. 18A shows that while unmodified BCMA CAR T cells underwent an initial expansion, its numbers quickly declined within 2 weeks of CAR T cell infusion. In contrast, CACCR-BCMA CAR T cells expanded comparably or better than their unmodified counterparts and showed prolonged persistence in vivo. FIG. 18B shows CAR expression levels (gMFI) in BCMA CAR T cells from peripheral blood. Although no differences in CAR expression was detected in the CAR T cell product in vitro (FIG. 11D), the EF1a-TpoR(478-582; H499L, S505N, W515K). IL2Rb(339-379, 393-433, 528-551)-BCMA CAR_noWPRE construct showed lower CAR expression relative to its WPRE-bearing counterparts in vivo. Data shows mean±sem.

Figure 19A:
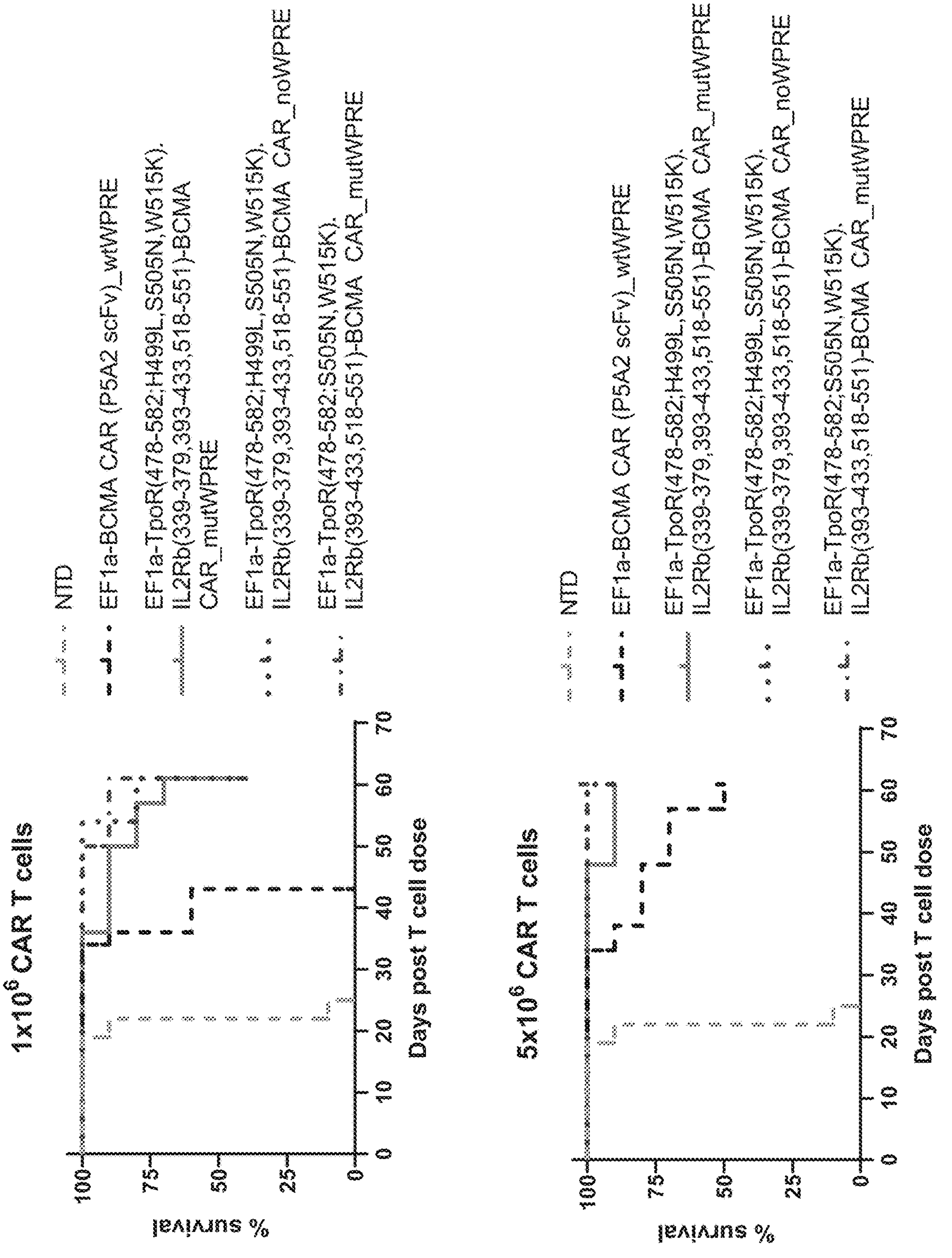
FIGS. 19A-19B show the overall survival of mice that had received either $1\times10^6$ or $5\times10^6$ CAR T cells up to Day 60 (FIG. 19A) and passing Day 100 (FIG. 19B).
Figure 19B:
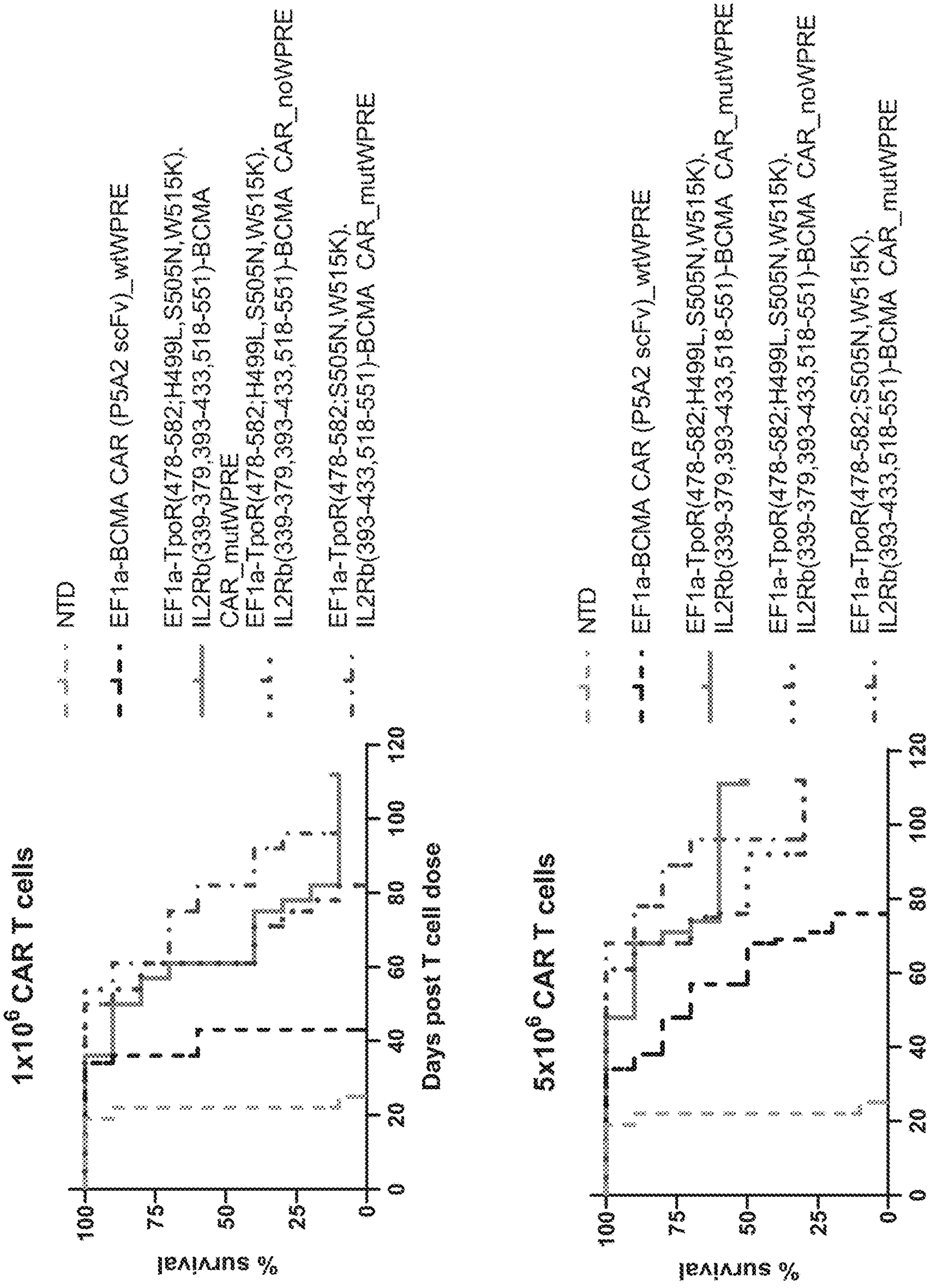

FIGS. 19A-19B show the overall survival of mice that had received either $1\times10^6$ or $5\times10^6$ CAR T cells. FIG. 19B shows the extended results. At both doses, CACCR-BCMA CAR T cells prolonged overall survival. Notably, median survival of $1\times10^6$ CACCR-BCMA CAR-treated mice was 61 days, which was comparable to the median survival of 57 days in mice treated with $5\times10^6$ unmodified BCMA CAR T cells.

Figure 20:
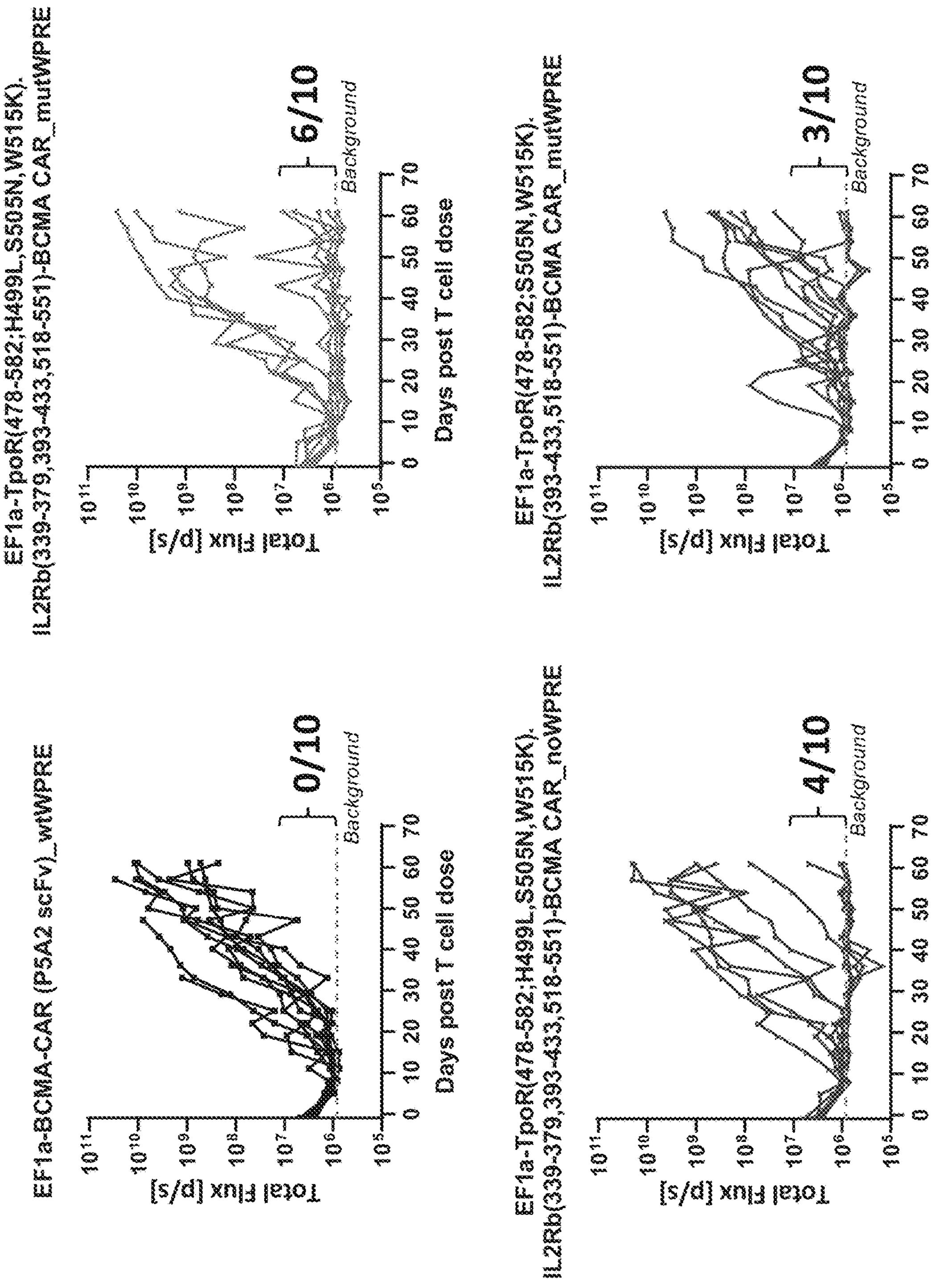
FIG. 20 shows the tumor burden of individual mouse that had received $5\times10^6$ CAR T cells as shown in FIG. 19.

FIG. 20 shows the tumor burden of individual mice that had received $5\times10^6$ CAR T cells. Mice treated with unmodified BCMA CAR T cells uniformly showed disease progression beyond Day 36. By contrast, infusions of CACCR-BCMA CAR T cells were able to substantially delay disease progression in a subset of mice. Therefore, the greater persistence of CACCR-BCMA CAR T cells correlates with improved tumor control.

Example 7: The Activity of CACCR-BCMA CART Cells is Target-Dependent

For CACCR-BCMA CAR T cells to be efficacious and safe, we next investigated whether their activity is governed by CAR-mediated target recognition, and that CACCR signaling in the absence of CAR engagement is insufficient to induce cytotoxic responses.

To evaluate whether the cytotoxicity and effector responses of CACCR-BCMA CAR T cells, an overnight cytotoxicity assay was performed using either REH-Luc-GFP stably overexpressing BCMA (REH-BCMA) or the parental BCMA-negative REH-Luc-GFP as target cells. TRAC/CD52 dKO CAR T cells were generated as previously described. Cryopreserved TRAC/CD52 dKO CAR T cells were thawed, and the percentage of CAR T cells across all samples were normalized to the sample with the lowest transduction efficiency by the addition of non-transduced (NTD) T cells. 10,000 target cells in a volume of 100 uL were added to each well of a white flat-bottomed 96-well tissue culture plate. CAR T cells in a volume of 100 uL were then added to each well of target cells at the indicated E:T ratios in triplicates. As a “Targets only” negative control, 100 uL of media, instead of T cells, was added to target cells. 24 hours later, the number of live target cells remaining was determined using the ONE-Glo Luciferase Assay System (Promega) according to manufacturer’s instructions. The percentage of live target cells was calculated by normalizing the luciferase signal of to that of “Targets only” wells, and percentage cytotoxicity was calculated as 100%-% live target cells.

To evaluate cytokine secretion profiles of CACCR-BCMA CART cells, $2.5\times10^5$ REH-BCMA or parental REH cells in a volume of 250 uL were plated in each well of a 24-well plate. Cryopreserved TRAC/CD52 dKO CAR T cells were thawed, and the percentage of CAR T cells across all samples were normalized to the sample with the lowest transduction efficiency by the addition of non-transduced (NTD) T cells. CAR T cells in a volume of 250 uL were then added to each well of target cells at and E:T=1:1 in duplicates. To assess whether CACCR-BCMA CAR T cells secreted elevated basal levels of cytokines, CAR T cells were cultured alone, and 250 uL media was added in place of target cells. 24 hours later, plates were spun down and 200 uL of supernatant from each well was harvested and stored at −80° C. for Luminex analysis. On the day of Luminex analysis, frozen culture supernatants were thawed and diluted either 4-fold or 16-fold prior to analysis using the MILLIPLEX MAP Human High Sensitivity T Cell Panel Premixed 21-plex—Immunology Multiplex Assay according to manufacturer’s instructions.

Figure 21A:
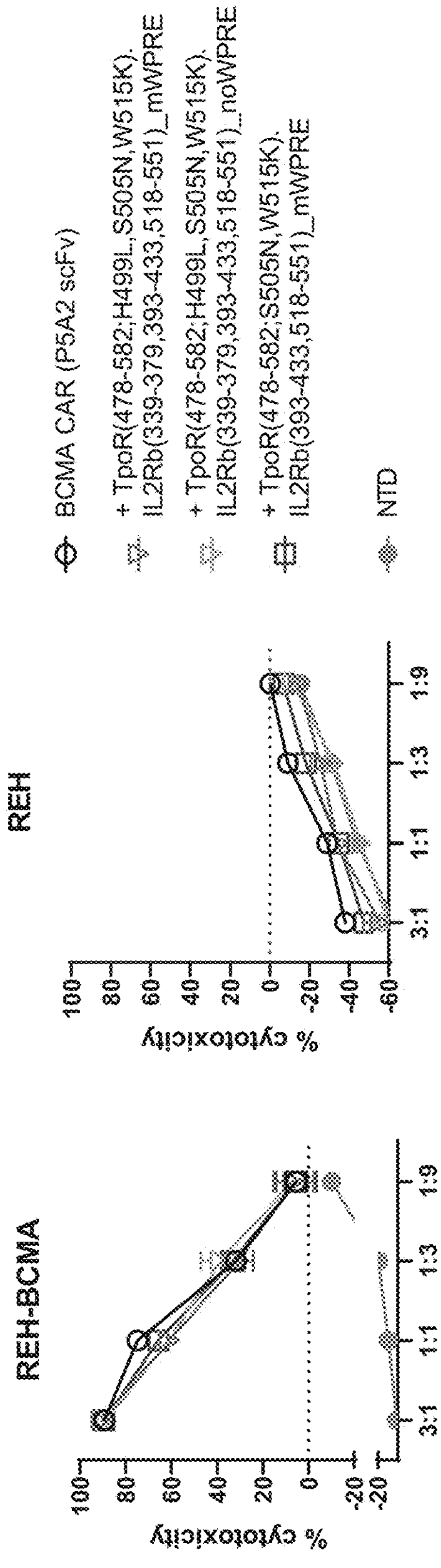
FIG. 21A depicts data showing target-dependent cytotoxicity of CACCR-BCMA CAR T cells and unmodified BCMA CAR T cells.
Figure 21B:
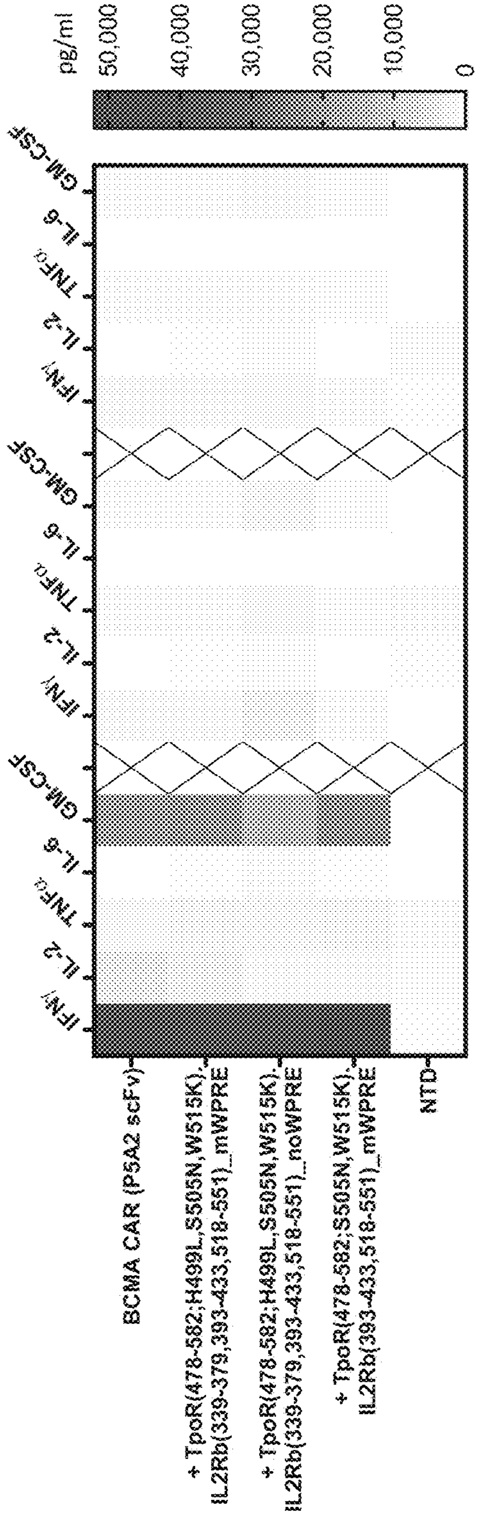
FIG. 21B depicts data showing target-dependent cytokine secretion profiles of CACCR-BCMA CAR T cells and unmodified BCMA CAR T cells.

FIG. 21 shows that CACCR-BCMA CAR T cells do not elaborate cytotoxic effector functions in the absence of BCMA. FIG. 21A shows the cytotoxicity of CACCR-BCMA CAR T cells after 24-hour coculture with either REH-BCMA or BCMA-negative REH. As expected, the unmodified BCMA CAR and CACCR-BCMA CART cells showed a dose-dependent killing of REH-BCMA target cells. By contrast, neither the unmodified BCMA CAR nor CACCR-BCMA CAR T cells were able to kill BCMA-negative REH cells. FIG. 21B shows the cytokine secretion profiles of CACCR-BCMA CAR T cells following 24 hour exposure to REH-BCMA, BCMA-negative REH or in media alone (T cells only). As expected, all BCMA CAR T cells secreted high and comparable levels of IFNγ and GM-CSF, and to a lesser degree IL-2, in response to REH-BCMA. In response to BCMA-negative REH, or with CAR T cells alone, all BCMA CAR T cells secreted little to no cytokines, with CACCR-BCMA CAR T cells showing a very similar profile to their unmodified counterpart. These data demonstrate that CACCRs do not increase the BCMA-independent cytotoxicity or effector functions of CACCR-BCMA CAR T cells.

To assess whether CACCR signaling alone is sufficient to drive the overt expansion of CACCR-BCMA CAR T cells, we performed a growth factor independent assay, where CACCR-BCMA CAR T cells were cultured in the absence of targets or exogenous cytokines. TRAC/CD52 dKO CAR T cells were generated as previously described. Cryopreserved TRAC/CD52 dKO CAR T cells were thawed, and the percentage of CAR T cells across all samples were normalized to the sample with the lowest transduction efficiency by the addition of non-transduced (NTD) T cells. $2.5\times10^5$ CAR T cells/mL were plated at a volume of 1.5-2 mL in 24-well tissue culture plates in duplicates. As a positive control, unmodified BCMA CAR T cells were cultured in the presence of 10 ng/mL recombinant human IL-15 that was replenished weekly. At the indicated timepoints, wells were mixed thoroughly by pipetting, and 100 uL was harvested from each well for CAR T cell enumeration by flow cytometric analysis. Briefly, cells were washed with PBS and stained with the Zombie-NIR Fixable Viability kit (Biolegend). Cells were then washed with PBS, Fc-blocked, and stained with a PE-conjugated anti-idiotype antibody for the detection of the P5A2 scFv, BV605-conjugated anti-human CD4 (Biolegend) and BV510-conjugated anti-human CD8 (Biolegend), diluted in PBS+1% BSA. After washing, cells were resuspended 100 uL PBS+1% BSA containing 123 count eBeads counting beads (Thermo Fisher) (10 uL counting beads in 90 uL PBS+1% BSA) prior to flow cytometric analysis. On Day 70 of the assay, each well was diluted 2-fold by the addition of media, and CAR T cell counts for subsequent timepoints were normalized accordingly by multiplying 2-fold.

Figure 22A:
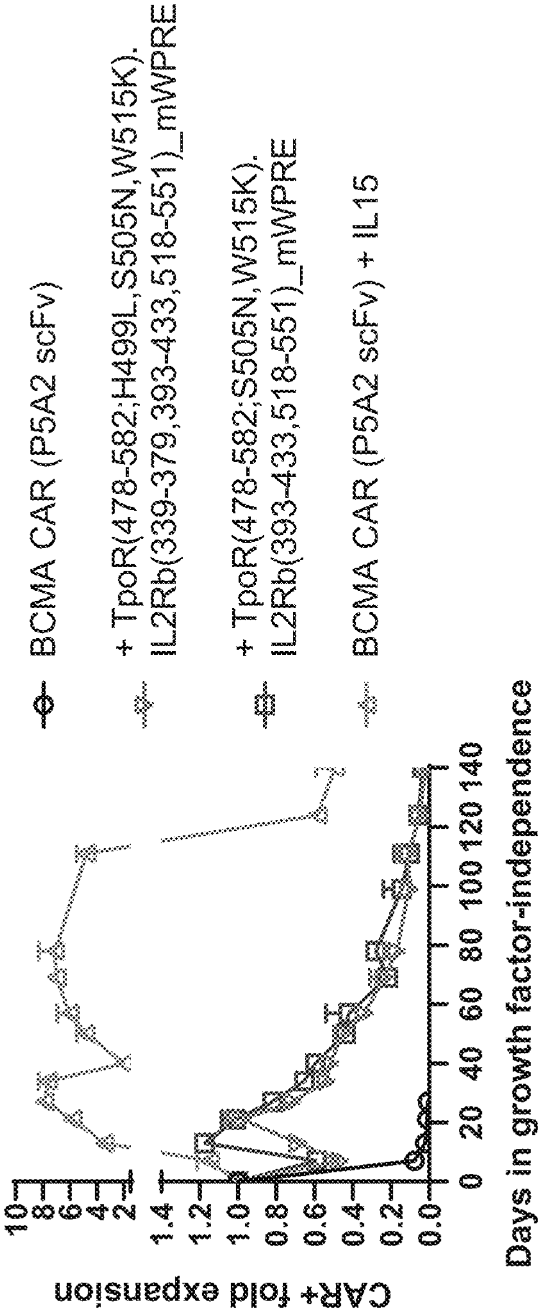

FIG. 22A shows CACCR-BCMA CAR T cells being more persistent than unmodified BCMA CAR T cells in the absence of targets and exogenous cytokines. Compared to unmodified CAR T cells that declined within 3 weeks, CACCR-BCMA CAR T cells showed prolonged persistence in the growth factor-independent assay. Nevertheless, CACCR-BCMA CAR T cells did not show overt proliferation, but instead underwent a slow but steady decline. The data indicate that while CACCR signaling can prolong CACCR-BCMA CAR T cell survival, CACCR signaling alone is insufficient to drive CACCR-BCMA CAR T cell expansion, nor can it sustain indefinite survival. Growth factor-independent assay was repeated using IL2 as the growth factor, and the ability of CACCR BCMA CAR T cells to expand in the absence of target and exogenous cytokine stimulation was further assessed in vitro by cell counting and Ki-67 analysis.

Briefly, TRAC/CD52 dKO CAR T cells were suspended in assay medium (X-VIVO15 medium (Lonza) containing 10% FBS (Hyclone)) to a final concentration of $1\times10^6$ cells/ml on Day 0.500 μl ($5\times10^5$ cells) of each sample was plated in quadruplicate wells in a 24-well tissue culture plate. 1 ml of assay medium was added to each well to bring the final volume to 1.5 ml. 1.5 ml of PBS were added to the outer wells of the 24-well plate to prevent media evaporation. Twice per week, cells in each well were mixed and 750 μl from each well was transferred to a new 24-well plate containing 750 μl of fresh assay medium. As a positive control, 1 ml of irradiated MM.1S cells suspended at a final concentration of $5\times10^5$ cells/ml was added in place of assay medium, along with the addition of IL-2 at a final concentration of 50 IU/ml. Twice per week, cells in each positive control well were mixed and 750 μl from each well was transferred to a new 24-well plate containing 750 μl of fresh assay medium, along with the addition IL-2 at a final concentration of 50 IU/ml. The volume remaining in each well was used to measure Total Viable Cells (TVC) using the NC-200 analyzer. The assay continued until all cell counts in each test sample read zero on the NC-200 instrument. The viable cell fold expansion was calculated by dividing the TVC of a specific time point by the TVC of Day 0. For each time point after day 0, the TVC value was normalized by a multiple of 2 to account for the sample dilution occurring twice per week.

For the Ki-67 analysis assessing cells in active cell cycle, on days 0, 3, 7 and 14, cells were harvested and washed with 2 mL of BSA-containing stain buffer (BD Biosciences). Cells were suspended in 100 μL of stain buffer containing pre-titrated amounts of each of the primary antibody. For CAR detection, 5 μL of FITC-conjugated soluble BCMA protein was added. Cells were stained for 30 min at 4° C. and washed twice with 2 mL of PBS. After the last wash, the supernatant was aspirated and the cell pellet was loosened up using a vortex. Two milliliters of cold 70% ethanol were added dropwise to the cell pellet while vortexing and then the mixture was vortexed for an additional 30 seconds. Cells in 70% ethanol were incubated at −20° C. for 1 hour and then washed three times with BioLegend Cell Staining buffer. Cells were suspended in 100 μL of BioLegend Cell Staining buffer and a pre-titrated amount of human anti-Ki-67 antibody was added. Cells were stained in the dark for 30 min at room temperature and then washed twice with BioLegend Cell Staining buffer. Finally, the cell pellet was suspended in BioLegend Cell Staining buffer for flow cytometry analysis.

The data show that CACCR BCMA CAR T cells do not display target- and IL-2-independent growth in vitro. FIG. 22B shows that BCMA and CACCR BCMA CAR T cells display minimal or no expansion during the first 3 days. After this, CACCR BCMA CAR T cells persisted for ~ 2 weeks, followed by a gradual decline over time. By Day 42, BCMA CAR T cells and CACCR BCMA CAR T cells were non-detectable. FIG. 22C shows that approximately 30-40% of $CAR^+$ cells in all three donors were expressing Ki-$67^+$ on Day 0. However, Ki-67 expression substantially decreased by day 3 of IL-2 independent culture and was undetectable by Day 14. FIG. 22D shows that both BCMA CAR T cells and CACCR BCMA CAR T cells were capable of robust and comparable expansion when cultured with irradiated target cells and IL-2.

The data confirmed that CACCR did not sustain indefinite survival of CACCR-BCMA CAR T cells growth in the absence of IL2 or target, either in T cell-based or PBMC-based CAR T cells derived from multiple donors.

The growth factor-independent assay presented is but one way for assessing aberrant growth, as the CAR T cells have never seen target and are therefore quiescent. We additionally sought to evaluate whether the expansion and persistence of CACCR-BCMA CART cells remained finite in recently activated CACCR-BCMA CAR T cells once targets had been cleared. To this end, CACCR-BCMA CAR T cells were first exposed repeatedly to BCMA-expressing target cells to drive their full activation and expansion, before target cells were withdrawn from these cultures. Briefly, TRAC/CD52 dKO CAR T cells were generated as previously described. On Day 0 of the assay, cryopreserved TRAC/CD52 dKO CAR T cells were thawed, and the percentage of CAR T cells across all samples were normalized to the sample with the lowest transduction efficiency by the addition of non-transduced (NTD) T cells. $3\times10^5$ CAR+ T cells and $1\times10^5$ MM.1S-Luc-GFP-target cells were plated at an E:T of 3:1 in a total volume of 750 uL per well in a 48-well tissue culture plate. As a comparator, 10 ng/mL recombinant human IL-15 (Miltenyi) was added to cocultures of unmodified CAR T cells and target cells. Every 2 or 3 days for the first 7 days, wells were mixed thoroughly by gentle pipetting, and 200 uL from each well was discarded. Wells were then replenished with $2\times10^5$ fresh MM.1S-Luc-GFP-target cells in a volume of 200 uL. On Day 9, target cells were either continued to be added every 2 or 3 days for the remainder of the assay, or withdrawn completely. In IL-15-treated wells, 10 ng/mL recombinant human IL-15 was replenished twice weekly. Duplicate wells were set up for each condition. At the indicated timepoints, wells were mixed thoroughly by pipetting, and 50-200 uL was harvested from each well for CAR T cell enumeration by flow cytometric analysis. Briefly, cells were washed with PBS and stained with the Zombie-NIR Fixable Viability kit (Biolegend). Cells were then washed with PBS, Fc-blocked, and stained with a PE-conjugated anti-idiotype antibody for the detection of the P5A2 scFv, BV605-conjugated anti-human CD4 (Biolegend) and BV510-conjugated anti-human CD8 (Biolegend), diluted in PBS+1% BSA. After washing, cells were resuspended 100 uL PBS+1% BSA containing 123 count eBeads counting beads (Thermo Fisher) (10 uL counting beads in 90 uL PBS+1% BSA) prior to flow cytometric analysis.

Figure 23A:
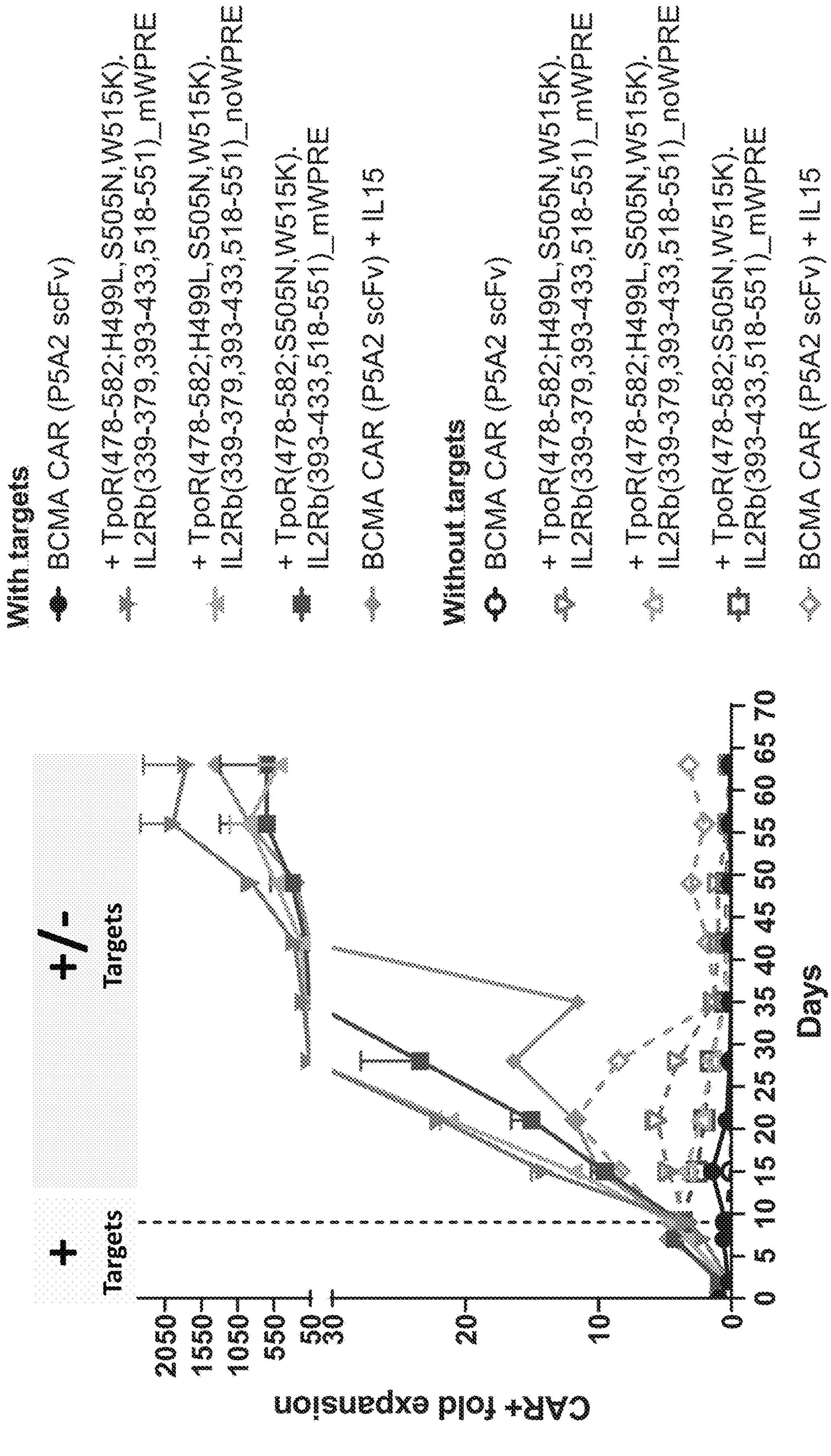
FIG. 23A shows the expansion profiles of recently activated BCMA CAR T cells that were either continually stimulated with target cells, or had targets withdrawn.

FIG. 23A shows the expansion profiles of recently activated BCMA CAR T cells that were either continually stimulated with target cells, or had targets withdrawn. BCMA CAR T cells that were continually stimulated with targets demonstrated proliferative potential. However, when targets were withdrawn, CACCR-BCMA CAR T cells ceased proliferation and instead underwent a slow and steady decline. This demonstrates that even after robust activation, the continued expansion and persistence of CACCR-BCMA CAR T cells is still dependent on target-induced CAR activation.

Long-term persistence of CACCR BCMA CAR T cells in the absence of target was next evaluated in vivo in non-tumor-bearing mice. To facilitate long-term in vivo tracking via bioluminescent imaging, CAR T cells labelled with the Click Beetle Red (CBR) luciferase reporter were generated. Briefly, lentivirus encoding the BCMA CARs and BFP-CBR were generated as described above. TRAC/CD52 dKO human CAR T cells were generated and cryopreserved as described above, with the exception that on Day 2, T cells resuspended at 0.5 million cells per mL were co-transduced with equal volumes of CAR and BFP-CBR crude lentiviral supernatants. The percentage of CAR- and CBR-transduced cells was determined by flow cytometry using a PE-conjugated anti-idiotype antibody specific for the BCMA scFv and the BFP fluorescent reporter, respectively. On the day of T cell dosing, cryopreserved CAR T cells were thawed and normalized to the sample with the lower transduction efficiency by the addition of non-transduced (NTD) T cells. $7\times10^6$ TRAC/CD52 $CAR^+$ T cells were intravenously infused into non-tumor-bearing 8-10 weeks old female NSG mice. Starting on the day of T cell dosing and 1-3 times per week thereafter, in vivo T cell pharmacokinetics was determined by bioluminescent imaging. At the indicated timepoints, mice were bled for the enumeration of BCMA CAR T cells in the periphery. Specifically, 50 uL of whole blood from each mouse was subjected to red blood cell lysis using ACK Lysing Buffer (Gibco), Fc-blocked and stained with the following antibody cocktail diluted in PBS+1% BSA: FITC-conjugated anti-mouse CD45 (Biolegend), AlexaFluor647-conjugated anti-human CD45 (Biolegend), PE-conjugated anti-idiotype antibody specific for the BCMA scFv and BUV395-conjugated anti-human CD3 (used as a surrogate for human T cell receptor; BD Biosciences). Finally, samples were washed in PBS and cell pellets were resuspended in 250 uL PBS+1% BSA containing 123 count eBeads counting beads (Thermo Fisher) (10 uL counting beads in 240 uL PBS+1% BSA) prior to flow cytometric analysis.

Figure 23B:
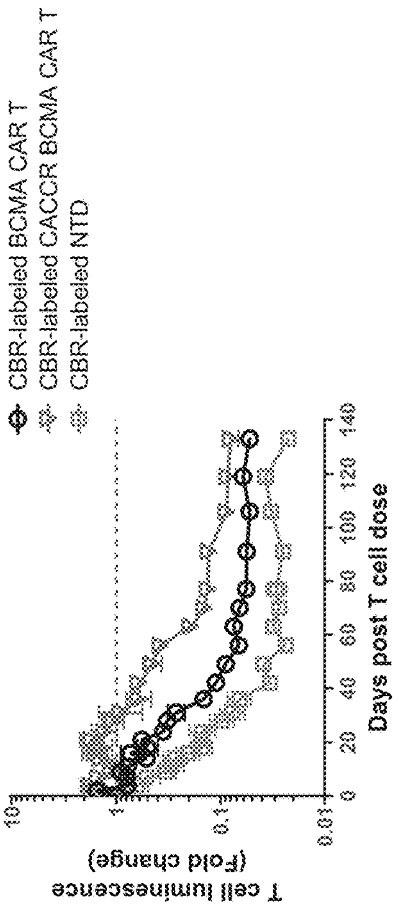
FIGS. 23B-23D depict data demonstrating that CACCR BCMA CAR T cells could not persist long term in vivo in the absence of target and exerted no negative effects on non-tumor bearing mice.
Figure 23C:
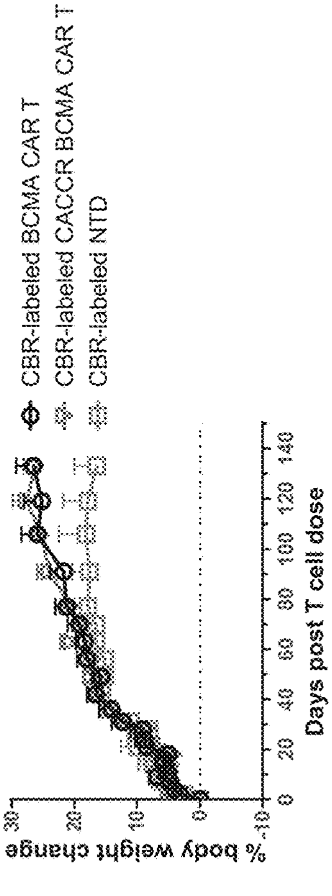
Figure 23D:
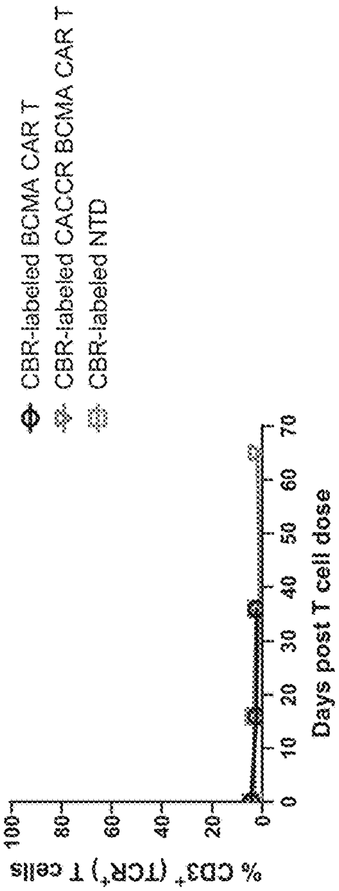

FIG. 23B shows that CACCR BCMA CAR T cells did not display aberrant target-independent growth in non-tumor bearing mice. Compared to NTD and BCMA CAR T cells, CACCR BCMA CAR T cells had increased persistence and survival. However, CACCR BCMA CAR T cells showed no evidence of overt target-independent expansion and instead underwent an eventual decline. T cell luminescence at each timepoint is expressed as a fold change relative to that of Day 0. FIG. 23C shows comparable weight gain between mice that had received CACCR BCMA CAR T cells and BCMA CAR T cells. FIG. 23D shows that no enrichment of T cell receptor (TCR)-expressing T cells was observed, suggesting that CACCR did not increase the xenoreactive potential of BCMA CAR T cells. The data suggest that BCMA CAR T expressing a CACCR will not likely increase the potential of GvHD when administered to patients.

CAR T cells that have recently undergone robust target-induced activation may have a higher threshold for their return to quiescence. To determine if the activity of CACCR BCMA CAR T cells could be reined in once target cells were cleared, the expansion and long-term persistence of CBR-labeled TRAC/CD52 dKO CAR T cells in mice bearing subcutaneous tumors was evaluated by bioluminescent imaging.

CBR-labeled TRAC/CD52 dKO CAR T cells were generated by two-vector co-transduction as described above, with the exception that CAR+CBR+ double-transduced T cells were FACS-sorted based on staining with a PE-conjugated anti-idiotype antibody specific for the BCMA scFv, as well as the BFP reporter. In parallel, unlabeled TRAC/CD52 dKO CAR T cells were generated. 8-10 weeks old female NSG mice were subcutaneously implanted with $3\times10^6$ unlabeled Molp8 cells. 17 days post tumor-implantation, mice were randomized based on tumor burden and a total of $10\times10^6$ ($9.5\times10^6$ unlabeled spiked with $0.5\times10^6$ CBR-labeled) TRAC/CD52 dKO CAR T cells were intravenously infused per mouse (n=7 or 8 mice per group). Starting 1 day after T cell dosing and 1 or 2 times per week thereafter, in vivo T cell pharmacokinetics was determined by bioluminescent imaging, and subcutaneous tumor burden was determined by caliper measurements. Tumor burden was calculated using the formula Tumor volume=(width^2×length/2).

Figure 23E:
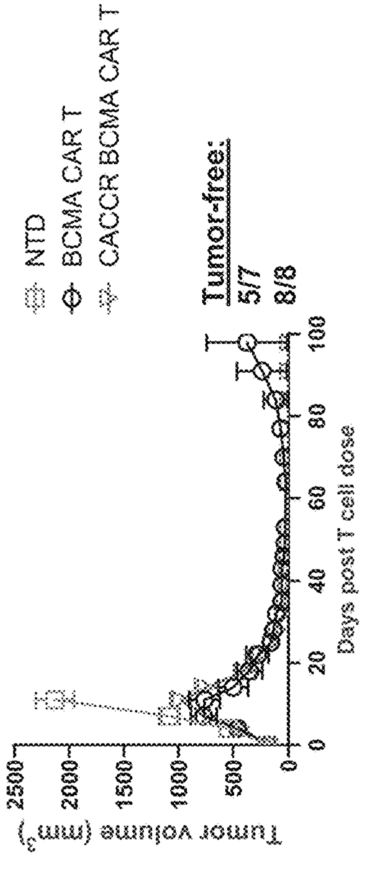
FIGS. 23E-23F show results demonstrating that in vivo expansion of CACCR BCMA CAR T cells was target-dependent, and that they returned to quiescence following target clearance. The weight gain of mice receiving BCMA CAR or CACCR BCMA CAR T cells was comparable (FIG. 23G).
Figure 23F:
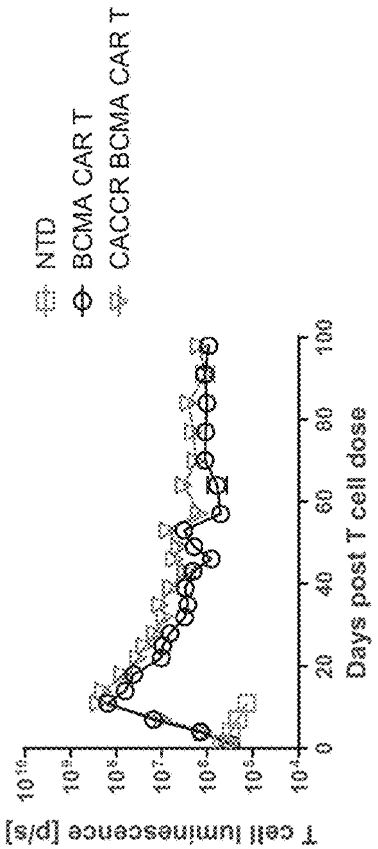
Figure 23G:
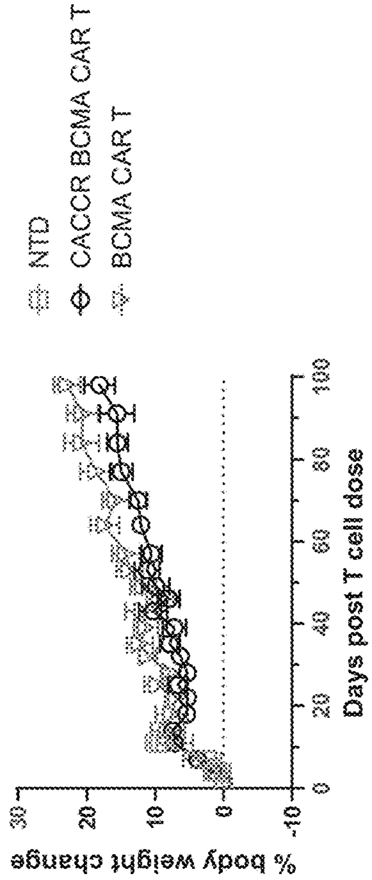

The data in FIGS. 23E-23G demonstrate that in vivo expansion of CACCR BCMA CAR T cells was target-dependent, and that they returned to quiescence following target clearance. FIG. 23E shows initial tumor progression in CAR T cell-treated mice, which was followed by tumor regression starting on Day 11. CACCR BCMA CAR T cells effectively eliminated tumors in 8/8 mice. By contrast, BCMA CAR T cells mediated tumor clearance in 5/7 mice. FIG. 23F shows the long-term CAR T cell pharmacokinetics in tumor-bearing mice. In response to tumor target, both BCMA and CACCR BCMA CAR T cells underwent robust expansion, with peak expansion on Day 11. This was followed by a comparable rate of decline in both BCMA and CACCR BCMA CAR T cells. FIG. 23G shows comparable weight gain between mice that had received CACCR BCMA CAR T cells and BCMA CAR T cells.

Example 8 Inhibition of the CACCR-BCMA CAR T Cells

Figure 24B:
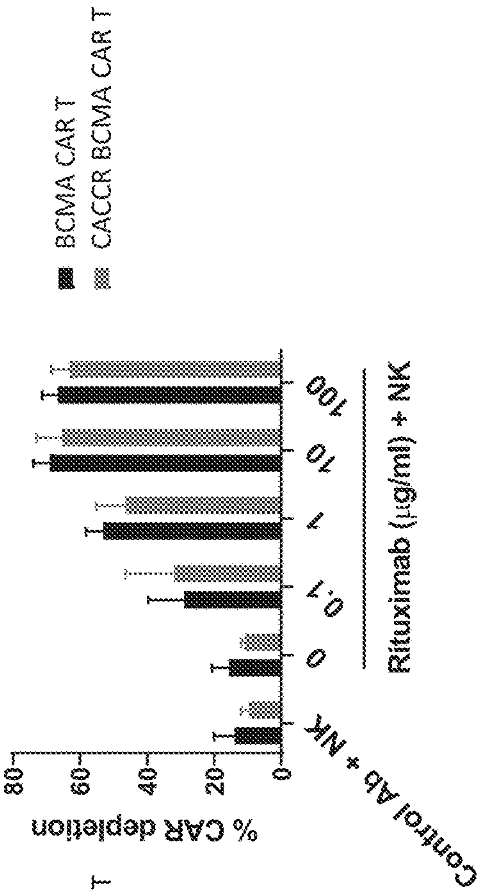
FIGS. 24A-24D show results of rituximab-mediated depletion assay of BCMA CAR or CACCR BCMA CAR T cells in vitro (FIG. 24A-24B) or in vivo (FIGS. 24C-24D).
Figure 24A:
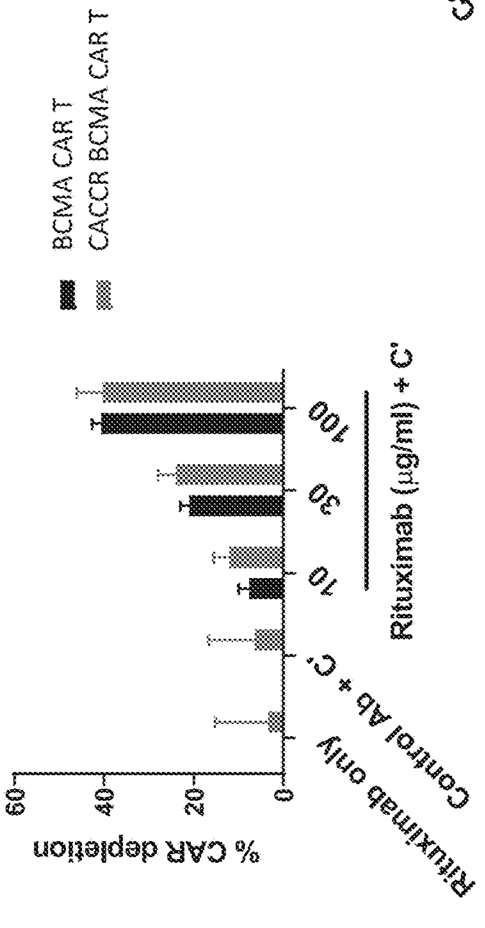

To minimize any potential safety concerns in clinical development, the BCMA CAR construct was designed to incorporate two rituximab mimotopes, which would sensitize the BCMA CAR T cells to rituximab-mediated depletion. We next tested the effects of rituximab on the BCMA CAR T cells with or without the CACCR. The results demonstrate that exposure of both types of BCMA CAR T cells to rituximab significantly decreased viable CAR T cells in a dose-responsive manner, as shown either in a complement-dependent cytotoxicity assay (FIG. 24A) or NK cell-mediated antibody-dependent cellular cytotoxicity assay (FIG. 24B).

Next, we tested the effect of rituximab on decreasing BCMA CAR T cells, with or without the CACCR, in vivo. Briefly, 8-10 weeks old female NSG mice were irradiated with 1 Gy one day prior to intravenous inoculation of $5\times10^6$ MM.1S-Luc-GFP. 14 days post tumor implantation, mice were randomized based on tumor burden and $3\times10^6$ TRAC/CD52 dKO CAR T cells were intravenously infused per mouse (n=10 mice per group). Rituximab (10 mg/kg) or PBS vehicle control was dosed intraperitoneally starting on the day of CAR T cell dosing and then daily for 4 additional days (n=9 or 10 per group). Tumor burden was monitored twice weekly by bioluminescent imaging. 7 days after CAR T cell dosing, mice were bled for the enumeration of BCMA CAR T cells in the periphery. Specifically, 50 uL of whole blood from each mouse was subjected to red blood cell lysis using ACK Lysing Buffer (Gibco), Fc-blocked and stained with the following antibody cocktail diluted in PBS+1% BSA: FITC-conjugated anti-mouse CD45 (Biolegend), BV421-conjugated anti-human CD45 (Biolegend) and PE-conjugated anti-idiotype antibody specific for the P5A2 scFv. Finally, samples were washed in PBS and cell pellets were resuspended in 250 uL PBS+1% BSA containing 123 count eBeads counting beads (Thermo Fisher) (10 uL counting beads in 240 uL PBS+1% BSA) prior to flow cytometric analysis.

Figure 24C:
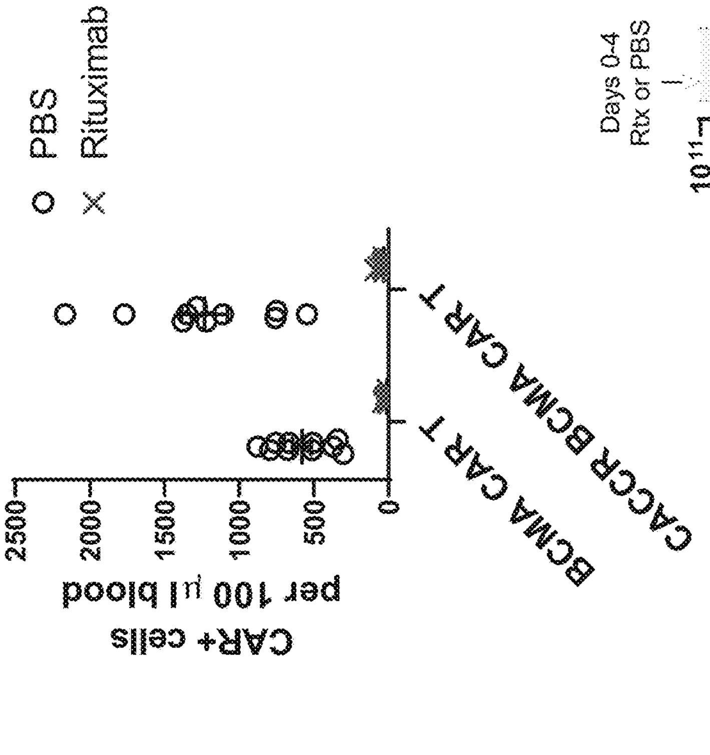
Figure 24D:
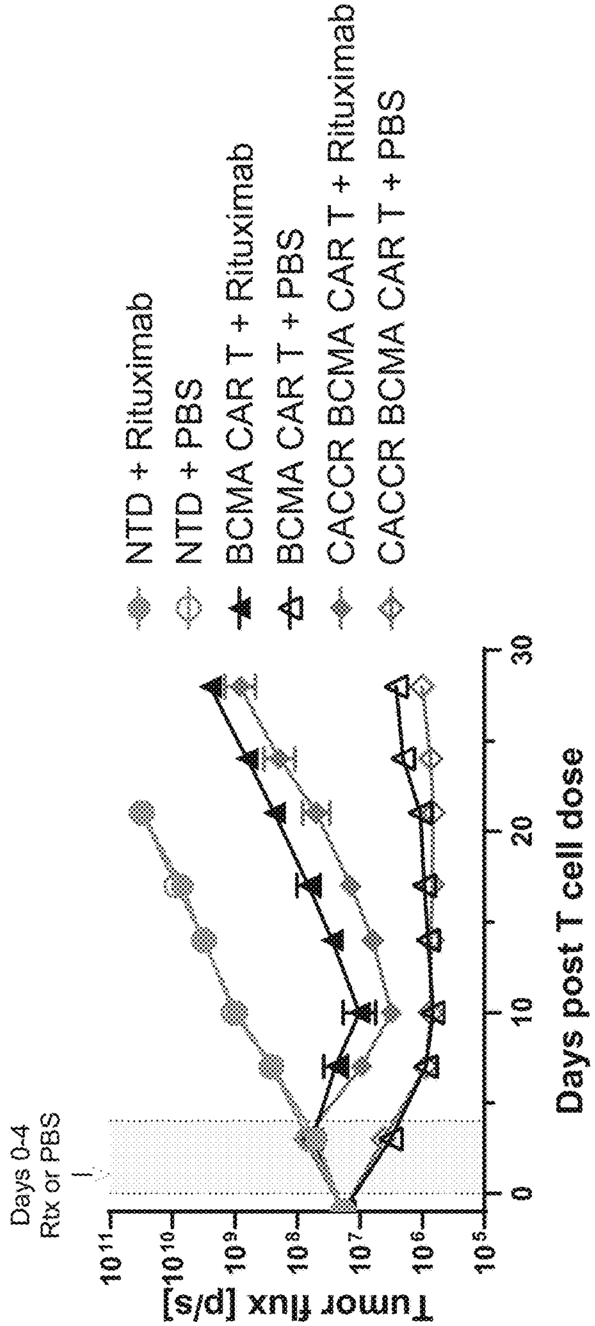

FIGS. 24C-24D show the effects of rituximab treatment on CAR T cell numbers and tumor growth kinetics. FIG. 24C shows the CAR T cell counts in peripheral blood 7 days post-CAR T cell dosing. In PBS-treated tumor-bearing mice, CACCR BCMA CAR T cells showed increased expansion compared to BCMA CAR T cells. However, treatment with rituximab resulted in efficient and complete elimination of both CAR T cells, demonstrating that CACCR BCMA CAR T cells remain susceptible to rituximab-mediated depletion in vivo. FIG. 24D shows tumor burden following rituximab-mediated CAR T cell depletion. While CAR T cells effectively controlled tumor growth in PBS-treated mice, CAR T cell elimination by rituximab compromised anti-tumor efficacy, as shown by suboptimal tumor clearance and subsequent tumor progression.

Figure 25A:
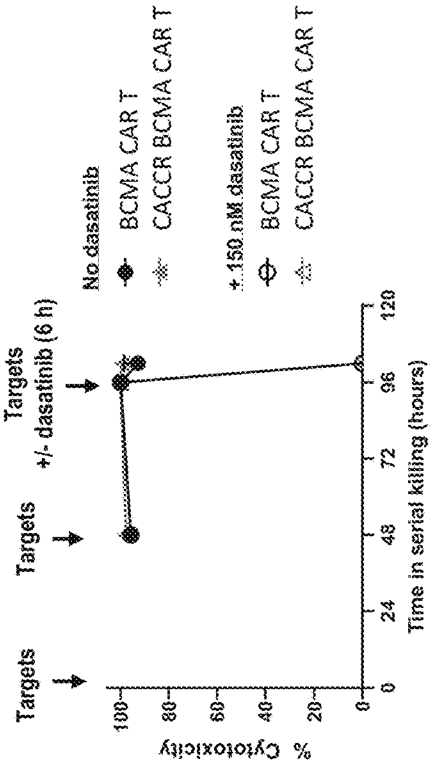
FIGS. 25A-25B show the effects of the tyrosine kinase inhibitor dasatinib on the activities of BCMA CAR T cells.
Figure 25B:
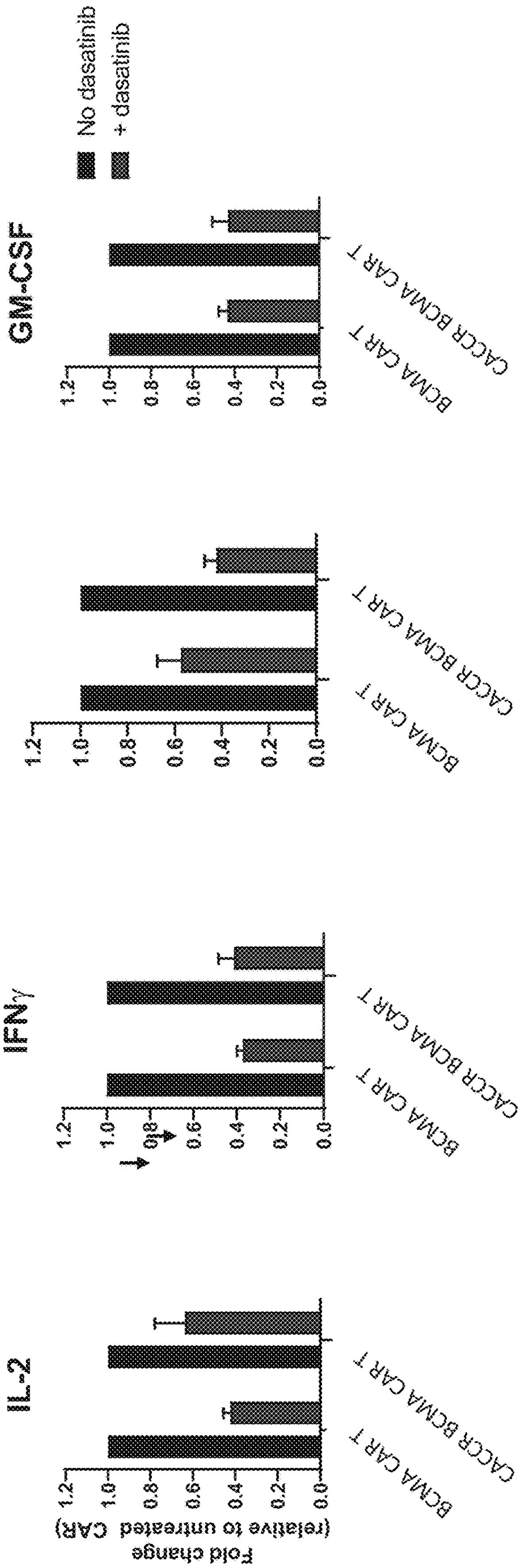

The data in FIGS. 25A-25B demonstrate that the activities of both the BCMA CAR T cells and CACCR BCMA CAR T cells can also be inhibited by the tyrosine kinase inhibitor dasatinib. It has been reported that dasatinib inhibits TCR signaling, T cell proliferation and effector function. We tested in an in vitro cell killing assay the effect of 150 nM dasatinib on the activities of the BCMA CAR T cells with or without the CACCR. The results in FIGS. 25A-25B show that dasatinib abolished the cytotoxicity (FIG. 25A) and inhibited cytokine secretion by both types of BCMA CAR T cells (FIG. 25B), though we observed that the effects were reversable when dasatinib was washed out of the cultures (data not shown).

Example 9 Long-Term In Vivo Pharmacokinetics of CACCR BCMA CAR T Cells

The long-term in vivo pharmacokinetics of CACCR BCMA CAR T cells was additionally evaluated in an orthotopic model of multiple myeloma. 8-10 weeks old female NSG mice were irradiated with 1 Gy one day prior to intravenous inoculation of $5 \times 10^6$ MM.1S-Luc-GFP. 15 days post tumor implantation, mice were randomized based on tumor burden and a suboptimal dose of $3 \times 10^6$ TRAC/CD52 dKO CACCR-BCMA CAR T cells were intravenously infused per mouse (n=10 mice per group). Thereafter, tumor burden was monitored twice weekly by bioluminescent imaging. At the indicated timepoints starting from Day 30, mice were bled for the enumeration of CACCR BCMA CAR T cells in the periphery. Specifically, 50 uL of whole blood from each mouse was subjected to red blood cell lysis using ACK Lysing Buffer (Gibco), Fc-blocked and stained with the following antibody cocktail diluted in PBS+1% BSA: FITC-conjugated anti-mouse CD45 (Biolegend), BV421-conjugated anti-human CD45 (Biolegend) and PE-conjugated anti-idiotype antibody specific for the BCMA scFv. Finally, samples were washed in PBS and cell pellets were resuspended in 250 uL PBS+1% BSA containing 123 count eBeads counting beads (Thermo Fisher) (10 uL counting beads in 240 uL PBS+1% BSA) prior to flow cytometric analysis.

Figures 26A, 26B, 26C:
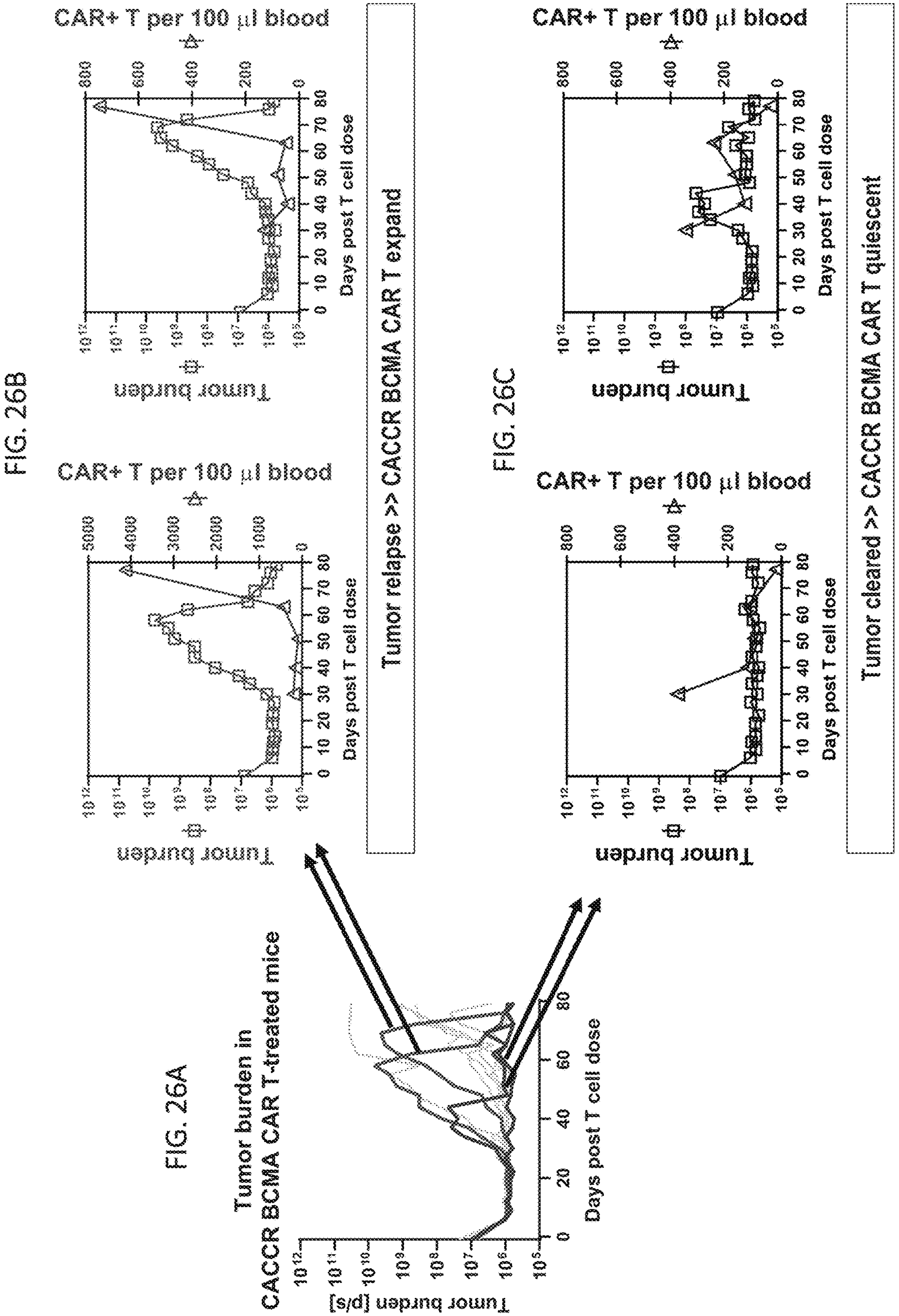
FIGS. 26A-26C show that active expansion of CACCR BCMA CAR T cells was target-dependent.

FIGS. 26A-26C again demonstrate that in vivo expansion of CACCR BCMA CAR T cells was target-dependent. FIG. 26A shows various anti-tumor response in individual mouse following treatment with a suboptimal dose of $3 \times 10^6$ TRAC/CD52 dKO CACCR BCMA CAR T cells, at which dose disease relapsed significantly in some mice, and completely regressed in others. FIG. 26B shows that disease relapse was followed by a sharp increase in CACCR BCMA CAR T cell expansion. FIG. 26C shows that in mice where tumors were cleared, no expansion of CACCR BCMA CAR T cells was observed, and the numbers of CACCR BCMA CAR T cells declined to the limit of detection by Day 80. Taken together, these demonstrate that active expansion of CACCR BCMA CAR T cells was target-dependent, and that constitutive signaling through the CACCR alone was insufficient to drive target-independent CAR T cell expansion or indefinite survival.

Example 10 the Effect of CACCR on BCMA CAR T Cell in an Orthotopic Model of Multiple Myeloma The effect of CACCR on BCMA CAR T cell in vivo activity and pharmacokinetics was next evaluated in an orthotopic model of multiple myeloma, in which disease initially establishes in the bone marrow and relapse subsequently occurs in extramedullary sites. 8-10 weeks old female NSG mice were irradiated with 1 Gy one day prior to intravenous inoculation of $5 \times 10^6$ MM.1S-Luc-GFP. 15 days post tumor implantation, mice were randomized based on tumor burden and the indicated numbers of TRAC/CD52 dKO CACCR-BCMA CAR T cells were intravenously infused per mouse (n=10 mice per group). Thereafter, tumor burden was monitored twice weekly by bioluminescent imaging. At the indicated timepoints, mice were bled for the enumeration of CACCR BCMA CAR T cells in the periphery.

Figures 27A, 27B, 27C, 27D:
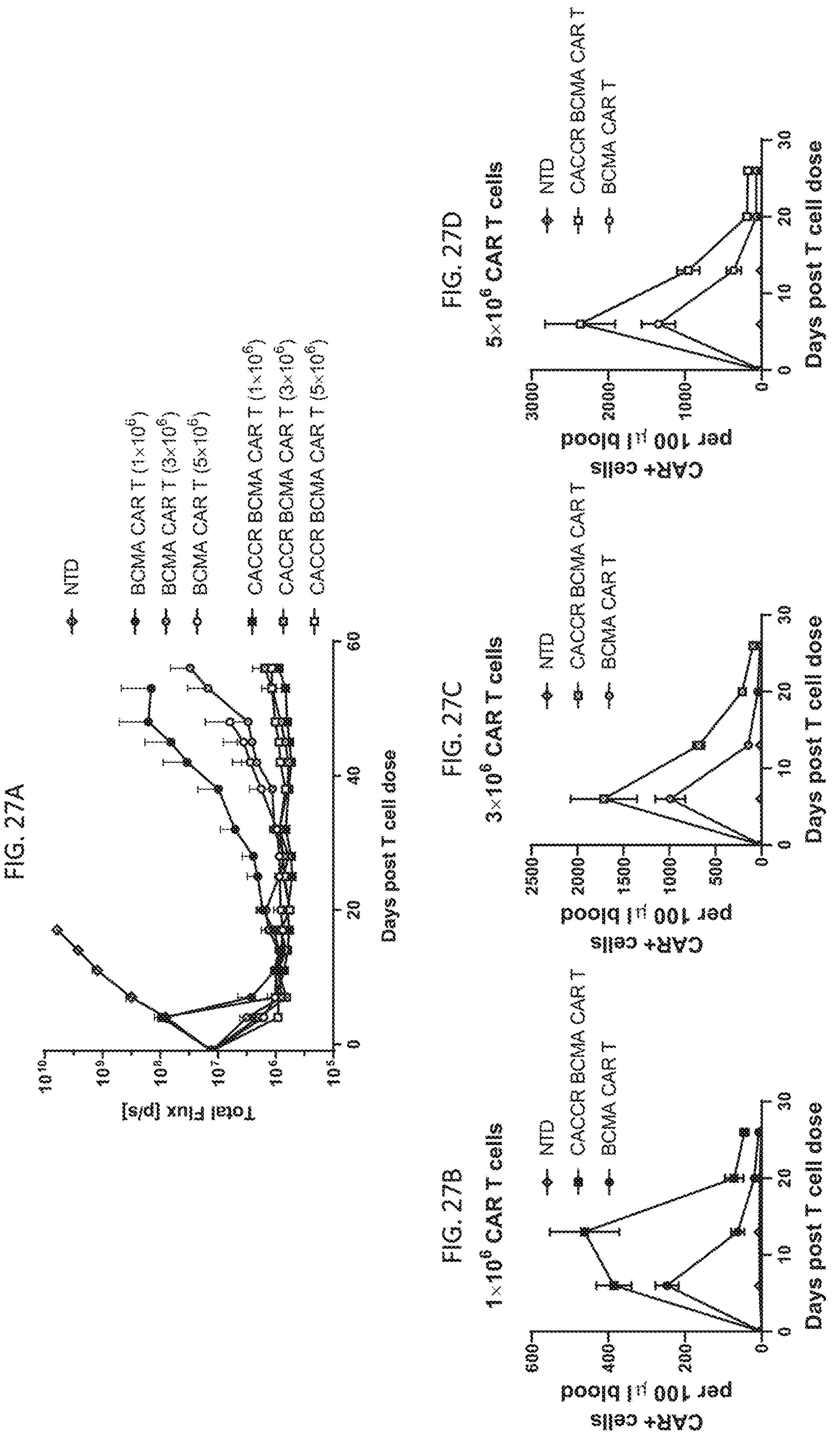
FIGS. 27A-27D show that CACCR improved anti-tumor efficacy and expansion of BCMA CAR T cells in an orthotopic model of multiple myeloma.

FIGS. 27A-27D show that CACCR improved the anti-tumor efficacy and expansion of BCMA CAR T cells in the orthotopic model of multiple myeloma. FIG. 27A shows the anti-tumor efficacy in response to the indicated numbers of CAR T cells. Compared to BCMA CAR T cell-treated groups that relapsed by Day 38, mice that had received CACCR BCMA CAR T cells showed improved durability of response. FIGS. 27B-27D show CAR T cell pharmacokinetics in the peripheral blood of mice that had received $1 \times 10^6$ (FIG. 27B), $3 \times 10^6$ (FIG. 27C), or $5 \times 10^6$ (FIG. 27D) CAR T cells. Consistent with improved anti-tumor efficacy, the results show that CACCR increased the expansion of BCMA CAR T cells in vivo.

What is claimed is:

1. An engineered immune cell comprising an anti-B cell maturation antigen (BCMA) chimeric antigen receptor (CAR) and a constitutively active chimeric cytokine receptor (CACCR), wherein the CACCR comprises two monomers, each monomer comprising:

a transmembrane domain;

a Janus Kinase (JAK)-binding domain; and a recruiting domain comprising the amino acid sequence of SEQ ID NO: 78, wherein the transmembrane domain and JAK-binding domain are present in a polypeptide (TM/JAK polypeptide) that comprises the amino acid sequence of SEQ ID NO: 12, wherein the CACCR does not comprise an extracellular ligand-binding domain, wherein the anti-BCMA CAR comprises an extracellular ligand-binding domain, a transmembrane domain, and an intracellular signaling domain, wherein the extracellular ligand-binding domain specifically recognizes and binds to human BCMA and comprises a single chain variable fragment (scFv), wherein the scFv comprises a heavy chain variable (VH) region and a light chain variable (VL) region; and wherein the VH region comprises a VH CDR1 comprising the amino acid sequence of SEQ ID NO: 146, 147, or 148; a VH CDR2 comprising the amino acid sequence of SEQ ID NO: 149 or 150; and a VH CDR3 comprising the amino acid sequence of SEQ ID NO: 151; and the VL region comprises a VL CDR1 comprising the amino acid sequence of SEQ ID NO: 152; a VL CDR2 comprising the amino acid sequence of SEQ ID NO: 153; and a VL CDR3 comprising the amino acid sequence of SEQ ID NO: 154.

2. The engineered immune cell of claim 1, wherein the CACCR comprises the amino acid sequence of SEQ ID NO: 100, 181, or 185.

3. The engineered immune cell of claim 1, wherein the VH region comprises the amino acid sequence of SEQ ID NO: 144 and the VL region comprises the amino acid sequence of SEQ ID NO: 145.

4. The engineered immune cell of claim 1, wherein the intracellular signaling domain of the BCMA CAR comprises a CD3ζ (CD3zeta) signaling domain and/or a 4-1BB signaling domain.

5. The engineered immune cell of claim 1, wherein the BCMA CAR comprises a safety switch comprising the CD20 mimotope.

6. The engineered immune cell of claim 1, wherein the BCMA CAR comprises the amino acid sequence of SEQ ID NO: 140, 141 or 166.

7. An engineered immune cell that comprises one or more polynucleotides that encode a BCMA CAR polypeptide that comprises the amino acid sequence of SEQ ID NO: 140, 141 or 166 and a CACCR polypeptide that comprises the amino acid sequence of SEQ ID NO: 100, 181, or 185.

8. The engineered immune cell of claim 7, wherein a single polynucleotide encodes both the polypeptide that comprises the amino acid sequence of SEQ ID NO: 140, 141 or 166 and the polypeptide that comprises the amino acid sequence of SEQ ID NO: 100, 181, or 185.

9. An engineered immune cell of claim 1 comprising a polynucleotide comprising the nucleic acid sequence of SEQ ID NO: 176.

10. The engineered immune cell of claim 7, wherein the one or more polynucleotides comprise a promoter.

11. The engineered immune cell of claim 10, wherein the promoter comprises an EF-1 alpha promoter.

12. The engineered immune cell of claim 1, wherein the engineered immune cell is an engineered T cell.

13. The engineered immune cell of claim 1, further comprising one or more genetic modifications in T cell receptor alpha constant region (TRAC) and/or CD52 gene to reduce or negate the expression of TCR alpha and/or CD52.

14. A method of treating a patient suffering from a disease or condition, wherein the method comprises administering an effective amount of the engineered immune cell of claim 1 to the patient in need thereof.

15. The method of claim 14, wherein the disease or condition is multiple myeloma.

16. The method of claim 14, wherein the engineered immune cell is allogeneic to the patient.

17. The method of claim 14, wherein the method comprises administering at least one dose of the engineered immune cell to the patient, and further wherein one dose contains between about 7×10^6 cells and about 480×10^6 cells.

18. The method of claim 17, wherein the dose ranges from about 20×10^6 cells/dose to about 480×10^6 cells/dose or the at least one dose is about 20×10^6 cells/dose, about 40×10^6 cells/dose, about 80×10^6 cells/dose, about 120×

$10^6$ cells/dose, about $240\times10^6$ cells/dose, about $320\times10^6$ cells/dose, about $360\times10^6$ cells/dose, or about $480\times10^6$ cells/dose.

19. One or more isolated polynucleotides encoding a BCMA CAR that comprises an amino acid sequence that is at least about 90% identical to the amino acid sequence of SEQ ID NO: 140, 141 or 166 and encoding a CACCR that comprises a polypeptide that is at least about 90% identical to the amino acid sequence of SEQ ID NO: 100, 181, or 185; wherein the CACCR comprises the amino acid sequence of SEQ ID NO: 78 and SEQ ID NO: 12.

20. A vector that comprises the one or more isolated polynucleotides of claim 19.

21. The vector of claim 20, wherein the BCMA CAR comprises the amino acid sequence of SEQ ID NO: 140, 141 or 166 and the CACCR comprises the amino acid sequence of SEQ ID NO: 100, 181, or 185.

22. The vector of claim 20, wherein the vector further comprises a promoter.

23. The vector of claim 22, wherein the promoter comprises an EF-1 alpha promoter.

24. The vector of claim 20, wherein the vector is a lentiviral vector.

25. The vector of claim 20 further comprising a mutant WPRE.

26. An engineered immune cell that comprises the one or more polynucleotides of claim 19.

27. A method of making an engineered immune cell of claim 1 comprising introducing into a cell: at least one polynucleotide that encodes a BCMA CAR and at least one polynucleotide that encodes a CACCR, wherein the engineered immune cell expresses a BCMA CAR and a CACCR.

28. The method of claim 27, wherein the immune cell is a T cell, dendritic cell, killer dendritic cell, mast cell, NK-cell, macrophage, monocyte, B-cell or an immune cell derived from a stem cell.

29. The method of claim 27, wherein the cell is autologous.

30. The method of claim 27, wherein the cell is allogeneic.

31. The method of claim 27, wherein the polynucleotide further encodes at least one selectable marker.

32. The method of claim 27, wherein the polynucleotide is introduced into the cell by electroporation, transfection and/or viral transduction.

* * * * *